US007906277B2

(12) United States Patent
Reed et al.

(10) Patent No.: US 7,906,277 B2
(45) Date of Patent: Mar. 15, 2011

(54) COMPOUND AND METHODS FOR DIAGNOSIS OF TUBERCULOSIS

(75) Inventors: Steven R. Reed, Bellevue, WA (US); Yasir A. W. Skeiky, Seattle, WA (US); Davin C. Dillon, Redmond, WA (US); Antonio Campos-Neto, Bainbridge Island, WA (US); Raymond Houghton, Bothell, WA (US); Thomas S. Vedvick, Federal Way, WA (US); Daniel R. Twardzik, Bainbridge Island, WA (US); Michael J. Lodes, Seattle, WA (US); Ronald C. Hendrickson, Seattle, WA (US)

(73) Assignee: Corixa Corporation, Seattle, WA (US)

( * ) Notice: Subject to any disclaimer, the term of this patent is extended or adjusted under 35 U.S.C. 154(b) by 103 days.

(21) Appl. No.: 11/505,569

(22) Filed: Aug. 16, 2006

(65) Prior Publication Data

US 2007/0141087 A1 Jun. 21, 2007

Related U.S. Application Data

(60) Continuation of application No. 11/082,005, filed on Mar. 15, 2005, now Pat. No. 7,122,196, which is a division of application No. 10/193,002, filed on Jul. 10, 2002, now Pat. No. 6,949,246, which is a continuation of application No. 09/072,596, filed on May 5, 1998, now Pat. No. 6,458,366, which is a continuation-in-part of application No. 09/024,753, filed on Feb. 18, 1998, now abandoned, which is a continuation-in-part of application No. 08/942,341, filed on Oct. 1, 1997, now abandoned, which is a continuation-in-part of application No. 08/818,111, filed on Mar. 13, 1997, now Pat. No. 6,338,852, which is a continuation-in-part of application No. 08/729,622, filed on Oct. 11, 1996, now abandoned, and a continuation-in-part of application No. 08/680,574, filed on Jul. 12, 1996, now abandoned, which is a continuation-in-part of application No. 08/658,800, filed on Jun. 5, 1996, now abandoned, which is a continuation-in-part of application No. 08/620,280, filed on Mar. 22, 1996, now abandoned, which is a continuation-in-part of application No. 08/532,136, filed on Sep. 22, 1995, now abandoned, which is a continuation of application No. 08/523,435, filed on Sep. 1, 1995, now abandoned.

(51) Int. Cl.

| | |
|---|---|
| *C12Q 1/00* | (2006.01) |
| *G01N 33/53* | (2006.01) |
| *A61K 39/04* | (2006.01) |

(52) U.S. Cl. ....... 435/4; 435/7.1; 424/130.1; 424/139.1; 424/150.1; 424/184.1; 424/185.1; 424/234.1; 424/248.1; 530/300; 530/350

(58) Field of Classification Search .................. 424/130, 424/139.1, 150.1, 184.1, 185.1, 234.1, 248.1; 435/4, 7.1; 530/300, 350
See application file for complete search history.

(56) References Cited

U.S. PATENT DOCUMENTS

| | | | |
|---|---|---|---|
| 3,943,119 | A | 3/1976 | Tsumita et al. |
| 4,235,877 | A | 11/1980 | Fullerton |
| 4,436,727 | A | 3/1984 | Ribi |
| 4,603,112 | A | 7/1986 | Paoletti et al. |
| 4,689,397 | A | 8/1987 | Shinnick et al. |
| 4,751,180 | A | 6/1988 | Cousens et al. |
| 4,769,330 | A | 9/1988 | Paoletti et al. |
| 4,777,127 | A | 10/1988 | Suni et al. |
| 4,866,034 | A | 9/1989 | Ribi |
| 4,876,089 | A | 10/1989 | Luciw et al. |
| 4,877,611 | A | 10/1989 | Cantrell |
| 4,879,213 | A | 11/1989 | Fox et al. |
| 4,897,268 | A | 1/1990 | Tice et al. |
| 4,912,094 | A | 3/1990 | Myers et al. |
| 4,935,233 | A | 6/1990 | Bell et al. |
| 4,946,778 | A | 8/1990 | Ladner et al. |
| 4,952,395 | A | 8/1990 | Shinnick et al. |
| 5,108,745 | A | 4/1992 | Horwitz |
| 5,145,684 | A | 9/1992 | Liversidge et al. |
| 5,240,856 | A | 8/1993 | Goffe et al. |
| 5,330,754 | A | 7/1994 | Kapoor et al. |
| 5,466,468 | A | 11/1995 | Schneider et al. |
| 5,478,726 | A | 12/1995 | Shinnick et al. |
| 5,504,005 | A | 4/1996 | Bloom et al. |
| 5,543,158 | A | 8/1996 | Ruzandra et al. |
| 5,565,213 | A | 10/1996 | Nakamori et al. |
| 5,567,434 | A | 10/1996 | Szoka |

(Continued)

FOREIGN PATENT DOCUMENTS

EP 345242 12/1989

(Continued)

OTHER PUBLICATIONS

Andersen and Hansen, "Structure and mapping of antigenic domains of protein antigen b. a 38,000-molecular-weight protein of Mycobacterium tuberculosis," *Infection and Immunity*, vol. 37, No. 8; pp. 2481-2488 (1989). Andersen and Heron "Specificity of a Protective Memory Immune Response against Mycobacteriurn tuberculosis" *Infection and Immunity* 61(3):844-851 (1993).
Andersen et al., "Identification of immunodominant antigens during infection with Mycobacterium tuberculosis," *Scand. J. Immunol.*, vol. 36, pp. 823-831 (1992).

(Continued)

*Primary Examiner* — Rodney P. Swartz
(74) *Attorney, Agent, or Firm* — Covergent Law Group LLP

(57) ABSTRACT

Compounds and methods for diagnosing tuberculosis are disclosed. The compounds provided include polypeptides that contain at least one antigenic portion of one or more *M. tuberculosis* proteins, and DNA sequences encoding such polypeptides. Diagnostic kits containing such polypeptides or DNA sequences and a suitable detection reagent may be used for the detection of *M. tuberculosis* infection in patients and biological samples. Antibodies directed against such polypeptides are also provided.

15 Claims, 19 Drawing Sheets

U.S. PATENT DOCUMENTS

| | | | |
|---|---|---|---|
| 5,580,579 | A | 12/1996 | Ruddy et al. |
| 5,583,112 | A | 12/1996 | Kensil et al. |
| 5,599,545 | A | 2/1997 | Stanford et al. |
| 5,616,500 | A | 4/1997 | Stanford et al. |
| 5,639,653 | A | 6/1997 | Bloom et al. |
| 5,714,593 | A | 2/1998 | Tsumita et al. |
| 5,780,045 | A | 7/1998 | McQuinn |
| 5,783,368 | A | 7/1998 | Jacobs, Jr. et al. |
| 5,795,587 | A | 8/1998 | Gao et al. |
| 5,804,212 | A | 9/1998 | Illum |
| 5,811,128 | A | 9/1998 | Tice et al. |
| 5,814,344 | A | 9/1998 | Tice et al. |
| 5,817,473 | A | 10/1998 | Das et al. |
| 5,820,883 | A | 10/1998 | Tice et al. |
| 5,853,763 | A | 12/1998 | Tice et al. |
| 5,856,462 | A | 1/1999 | Agrawal |
| 5,928,647 | A | 7/1999 | Rock |
| 5,942,252 | A | 8/1999 | Tice et al. |
| 5,955,077 | A | 9/1999 | Andersen et al. |
| 5,985,287 | A | 11/1999 | Tan et al. |
| 6,001,361 | A | 12/1999 | Tan et al. |
| 6,034,218 | A | 3/2000 | Reed et al. |
| 6,037,135 | A | 3/2000 | Kubo et al. |
| 6,113,918 | A | 9/2000 | Johnson et al. |
| 6,290,969 | B1 | 11/2001 | Reed et al. |
| 6,338,852 | B1 | 1/2002 | Reed et al. |
| 6,350,456 | B1 | 2/2002 | Reed et al. |
| 6,355,257 | B1 | 3/2002 | Johnson et al. |
| 6,458,366 | B1 | 10/2002 | Reed et al. |
| 6,465,633 | B1 | 10/2002 | Skeiky |
| 6,544,522 | B1 | 4/2003 | Skeiky et al. |
| 6,555,653 | B2 | 4/2003 | Alderson et al. |
| 6,592,877 | B1 | 7/2003 | Reed et al. |
| 6,613,881 | B1 | 9/2003 | Alderson et al. |
| 6,627,198 | B2 | 9/2003 | Reed et al. |
| 6,949,246 | B2 | 9/2005 | Reed et al. |
| 6,962,710 | B2 | 11/2005 | Reed et al. |
| 6,977,069 | B2 | 12/2005 | Reed et al. |
| 7,026,465 | B2 | 4/2006 | Skeiky et al. |
| 7,064,195 | B2 | 6/2006 | Skeiky et al. |
| 7,083,796 | B2 | 8/2006 | Skeiky et al. |
| 7,087,713 | B2 | 8/2006 | Campos-Neto et al. |
| 7,122,196 | B2 | 10/2006 | Reed et al. |
| 7,186,412 | B1 | 3/2007 | Skeiky et al. |
| 7,261,897 | B2 | 8/2007 | Skeiky et al. |
| 7,311,922 | B1 | 12/2007 | Skeiky et al. |
| 7,335,369 | B2 | 2/2008 | Reed et al. |
| 7,678,375 | B2 | 3/2010 | Skeiky et al. |
| 7,691,993 | B2 | 4/2010 | Skeiky et al. |
| 2006/0193876 | A1 | 8/2006 | Skeiky et al. |
| 2007/0054336 | A1 | 3/2007 | Campos-Neto et al. |
| 2007/0141087 | A1 | 6/2007 | Reed et al. |
| 2008/0176798 | A1 | 7/2008 | Campos-Neto et al. |
| 2008/0199405 | A1 | 8/2008 | Reed et al. |
| 2008/0269151 | A1 | 10/2008 | Skeiky et al. |
| 2008/0317716 | A1 | 12/2008 | Skeiky et al. |
| 2009/0017077 | A1 | 1/2009 | Reed et al. |
| 2009/0018095 | A1 | 1/2009 | Skeiky et al. |
| 2009/0022742 | A1 | 1/2009 | Campos-Neto et al. |
| 2009/0281168 | A1 | 11/2009 | Reed et al. |
| 2009/0306195 | A1 | 12/2009 | Skeiky et al. |
| 2010/0015096 | A1 | 1/2010 | Skeiky et al. |
| 2010/0183657 | A1 | 7/2010 | Skeiky et al. |
| 2010/0183677 | A1 | 7/2010 | Skeiky et al. |

FOREIGN PATENT DOCUMENTS

| | | | |
|---|---|---|---|
| EP | 413 355 | A1 | 3/1991 |
| EP | 519 218 | A2 | 12/1992 |
| FR | 2 244 539 | | 5/1975 |
| FR | 2 265 402 | | 11/1975 |
| GB | 2200651 | | 8/1988 |
| GB | 2298862 | | 9/1996 |
| HU | 158035 | | 3/1971 |
| RU | 2024021 | | 11/1994 |
| WO | WO 88/05823 | | 8/1988 |
| WO | WO 88/06591 | | 9/1988 |
| WO | WO 89/01973 | | 3/1989 |
| WO | WO 89/06280 | | 7/1989 |
| WO | WO 91/02805 | | 3/1991 |
| WO | WO 91/04272 | | 4/1991 |
| WO | WO 91/14448 | | 10/1991 |
| WO | WO 91/18926 | | 12/1991 |
| WO | WO 92/04049 | | 3/1992 |
| WO | WO 92/07243 | | 4/1992 |
| WO | WO 92/14154 | | 8/1992 |
| WO | WO 92/14823 | | 9/1992 |
| WO | WO 92/16628 | | 10/1992 |
| WO | WO 92/21697 | | 12/1992 |
| WO | WO 92/21758 | | 12/1992 |
| WO | WO 94/00153 | | 1/1994 |
| WO | WO 94/00228 | | 1/1994 |
| WO | WO 94/00492 | | 1/1994 |
| WO | WO 94/00493 | | 1/1994 |
| WO | WO 94/14069 | | 6/1994 |
| WO | WO 94/20078 | | 9/1994 |
| WO | WO 94/23701 | | 10/1994 |
| WO | WO 95/01440 | | 1/1995 |
| WO | WO 95/01441 | | 1/1995 |
| WO | WO 95/14713 | | 6/1995 |
| WO | WO 95/17210 | | 6/1995 |
| WO | WO 95/17511 | | 6/1995 |
| WO | WO 95/31216 | | 11/1995 |
| WO | WO 96/02555 | | 2/1996 |
| WO | WO 96/06638 | | 3/1996 |
| WO | WO 96/15241 | | 5/1996 |
| WO | WO 96/23885 | | 8/1996 |
| WO | WO 96/28551 | | 9/1996 |
| WO | WO 96/33739 | | 10/1996 |
| WO | WO 96/38591 | | 12/1996 |
| WO | WO 97/09248 | | 3/1997 |
| WO | WO 97/09249 | | 3/1997 |
| WO | WO 97/09428 | | 3/1997 |
| WO | WO 97/09429 | | 3/1997 |
| WO | WO 97/24447 | | 10/1997 |
| WO | WO 98/07868 | | 2/1998 |
| WO | WO 98/16645 | | 4/1998 |
| WO | WO 98/16646 | | 4/1998 |
| WO | WO 98/44119 | | 10/1998 |
| WO | WO 98/53075 | | 11/1998 |
| WO | WO 98/53076 | | 11/1998 |
| WO | WO 99/09186 | | 2/1999 |
| WO | WO 99/33488 | | 7/1999 |
| WO | WO 99/42076 | | 8/1999 |
| WO | WO 99/42118 | | 8/1999 |
| WO | WO/99/51748 | | 10/1999 |
| WO | WO 99/5254900 | | 10/1999 |
| WO | WO 00/09159 | | 2/2000 |
| WO | WO 01/24820 | | 4/2001 |
| WO | WO 01/34802 | | 5/2001 |
| WO | WO 01/034803 | | 5/2001 |
| WO | WO 01/51633 | | 7/2001 |
| WO | WO 01/62893 | | 8/2001 |
| WO | WO 01/73032 | | 10/2001 |
| WO | WO 01/90152 | | 11/2001 |
| WO | WO 01/090152 | | 11/2001 |
| WO | WO 01/98460 | | 12/2001 |
| WO | WO 2005/076101 | | 8/2005 |
| WO | WO 2008/107370 | | 9/2008 |

OTHER PUBLICATIONS

Andersen P., "Effective vaccination of mice against Mycobacterium tuberculosis with a soluble mixture of secreted mycobacterial proteins," *Infection and Immunity*, vol, 62, No. 6, pp. 2536-2544 (1994).
Ausebel et al., "Isolation of proteins for microsequence analysis," *Current Protocols in Molecular Biology*, Wiley & Sons, New York, pp. 10.19.1-10.19-12 (1993).
Barnes et al., "Immunoreactivity of a 10-kDa antigen of Mycobacterium tuberculosis," *J. Immunol.*, vol. 148, No. 6; pp. 1835-1840 (1992).
Boesen et al., "Human T-cell responses to secreted antigen fractions of Mycobacterium tuberculosis." *Infection and Immunity*, vol. 63, No. 4; pp. 1491-1497 (1995).
Borremans et al., "Cloning, sequencing determination, and expression of a 32-kilodalton-protein gene of Mycobacterium tuberculosis," *Infection and Immunity*, vol. 57, No. 10. pp. 3123-3130 (1989).

Burgess et al. "Possible Dissociation of the Heparin-binding and Mitogenic Activities of 1-Heparin-Binding (Acidic Fibroblast) Growth Factor-1 from its Receptor-binding Activities by Site-Directed Mutagenesis of a Single Lysine Residue." *J. Cell. Biol.* 111:2129-2138 (1990).
Content et al., "The genes coding for antigen 85 complexes of Mycobacterium tuberculosis anti Mycobacterium bovis BCG are members of a gene family: Cloning, sequence determination, and genomic organization of the gene coding for antigen 85-C of M. tuberculosis," *Infection and Immunity*, vol. 59; pp. 3205-3212 (1991).
Eiglmeier et al. "Use of an ordered cosmid library deduce the genomic organization of Mycobacterium leprae" *Mol. Microbiol.* 7(2)197-208 (1993).
Fifis et al. "Purification and Characterization of Major Antigens from Mycobacterium bovis Culture Filtrate" *Infection and Immunity* 59(3) 800-807 (1991).
Geysen et al. "Cognitive features of continuous antigenic determinants" *J. Mol. Recognition* 1:32-41 (1988).
Greenway et al, "Enhancement of protective immune responses to Venezuelan equine encephalitis (VEE) virus with microencapsulated vaccine" *Vaccine* 13:1411-1420 (1995).
Horowitz, et al., "Protective immunity against tuberculosis induced by vaccination with major extraceiluiar proteins of Mycobacterium tuberculosis," *PNAS USA*, vol. 92; pp. 1530-1534 (1995).
Kadival et al. "Radioimmunoassay of tuberculous antigen" *Indian J. Med. Res.* 75:765-770 (1982).
Lazar et al. "Transforming Growth Factor : Mutation of Aspartic Acid 47 and Leucine 48 results in Different Biological Activities" *Mol. Cell. Biol.* 8(3):1247-1252 (1988).
Lee et al. "Characterization of the Major Membrane Protein of virulent Mycobacterium tuberculosis" *Infection and Immunity* 60:2086-2074 (1992).
Lerner, at al. "Cloning and structure of the *Bacillus subtilis* aspartate transcarbamylase gene (pyrB)," *J. Biol. Chem.*, vol. 261(24): 11156-11165 (Aug. 25, 1986).
Lowrie et al., "Towards a DNA vaccine against tuberculosis," *Vaccine*, vol. 12, No. 16: pp. 1537-1540 (1994).
Mahairas, Gregory G. et al.; "Molecular Analysis of Genetic Differences between *Mycobacterium bovis* BCG and Virulent *M. bovis*"; 1996, *Journal of Bacteriology*, vol. 178, No. 5, pp. 1274-1282.
Mathur and Kolttukudy "Molecular cloning and sequencing of the gene for mycocerosic acid synthase, a novel fatty acid elongating muitifunctional enzyme, from Mycobacterium tuberculosis var. bovis Bacillus Calmette-Guerin" *J. Biol. Chem.* 267:19388-19395(1992).
Matsumoto et al, "Cloning and sequencing of a unique antigen MPT7O from Mycrobacterium tuberculosis H37Rv and expression in BCG using *E. coli*—Mycobacteria shuttle vector," *Scand. J. Immunol.*, vol. 41, pp. 281-287 (1995).
Nagai et al., "Isolation and partial characterization of major protein antigens in the culture fluid of Mycobacterium tuberculosis," *Infection and Immunity*, vol. 59, No. 1: pp. 372-382 (1991).
Oettinger and Andersen, "Cloning and B-cell-epitope mapping of MPT64 from Mycobacteriurn tuberculosis H37Rv," *Infection and Immunity*. vol. 62, No. 5; pp. 2058-2064 (1994).
Orme "Prospects for new vaccines gainst tuberculosis" *Trends in Microbiology* 3(10):401-404 (1995).
Pal and Horwitz, "Immunization with extracellular proteins of Mycobacterium tuberculosis induces cell-mediated immune responses and substantial protective immunity in a guinea pig model of pulmonary tuberculosis," *Infection and Immunity*, vol. 60, No. 11; pp. 4781-4792 (1992).
Pancholi et al. "Dendritic cells efficiently immunoselect mycobacterial-reactive T cells in human blood, including clonable antigen-reactive precursors" *Immunology* 76(2):217-224 (1992).
Philipp at al. "An integrated map of the genome of the tubercle baciiius, Mycobacterium tuberculosis H37Rv, and comparison with Mymbacteriumum leprae" *Proc. Natl. Acad. Sci. USA* 93(7):3132-3137 (1996).
Rinke de Wit et al. "A Mycobacterium leprae-specific gene encoding an immunologically recognized 45 kDa protein" *Mol. Microbiol.* 10(4):829-838 (1993).
Rinke de Wit et al. "A Mycobacteria contains two groEL genes: the second Mycobacterium leprae groEL gene is arranged in an operon with groES" *Mol. Microbiol.* 6(14):1995-2007 (1992).
Romain et al. "Identification of a Mycobacterium bovis BCG 45/47-Kilodalton Antigen Complex, an Immunodominant Target for Antibody Response after immunization with Living Bacteria" *Infection and Immunity* 61(2):742-750 (1993).
Romain et al, "Isolation of a proline-rich mycobacteriai protein eliciting delayed-type hypersensitivity reactions only in guinea pigs immunized with living mycobacteria," *PNAS USA*, vol. 90, pp. 5322-5326 (1993).
Romain, et al., "Preparation of Tuberculin Antigen L," *Ann. Inst. Pasteur/Microbiol.*, vol. 135B: 235-248 (1985).
Sanderson et al. "identification of a CD4+ T Cell-stimulating Antigen of Pathogenic Bacteria by Expression Cloning" *J. Exp. Med.* 182(6)1751-1757 (1995).
Vega-Lopez et al. "Sequence and immunological characterization of a serine-rich antigen from Mycobacterium leprae" *Infection and Immunity* 61 (5):2145-2153 (1993).
Wallis et al, "Identification of antigens of Mycobacterium tuberculosis using human monoclonal antibodies," *J. Clin Invest.* vol. 84; pp. 214-219 (1989).
Wieles et al. "Characterization of a Mycobacterium leprae Antigen Related to the Secreted Mycobacterium tuberculosis Protein MPT32" *Infection and Immunity* 62(1):252-258 (1994).
Wiker and Harboe, "The antigen 85 complex: A major secretion product of Mycobacterium tuberculosis," *Microbiological Reviews*, vol. 56, No. 4, pp. 648-661 (1992).
Yamaguchi et al., "Cloning and characterization of the gene for immunogenic protein MP864 of Mycotocterium bovis BCG", *Infection and Immunity*, vol. 57, No. 1; pp. 283-288 (1989).
Young et al., "Screening of a recombinant mycobacterial DNA library with polyclonal antiserum and molecular weight analysis of expressed antigens," *Infection and Immunity*, vol. 55, No. 6; pp. 1421-1425 (1987).
Sorenson, et al., "Purification and Characterization of a Low-Molecular-Mass T-Cell Antigen Secreted by *Mycobacterium tuberculosis*", Infection and Immunity, vol. 63, No. 5, pp. 1710-17 (May 1995).
EMBL Sequence Version Archive U34848 (Dec. 4, 1995) *Microbacterium bovis*, ID MB34848.
Hobbs, McGraw Hill Yearbook of Science and Technology, pp. 191-196 (1992).
Horn, et al., "Synthesis of oligonucleotides on cellulose," Nucl. Acids Res. Symposia Series, pp. 225-232 (1980).
Jacobs, "Advances in mycobacterial genetics: new promises for old diseases," Immunobiology 184(2-3):147-156 (1992).
Jurcevic, et al., "T cell responses to a mixture of *Mycobacterium tuberculosis* peptide with complementary HLA-DR binding profiles," Clinical and Experimental Immunology 105(3): 416-421 (1996).
Kalinowski, et al., "Genetic and biochemcial analysis of the aspartokinase from *Corynebacterium glutamicum* ," Molecular Microbiology 5:1197-1204 (1991).
Kass-Eisler, et al., "Quantitative determination of Adenoviral-mediated gene delivery to rat cardiac myocytes in vitro and in vivo," PNAS USA 90:11498-11502 (1993).
Karlin and Altschul, "Applications and statistics for multiple high-scoring segments in molecular sequences," PNAS USA 90: 5873-5787 (1993).
Kaufmann, et al., "Vaccination against tuberculosis and leprosy," Immunobiology 184(2-3): 208-229 (1992).
Khanolkar-Young, et al., "Results of the Third Immunology of Tuberculosis Anitmycobacterial Monoclonal Anitbody Workshop" Infection and Immunity 60(9):3925-927 (1992).
Kohler and Milstein, "Continuous cultures of fused cells secreting antibodies of predefined sequence," Nature 256:495-497 (1975).
Kolls, "Prolonged and effective blockade of TNF activity through Adenoviral-mediated gene transfer," PNAS USA 91: 215-219 (1994).
Kozak, "Comparison of Initiation of Protein Synthesis in Procaryotes, Eucaryotes, and Organelles;" Microbiological Review, pp. 1-45 (1983).

Kroll, et al., "A Multifunctional Prokaryotic Protein Expression System: Overproduction, Affinity Purification, and Selective Detection," DNA Cell Biol. 12:441-453 (1993).
Labouesse, et al., "Conformational changes in enzyme catalysis," Biochemistry 48:2137-2145 (1962).
Launois, et al., "T-Cell Epitope Mapping of the Major Secreted Mycobacterial Antigen AG85A in Tuberculosis and Leprosy," Infection and Immunity 62:3679-87 (1994).
Leao, et al., "Immunological and functional characterization of proteins of the *Mycobacterium tuberculosis* antigen 85 complex using synthetic pepides," J. Gen. Microbiol. 139:1543-1549 (1993).
Lewin, Genes IV, Oxford University Press, pp. 124-26 (1990).
Lewinshohn, et al., "Characterization of HumanCD8+ T Cells Reactive with *Mycrobacterium tuberculosis*-infected Antigen-presenting Cells," J. Exp. Med. 187(10):1633-1640 (1998).
Li, et al., "Important Role of the Amino Acid Attached to tRNA in Formylation and in Initiation of Protein Synthesis in *Escherichia coli*, " J. Biol. Chem., 271:1022-1028 (1996).
Ljungqvist, et al., "Antibody Responses Against Mycobacterium Tuberculosis in 11 Strains of Inbred Mice Novel Monoclonal Antibody Specificites Generated by Fusion Using Spleens from BALB B10 nd CBA-J Mice," Infections and Immunity 56(8):1994-98 (1988).
Logan and Shenk, "Advenovirus tripartite leader sequence enhances translation of mRNAs late after infection," PNAS USA 81: 365-3659 (1984).
Lowrie, et al., "Towards a DNA vaccine against tuberculosis," Vaccine 12(16);1537-1540 (1994).
Lowy, et al., "Isolation of transforming DNA: Cloning the Hamster aprt Gene," Cell 22:817-23 (1990).
Maddox, et al., "Elevated Serum Levels in Human Pregnancy of a Molecule Immunochemically similar to Eosinophil Granule Major Basic Protein," J. Exp. Med. 158:1211-1216 (1983).
Mahvi, et al., "DNA Cancer Vaccines—A Gene Gun Approach," Imm. and Cell Bio. 75: 456-460 (1997).
Manca, et al., "Molecular cloning, prufication and serological characterization of MPT63, a novel antigen secreted by *Mycobacterium tuberculosis*, " Infection and Immunity 65(1):16-23 (1997).
Maratea, et al., "Deletion and fusion analysis of phage phi-X-174 lysis gene E," Gene 40:39-46 (1985).
Merrifield, "Solid Phase Peptide Synthesis," J. Am. Chem. Soc. 85:2149-2146 (1963).
Moos, Isolation of Proteins for Microsequence Analysis, Current Protocols in Molecular Biology, pp. 10.19.1-1019.12 (2000).
Mosmann and Coffan, "Th1 and TH2 Cells: Different Patterns of Lymphokine Secretion Lead to Different Functional Properties," Ann. Rev. Immunol. 7:145-173 (1989).
Murphy, et al., "Genetic construction, expression and melanoma-selective cytotoxicity of a diphtheria toxin-related alpha-melanocyte stimulating hormone fusion protein," PNAS USA 83: 8258-8262 (1986).
Needleman and Wunsch, "A General Method Applicable to the Search for Similarities in the Amino Acid Sequence of Two Proteins," J. Mol. Biol. 48:443 (1970).
Newport, et al., "A Mutation in the Interferon-β-Receptor Gene and Susceptibility to Mycobacterial Infection," New Eng. J. of Medicine 335(26):1941-1949 (1996).
Nosoh, et al., Protein Stability and Stabilization through Protein Engineering, chap. 7, p. 197 (1991).
Ortega, et al., "Single-step purification on DEAE-sephacel of recombinant polypeptides produced in *Escherichia coli*," Biotechnology 10:795-798 (1992).
Parker, et al., "Targeted Gene Walking Polymerase Chain Reactions," Nuc. Acids Res. 19: 3055-60 (1991).
Paul, Fundamental Immunology, chap. 8, 243—247 (1993).
Porath, et al., "Immobilized Metal Ion Affinity Chromatography, " Proto Exp. Purif. 3:263-281 (1992).
Pouthier, et al., "Anti-A60 immunoglobulin G in the serodiagnosis of tuberculosis in HIV-seropositive and seronegative patients," AIDS 8(9):1277-80 (1994).
Reed, et al., "Tuberculosis vaccine development: from mouse to man," Microbes and Infection 7(5-6):992-31 (2005).
Reed, et al., "Defined tuberculosis vaccine, Mtb72F/AS02A,evidence of protection in cynomolgus monkeys," PNAS 106(7):2301-06 (2009).
Rhodes, et al., "Transformations of Maize by the Electroporation of Embryos," Methods Mol. Biol. 55:121-131 (1995).
Riveau, et al., "Synthetic peptide vaccines against peptides and biological mediators," Trends in Pharmacological Sciences 11:194-198 (1990).
Roberts, et al., "Prediction of HIV peptide epitopes by a novel algorithm," AIDS Research and Human Retroviruses 12:593-610 (1996).
Romano, et al., "Immunogenicity and protective efficacy of tuberculosis subunit vaccines expression PPE44 (Rv2770c)," Vaccine, 26(48):6053-63 (2008).
Rolland, "From Genes to Gene Medicines: Recent Advances in Nonviral Gene Delivery," Crit. Rev. Therap. Drug Carrier Systems 15:143-198 (1998).
Rosenfeld, et al., "Adenovirus-Mediated Transfere of a Recombinant Alpha-1 Antitrypsin Gene to Lung Epithelium in Vivo," Science 252:431-434 (1991).
Rossolini, et al., "Use of deoxyinosine-containing primers versus degenerate primers," Mol. Cell. Probes 8:91-98 (1994).
Sato, et al., "Immunostimulatory DNA Sequences Necessary for Effective Intradermal Gene Immunization," Science 273:352 (1996).
Scharf, et al., "Heat Stress Promoters and Transcription Factors," Results Probl. Cell Differ. 20:125-162 (1994).
Schorey, "A *Mycobacterium leprae* Gene Encoding a Fibronectin Binding Protein is Used for Efficient Invasion of Epithelial Cells and Schwann Cells," Infection and Immunity 63(7):2652-2657 (1995).
Shinnick, "The 65-Kilodalton Antigen of *Mycobacterioum tuberculosis*, " J. of Bacteriology 169(3): 1080-1088 (1997).
Singh, et al., "In Vitro Characterization of T Cells from Mycobacterium W-Vaccinated Mice," Infection and Immunity 60(1):257-263 (1992).
Sinha, et al., "Immunological properties of a 30 Kda secretory proteion of *Mycobacterium tuberculosis* H37RA," Vaccine 15(6-7): 689-99 (1997).
Simmonney et al., "Analysis of the immunological humoral response to *Mycobacterium tuberculosis* glycolipid antigens (DAT, PGLTb1) for diagnosis of tuberculosis in HIV-seropositive and seronegative patients," Eur. J. of Clin. Microbiology and Infectious Disease 14(10):883-891 (1995).
Skeiky, et al., "Cloning Expression and Immunological Evaluation of Two Putative Secreted Serine Protease Antigens of *Mycrobacterium tuberculosis*, " Infection and Immunity 67(8): 3998-4007 (1999).
Skeiky, et al., "LeIF: a recombinant leishmania protein that induces an IL-12 mediated Th cytokine profile," J. of Immunology 161: 6171-79 (1998).
Skeiky, et al., "Differential immune response and protective efficacy induced by components of a tuberculosis polyprotein vaccine, Mtb72F, delivered as naked DNA or recombinant protein," J. of Immunology 172(12):7618-28 (2004).
Skorko-Glonek, "Comparison of the structure of wild-type HtrA heat shock protease and mutant HtrA proteins. A Fourier transform infrared spectroscopic study," JBC 270(19); 11140-11146 (1995).
Skuce, et al., " Discrimination of M. tuberculosis complex bacterial using novel VNTR-PCR targets," Microbiology 148(2):519-28 (2002).
Stoute, et al., "A Preliminary Evaluation of a Recombinant Circumsporozoite Protein Vaccine Against Plasmodium Falciparum Malaria," New Engl. J. Med. 336:86-91 (1997).
St. Pierre, et al., "A refined vector system for the in vitro construction of single-copy transciptional or translational fusions to lacZ," Gene 169:65-68 (1996).
Timmerman and Levy, "Dendritic Cell Vaccines for Cancer Immunotherapy," Ann. Rev. Med 50: 507-529 (1999).
Triglia, et al., "A Procedure for in Vitro Amplification of DNA Squences that Lie Outside the Boundaries of Known Sequences," Nucl. Acids Res. 16:8186 (1988).
Tsenova, et al., "Evaluation of the Mtb72F Polyprotein Vaccine in a Rabbit Model," Infection and Immunity 74(4):2922-401 (2006).
Ulmer, et al., "Heterologous Protection Against Influenze by Injection of DNA Encoding a Viral Protein," Scinece 259:1745-1749 (1993).

Van Pittius, et al., "Evolution and expansion of the M. tuberculosis PE and PPE multigene families and their association with the duplication of the ESAT-6 (esx) gene cluster regions," BML Evolutionary Biology 6(1):95 (2006).
Van Soolingen, et al., "Host-Mediated Modification fo Pvull Restriction in *Mycobacterium tuberculosis*, " J. of Bactreriology 178(1):78-84 (1996).
Vekemans et al., "Immune Responses to Mycobacterial Antigens in the Gambian Population,", Infection and Immunity 72(1):381-88 z92004).
Von Eschen, et al., " The candidate tuberculosis vaccine Mtb72F/AS02A," Human Vaccines 5(7):475-82 (2009).
Verbon, et al., "The 14,000-Molecular-Weight Antigen of *Mycobacterium tuberculosis* Is Related to the Alpha-Crystallin Family of Low-Molecular-Weight Heat Shock Proteins," J. of Bacteriology 174(4):1352-1359 (1992).
Vordemeier, et al., "Synthetic delivery system for tuberculosis vaccines: Immunological evaluation of the *M. tuberculosis* 38 kDa protein entrapped in biodegradable PLG microparticles," Vaccine 13(16):1576-1582 (1995).
Wang et al., "Tuberculosis Vaccines: Past, Present and Future," Expert Rev. Vaccines 1(3):341-54 (2002).
Wang, et al., "A novel method for increasing the expression level of recombinant proteins," Protein Expression and Pruification 30(1):124-133 (2003).
Webb, et al., "Molecular Cloning, Expression and Immunogenicity of MTB12," Infection & Immunity 66(9):4208-4214 (1998).
Wiegeshaus, et al., "Evaluation of the protective potency of new tuberculosis vaccines," Reviews of Infectious Diseases 11(Suppl. 2):S484-S490 (1989).
Wigler, et al., "Transformation of mammalian cells with an amplifiable dominant-acting gene," PNAS USA 77:3567-70 (1980).
Winter, "The Expression of Heat Shock Proteins and Cognate Genes During Plant Development," Results Probl. Cell Differ. 17: 85-105 (1991).
Zimmerman, et al. "Immunization with peptide heteroconjugates primes a T helper cell type 1-associated antibody (IgG2a) response that recognizes the native epitope on the 38-kDa protein of *Mycobacterium tuberculosis*, " Vaccine Res. 5(2):103-118 (1996).
Zitvogel, et al., "Eradiation of established murine tumors using a novel cell-free vaccine: dedritic cell-derived exosomes," Nature Med. 4:594-600 (1998).
Seq_NCBI_AF2122897, 1 page.
Seq_XP002416348_CDC1551, 2 pages.
Seq_NCBI AD000020 gi: 1717739 Dec. 10, 1996, 10 pages.
Seq_NCBI_AL021930.1, 2 pages.
Seq_NCBI_AL021930, 17 pages.
Seq_NCBI_CAA17362.
Seq_Accession No. O05907, Database:stpremb119, publicly available Jul. 1, 1997.
Seq_Accession No. O05908, Database:stpremb119, publicly available Jul. 1, 1997.
Seq_EMBL_MTCY7H7Bc, Accession No. Z95557, May 20, 1997.
Seq_EMBL_MTCY24G1, Accession No. Z83858, Jan. 13, 1997.
Seq_EMBL_MTCY19G5, Accession No. Z77826, Jul. 31, 1996.
Seq_EMBL_MTCY261, Accession No. Z97559, Jul. 10, 1997.
Seq_EMBL_Z78020, XP002224823.
Seq_EMBL_P41403, XP002224824.
Seq_EMBL_Q50596, XP002224822.
Seq_EMBL_Z17372, XP002224825.
Seq_EMBL_U90239, XP002224826.
Seq_EMBL_P97048, XP002224827.
Seq_Accession_No_AU077540.
Seq_EMBL_P15712, (Apr. 1, 1990) "PBP-1 from *M. tuberculosis*" XP002359448.
Seq_Uniprot_Q79FV1.
Seq_Uniprot_O06267.
Seq_Uniprot_P96364.
Seq_Uniprot_O05300.
Seq_Sequence Alignment_SEQ ID NO: 163-*Mycobacterium smegmatis* (Cirillo et al.).
Seq_Sequence Alignment_*C orynebacterium glutamicum* .
Seq_Sequence alignment_*Mycobacterium segmatis*_P41403, created Nov. 1995.
Seq_NCBI_214801_Rv0287 [*Mycobacterium tuberculosisi* H37Rv].
Seq_EMBL_Q7U0G8-Hypothetical Protein Mb1207c, Oct. 31, 2006 XP002416347.
Seq_EMBL_050430-Hypothetical Protein Mb1207c, Oct. 31, 2006 XP002416348.
Seq_Compugen_Q10813, 1996.
Seq_Compugen_P95242, 1997.
Seq_Compugen_P96363, 1997.
Seq_Compugen_P95243, 1997.
Seq_Compugen_P96361, 1997.
Seq_Compugen_P95012, 1997.
Seq_Compugen_Q49722, 1996.
Seq_EMBL_X84741-Mycrobacteriumbovis BCG IS1081 DNA Sequence, Van Soolingen, D.
U.S. Appl. No. 09/724,685; filed Oct. 11, 1996.
First Office Action for U.S. Appl. No. 08/658,800.
Second Office Action for U.S. Appl. No. 08/658,800.
First Office Action for U.S. Appl. No. 08/659,683.
Second Office Action for U.S. Appl. No. 08/659,683.
First Office Action for U.S. Appl. No. 08/680,573.
Second Office Action for U.S. Appl. No. 08/680,573.
First Office Action for U.S. Appl. No. 08/680,574.
Second Office Action for U.S. Appl. No. 08/680,574.
First Office Action for U.S. Appl. No. 08/729,622.
Second Office Action for U.S. Appl. No. 08/729,622.
First Office Action for U.S. Appl. No. 08/730,510.
First Office Action for U.S. Appl. No. 08/818,111.
Second Office Action for U.S. Appl. No. 08/818,111.
First Office Action for U.S. Appl. No. 08/818,112.
Second Office Action for U.S. Appl. No. 08/818,112.
First Office Action for U.S. Appl. No. 08/858,998.
First Office Action for U.S. Appl. No. 08/859,381.
First Office Action for U.S. Appl. No. 08/942,341.
First Office Action for U.S. Appl. No. 08/928,78.
First Office Action for U.S. Appl. No. 09/056,556.
Second Office Action for U.S. Appl. No. 09/056,556.
First Office Action for U.S. Appl. No. 09/072,967.
First Office Action for U.S. Appl. No. 09/073,009.
Second Office Action for U.S. Appl. No. 09/073,009.
Third Office Action for U.S. Appl. No. 09/073,009.
Fourth Office Action for U.S. Appl. No. 09/073,009.
First Office Action for U.S. Appl. No. 09/073,010.
Second Office Action for U.S. Appl. No. 09/073,010.
Third Office Action for U.S. Appl. No. 09/073,010.
Office Action for U.S. Appl. No. 08/730,510.
Office Action for U.S. Appl. No. 09/470,191.
First Office Action for U.S. Appl. No. 09/072,596.
Altschul, et al., "Gapped BLAST and PSI-BLAST: a new generation of protein database search programs," Nuc. Acids Res. (25):3389-3402 (1977).
Alderson, et al., "Expression Cloning of an Immunodominant Family of *Mycobacterium tuberculosis* Antigens Using Human Cd4+ T Cells," J. Exp. Med. 191(3): 551-559 (2000).
Andersen, et al., "The T Cell Response to Secreted Antigens and *Mycobacterium tuberculosis*, " Immunobiol 191:537-547 (1994).
Andersen, et al., "Structure and Mapping of Antigenic Domains of Protein Antigenb, a 38,00-Molecular-Weight Protein of *Mycobacterium tuberculosis*, " Infection and Immunity 57(8):2481-2488 (1989).
Arnon, "Synthetic Peptids as a Basic for Vaccine Design," Molecular Immunology 28(2):209-215 (1991).
Banchereau, et al. "Dendritic cells and the control of immunity," Naure 392:245-251 (1998).
Barrera, et al., Humoral Response to Mycobacterium Tuberculosis in Patients with Human Immunodeficienty Virus Infection Tuberde and Lung Disease 73(4):187-91 (1992).
Batzer, et al., "Enhances evolutionary PCR using oligonucleotides with inosine at the 3' terminus" Nuc. Acids Res. 19:5081 (1991).
Berkner, "Development of Adenovirus Vectors for the Expression of Heterologous Genes," Biotechniques 6:616-627 (1988).

Bowie, et al., "Deciphering the Message of Protein Sequences: Tolerance to Amino Acid Sbustitutions" Science 257:1306-10 (1990).
Brandt, et al. "ESAT-6 subunit vaccination against *Mycobacterium tuberculosis*, " Infection and Immunity 68(2):791-795 (2000).
Brandt, et al. "The Protective Effect of the *Mycobacterium bovis* BCG Vaccine is Increased by Coadministration with the *Mycobacterium tuberculosis* 72-Kilodalton Fusion Polyprotein Mtb72F in *M. tuberculosis* -Infected Guinea Pigs" Infection and Immunity 72(11):6622-32 (2004).
Cameron, et al., "Identification and characterization of a putative serine protease expressed in vivo by *Mycobacterium avium* subsp. Paratuberculosisi," Microbiology 140(8):1977-1982 (1994).
Campos-Neto, et al., "Cutting Edge: CD40 Ligand Is Not Essential for the Development of Cell-Mediated Immunity and Resistance to *Mycobacterium tuberculosis*, " J. Immunol. 160(5):2037-2041 (1988).
Carter and Wells, "Dissecting the catalytic triad of a serine protease," Nature 332: 564-568 (1988).
Carter, "Peptide Analysis Protocols," Methoda in Molecular Biology, Chapter 1.1, 36:193-206 (1994).
Chaitra, et al., "Defining putative T cell epitopes from PE and PPE families of protein of *M. tuberculosis* with vaccine potential" Vaccine 23(10):1265-72 (2005).
Chaitra, et al., "HLAA0201-restricted cytotoxic T-cell epitopes in three PE/PPE family proteins of *M. tuberculosis*" Scand. J. of Immunology 67(4):411-17 (2008).
Chan and Kaufmann, Tuberculosis: Pathogenesis, Protection and Control, Chap. 24, ASM PRESS (1994)
Chen, et al., "T Cells for Tumor Therapy can be Obtained from Antigen-loaded Sponge Implants" Cancer Res. 54: 1065-1070 (1994).
Cirillo, et al., "Isolation and characterization of the aspartokinase and aspartate semiadldehyde dehydrogenase operon from mycobacteria," Molecular Microbiology 11(4): 629-639 (1994).
Cohen, "Naked DNA Points Way to Vaccines" Science 259: 1691-1692 (1993).
Colbere-Garapin, et al., "A New Dominant Hybrid Selective Marker for Higher Eurcaryotic Cells," J. Mol. Biol. 1501:1-14 (1981).
Cole et al., "Deciphering the biology of *Mycobacterium tuberculosis* from the complete genome sequence," Nature 393: 537-544 (1998).
Coler, et al. "Molecular cloning and immunologic reactivity of a novel low molecular mass antigen for *Mycobacterium tuberculosis*, " J. Immunol. 161(5):2356-2364 (1998).
Collins, "New Generation of tuberculosis vaccines," Clincial Microbiology Newsletter 23(3):17-23 (2001).
Coombes, et al., "Single dose, polymeric, microparticle-based vaccines: the influence of formulation conditions on the magnitude and duration of the immune response to a protein antigen," Vaccine 14: 1429-1438 (1996).
Coruzzi, et al., "Tissue-specific and light-regulated expression of a pea nuclear gene enconding the small subunit of ribulose-1,5-biphosphate carboxylase," EMBO 3: 1671-1680 (1984).
Creighton, Protein Structure: A Practical Approach, pp. 184-186 (1989).
Creighton, Proteins: Structures and Molecular Properties, pp. 314-315 (1984).
Daleine, et al., "Preliminary evaluation of a *Mycobacterium tuberculosis* lipoligosaccharide (LOS) antigen in the serological diagnosis of tuberculosis in HIV seropositive and seronegative patients," Tuberde and Lung Disease, 76(3): 234-39 (1995).
Devereaux, et al., "A Comprehensive System of Sequence Analysis Tools for the VAX," Nuc. Acides Res. 12:387-395 (1984).
Dillon, et al., "Molecular Characterization and Human T-Cell Responses to a Member of Novel *Mycobacterium tyberculosis* mtb39 Gene Family," Infection and Immunity 67(6): 2941-2950 (1999).
Doran, et al., "Characertisation of a Novel Repetitive DNA sequence from *Mycrobacerium bovis*, " FEMS Microbiology Letters 96: 179-186 (1992).
Fisher-Hoch, et al., "Protection of rhesus monkey from fatal Lassa feve by vaccination with a recombinatn vaccinia virus containing the Lassa virus glycoprotein gene" PNAS USA 86: 317-321 (1989).
Flexner, et al., "Vaccinia Virus Expression Vectors" Vaccine 8: 17-21 (1989).
Flexner, "Attenuation and immugenicity in primates of vaccinia virus recombinants expression human interleukin-2," Ann. NY. Acad. Sci. 569:86-103 (1989).
Flynn, et al., "An essential Role for Interferon γ in Resistance to *Mycobacterium tuberculosis* infection," J. of Experimental Medicine 178: 2249-2254 (1993).
Fsihi, et al. "The Mycrobacterium Leprae genome: systematic sequence ananlysis indentifies key catabolic enzymes, ATP-dependaent transport system and a novel PolA locus associated with genomic variability," Molecular Microbiology 16(5):909-919 (1995).
Garcia, "Nucleotide Sequence and Expression of pneumococcal autolysin gene from its own promoter in *E. Coli*," Gene (43):265-292 (1986).
Goodman-Smitkoff, et al., "Defining minimal requirements for antibody production to peptide antigens," Vaccine 8: 257-262 (1990).
Grant, et al., "Expression and Secretion Vectors for Yeast, "Methods Enzymol. 153: 516—544 (1987).
Greenspan and Di Cera, "Defining epitopes: It's not as easy as it seems," Nature Biotechnology 17: 936-937 (1999).
Griffin, et al., "Animal Models of Protective Immunity in Tuberculosis to Evaluate Candidate Vaccines;" Trends in Microbiology 3(11): 418-423 (1995).
Guzman, et al., "Efficient Gene Transfer into Myocardium by Direct Injection of Adenovirus," Cir. Res. 73: 1202- 1207 (1993).
Harrison's Principles of Internal Medicine, vol. 1, pp. 1004-1014 (1998).
Harrison's Principles of Internal Medicine, vol. 1, pp. 1019-1023 (1998).
Hartman and Mulligan, "Two dominant-acting selectable markers for gene transfer studies in mammalian cells," Pnas Usa 85: 8047-51 (1988).
Hendrickson, et al., "Mass Spectrometric Identification of Mtb81, A Novel Serological Marker for Tuberculosis," J. Clin. Microbiol 38(6):2354-2361 (2000).
Higgins and Sharp, "Fast and sensitive multiple sequence alignments on a microcomputer," Cabios 5:151- 153 (1989).

a - Tb lysate (5µg)
b - CSP + LAM (5µg)
c - 38.1 (50ng)
d - TbH-9 (50ng)
e - 85b (50ng)

a b c d e

Rαm TbsP

O/N exposure

SEQUENCE LISTING

```
<160> NUMBER OF SEQ ID NOS: 351

<210> SEQ ID NO 1
<211> LENGTH: 766
<212> TYPE: DNA
<213> ORGANISM: Mycobacterium tuberculosis
<220> FEATURE:
<221> NAME/KEY: modified_base
<222> LOCATION: (1)..(766)
<223> OTHER INFORMATION: n = g, a, c or t

<400> SEQUENCE: 1

cgaggcaccg gtagtttgaa ccaaacgcac aatcgacggg caaacgaacg gaagaacaca     60

accatgaaga tggtgaaatc gatcgccgca ggtctgaccg ccgcggctgc aatcggcgcc    120

gctgcggccg gtgtgacttc gatcatggct ggcggcccgg tcgtatacca gatgcagccg    180

gtcgtcttcg gcgcgccact gccgttggac ccggcatccg cccctgacgt cccgaccgcc    240

gcccagttga ccagcctgct caacagcctc gccgatccca acgtgtcgtt tgcgaacaag    300

ggcagtctgg tcgagggcgg catcgggggc accgaggcgc gcatcgccga ccacaagctg    360

aagaaggccg ccgagcacgg ggatctgccg ctgtcgttca gcgtgacgaa catccagccg    420

gcggccgccg gttcggccac cgccgacgtt tccgtctcgg gtccgaagct ctcgtcgccg    480

gtcacgcaga acgtcacgtt cgtgaatcaa ggcggctgga tgctgtcacg cgcatcggcg    540

atggagttgc tgcaggccgc agggnaactg attggcgggc cggnttcagc ccgctgttca    600

gctacgccgc ccgcctggtg acgcgtccat gtcgaacact cgcgcgtgta gcacggtgcg    660

gtntgcgcag ggncgcacgc accgcccggt gcaagccgtc ctcgagatag gtggtgnctc    720

gncaccagng ancaccccn nntcgncnnt tctcgntgnt gnatga                    766


<210> SEQ ID NO 2
<211> LENGTH: 752
<212> TYPE: DNA
<213> ORGANISM: Mycobacterium tuberculosis
<220> FEATURE:
<221> NAME/KEY: modified_base
<222> LOCATION: (1)..(752)
<223> OTHER INFORMATION: n = g, a, c or t

<400> SEQUENCE: 2

atgcatcacc atcaccatca cgatgaagtc acggtagaga cgacctccgt cttccgcgca     60

gacttcctca gcgagctgga cgctcctgcg caagcgggta cggagagcgc ggtctccggg    120

gtggaagggc tcccgccggg ctcggcgttg ctggtagtca aacgaggccc caacgccggg    180

tcccggttcc tactcgacca agccatcacg tcggctggtc ggcatcccga cagcgacata    240

tttctcgacg acgtgaccgt gagccgtcgc catgctgaat tccggttgga aaacaacgaa    300

ttcaatgtcg tcgatgtcgg gagtctcaac ggcacctacg tcaaccgcga gcccgtggat    360

tcggcggtgc tggcgaacgg cgacgaggtc cagatcggca agctccggtt ggtgttcttg    420

accggaccca agcaaggcga ggatgacggg agtaccgggg gcccgtgagc gcacccgata    480

gccccgcgct ggccgggatg tcgatcgggg cggtcctccg acctgctacg accggatttt    540
```

-continued ccctgatgtc caccatctcc aagattcgat tcttgggagg cttgagggtc ngggtgaccc 600
ccccgcgggc ctcattcngg ggtntcggcn ggtttcaccc cntaccnact gccnccccggn 660 ttgcnaattc nttcttcnct gcccnnaaag ggaccnttan cttgccgctn gaaanggtna 720
tccngggccc ntcctngaan ccccntcccc ct 752

<210> SEQ ID NO 3
<211> LENGTH: 813
<212> TYPE: DNA
<213> ORGANISM: Mycobacterium tuberculosis
<220> FEATURE:
<221> NAME/KEY: modified_base
<222> LOCATION: (1)..(813)
<223> OTHER INFORMATION: n = g, a, c or t

<400> SEQUENCE: 3
catatgcatc accatcacca tcacacttct aaccgcccag cgcgtcgggg gcgtcgagca 60
ccacgcgaca ccgggcccga tcgatctgct agcttgagtc tggtcaggca tcgtcgtcag 120
cagcgcgatg ccctatgttt gtcgtcgact cagatatcgc ggcaatccaa tctcccgcct 180
gcggccggcg gtgctgcaaa ctactcccgg aggaatttcg acgtgcgcat caagatcttc 240
atgctggtca cggctgtcgt tttgctctgt tgttcgggtg tggccacggc cgcgcccaag 300
acctactgcg aggagttgaa aggcaccgat accggccagg cgtgccagat tcaaatgtcc 360
gacccggcct acaacatcaa catcagcctg cccagttact accccgacca gaagtcgctg 420
gaaaattaca tcgcccagac gcgcgacaag ttcctcagcg cggccacatc gtccactcca 480
cgcgaagccc cctacgaatt gaatatcacc tcggccacat accagtccgc gataccgccg 540
cgtggtacgc aggccgtggt gctcamggtc taccacaacg ccggcggcac gcacccaacg 600
accacgtaca aggccttcga ttgggaccag gcctatcgca agccaatcac ctatgacacg 660
ctgtggcagg ctgacaccga tccgctgcca gtcgtcttcc ccattgttgc aaggtgaact 720
gagcaacgca gaccgggaca acwggtatcg atagccgccn aatgccggct tggaacccng 780
tgaaattatc acaacttcgc agtcacnaaa naa 813

<210> SEQ ID NO 4
<211> LENGTH: 447
<212> TYPE: DNA
<213> ORGANISM: Mycobacterium tuberculosis

<400> SEQUENCE: 4
cggtatgaac acggccgcgt ccgataactt ccagctgtcc cagggtgggc agggattcgc 60
cattccgatc gggcaggcga tggcgatcgc gggccagatc cgatcgggtg gggggtcacc 120
caccgttcat atcgggccta ccgccttcct cggcttgggt gttgtcgaca acaacggcaa 180
cggcgcacga gtccaacgcg tggtcgggag cgctccggcg gcaagtctcg gcatctccac 240
cggcgacgtg atcaccgcgg tcgacggcgc tccgatcaac tcggccaccg cgatggcgga 300
cgcgcttaac gggcatcatc ccggtgacgt catctcggtg aactggcaaa ccaagtcggg 360
cggcacgcgt acagggaacg tgacattggc cgagggaccc ccggcctgat ttcgtcgygg 420
ataccacccg ccggccggcc aattgga 447

<210> SEQ ID NO 5
<211> LENGTH: 604
<212> TYPE: DNA
<213> ORGANISM: Mycobacterium tuberculosis
<220> FEATURE:
<221> NAME/KEY: modified_base
<222> LOCATION: (1)..(604)

<223> OTHER INFORMATION: n = g, a, c or t

<400> SEQUENCE: 5
gtcccactgc ggtcgccgag tatgtcgccc agcaaatgtc tggcagccgc ccaacggaat 60
ccggtgatcc gacgtcgcag gttgtcgaac ccgccgccgc ggaagtatcg gtccatgcct 120
agcccggcga cggcgagcgc cggaatggcg cgagtgagga ggcgggcaat ttggcggggc 180
ccggcgacgg ngagcgccgg aatggcgcga gtgaggaggt ggncagtcat gcccagngtg 240
atccaatcaa cctgnattcg gnctgngggn ccatttgaca atcgaggtag tgagcgcaaa 300
tgaatgatgg aaaacgggng gngacgtccg ntgttctggt ggtgntaggt gnctgnctgg 360
ngtngnggnt atcaggatgt tcttcgncga aanctgatgn cgaggaacag ggtgtncccg 420
nnannccnan ggngtccnan cccnnnntcc tcgncganat cananagncg nttgatgnga 480
naaaagggtg gancagnnnn aantngnggn ccnaanaanc nnnanngnng nnagntngnt 540
nnntnttnnc annnnnnntg nngnngnncn nnncaancnn ntnnnngnaa nnggnttntt 600 naat 604

<210> SEQ ID NO 6
<211> LENGTH: 633
<212> TYPE: DNA
<213> ORGANISM: Mycobacterium tuberculosis
<220> FEATURE:
<221> NAME/KEY: modified_base
<222> LOCATION: (1)..(633)
<223> OTHER INFORMATION: n = g, a, c or t

<400> SEQUENCE: 6
ttgcangtcg aaccacctca ctaaagggaa caaaagctng agctccaccg cggtggcggc 60
cgctctagaa ctagtgkatm yyyckggctg cagsaatycg gyacgagcat taggacagtc 120
taacggtcct gttacggtga tcgaatgacc gacgacatcc tgctgatcga caccgacgaa 180
cgggtgcgaa ccctcaccct caaccggccg cagtcccgya acgcgctctc ggcggcgcta 240
cgggatcggt ttttcgcggy gttggycgac gccgaggycg acgacgacat cgacgtcgtc 300
atcctcaccg gygccgatcc ggtgttctgc gccggactgg acctcaaggt agctggccgg 360
gcagaccgcg ctgccggaca tctcaccgcg gtgggcggcc atgaccaagc cggtgatcgg 420
cgcgatcaac ggcgccgcgg tcaccggcgg gctcgaactg gcgctgtact gcgacatcct 480
gatcgcctcc gagcacgccc gcttcgncga cacccacgcc cgggtggggc tgctgcccac 540
ctggggactc agtgtgtgct tgccgcaaaa ggtcggcatc ggnctgggcc ggtggatgag 600
cctgaccggc gactacctgt ccgtgaccga cgc 633

<210> SEQ ID NO 7
<211> LENGTH: 1362
<212> TYPE: DNA
<213> ORGANISM: Mycobacterium tuberculosis

<400> SEQUENCE: 7
cgacgacgac ggcgccggag agcgggcgcg aacggcgatc gacgcggccc tggccagagt 60
cggcaccacc caggagggag tcgaatcatg aaatttgtca accatattga gcccgtcgcg 120
ccccgccgag ccggcggcgc ggtcgccgag gtctatgccg aggcccgccg cgagttcggc 180
cggctgcccg agccgctcgc catgctgtcc ccggacgagg gactgctcac cgccggctgg 240
gcgacgttgc gcgagacact gctggtgggc caggtgccgc gtggccgcaa ggaagccgtc 300
gccgccgccg tcgcggccag cctgcgctgc ccctggtgcg tcgacgcaca caccaccatg 360

-continued

```
ctgtacgcgg caggccaaac cgacaccgcc gcggcgatct tggccggcac agcacctgcc    420

gccggtgacc cgaacgcgcc gtatgtggcg tgggcggcag gaaccgggac accggcggga    480

ccgccggcac cgttcggccc ggatgtcgcc gccgaatacc tgggcaccgc ggtgcaattc    540

cacttcatcg cacgcctggt cctggtgctg ctggacgaaa ccttcctgcc ggggggcccg    600

cgcgcccaac agctcatgcg ccgcgccggt ggactggtgt tcgcccgcaa ggtgcgcgcg    660

gagcatcggc cgggccgctc cacccgccgg ctcgagccgc gaacgctgcc cgacgatctg    720

gcatgggcaa caccgtccga gcccatagca accgcgttcg ccgcgctcag ccaccacctg    780

gacaccgcgc cgcacctgcc gccaccgact cgtcaggtgg tcaggcgggt cgtggggtcg    840

tggcacggcg agccaatgcc gatgagcagt cgctggacga acgagcacac cgccgagctg    900

cccgccgacc tgcacgcgcc cacccgtctt gccctgctga ccggcctggc cccgcatcag    960

gtgaccgacg acgacgtcgc cgcggcccga tccctgctcg acaccgatgc ggcgctggtt   1020

ggcgccctgg cctgggccgc cttcaccgcc gcgcggcgca tcggcacctg gatcggcgcc   1080

gccgccgagg gccaggtgtc gcggcaaaac ccgactgggt gagtgtgcgc gccctgtcgg   1140

tagggtgtca tcgctggccc gagggatctc gcggcggcga acggaggtgg cgacacaggt   1200

ggaagctgcg cccactggct tgcgccccaa cgccgtcgtg ggcgttcggt tggccgcact   1260

ggccgatcag gtcggcgccg gcccttggcc gaaggtccag ctcaacgtgc cgtcaccgaa   1320

ggaccggacg gtcaccgggg gtcaccctgc gcgcccaagg aa                      1362
```

<210> SEQ ID NO 8
<211> LENGTH: 1458
<212> TYPE: DNA
<213> ORGANISM: Mycobacterium tuberculosis

<400> SEQUENCE: 8

```
gcgacgaccc cgatatgccg ggcaccgtag cgaaagccgt cgccgacgca ctcgggcgcg     60

gtatcgctcc cgttgaggac attcaggact gcgtggaggc ccggctgggg gaagccggtc    120

tggatgacgt ggcccgtgtt tacatcatct accggcagcg gcgcgccgag ctgcggacgg    180

ctaaggcctt gctcggcgtg cgggacgagt taaagctgag cttggcggcc gtgacggtac    240

tgcgcgagcg ctatctgctg cacgacgagc agggccggcc ggccgagtcg accggcgagc    300

tgatggaccg atcggcgcgc tgtgtcgcgg cggccgagga ccagtatgag ccgggctcgt    360

cgaggcggtg ggccgagcgg ttcgccacgc tattacgcaa cctggaattc ctgccgaatt    420

cgcccacgtt gatgaactct ggcaccgacc tgggactgct cgccggctgt tttgttctgc    480

cgattgagga ttcgctgcaa tcgatctttg cgacgctggg acaggccgcc gagctgcagc    540

gggctggagg cggcaccgga tatgcgttca gccacctgcg acccgccggg gatcgggtgg    600

cctccacggg cggcacggcc agcggaccgg tgtcgtttct acggctgtat gacagtgccg    660

cgggtgtggt ctccatgggc ggtcgccggc gtggcgcctg tatggctgtg cttgatgtgt    720

cgcacccgga tatctgtgat ttcgtcaccg ccaaggccga atcccccagc gagctcccgc    780

atttcaacct atcggttggt gtgaccgacg cgttcctgcg ggccgtcgaa cgcaacggcc    840

tacaccggct ggtcaatccg cgaaccggca agatcgtcgc gcggatgccc gccgccgagc    900

tgttcgacgc catctgcaaa gccgcgcacg ccggtggcga tcccgggctg gtgtttctcg    960

acacgatcaa tagggcaaac ccggtgccgg ggagaggccg catcgaggcg accaacccgt   1020

gcggggaggt cccactgctg ccttacgagt catgtaatct cggctcgatc aacctcgccc   1080

ggatgctcgc cgacggtcgc gtcgactggg accggctcga ggaggtcgcc ggtgtggcgg   1140
```

-continued tgcggttcct tgatgacgtc atcgatgtca gccgctaccc cttccccgaa ctgggtgagg 1200
cggcccgcgc cacccgcaag atcgggctgg gagtcatggg tttggcggaa ctgcttgccg 1260
cactgggtat tccgtacgac agtgaagaag ccgtgcggtt agccacccgg ctcatgcgtc 1320
gcatacagca ggcggcgcac acggcatcgc ggaggctggc cgaagagcgg ggcgcattcc 1380
cggcgttcac cgatagccgg ttcgcgcggt cgggcccgag gcgcaacgca caggtcacct 1440
ccgtcgctcc gacgggca 1458

<210> SEQ ID NO 9
<211> LENGTH: 862
<212> TYPE: DNA
<213> ORGANISM: Mycobacterium tuberculosis

<400> SEQUENCE: 9
acggtgtaat cgtgctggat ctggaaccgc gtggcccgct acctaccgag atctactggc 60
ggcgcagggg gctggccctg ggcatcgcgg tcgtcgtagt cgggatcgcg gtggccatcg 120
tcatcgcctt cgtcgacagc agcgccggtg ccaaaccggt cagcgccgac aagccggcct 180
ccgcccagag ccatccgggc tcgccggcac cccaagcacc ccagccggcc gggcaaaccg 240
aaggtaacgc cgccgcggcc ccgccgcagg gccaaaaccc cgagacaccc acgcccaccg 300
ccgcggtgca gccgccgccg gtgctcaagg aaggggacga ttgccccgat tcgacgctgg 360
ccgtcaaagg tttgaccaac gcgccgcagt actacgtcgg cgaccagccg aagttcacca 420
tggtggtcac caacatcggc ctggtgtcct gtaaacgcga cgttggggcc gcggtgttgg 480
ccgcctacgt ttactcgctg gacaacaagc ggttgtggtc caacctggac tgcgcgccct 540
cgaatgagac gctggtcaag acgttttccc ccggtgagca ggtaacgacc gcggtgacct 600
ggaccgggat gggatcggcg ccgcgctgcc cattgccgcg gccggcgatc gggccgggca 660
cctacaatct cgtggtacaa ctgggcaatc tgcgctcgct gccggttccg ttcatcctga 720
atcagccgcc gccgccgccc gggccggtac ccgctccggg tccagcgcag gcgcctccgc 780
cggagtctcc cgcgcaaggc ggataattat tgatcgctga tggtcgattc cgccagctgt 840
gacaacccct cgcctcgtgc cg 862

<210> SEQ ID NO 10
<211> LENGTH: 622
<212> TYPE: DNA
<213> ORGANISM: Mycobacterium tuberculosis
<220> FEATURE:
<221> NAME/KEY: modified_base
<222> LOCATION: (1)..(622)
<223> OTHER INFORMATION: n = g, a, c or t

<400> SEQUENCE: 10
ttgatcagca ccggcaaggc gtcacatgcc tccctgggtg tgcaggtgac caatgacaaa 60
gacaccccgg gcgccaagat cgtcgaagta gtggccggtg gtgctgccgc gaacgctgga 120
gtgccgaagg gcgtcgttgt caccaaggtc gacgaccgcc cgatcaacag cgcggacgcg 180
ttggttgccg ccgtgcggtc caaagcgccg ggcgccacgg tggcgctaac ctttcaggat 240
ccctcgggcg gtagccgcac agtgcaagtc accctcggca aggcggagca gtgatgaagg 300
tcgccgcgca gtgttcaaag ctcggatata cggtggcacc catggaacag cgtgcggagt 360
tggtggttgg ccgggcactt gtcgtcgtcg ttgacgatcg cacggcgcac ggcgatgaag 420
accacagcgg gccgcttgtc accgagctgc tcaccgaggc cgggtttgtt gtcgacggcg 480
tggtggcggt gtcggccgac gaggtcgaga tccgaaatgc gctgaacaca gcggtgatcg 540
gcggggtgga cctggtggtg tcggtcggcg ggaccggngt gacgnctcgc gatgtcaccc 600
cggaagccac ccgngacatt ct 622

<210> SEQ ID NO 11
<211> LENGTH: 1200
<212> TYPE: DNA
<213> ORGANISM: Mycobacterium tuberculosis

<400> SEQUENCE: 11
ggcgcagcgg taagcctgtt ggccgccggc acactggtgt tgacagcatg cggcggtggc 60
accaacagct cgtcgtcagg cgcaggcgga acgtctgggt cggtgcactg cggcggcaag 120
aaggagctcc actccagcgg ctcgaccgca caagaaaatg ccatggagca gttcgtctat 180
gcctacgtgc gatcgtgccc gggctacacg ttggactaca acgccaacgg gtccggtgcc 240
ggggtgaccc agtttctcaa caacgaaacc gatttcgccg gctcggatgt cccgttgaat 300
ccgtcgaccg gtcaacctga ccggtcggcg gagcggtgcg gttccccggc atgggacctg 360
ccgacggtgt tcggcccgat cgcgatcacc tacaatatca agggcgtgag cacgctgaat 420
cttgacggac ccactaccgc caagattttc aacggcacca tcaccgtgtg gaatgatcca 480
cagatccaag ccctcaactc cggcaccgac ctgccgccaa caccgattag cgttatcttc 540
cgcagcgaca agtccggtac gtcggacaac ttccagaaat acctcgacgg tgtatccaac 600
ggggcgtggg gcaaaggcgc cagcgaaacg ttcagcgggg gcgtcggcgt cggcgccagc 660
gggaacaacg gaacgtcggc cctactgcag acgaccgacg ggtcgatcac ctacaacgag 720
tggtcgtttg cggtgggtaa gcagttgaac atggcccaga tcatcacgtc ggcgggtccg 780
gatccagtgg cgatcaccac cgagtcggtc ggtaagacaa tcgccggggc caagatcatg 840
ggacaaggca acgacctggt attggacacg tcgtcgttct acagacccac ccagcctggc 900
tcttacccga tcgtgctggc gacctatgag atcgtctgct cgaaataccc ggatgcgacg 960
accggtactg cggtaagggc gtttatgcaa gccgcgattg gtccaggcca agaaggcctg 1020
gaccaatacg gctccattcc gttgcccaaa tcgttccaag caaaattggc ggccgcggtg 1080
aatgctattt cttgacctag tgaagggaat tcgacggtga gcgatgccgt tccgcaggta 1140
gggtcgcaat ttgggccgta tcagctattg cggctgctgg gccgaggcgg gatgggcgag 1200

<210> SEQ ID NO 12
<211> LENGTH: 1155
<212> TYPE: DNA
<213> ORGANISM: Mycobacterium tuberculosis

<400> SEQUENCE: 12
gcaagcagct gcaggtcgtg ctgttcgacg aactgggcat gccgaagacc aaacgcacca 60
agaccggcta caccacggat gccgacgcgc tgcagtcgtt gttcgacaag accgggcatc 120
cgtttctgca acatctgctc gcccaccgcg acgtcacccg gctcaaggtc accgtcgacg 180
ggttgctcca agcggtggcc gccgacggcc gcatccacac cacgttcaac cagacgatcg 240
ccgcgaccgg ccggctctcc tcgaccgaac ccaacctgca gaacatcccg atccgcaccg 300
acgcgggccg gcggatccgg gacgcgttcg tggtcgggga cggttacgcc gagttgatga 360
cggccgacta cagccagatc gagatgcgga tcatggggca cctgtccggg gacgagggcc 420
tcatcgaggc gttcaacacc ggggaggacc tgtattcgtt cgtcgcgtcc cgggtgttcg 480
gtgtgcccat cgacgaggtc accggcgagt tgcggcgccg ggtcaaggcg atgtcctacg 540
ggctggttta cgggttgagc gcctacggcc tgtcgcagca gttgaaaatc tccaccgagg 600

-continued

```
aagccaacga gcagatggac gcgtatttcg cccgattcgg cggggtgcgc gactacctgc    660

gcgccgtagt cgagcgggcc cgcaaggacg gctacacctc gacggtgctg ggccgtcgcc    720

gctacctgcc cgagctggac agcagcaacc gtcaagtgcg ggaggccgcc gagcgggcgg    780

cgctgaacgc gccgatccag ggcagcgcgg ccgacatcat caaggtggcc atgatccagg    840

tcgacaaggc gctcaacgag gcacagctgg cgtcgcgcat gctgctgcag gtccacgacg    900

agctgctgtt cgaaatcgcc cccggtgaac gcgagcgggt cgaggccctg gtgcgcgaca    960

agatgggcgg cgcttacccg ctcgacgtcc cgctggaggt gtcggtgggc tacggccgca   1020

gctgggacgc ggcggcgcac tgagtgccga gcgtgcatct ggggcgggaa ttcggcgatt   1080

tttccgccct gagttcacgc tcggcgcaat cgggaccgag tttgtccagc gtgtacccgt   1140

cgagtagcct cgtca                                                     1155
```

```
<210> SEQ ID NO 13
<211> LENGTH: 1771
<212> TYPE: DNA
<213> ORGANISM: Mycobacterium tuberculosis

<400> SEQUENCE: 13

gagcgccgtc tggtgtttga acggttttac cggtcggcat cggcacgggc gttgccgggt     60

tcgggcctcg ggttggcgat cgtcaaacag gtggtgctca accacggcgg attgctgcgc    120

atcgaagaca ccgacccagg cggccagccc cctggaacgt cgatttacgt gctgctcccc    180

ggccgtcgga tgccgattcc gcagcttccc ggtgcgacgg ctggcgctcg gagcacggac    240

atcgagaact ctcggggttc ggcgaacgtt atctcagtgg aatctcagtc cacgcgcgca    300

acctagttgt gcagttactg ttgaaagcca cacccatgcc agtccacgca tggccaagtt    360

ggcccgagta gtgggcctag tacaggaaga gcaacctagc gacatgacga atcacccacg    420

gtattcgcca ccgccgcagc agccgggaac cccaggttat gctcaggggc agcagcaaac    480

gtacagccag cagttcgact ggcgttaccc accgtccccg cccccgcagc caacccagta    540

ccgtcaaccc tacgaggcgt tgggtggtac ccggccgggt ctgatacctg gcgtgattcc    600

gaccatgacg ccccctcctg ggatggttcg ccaacgccct cgtgcaggca tgttggccat    660

cggcgcggtg acgatagcgg tggtgtccgc cggcatcggc ggcgcggccg catccctggt    720

cgggttcaac cgggcacccg ccggccccag cggcggccca gtggctgcca gcgcggcgcc    780

aagcatcccc gcagcaaaca tgccgccggg gtcggtcgaa caggtggcgg ccaaggtggt    840

gcccagtgtc gtcatgttgg aaaccgatct gggccgccag tcggaggagg gctccggcat    900

cattctgtct gccgaggggc tgatcttgac caacaaccac gtgatcgcgg cggccgccaa    960

gcctcccctg ggcagtccgc cgccgaaaac gacggtaacc ttctctgacg ggcggaccgc   1020

acccttcacg gtggtggggg ctgaccccac cagtgatatc gccgtcgtcc gtgttcaggg   1080

cgtctccggg ctcaccccga tctccctggg ttcctcctcg gacctgaggg tcggtcagcc   1140

ggtgctggcg atcgggtcgc cgctcggttt ggagggcacc gtgaccacgg ggatcgtcag   1200

cgctctcaac cgtccagtgt cgacgaccgg cgaggccggc aaccagaaca ccgtgctgga   1260

cgccattcag accgacgccg cgatcaaccc cggtaactcc gggggcgcgc tggtgaacat   1320

gaacgctcaa ctcgtcggag tcaactcggc cattgccacg ctgggcgcgg actcagccga   1380

tgcgcagagc ggctcgatcg gtctcggttt tgcgattcca gtcgaccagg ccaagcgcat   1440

cgccgacgag ttgatcagca ccggcaaggc gtcacatgcc tccctgggtg tgcaggtgac   1500

caatgacaaa gacaccccgg gcgccaagat cgtcgaagta gtggccggtg gtgctgccgc   1560
```

-continued

```
gaacgctgga gtgccgaagg gcgtcgttgt caccaaggtc gacgaccgcc cgatcaacag   1620

cgcggacgcg ttggttgccg ccgtgcggtc caaagcgccg ggcgccacgg tggcgctaac   1680

ctttcaggat ccctcgggcg gtagccgcac agtgcaagtc accctcggca aggcggagca   1740

gtgatgaagg tcgccgcgca gtgttcaaag c                                  1771
```

<210> SEQ ID NO 14
<211> LENGTH: 1058
<212> TYPE: DNA
<213> ORGANISM: Mycobacterium tuberculosis
<220> FEATURE:
<221> NAME/KEY: modified_base
<222> LOCATION: (1)..(1058)
<223> OTHER INFORMATION: n = g, a, c or t

<400> SEQUENCE: 14

```
ctccaccgcg gtggcggccg ctctagaact agtggatccc ccgggctgca ggaattcggc     60

acgaggatcc gacgtcgcag gttgtcgaac ccgccgccgc ggaagtatcg gtccatgcct    120

agcccggcga cggcgagcgc cggaatggcg cgagtgagga ggcgggcaat ttggcggggc    180

ccggcgacgg cgagcgccgg aatggcgcga gtgaggaggc gggcagtcat gcccagcgtg    240

atccaatcaa cctgcattcg gcctgcgggc ccatttgaca atcgaggtag tgagcgcaaa    300

tgaatgatgg aaaacgggcg gtgacgtccg ctgttctggt ggtgctaggt gcctgcctgg    360

cgttgtggct atcaggatgt tcttcgccga aacctgatgc cgaggaacag ggtgttcccg    420

tgagcccgac ggcgtccgac cccgcgctcc tcgccgagat caggcagtcg cttgatgcga    480

caaaagggtt gaccagcgtg cacgtagcgg tccgaacaac cgggaaagtc gacagcttgc    540

tgggtattac cagtgccgat gtcgacgtcc gggccaatcc gctcgcggca aagggcgtat    600

gcacctacaa cgacgagcag ggtgtcccgt ttcgggtaca aggcgacaac atctcggtga    660

aactgttcga cgactggagc aatctcggct cgatttctga actgtcaact tcacgcgtgc    720

tcgatcctgc cgctggggtg acgcagctgc tgtccggtgt cacgaacctc caagcgcaag    780

gtaccgaagt gatagacgga atttcgacca ccaaaatcac cgggaccatc cccgcgagct    840

ctgtcaagat gcttgatcct ggcgccaaga gtgcaaggcc ggcgaccgtg tggattgccc    900

aggacggctc gcaccacctc gtccgagcga gcatcgacct cggatccggg tcgattcagc    960

tcacgcagtc gaaatggaac gaacccgtca acgtcgacta ggccgaagtt gcgtcgacgc   1020

gttgntcgaa acgcccttgt gaacggtgtc aacggnac                           1058
```

<210> SEQ ID NO 15
<211> LENGTH: 542
<212> TYPE: DNA
<213> ORGANISM: Mycobacterium tuberculosis
<220> FEATURE:
<221> NAME/KEY: modified_base
<222> LOCATION: (406)
<223> OTHER INFORMATION: n = g, a, c or t

<400> SEQUENCE: 15

```
gaattcggca cgagaggtga tcgacatcat cgggaccagc cccacatcct gggaacaggc     60

ggcggcggag gcggtccagc gggcgcggga tagcgtcgat gacatccgcg tcgctcgggt    120

cattgagcag gacatggccg tggacagcgc cggcaagatc acctaccgca tcaagctcga    180

agtgtcgttc aagatgaggc cggcgcaacc gcgctagcac gggccggcga gcaagacgca    240

aaatcgcacg gtttgcggtt gattcgtgcg attttgtgtc tgctcgccga ggcctaccag    300

gcgcggccca ggtccgcgtg ctgccgtatc caggcgtgca tcgcgattcc ggcggccacg    360
```

-continued ccggagttaa tgcttcgcgt cgacccgaac tgggcgatcc gccggngagc tgatcgatga 420
ccgtggccag cccgtcgatg cccgagttgc ccgaggaaac gtgctgccag gccggtagga 480
agcgtccgta ggcggcggtg ctgaccggct ctgcctgcgc cctcagtgcg gccagcgagc 540
gg 542

<210> SEQ ID NO 16
<211> LENGTH: 913
<212> TYPE: DNA
<213> ORGANISM: Mycobacterium tuberculosis
<220> FEATURE:
<221> NAME/KEY: modified_base
<222> LOCATION: (1)..(913)
<223> OTHER INFORMATION: n = g, a, c or t

<400> SEQUENCE: 16
cggtgccgcc cgcgcctccg ttgcccccat tgccgccgtc gccgatcagc tgcgcatcgc 60
caccatcacc gcctttgccg ccggcaccgc cggtggcgcc ggggccgccg atgccaccgc 120
ttgaccctgg ccgccggcgc cgccattgcc atacagcacc ccgccggggg caccgttacc 180
gccgtcgcca ccgtcgccgc cgctgccgtt tcaggccggg gaggccgaat gaaccgccgc 240
caagcccgcc gccggcaccg ttgccgcctt ttccgcccgc cccgccggcg ccgccaattg 300
ccgaacagcc amgcaccgtt gccgccagcc ccgccgccgt taacggcgct gccgggcgcc 360
gccgccggac ccgccattac cgccgttccc gttcggtgcc ccgccgttac cggcgccgcc 420
gtttgccgcc aatattcggc gggcaccgcc agacccgccg gggccaccat tgccgccggg 480
caccgaaaca acagcccaac ggtgccgccg gccccgccgt ttgccgccat caccggccat 540
tcaccgccag caccgccgtt aatgtttatg aacccggtac cgccagcgcg gcccctattg 600
ccgggcgccg gagngcgtgc ccgccggcgc cgccaacgcc caaaagcccg gggttgccac 660
cggccccgcc ggacccaccg gtcccgccga tccccccgtt gccgccggtg ccgccgccat 720
tggtgctgct gaagccgtta gcgccggttc cgcsggttcc ggcggtggcg ccntggccgc 780
cggccccgcc gttgccgtac agccaccccc cggtggcgcc gttgccgcca ttgccgccat 840
tgccgccgtt gccgccattg ccgccgttcc cgccgccacc gccggnttgg ccgccggcgc 900
cgccggcggc cgc 913

<210> SEQ ID NO 17
<211> LENGTH: 1872
<212> TYPE: DNA
<213> ORGANISM: Mycobacterium tuberculosis
<220> FEATURE:
<221> NAME/KEY: modified_base
<222> LOCATION: (1)..(1872)
<223> OTHER INFORMATION: n = g, a, c or t

<400> SEQUENCE: 17
gactacgttg gtgtagaaaa atcctgccgc ccggaccctt aaggctggga caatttctga 60
tagctacccc gacacaggag gttacgggat gagcaattcg cgccgccgct cactcaggtg 120
gtcatggttg ctgagcgtgc tggctgccgt cgggctgggc ctggccacgg cgccggccca 180
ggcggccccg ccggccttgt cgcaggaccg gttcgccgac ttccccgcgc tgcccctcga 240
cccgtccgcg atggtcgccc aagtggcgcc acaggtggtc aacatcaaca ccaaactggg 300
ctacaacaac gccgtgggcg ccgggaccgg catcgtcatc gatcccaacg gtgtcgtgct 360
gaccaacaac cacgtgatcg cgggcgccac cgacatcaat gcgttcagcg tcggctccgg 420
ccaaacctac ggcgtcgatg tggtcgggta tgaccgcacc caggatgtcg cggtgctgca 480

-continued gctgcgcggt gccggtggcc tgccgtcggc ggcgatcggt ggcggcgtcg cggttggtga 540
gcccgtcgtc gcgatgggca acagcggtgg gcagggcgga acgccccgtg cggtgcctgg 600
cagggtggtc gcgctcggcc aaaccgtgca ggcgtcggat tcgctgaccg gtgccgaaga 660
gacattgaac gggttgatcc agttcgatgc cgcaatccag cccggtgatt cgggcgggcc 720
cgtcgtcaac ggcctaggac aggtggtcgg tatgaacacg gccgcgtccg ataacttcca 780
gctgtcccag ggtgggcagg gattcgccat tccgatcggg caggcgatgg cgatcgcggg 840
ccaaatccga tcgggtgggg ggtcacccac cgttcatatc gggcctaccg ccttcctcgg 900
cttgggtgtt gtcgacaaca acggcaacgg cgcacgagtc caacgcgtgg tcggaagcgc 960
tccggcggca agtctcggca tctccaccgg cgacgtgatc accgcggtcg acggcgctcc 1020
gatcaactcg gccaccgcga tggcggacgc gcttaacggg catcatcccg gtgacgtcat 1080
ctcggtgaac tggcaaacca agtcgggcgg cacgcgtaca gggaacgtga cattggccga 1140
gggacccccg gcctgatttg tcgcggatac cacccgccgg ccggccaatt ggattggcgc 1200
cagccgtgat tgccgcgtga gcccccgagt tccgtctccc gtgcgcgtgg cattgtggaa 1260
gcaatgaacg aggcagaaca cagcgttgag caccctcccg tgcagggcag ttacgtcgaa 1320
ggcggtgtgg tcgagcatcc ggatgccaag gacttcggca gcgccgccgc cctgcccgcc 1380
gatccgacct ggtttaagca cgccgtcttc tacgaggtgc tggtccgggc gttcttcgac 1440
gccagcgcgg acggttccgn cgatctgcgt ggactcatcg atcgcctcga ctacctgcag 1500
tggcttggca tcgactgcat ctgttgccgc cgttcctacg actcaccgct gcgcgacggc 1560
ggttacgaca ttcgcgactt ctacaaggtg ctgcccgaat tcggcaccgt cgacgatttc 1620
gtcgccctgg tcgacaccgc tcaccggcga ggtatccgca tcatcaccga cctggtgatg 1680
aatcacacct cggagtcgca cccctggttt caggagtccc gccgcgaccc agacggaccg 1740
tacggtgact attacgtgtg gagcgacacc agcgagcgct acaccgacgc ccggatcatc 1800
ttcgtcgaca ccgaagagtc gaactggtca ttcgatcctg tccgccgaca gttnctactg 1860
gcaccgattc tt 1872

<210> SEQ ID NO 18
<211> LENGTH: 1482
<212> TYPE: DNA
<213> ORGANISM: Mycobacterium tuberculosis

<400> SEQUENCE: 18
cttcgccgaa acctgatgcc gaggaacagg gtgttcccgt gagcccgacg gcgtccgacc 60
ccgcgctcct cgccgagatc aggcagtcgc ttgatgcgac aaaagggttg accagcgtgc 120
acgtagcggt ccgaacaacc gggaaagtcg acagcttgct gggtattacc agtgccgatg 180
tcgacgtccg ggccaatccg ctcgcggcaa agggcgtatg cacctacaac gacgagcagg 240
gtgtcccgtt tcgggtacaa ggcgacaaca tctcggtgaa actgttcgac gactggagca 300
atctcggctc gatttctgaa ctgtcaactt cacgcgtgct cgatcctgcc gctggggtga 360
cgcagctgct gtccggtgtc acgaacctcc aagcgcaagg taccgaagtg atagacggaa 420
tttcgaccac caaaatcacc gggaccatcc ccgcgagctc tgtcaagatg cttgatcctg 480
gcgccaagag tgcaaggccg gcgaccgtgt ggattgccca ggacggctcg caccacctcg 540
tccgagcgag catcgacctc ggatccgggt cgattcagct cacgcagtcg aaatggaacg 600
aacccgtcaa cgtcgactag gccgaagttg cgtcgacgcg ttgctcgaaa cgcccttgtg 660
aacggtgtca acggcacccg aaaactgacc ccctgacggc atctgaaaat tgacccccta 720

-continued

```
gaccgggcgg ttggtggtta ttcttcggtg gttccggctg gtgggacgcg gccgaggtcg     780

cggtctttga gccggtagct gtcgcctttg agggcgacga cttcagcatg gtggacgagg     840

cggtcgatca tggcggcagc aacgacgtcg tcgccgccga aaacctcgcc ccaccggccg     900

aaggccttat tggacgtgac gatcaagctg gcccgctcat accgggagga caccagctgg     960

aagaagaggt tggcggcctc gggctcaaac ggaatgtaac cgacttcgtc aaccaccagg    1020

agcggatagc ggccaaaccg ggtgagttcg gcgtagatgc gcccggcgtg gtgagcctcg    1080

gcgaaccgtg ctacccattc ggcggcggtg gcgaacagca cccgatgacc ggcctgacac    1140

gcgcgtatcg ccaggccgac cgcaagatga gtcttcccgg tgccaggcgg ggcccaaaaa    1200

cacgacgtta tcgcgggcgg tgatgaaatc cagggtgccc agatgtgcga tggtgtcgcg    1260

tttgaggcca cgagcatgct caaagtcgaa ctcttccaac gacttccgaa ccgggaagcg    1320

ggcggcgcgg atgcggccct caccaccatg ggactcccgg gctgacactt cccgctgcag    1380

gcaggcggcc aggtattctt cgtggctcca gttctcggcg cgggcgcgat cggccagccg    1440

ggacactgac tcacgcaggg tgggagcttt caatgctctt gt                       1482


<210> SEQ ID NO 19
<211> LENGTH: 876
<212> TYPE: DNA
<213> ORGANISM: Mycobacterium tuberculosis
<220> FEATURE:
<221> NAME/KEY: modified_base
<222> LOCATION: (1)..(876)
<223> OTHER INFORMATION: n = g, a, c or t

<400> SEQUENCE: 19

gaattcggca cgagccggcg atagcttctg ggccgcggcc gaccagatgg ctcgagggtt      60

cgtgctcggg gccaccgccg ggcgcaccac cctgaccggt gagggcctgc aacacgccga     120

cggtcactcg ttgctgctgg acgccaccaa cccggcggtg gttgcctacg acccggcctt     180

cgcctacgaa atcggctaca tcgnggaaag cggactggcc aggatgtgcg gggagaaccc     240

ggagaacatc ttcttctaca tcaccgtcta caacgagccg tacgtgcagc cgccggagcc     300

ggagaacttc gatcccgagg gcgtgctggg gggtatctac cgntatcacg cggccaccga     360

gcaacgcacc aacaaggngc agatcctggc ctccggggta gcgatgcccg cggcgctgcg     420

ggcagcacag atgctggccg ccgagtggga tgtcgccgcc gacgtgtggt cggtgaccag     480

ttggggcgag ctaaaccgcg acggggtggt catcgagacc gagaagctcc gccaccccga     540

tcggccggcg ggcgtgccct acgtgacgag agcgctggag aatgctcggg gcccggtgat     600

cgcggtgtcg gactggatgc gcgcggtccc cgagcagatc cgaccgtggg tgccgggcac     660

atacctcacg ttgggcaccg acgggttcgg tttttccgac actcggcccg ccggtcgtcg     720

ttacttcaac accgacgccg aatcccaggt tggtcgcggt tttgggaggg gttggccggg     780

tcgacgggtg aatatcgacc cattcggtgc cggtcgtggg ccgcccgccc agttacccgg     840

attcgacgaa ggtgggggt tgcgcccgan taagtt                                876


<210> SEQ ID NO 20
<211> LENGTH: 1021
<212> TYPE: DNA
<213> ORGANISM: Mycobacterium tuberculosis
<220> FEATURE:
<221> NAME/KEY: modified_base
<222> LOCATION: (1)..(1021)
<223> OTHER INFORMATION: n = g, a, c or t

<400> SEQUENCE: 20
```

-continued

```
atccccccgg gctgcaggaa ttcggcacga gagacaaaat tccacgcgtt aatgcaggaa      60

cagattcata acgaattcac agcggcacaa caatatgtcg cgatcgcggt ttatttcgac     120

agcgaagacc tgccgcagtt ggcgaagcat ttttacagcc aagcggtcga ggaacgaaac     180

catgcaatga tgctcgtgca acacctgctc gaccgcgacc ttcgtgtcga aattcccggc     240

gtagacacgg tgcgaaacca gttcgacaga ccccgcgagg cactggcgct ggcgctcgat     300

caggaacgca cagtcaccga ccaggtcggt cggctgacag cggtggcccg cgacgagggc     360

gatttcctcg gcgagcagtt catgcagtgg ttcttgcagg aacagatcga agaggtggcc     420

ttgatggcaa ccctggtgcg ggttgccgat cgggccgggg ccaacctgtt cgagctagag     480

aacttcgtcg cacgtgaagt ggatgtggcg ccggccgcat caggcgcccc gcacgctgcc     540

gggggccgcc tctagatccc tggggggat cagcgagtgg tcccgttcgc ccgcccgtct     600

tccagccagg ccttggtgcg gccggggtgg tgagtaccaa tccaggccac cccgacctcc     660

cggnaaaagt cgatgtcctc gtactcatcg acgttccagg agtacaccgc ccggccctga     720

gctgccgagc ggtcaacgag ttgcggatat tcctttaacg caggcagtga gggtcccacg     780

gcggttggcc cgaccgccgt ggccgcactg ctggtcaggt atcgggggt cttggcgagc     840

aacaacgtcg gcaggagggg tggagcccgc cggatccgca gaccgggggg gcgaaaacga     900

catcaacacc gcacgggatc gatctgcgga ggggggtgcg ggaataccga accggtgtag     960

gagcgccagc agttgttttt ccaccagcga agcgttttcg ggtcatcggn ggcnnttaag    1020

t                                                                    1021
```

<210> SEQ ID NO 21
<211> LENGTH: 321
<212> TYPE: DNA
<213> ORGANISM: Mycobacterium tuberculosis
<220> FEATURE:
<221> NAME/KEY: modified_base
<222> LOCATION: (1)..(321)
<223> OTHER INFORMATION: n = g, a, c or t

<400> SEQUENCE: 21

```
cgtgccgacg aacggaagaa cacaaccatg aagatggtga aatcgatcgc cgcaggtctg      60

accgccgcgg ctgcaatcgg cgccgctgcg gccggtgtga cttcgatcat ggctggcggn     120

ccggtcgtat accagatgca gccggtcgtc ttcggcgcgc cactgccgtt ggacccggna     180

tccgcccctg angtcccgac cgccgcccag tggaccagnc tgctcaacag nctcgncgat     240

cccaacgtgt cgtttgngaa caagggnagt ctggtcgagg gnggnatcgg nggnancgag     300

ggngngnatc gncgancaca a                                               321
```

<210> SEQ ID NO 22
<211> LENGTH: 373
<212> TYPE: DNA
<213> ORGANISM: Mycobacterium tuberculosis
<220> FEATURE:
<221> NAME/KEY: modified_base
<222> LOCATION: (1)..(373)
<223> OTHER INFORMATION: n = g, a, c or t

<400> SEQUENCE: 22

```
tcttatcggt tccggttggc gacgggtttt gggngcgggt ggttaacccg ctcggccagc      60

cgatcgacgg gcgcggagac gtcgactccg atactcggcg cgcgctggag ctccaggcgc     120

cctcggtggt gnaccggcaa ggcgtgaagg agccgttgna gaccgggatc aaggcgattg     180

acgcgatgac cccgatcggc cgcgggcagc gccagctgat catcggggac cgcaagaccg     240
```

gcaaaaaccg ccgtctgtgt cggacaccat cctcaaacca gcgggaagaa ctgggagtcc 300
ggtggatccc aagaagcagg tgcgcttgtg tatacgttgg ccatcgggca agaaggggaa 360
cttaccatcg ccg 373

<210> SEQ ID NO 23
<211> LENGTH: 352
<212> TYPE: DNA
<213> ORGANISM: Mycobacterium tuberculosis
<220> FEATURE:
<221> NAME/KEY: modified_base
<222> LOCATION: (1)..(352)
<223> OTHER INFORMATION: n = g, a, c or t

<400> SEQUENCE: 23
gtgacgccgt gatgggattc ctgggcgggg ccggtccgct ggcggtggtg gatcagcaac 60
tggttacccg ggtgccgcaa ggctggtcgt ttgctcaggc agccgctgtg ccggtggtgt 120
tcttgacggc ctggtacggg ttggccgatt tagccgagat caaggcgggc gaatcggtgc 180
tgatccatgc cggtaccggc ggtgtgggca tggcggctgt gcagctggct cgccagtggg 240
gcgtggaggt tttcgtcacc gccagccgtg gnaagtggga cacgctgcgc gccatngngt 300
ttgacgacga nccatatcgg ngattcccnc acatncgaag ttccgangga ga 352

<210> SEQ ID NO 24
<211> LENGTH: 726
<212> TYPE: DNA
<213> ORGANISM: Mycobacterium tuberculosis

<400> SEQUENCE: 24
gaaatccgcg ttcattccgt tcgaccagcg gctggcgata atcgacgaag tgatcaagcc 60
gcggttcgcg gcgctcatgg gtcacagcga gtaatcagca agttctctgg tatatcgcac 120
ctagcgtcca gttgcttgcc agatcgcttt cgtaccgtca tcgcatgtac cggttcgcgt 180
gccgcacgct catgctggcg gcgtgcatcc tggccacggg tgtggcgggt ctcggggtcg 240
gcgcgcagtc cgcagcccaa accgcgccgg tgcccgacta ctactggtgc ccggggcagc 300
ctttcgaccc cgcatggggg cccaactggg atccctacac ctgccatgac gacttccacc 360
gcgacagcga cggccccgac cacagccgcg actaccccgg acccatcctc gaaggtcccg 420
tgcttgacga tcccggtgct gcgccgccgc ccccggctgc cggtggcggc gcatagcgct 480
cgttgaccgg gccgcatcag cgaatacgcg tataaacccg ggcgtgcccc cggcaagcta 540
cgacccccgg cggggcagat ttacgctccc gtgccgatgg atcgcgccgt ccgatgacag 600
aaaataggcg acggttttgg caaccgcttg gaggacgctt gaagggaacc tgtcatgaac 660
ggcgacagcg cctccaccat cgacatcgac aaggttgtta cccgcacacc cgttcgccgg 720
atcgtg 726

<210> SEQ ID NO 25
<211> LENGTH: 580
<212> TYPE: DNA
<213> ORGANISM: Mycobacterium tuberculosis

<400> SEQUENCE: 25
cgcgacgacg acgaacgtcg ggcccaccac cgcctatgcg ttgatgcagg cgaccgggat 60
ggtcgccgac catatccaag catgctgggt gcccactgag cgaccttttg accagccggg 120
ctgcccgatg gcggcccggt gaagtcattg cgccggggct tgtgcacctg atgaacccga 180
atagggaaca atagggggt gatttggcag ttcaatgtcg ggtatggctg gaaatccaat 240

-continued

```
ggcggggcat gctcggcgcc gaccaggctc gcgcaggcgg gccagcccga atctggaggg    300

agcactcaat ggcggcgatg aagccccgga ccggcgacgg tcctttggaa gcaactaagg    360

aggggcgcgg cattgtgatg cgagtaccac ttgagggtgg cggtcgcctg gtcgtcgagc    420

tgacacccga cgaagccgcc gcactgggtg acgaactcaa aggcgttact agctaagacc    480

agcccaacgg cgaatggtcg gcgttacgcg cacaccttcc ggtagatgtc cagtgtctgc    540

tcggcgatgt atgcccagga gaactcttgg atacagcgct                          580


<210> SEQ ID NO 26
<211> LENGTH: 160
<212> TYPE: DNA
<213> ORGANISM: Mycobacterium tuberculosis

<400> SEQUENCE: 26

aacggaggcg ccgggggttt tggcggggcc ggggcggtcg gcggcaacgg cggggccggc     60

ggtaccgccg ggttgttcgg tgtcggcggg gccggtgggg ccggaggcaa cggcatcgcc    120

ggtgtcacgg gtacgtcggc cagcacaccg ggtggatccg                          160


<210> SEQ ID NO 27
<211> LENGTH: 272
<212> TYPE: DNA
<213> ORGANISM: Mycobacterium tuberculosis

<400> SEQUENCE: 27

gacaccgata cgatggtgat gtacgccaac gttgtcgaca cgctcgaggc gttcacgatc     60

cagcgcacac ccgacggcgt gaccatcggc gatgcggccc cgttcgcgga ggcggctgcc    120

aaggcgatgg gaatcgacaa gctgcgggta attcataccg gaatggaccc cgtcgtcgct    180

gaacgcgaac agtgggacga cggcaacaac acgttggcgt tggcgcccgg tgtcgttgtc    240

gcctacgagc gcaacgtaca gaccaacgcc cg                                  272


<210> SEQ ID NO 28
<211> LENGTH: 317
<212> TYPE: DNA
<213> ORGANISM: Mycobacterium tuberculosis

<400> SEQUENCE: 28

gcagccggtg gttctcggac tatctgcgca cggtgacgca gcgcgacgtg cgcgagctga     60

agcggatcga gcagacggat cgcctgccgc ggttcatgcg ctacctggcc gctatcaccg    120

cgcaggagct gaacgtggcc gaagcggcgc gggtcatcgg ggtcgacgcg gggacgatcc    180

gttcggatct ggcgtggttc gagacggtct atctggtaca tcgcctgccc gcctggtcgc    240

ggaatctgac cgcgaagatc aagaagcggt caaagatcca cgtcgtcgac agtggcttcg    300

cggcctggtt gcgcggg                                                   317


<210> SEQ ID NO 29
<211> LENGTH: 182
<212> TYPE: DNA
<213> ORGANISM: Mycobacterium tuberculosis

<400> SEQUENCE: 29

gatcgtggag ctgtcgatga acagcgttgc cggacgcgcg gcggccagca cgtcggtgta     60

gcagcgccgg accacctcgc cggtgggcag catggtgatg accacgtcgg cctcggccac    120

cgcttcgggc gcgctacgaa acaccgcgac accgtgcgcg gcggcgccgg acgccgccgt    180

gg                                                                   182
```

<210> SEQ ID NO 30
<211> LENGTH: 308
<212> TYPE: DNA
<213> ORGANISM: Mycobacterium tuberculosis
<400> SEQUENCE: 30
gatcgcgaag tttggtgagc aggtggtcga cgcgaaagtc tgggcgcctg cgaagcgggt 60
cggcgttcac gaggcgaaga cacgcctgtc cgagctgctg cggctcgtct acggcgggca 120
gaggttgaga ttgcccgccg cggcgagccg gtagcaaagc ttgtgccgct gcatcctcat 180
gagactcggc ggttaggcat tgaccatggc gtgtaccgcg tgcccgacga tttggacgct 240
ccgttgtcag acgacgtgct cgaacgcttt caccggtgaa gcgctacctc atcgacaccc 300
acgtttgg 308

<210> SEQ ID NO 31
<211> LENGTH: 267
<212> TYPE: DNA
<213> ORGANISM: Mycobacterium tuberculosis
<400> SEQUENCE: 31
ccgacgacga gcaactcacg tggatgatgg tcggcagcgg cattgaggac ggagagaatc 60
cggccgaagc tgccgcgcgg caagtgctca tagtgaccgg ccgtagaggg ctcccccgat 120
ggcaccggac tattctggtg tgccgctggc cggtaagagc gggtaaaaga atgtgagggg 180
acacgatgag caatcacacc taccgagtga tcgagatcgt cgggacctcg cccgacggcg 240
tcgacgcggc aatccagggc ggtctgg 267

<210> SEQ ID NO 32
<211> LENGTH: 1539
<212> TYPE: DNA
<213> ORGANISM: Mycobacterium tuberculosis
<400> SEQUENCE: 32
ctcgtgccga aagaatgtga ggggacacga tgagcaatca cacctaccga gtgatcgaga 60
tcgtcgggac ctcgcccgac ggcgtcgacg cggcaatcca gggcggtctg gcccgagctg 120
cgcagaccat gcgcgcgctg gactggttcg aagtacagtc aattcgaggc cacctggtcg 180
acggagcggt cgcgcacttc caggtgacta tgaaagtcgg cttccgctgg aggattcctg 240
aaccttcaag cgcggccgat aactgaggtg catcattaag cgacttttcc agaacatcct 300
gacgcgctcg aaacgcggtt cagccgacgg tggctccgcc gaggcgctgc ctccaaaatc 360
cctgcgacaa ttcgtcggcg gcgcctacaa ggaagtcggt gctgaattcg tcgggtatct 420
ggtcgacctg tgtgggctgc agccggacga agcggtgctc gacgtcggct gcggctcggg 480
gcggatggcg ttgccgctca ccggctatct gaacagcgag ggacgctacg ccggcttcga 540
tatctcgcag aaagccatcg cgtggtgcca ggagcacatc acctcggcgc accccaactt 600
ccagttcgag gtctccgaca tctacaactc gctgtacaac ccgaaaggga aataccagtc 660
actagacttt cgctttccat atccggatgc gtcgttcgat gtggtgtttc ttacctcggt 720
gttcacccac atgtttccgc cggacgtgga gcactatctg gacgagatct cccgcgtgct 780
gaagcccggc ggacgatgcc tgtgcacgta cttcttgctc aatgacgagt cgttagccca 840
catcgcggaa ggaaagagtg cgcacaactt ccagcatgag ggaccgggtt atcggacaat 900
ccacaagaag cggcccgaag aagcaatcgg cttgccggag accttcgtca gggatgtcta 960
tggcaagttc ggcctcgccg tgcacgaacc attgcactac ggctcatgga gtggccggga 1020

-continued accacgccta agcttccagg acatcgtcat cgcgaccaaa accgcgagct aggtcggcat 1080
ccgggaagca tcgcgacacc gtggcgccga gcgccgctgc cggcaggccg attaggcggg 1140
cagattagcc cgccgcggct cccggctccg agtacggcgc cccgaatggc gtcaccggct 1200
ggtaaccacg cttgcgcgcc tgggcggcgg cctgccggat caggtggtag atgccgacaa 1260
agcctgcgtg atcggtcatc accaacggtg acagcagccg gttgtgcacc agcgcgaacg 1320
ccaccccggt ctccgggtct gtccagccga tcgagccgcc caagcccaca tgaccaaacc 1380
ccggcatcac gttgccgatc ggcataccgt gatagccaag atgaaaattt aagggcacca 1440
atagatttcg atccggcaga acttgccgtc ggttgcgggt caggcccgtg accagctccc 1500
gcgacaagaa ccgtatgccg tcgatctcgc ctcgtgccg 1539

<210> SEQ ID NO 33
<211> LENGTH: 851
<212> TYPE: DNA
<213> ORGANISM: Mycobacterium tuberculosis
<220> FEATURE:
<221> NAME/KEY: modified_base
<222> LOCATION: (767)
<223> OTHER INFORMATION: n = g, a, c or t

<400> SEQUENCE: 33
ctgcagggtg gcgtggatga gcgtcaccgc ggggcaggcc gagctgaccg ccgcccaggt 60
ccgggttgct gcggcggcct acgagacggc gtatgggctg acggtgcccc cgccggtgat 120
cgccgagaac cgtgctgaac tgatgattct gatagcgacc aacctcttgg ggcaaaacac 180
cccggcgatc gcggtcaacg aggccgaata cggcgagatg tgggcccaag acgccgccgc 240
gatgtttggc tacgccgcgg cgacggcgac ggcgacggcg acgttgctgc cgttcgagga 300
ggcgccggag atgaccagcg cgggtgggct cctcgagcag gccgccgcgg tcgaggaggc 360
ctccgacacc gccgcggcga accagttgat gaacaatgtg ccccaggcgc tgaaacagtt 420
ggcccagccc acgcagggca ccacgccttc ttccaagctg ggtggcctgt ggaagacggt 480
ctcgccgcat cggtcgccga tcagcaacat ggtgtcgatg gccaacaacc acatgtcgat 540
gaccaactcg ggtgtgtcga tgaccaacac cttgagctcg atgttgaagg gctttgctcc 600
ggcggcggcc gcccaggccg tgcaaaccgc ggcgcaaaac ggggtccggg cgatgagctc 660
gctgggcagc tcgctgggtt cttcgggtct gggcggtggg gtggccgcca acttgggtcg 720
ggcggcctcg gtacggtatg gtcaccggga tggcggaaaa tatgcanagt ctggtcggcg 780
gaacggtggt ccggcgtaag gtttaccccc gttttctgga tgcggtgaac ttcgtcaacg 840
gaaacagtta c 851

<210> SEQ ID NO 34
<211> LENGTH: 254
<212> TYPE: DNA
<213> ORGANISM: Mycobacterium tuberculosis

<400> SEQUENCE: 34
gatcgatcgg gcggaaattt ggaccagatt cgcctccggc gataacccaa tcaatcgaac 60
ctagatttat tccgtccagg ggcccgagta atggctcgca ggagaggaac cttactgctg 120
cgggcacctg tcgtaggtcc tcgatacggc ggaaggcgtc gacattttcc accgacaccc 180
ccatccaaac gttcgagggc cactccagct tgtgagcgag gcgacgcagt cgcaggctgc 240
gcttggtcaa gatc 254

<210> SEQ ID NO 35

<211> LENGTH: 1227
<212> TYPE: DNA
<213> ORGANISM: Mycobacterium tuberculosis

<400> SEQUENCE: 35
gatcctgacc gaagcggccg ccgccaaggc gaagtcgctg ttggaccagg agggacggga 60
cgatctggcg ctgcggatcg cggttcagcc ggggggggtgc gctggattgc gctataacct 120
tttcttcgac gaccggacgc tggatggtga ccaaaccgcg gagttcggtg gtgtcaggtt 180
gatcgtggac cggatgagcg cgccgtatgt ggaaggcgcg tcgatcgatt tcgtcgacac 240
tattgagaag caaggttcac catcgacaat cccaacgcca ccggctcctg cgcgtgcggg 300
gattcgttca actgataaaa cgctagtacg accccgcggt gcgcaacacg tacgagcaca 360
ccaagacctg accgcgctgg aaaagcaact gagcgatgcc ttgcacctga ccgcgtggcg 420
ggccgccggc ggcaggtgtc acctgcatgg tgaacagcac ctgggcctga tattgcgacc 480
agtacacgat tttgtcgatc gaggtcactt cgacctggga gaactgcttg cggaacgcgt 540
cgctgctcag cttggccaag gcctgatcgg agcgcttgtc gcgcacgccg tcgtggatac 600
cgcacagcgc attgcgaacg atggtgtcca catcgcggtt ctccagcgcg ttgaggtatc 660
cctgaatcgc ggttttggcc ggtccctccg agaatgtgcc tgccgtgttg gctccgttgg 720
tgcggacccc gtatatgatc gccgccgtca tagccgacac cagcgcgagg gctaccacaa 780
tgccgatcag cagccgcttg tgccgtcgct tcgggtagga cacctgcggc ggcacgccgg 840
gatatgcggc gggcggcagc gccgcgtcgt ctgccggtcc cggggcgaag gccggttcgg 900
cggcgccgag gtcgtggggg tagtccaggg cttggggttc gtgggatgag ggctcggggt 960
acggcgccgg tccgttggtg ccgacaccgg ggttcggcga gtggggaccg ggcattgtgg 1020
ttctcctagg gtggtggacg ggaccagctg ctagggcgac aaccgcccgt cgcgtcagcc 1080
ggcagcatcg gcaatcaggt gagctcccta ggcaggctag cgcaacagct gccgtcagct 1140
ctcaacgcga cggggcgggc cgcggcgccg ataatgttga aagactaggc aaccttagga 1200
acgaaggacg gagattttgt gacgatc 1227

<210> SEQ ID NO 36
<211> LENGTH: 181
<212> TYPE: DNA
<213> ORGANISM: Mycobacterium tuberculosis
<220> FEATURE:
<221> NAME/KEY: modified_base
<222> LOCATION: (1)..(181)
<223> OTHER INFORMATION: n = g, a, c or t

<400> SEQUENCE: 36
gcggtgtcgg cggatccggc gggtggttga acggcaacgg cggggccggc ggggccggcg 60
ggaccggcgc taacggtggt gccggcggca acgcctggtt gttcggggcc ggcgggtccg 120
gcggngccgg caccaatggt ggngtcggcg ggtccggcgg atttgtctac ggcaacggcg 180
g 181

<210> SEQ ID NO 37
<211> LENGTH: 290
<212> TYPE: DNA
<213> ORGANISM: Mycobacterium tuberculosis
<220> FEATURE:
<221> NAME/KEY: modified_base
<222> LOCATION: (1)..(290)
<223> OTHER INFORMATION: n = g, a, c or t

<400> SEQUENCE: 37

-continued gcggtgtcgg cggatccggc gggtggttga acggcaacgg cggtgtcggc ggccggggcg 60
gcgacggcgt ctttgccggt gccggcggcc agggcggcct cggtgggcag ggcggcaatg 120
gcggcggctc caccggcggc aacggcggtc ttggcggcgc gggcggtggc ggaggcaacg 180
ccccggacgg cggcttcggt ggcaacggcg gtaagggtgg ccagggcggn attggcggcg 240
gcactcagag cgcgaccggc ctcggnggtg acggcggtga cggcggtgac 290

<210> SEQ ID NO 38
<211> LENGTH: 34
<212> TYPE: DNA
<213> ORGANISM: Mycobacterium tuberculosis
<220> FEATURE:
<221> NAME/KEY: modified_base
<222> LOCATION: (16)
<223> OTHER INFORMATION: n = g, a, c or t

<400> SEQUENCE: 38
gatccagtgg catggngggt gtcagtggaa gcat 34

<210> SEQ ID NO 39
<211> LENGTH: 155
<212> TYPE: DNA
<213> ORGANISM: Mycobacterium tuberculosis
<220> FEATURE:
<221> NAME/KEY: modified_base
<222> LOCATION: (142)
<223> OTHER INFORMATION: n = g, a, c or t

<400> SEQUENCE: 39
gatcgctgct cgtccccccc ttgccgccga cgccaccggt cccaccgtta ccgaacaagc 60
tggcgtggtc gccagcaccc ccggcaccgc cgacgccgga gtcgaacaat ggcaccgtcg 120
tatccccacc attgccgccg gncccaccgg caccg 155

<210> SEQ ID NO 40
<211> LENGTH: 53
<212> TYPE: DNA
<213> ORGANISM: Mycobacterium tuberculosis
<220> FEATURE:
<221> NAME/KEY: modified_base
<222> LOCATION: (38)
<223> OTHER INFORMATION: n = g, a, c or t

<400> SEQUENCE: 40
atggcgttca cggggcgccg gggaccgggc agcccggngg ggccgggggg tgg 53

<210> SEQ ID NO 41
<211> LENGTH: 132
<212> TYPE: DNA
<213> ORGANISM: Mycobacterium tuberculosis
<220> FEATURE:
<221> NAME/KEY: modified_base
<222> LOCATION: (98)
<223> OTHER INFORMATION: n = g, a, c or t

<400> SEQUENCE: 41
gatccaccgc gggtgcagac ggtgcccgcg gcgccacccc gaccagcggc ggcaacggcg 60
gcaccggcgg caacggcgcg aacgccaccg tcgtcggngg ggccggcggg gccggcggca 120
agggcggcaa cg 132

<210> SEQ ID NO 42
<211> LENGTH: 132
<212> TYPE: DNA
<213> ORGANISM: Mycobacterium tuberculosis
<220> FEATURE:

<221> NAME/KEY: modified_base
<222> LOCATION: (1)..(132)
<223> OTHER INFORMATION: n = g, a, c or t

<400> SEQUENCE: 42
gatcggcggc cggnacggnc ggggacggcg gcaagggcgg naacgggggc gccgnagcca 60
ccngccaaga atcctccgng tccnccaatg gcgcgaatgg cggacagggc ggcaacggcg 120
gcancggcgg ca 132

<210> SEQ ID NO 43
<211> LENGTH: 702
<212> TYPE: DNA
<213> ORGANISM: Mycobacterium tuberculosis
<220> FEATURE:
<221> NAME/KEY: modified_base
<222> LOCATION: (1)..(702)
<223> OTHER INFORMATION: n = g, a, c or t

<400> SEQUENCE: 43
cggcacgagg atcggtaccc cgcggcatcg gcagctgccg attcgccggg tttccccacc 60
cgaggaaagc cgctaccaga tggcgctgcc gaagtagggc gatccgttcg cgatgccggc 120
atgaacgggc ggcatcaaat tagtgcagga acctttcagt ttagcgacga taatggctat 180
agcactaagg aggatgatcc gatatgacgc agtcgcagac cgtgacggtg gatcagcaag 240
agattttgaa cagggccaac gaggtggagg ccccgatggc ggacccaccg actgatgtcc 300
ccatcacacc gtgcgaactc acggnggnta aaaacgccgc ccaacagntg gtnttgtccg 360
ccgacaacat gcgggaatac ctggcggccg gtgccaaaga gcggcagcgt ctggcgacct 420
cgctgcgcaa cgcggccaag gngtatggcg aggttgatga ggaggctgcg accgcgctgg 480
acaacgacgg cgaaggaact gtgcaggcag aatcggccgg ggccgtcgga ggggacagtt 540
cggccgaact aaccgatacg ccgagggtgg ccacggccgg tgaacccaac ttcatggatc 600
tcaaagaagc ggcaaggaag ctcgaaacgg gcgaccaagg cgcatcgctc gcgcactgng 660
gggatgggtg gaacacttnc accctgacgc tgcaaggcga cg 702

<210> SEQ ID NO 44
<211> LENGTH: 298
<212> TYPE: DNA
<213> ORGANISM: Mycobacterium tuberculosis

<400> SEQUENCE: 44
gaagccgcag cgctgtcggg cgacgtggcg gtcaaagcgg catcgctcgg tggcggtgga 60
ggcggcgggg tgccgtcggc gccgttggga tccgcgatcg gggcgccga atcggtgcgg 120 cccgctggcg ctggtgacat tgccggctta ggccagggaa gggccggcgg cggcgccgcg 180
ctgggcggcg gtggcatggg aatgccgatg ggtgccgcgc atcagggaca agggggcgcc 240
aagtccaagg gttctcagca ggaagacgag gcgctctaca ccgaggatcc tcgtgccg 298

<210> SEQ ID NO 45
<211> LENGTH: 1058
<212> TYPE: DNA
<213> ORGANISM: Mycobacterium tuberculosis

<400> SEQUENCE: 45
cggcacgagg atcgaatcgc gtcgccggga gcacagcgtc gcactgcacc agtggaggag 60
ccatgaccta ctcgccgggt aaccccggat acccgcaagc gcagcccgca ggctcctacg 120
gaggcgtcac accctcgttc gcccacgccg atgagggtgc gagcaagcta ccgatgtacc 180

```
tgaacatcgc ggtggcagtg ctcggtctgg ctgcgtactt cgccagcttc ggcccaatgt    240

tcaccctcag taccgaactc ggggggggtg atggcgcagt gtccggtgac actgggctgc    300

cggtcggggt ggctctgctg gctgcgctgc ttgccggggt ggttctggtg cctaaggcca    360

agagccatgt gacggtagtt gcggtgctcg gggtactcgg cgtatttctg atggtctcgg    420

cgacgtttaa caagcccagc gcctattcga ccggttgggc attgtgggtt gtgttggctt    480

tcatcgtgtt ccaggcggtt gcggcagtcc tggcgctctt ggtggagacc ggcgctatca    540

ccgcgccggc gccgcggccc aagttcgacc cgtatggaca gtacgggcgg tacgggcagt    600

acgggcagta cggggtgcag ccgggtgggt actacggtca gcagggtgct cagcaggccg    660

cgggactgca gtcgcccggc ccgcagcagt ctccgcagcc tcccggatat gggtcgcagt    720

acggcggcta ttcgtccagt ccgagccaat cgggcagtgg atacactgct cagccccccgg    780

cccagccgcc ggcgcagtcc gggtcgcaac aatcgcacca gggcccatcc acgccaccta    840

ccggctttcc gagcttcagc ccaccaccac cggtcagtgc cgggacgggg tcgcaggctg    900

gttcggctcc agtcaactat tcaaacccca gcgggggcga gcagtcgtcg tcccccgggg    960

gggcgccggt ctaaccgggc gttcccgcgt ccggtcgcgc gtgtgcgcga agagtgaaca   1020

gggtgtcagc aagcgcggac gatcctcgtg ccgaattc                           1058


<210> SEQ ID NO 46
<211> LENGTH: 327
<212> TYPE: DNA
<213> ORGANISM: Mycobacterium tuberculosis

<400> SEQUENCE: 46

cggcacgaga gaccgatgcc gctaccctcg cgcaggaggc aggtaatttc gagcggatct     60

ccggcgacct gaaaacccag atcgaccagg tggagtcgac ggcaggttcg ttgcagggcc    120

agtggcgcgg cgcggcgggg acggccgccc aggccgcggt ggtgcgcttc caagaagcag    180

ccaataagca gaagcaggaa ctcgacgaga tctcgacgaa tattcgtcag gccggcgtcc    240

aatactcgag ggccgacgag gagcagcagc aggcgctgtc ctcgcaaatg ggcttctgac    300

ccgctaatac gaaaagaaac ggagcaa                                        327


<210> SEQ ID NO 47
<211> LENGTH: 170
<212> TYPE: DNA
<213> ORGANISM: Mycobacterium tuberculosis
<220> FEATURE:
<221> NAME/KEY: modified_base
<222> LOCATION: (1)..(170)
<223> OTHER INFORMATION: n = g, a, c or t

<400> SEQUENCE: 47

cggtcgcgat gatggcgttg tcgaacgtga ccgattctgt accgccgtcg ttgagatcaa     60

ccaacaacgt gttggcgtcg gcaaatgtgc cgnacccgtg gatctcggtg atcttgttct    120

tcttcatcag gaagtgcaca ccggccaccc tgccctcggn tacctttcgg                170


<210> SEQ ID NO 48
<211> LENGTH: 127
<212> TYPE: DNA
<213> ORGANISM: Mycobacterium tuberculosis

<400> SEQUENCE: 48

gatccggcgg cacgggggt gccggcggca gcaccgctgg cgctggcggc aacggcgggg     60

ccgggggtgg cggcggaacc ggtgggttgc tcttcggcaa cggcggtgcc ggcgggcacg    120
```

gggccgt 127

<210> SEQ ID NO 49
<211> LENGTH: 81
<212> TYPE: DNA
<213> ORGANISM: Mycobacterium tuberculosis

<400> SEQUENCE: 49
cggcggcaag ggcggcaccg ccggcaacgg gagcggcgcg gccggcggca acggcggcaa 60
cggcggctcc ggcctcaacg g 81

<210> SEQ ID NO 50
<211> LENGTH: 149
<212> TYPE: DNA
<213> ORGANISM: Mycobacterium tuberculosis
<220> FEATURE:
<221> NAME/KEY: modified_base
<222> LOCATION: (1)..(149)
<223> OTHER INFORMATION: n = g, a, c or t

<400> SEQUENCE: 50
gatcagggct ggccggctcc ggccagaagg gcggtaacgg aggagctgcc ggattgtttg 60
gcaacggcgg ggccggnggt gccggcgcgt ccaaccaagc cggtaacggc ggngccggcg 120
gaaacggtgg tgccggtggg ctgatctgg 149

<210> SEQ ID NO 51
<211> LENGTH: 355
<212> TYPE: DNA
<213> ORGANISM: Mycobacterium tuberculosis
<220> FEATURE:
<221> NAME/KEY: modified_base
<222> LOCATION: (67)
<223> OTHER INFORMATION: n = g, a, c or t

<400> SEQUENCE: 51
cggcacgaga tcacacctac cgagtgatcg agatcgtcgg gacctcgccc gacggtgtcg 60
acgcggnaat ccagggcggt ctggcccgag ctgcgcagac catgcgcgcg ctggactggt 120
tcgaagtaca gtcaattcga ggccacctgg tcgacggagc ggtcgcgcac ttccaggtga 180
ctatgaaagt cggcttccgc ctggaggatt cctgaacctt caagcgcggc cgataactga 240
ggtgcatcat taagcgactt ttccagaaca tcctgacgcg ctcgaaacgc ggttcagccg 300
acggtggctc cgccgaggcg ctgcctccaa aatccctgcg acaattcgtc ggcgg 355

<210> SEQ ID NO 52
<211> LENGTH: 999
<212> TYPE: DNA
<213> ORGANISM: Mycobacterium tuberculosis

<400> SEQUENCE: 52
atgcatcacc atcaccatca catgcatcag gtggaccccca acttgacacg tcgcaaggga 60
cgattggcgg cactggctat cgcggcgatg gccagcgcca gcctggtgac cgttgcggtg 120
cccgcgaccg ccaacgccga tccggagcca gcgcccccgg tacccacaac ggccgcctcg 180
ccgccgtcga ccgctgcagc gccacccgca ccggcgacac ctgttgcccc cccaccaccg 240
gccgccgcca acacgccgaa tgcccagccg ggcgatccca acgcagcacc tccgccggcc 300
gacccgaacg caccgccgcc acctgtcatt gccccaaacg caccccaacc tgtccggatc 360
gacaacccgg ttggaggatt cagcttcgcg ctgcctgctg gctgggtgga gtctgacgcc 420
gcccacttcg actacggttc agcactcctc agcaaaacca ccggggaccc gccatttccc 480

-continued

```
ggacagccgc cgccggtggc caatgacacc cgtatcgtgc tcggccggct agaccaaaag    540

ctttacgcca gcgccgaagc caccgactcc aaggccgcgg cccggttggg ctcggacatg    600

ggtgagttct atatgcccta cccgggcacc cggatcaacc aggaaaccgt ctcgctcgac    660

gccaacgggg tgtctggaag cgcgtcgtat tacgaagtca agttcagcga tccgagtaag    720

ccgaacggcc agatctggac gggcgtaatc ggctcgcccg cggcgaacgc accggacgcc    780

gggccccctc agcgctggtt tgtggtatgg ctcgggaccg ccaacaaccc ggtggacaag    840

ggcgcggcca aggcgctggc cgaatcgatc cggcctttgg tcgccccgcc gccggcgccg    900

gcaccggctc ctgcagagcc cgctccggcg ccggcgccgg ccggggaagt cgctcctacc    960

ccgacgacac cgacaccgca gcggacctta ccggcctga                           999
```

<210> SEQ ID NO 53
<211> LENGTH: 332
<212> TYPE: PRT
<213> ORGANISM: Mycobacterium tuberculosis

<400> SEQUENCE: 53

```
Met His His His His His His Met His Gln Val Asp Pro Asn Leu Thr
  1               5                  10                  15

Arg Arg Lys Gly Arg Leu Ala Ala Leu Ala Ile Ala Ala Met Ala Ser
             20                  25                  30

Ala Ser Leu Val Thr Val Ala Val Pro Ala Thr Ala Asn Ala Asp Pro
         35                  40                  45

Glu Pro Ala Pro Pro Val Pro Thr Thr Ala Ala Ser Pro Pro Ser Thr
     50                  55                  60

Ala Ala Ala Pro Pro Ala Pro Ala Thr Pro Val Ala Pro Pro Pro Pro
 65                  70                  75                  80

Ala Ala Ala Asn Thr Pro Asn Ala Gln Pro Gly Asp Pro Asn Ala Ala
                 85                  90                  95

Pro Pro Pro Ala Asp Pro Asn Ala Pro Pro Pro Pro Val Ile Ala Pro
            100                 105                 110

Asn Ala Pro Gln Pro Val Arg Ile Asp Asn Pro Val Gly Gly Phe Ser
        115                 120                 125

Phe Ala Leu Pro Ala Gly Trp Val Glu Ser Asp Ala Ala His Phe Asp
    130                 135                 140

Tyr Gly Ser Ala Leu Leu Ser Lys Thr Thr Gly Asp Pro Pro Phe Pro
145                 150                 155                 160

Gly Gln Pro Pro Pro Val Ala Asn Asp Thr Arg Ile Val Leu Gly Arg
                165                 170                 175

Leu Asp Gln Lys Leu Tyr Ala Ser Ala Glu Ala Thr Asp Ser Lys Ala
            180                 185                 190

Ala Ala Arg Leu Gly Ser Asp Met Gly Glu Phe Tyr Met Pro Tyr Pro
        195                 200                 205

Gly Thr Arg Ile Asn Gln Glu Thr Val Ser Leu Asp Ala Asn Gly Val
    210                 215                 220

Ser Gly Ser Ala Ser Tyr Tyr Glu Val Lys Phe Ser Asp Pro Ser Lys
225                 230                 235                 240

Pro Asn Gly Gln Ile Trp Thr Gly Val Ile Gly Ser Pro Ala Ala Asn
                245                 250                 255

Ala Pro Asp Ala Gly Pro Pro Gln Arg Trp Phe Val Val Trp Leu Gly
            260                 265                 270

Thr Ala Asn Asn Pro Val Asp Lys Gly Ala Ala Lys Ala Leu Ala Glu
        275                 280                 285
```

-continued

```
Ser Ile Arg Pro Leu Val Ala Pro Pro Pro Ala Pro Ala Pro Ala Pro
    290                 295                 300

Ala Glu Pro Ala Pro Ala Pro Ala Pro Ala Gly Glu Val Ala Pro Thr
305                 310                 315                 320

Pro Thr Thr Pro Thr Pro Gln Arg Thr Leu Pro Ala
                325                 330


<210> SEQ ID NO 54
<211> LENGTH: 20
<212> TYPE: PRT
<213> ORGANISM: Mycobacterium tuberculosis
<220> FEATURE:
<221> NAME/KEY: MOD_RES
<222> LOCATION: (11)
<223> OTHER INFORMATION: Xaa = any amino acid

<400> SEQUENCE: 54

Asp Pro Val Asp Ala Val Ile Asn Thr Thr Xaa Asn Tyr Gly Gln Val
  1               5                  10                  15

Val Ala Ala Leu
             20


<210> SEQ ID NO 55
<211> LENGTH: 15
<212> TYPE: PRT
<213> ORGANISM: Mycobacterium tuberculosis

<400> SEQUENCE: 55

Ala Val Glu Ser Gly Met Leu Ala Leu Gly Thr Pro Ala Pro Ser
  1               5                  10                  15


<210> SEQ ID NO 56
<211> LENGTH: 19
<212> TYPE: PRT
<213> ORGANISM: Mycobacterium tuberculosis

<400> SEQUENCE: 56

Ala Ala Met Lys Pro Arg Thr Gly Asp Gly Pro Leu Glu Ala Ala Lys
  1               5                  10                  15

Glu Gly Arg


<210> SEQ ID NO 57
<211> LENGTH: 15
<212> TYPE: PRT
<213> ORGANISM: Mycobacterium tuberculosis

<400> SEQUENCE: 57

Tyr Tyr Trp Cys Pro Gly Gln Pro Phe Asp Pro Ala Trp Gly Pro
  1               5                  10                  15


<210> SEQ ID NO 58
<211> LENGTH: 14
<212> TYPE: PRT
<213> ORGANISM: Mycobacterium tuberculosis
<220> FEATURE:
<221> NAME/KEY: MOD_RES
<222> LOCATION: (12)
<223> OTHER INFORMATION: Xaa = any amino acid

<400> SEQUENCE: 58

Asp Ile Gly Ser Glu Ser Thr Glu Asp Gln Gln Xaa Ala Val
  1               5                  10


<210> SEQ ID NO 59
<211> LENGTH: 13
```

<212> TYPE: PRT
<213> ORGANISM: Mycobacterium tuberculosis
<220> FEATURE:
<221> NAME/KEY: MOD_RES
<222> LOCATION: (1)..(13)
<223> OTHER INFORMATION: Xaa = any amino acid

<400> SEQUENCE: 59

Ala Glu Glu Ser Ile Ser Thr Xaa Glu Xaa Ile Val Pro
1 5 10

<210> SEQ ID NO 60
<211> LENGTH: 17
<212> TYPE: PRT
<213> ORGANISM: Mycobacterium tuberculosis

<400> SEQUENCE: 60

Asp Pro Glu Pro Ala Pro Pro Val Pro Thr Ala Ala Ala Ala Pro Pro
1 5 10 15

Ala

<210> SEQ ID NO 61
<211> LENGTH: 15
<212> TYPE: PRT
<213> ORGANISM: Mycobacterium tuberculosis
<220> FEATURE:
<221> NAME/KEY: MOD_RES
<222> LOCATION: (6)
<223> OTHER INFORMATION: Xaa = any amino acid

<400> SEQUENCE: 61

Ala Pro Lys Thr Tyr Xaa Glu Glu Leu Lys Gly Thr Asp Thr Gly
1 5 10 15

<210> SEQ ID NO 62
<211> LENGTH: 30
<212> TYPE: PRT
<213> ORGANISM: Mycobacterium tuberculosis

<400> SEQUENCE: 62

Asp Pro Ala Ser Ala Pro Asp Val Pro Thr Ala Ala Gln Gln Thr Ser
1 5 10 15

Leu Leu Asn Asn Leu Ala Asp Pro Asp Val Ser Phe Ala Asp
20 25 30

<210> SEQ ID NO 63
<211> LENGTH: 24
<212> TYPE: PRT
<213> ORGANISM: Artificial Sequence
<220> FEATURE:
<223> OTHER INFORMATION: Description of Artificial Sequence:synthetic
peptide containing one and a half repeats of a
TbM-1 sequence

<400> SEQUENCE: 63

Gly Cys Gly Asp Arg Ser Gly Gly Asn Leu Asp Gln Ile Arg Leu Arg
1 5 10 15

Arg Asp Arg Ser Gly Gly Asn Leu
20

<210> SEQ ID NO 64
<211> LENGTH: 187
<212> TYPE: PRT
<213> ORGANISM: Mycobacterium tuberculosis
<220> FEATURE:
<221> NAME/KEY: MOD_RES
<222> LOCATION: (187)

<223> OTHER INFORMATION: Xaa = any amino acid

<400> SEQUENCE: 64

Thr Gly Ser Leu Asn Gln Thr His Asn Arg Arg Ala Asn Glu Arg Lys
1 5 10 15

Asn Thr Thr Met Lys Met Val Lys Ser Ile Ala Ala Gly Leu Thr Ala
20 25 30

Ala Ala Ala Ile Gly Ala Ala Ala Ala Gly Val Thr Ser Ile Met Ala
35 40 45

Gly Gly Pro Val Val Tyr Gln Met Gln Pro Val Val Phe Gly Ala Pro
50 55 60

Leu Pro Leu Asp Pro Ala Ser Ala Pro Asp Val Pro Thr Ala Ala Gln
65 70 75 80

Leu Thr Ser Leu Leu Asn Ser Leu Ala Asp Pro Asn Val Ser Phe Ala
85 90 95

Asn Lys Gly Ser Leu Val Glu Gly Gly Ile Gly Gly Thr Glu Ala Arg
100 105 110

Ile Ala Asp His Lys Leu Lys Lys Ala Ala Glu His Gly Asp Leu Pro
115 120 125

Leu Ser Phe Ser Val Thr Asn Ile Gln Pro Ala Ala Ala Gly Ser Ala
130 135 140

Thr Ala Asp Val Ser Val Ser Gly Pro Lys Leu Ser Ser Pro Val Thr
145 150 155 160

Gln Asn Val Thr Phe Val Asn Gln Gly Gly Trp Met Leu Ser Arg Ala
165 170 175

Ser Ala Met Glu Leu Leu Gln Ala Ala Gly Xaa
180 185

<210> SEQ ID NO 65
<211> LENGTH: 148
<212> TYPE: PRT
<213> ORGANISM: Mycobacterium tuberculosis

<400> SEQUENCE: 65

Asp Glu Val Thr Val Glu Thr Thr Ser Val Phe Arg Ala Asp Phe Leu
1 5 10 15

Ser Glu Leu Asp Ala Pro Ala Gln Ala Gly Thr Glu Ser Ala Val Ser
20 25 30

Gly Val Glu Gly Leu Pro Pro Gly Ser Ala Leu Leu Val Val Lys Arg
35 40 45

Gly Pro Asn Ala Gly Ser Arg Phe Leu Leu Asp Gln Ala Ile Thr Ser
50 55 60

Ala Gly Arg His Pro Asp Ser Asp Ile Phe Leu Asp Asp Val Thr Val
65 70 75 80

Ser Arg Arg His Ala Glu Phe Arg Leu Glu Asn Asn Glu Phe Asn Val
85 90 95

Val Asp Val Gly Ser Leu Asn Gly Thr Tyr Val Asn Arg Glu Pro Val
100 105 110

Asp Ser Ala Val Leu Ala Asn Gly Asp Glu Val Gln Ile Gly Lys Leu
115 120 125

Arg Leu Val Phe Leu Thr Gly Pro Lys Gln Gly Glu Asp Asp Gly Ser
130 135 140

Thr Gly Gly Pro
145

<210> SEQ ID NO 66

-continued

<211> LENGTH: 230
<212> TYPE: PRT
<213> ORGANISM: Mycobacterium tuberculosis
<220> FEATURE:
<221> NAME/KEY: MOD_RES
<222> LOCATION: (181)
<223> OTHER INFORMATION: Xaa = any amino acid

<400> SEQUENCE: 66

```
Thr Ser Asn Arg Pro Ala Arg Arg Gly Arg Arg Ala Pro Arg Asp Thr
  1               5                  10                  15

Gly Pro Asp Arg Ser Ala Ser Leu Ser Leu Val Arg His Arg Arg Gln
             20                  25                  30

Gln Arg Asp Ala Leu Cys Leu Ser Ser Thr Gln Ile Ser Arg Gln Ser
         35                  40                  45

Asn Leu Pro Pro Ala Ala Gly Gly Ala Ala Asn Tyr Ser Arg Arg Asn
     50                  55                  60

Phe Asp Val Arg Ile Lys Ile Phe Met Leu Val Thr Ala Val Val Leu
 65                  70                  75                  80

Leu Cys Cys Ser Gly Val Ala Thr Ala Ala Pro Lys Thr Tyr Cys Glu
                 85                  90                  95

Glu Leu Lys Gly Thr Asp Thr Gly Gln Ala Cys Gln Ile Gln Met Ser
            100                 105                 110

Asp Pro Ala Tyr Asn Ile Asn Ile Ser Leu Pro Ser Tyr Tyr Pro Asp
        115                 120                 125

Gln Lys Ser Leu Glu Asn Tyr Ile Ala Gln Thr Arg Asp Lys Phe Leu
    130                 135                 140

Ser Ala Ala Thr Ser Ser Thr Pro Arg Glu Ala Pro Tyr Glu Leu Asn
145                 150                 155                 160

Ile Thr Ser Ala Thr Tyr Gln Ser Ala Ile Pro Pro Arg Gly Thr Gln
                165                 170                 175

Ala Val Val Leu Xaa Val Tyr His Asn Ala Gly Gly Thr His Pro Thr
            180                 185                 190

Thr Thr Tyr Lys Ala Phe Asp Trp Asp Gln Ala Tyr Arg Lys Pro Ile
        195                 200                 205

Thr Tyr Asp Thr Leu Trp Gln Ala Asp Thr Asp Pro Leu Pro Val Val
    210                 215                 220

Phe Pro Ile Val Ala Arg
225                 230
```

<210> SEQ ID NO 67
<211> LENGTH: 132
<212> TYPE: PRT
<213> ORGANISM: Mycobacterium tuberculosis

<400> SEQUENCE: 67

```
Thr Ala Ala Ser Asp Asn Phe Gln Leu Ser Gln Gly Gly Gln Gly Phe
  1               5                  10                  15

Ala Ile Pro Ile Gly Gln Ala Met Ala Ile Ala Gly Gln Ile Arg Ser
             20                  25                  30

Gly Gly Gly Ser Pro Thr Val His Ile Gly Pro Thr Ala Phe Leu Gly
         35                  40                  45

Leu Gly Val Val Asp Asn Asn Gly Asn Gly Ala Arg Val Gln Arg Val
     50                  55                  60

Val Gly Ser Ala Pro Ala Ala Ser Leu Gly Ile Ser Thr Gly Asp Val
 65                  70                  75                  80

Ile Thr Ala Val Asp Gly Ala Pro Ile Asn Ser Ala Thr Ala Met Ala
                 85                  90                  95
```

```
Asp Ala Leu Asn Gly His His Pro Gly Asp Val Ile Ser Val Asn Trp
            100                 105                 110

Gln Thr Lys Ser Gly Gly Thr Arg Thr Gly Asn Val Thr Leu Ala Glu
        115                 120                 125

Gly Pro Pro Ala
    130
```

<210> SEQ ID NO 68
<211> LENGTH: 100
<212> TYPE: PRT
<213> ORGANISM: Mycobacterium tuberculosis
<220> FEATURE:
<221> NAME/KEY: MOD_RES
<222> LOCATION: (1)..(100)
<223> OTHER INFORMATION: Xaa = any amino acid

<400> SEQUENCE: 68

```
Val Pro Leu Arg Ser Pro Ser Met Ser Pro Ser Lys Cys Leu Ala Ala
  1               5                  10                  15

Ala Gln Arg Asn Pro Val Ile Arg Arg Arg Arg Leu Ser Asn Pro Pro
             20                  25                  30

Pro Arg Lys Tyr Arg Ser Met Pro Ser Pro Ala Thr Ala Ser Ala Gly
         35                  40                  45

Met Ala Arg Val Arg Arg Arg Ala Ile Trp Arg Gly Pro Ala Thr Xaa
     50                  55                  60

Ser Ala Gly Met Ala Arg Val Arg Arg Trp Xaa Val Met Pro Xaa Val
 65                  70                  75                  80

Ile Gln Ser Thr Xaa Ile Arg Xaa Xaa Gly Pro Phe Asp Asn Arg Gly
                 85                  90                  95

Ser Glu Arg Lys
            100
```

<210> SEQ ID NO 69
<211> LENGTH: 163
<212> TYPE: PRT
<213> ORGANISM: Mycobacterium tuberculosis
<220> FEATURE:
<221> NAME/KEY: MOD_RES
<222> LOCATION: (1)..(163)
<223> OTHER INFORMATION: Xaa = any amino acid

<400> SEQUENCE: 69

```
Met Thr Asp Asp Ile Leu Leu Ile Asp Thr Asp Glu Arg Val Arg Thr
  1               5                  10                  15

Leu Thr Leu Asn Arg Pro Gln Ser Arg Asn Ala Leu Ser Ala Ala Leu
             20                  25                  30

Arg Asp Arg Phe Phe Ala Xaa Leu Xaa Asp Ala Glu Xaa Asp Asp Asp
         35                  40                  45

Ile Asp Val Val Ile Leu Thr Gly Ala Asp Pro Val Phe Cys Ala Gly
     50                  55                  60

Leu Asp Leu Lys Val Ala Gly Arg Ala Asp Arg Ala Ala Gly His Leu
 65                  70                  75                  80

Thr Ala Val Gly Gly His Asp Gln Ala Gly Asp Arg Arg Asp Gln Arg
                 85                  90                  95

Arg Arg Gly His Arg Arg Ala Arg Thr Gly Ala Val Leu Arg His Pro
            100                 105                 110

Asp Arg Leu Arg Ala Arg Pro Leu Arg Arg His Pro Arg Pro Gly Gly
        115                 120                 125

Ala Ala Ala His Leu Gly Thr Gln Cys Val Leu Ala Ala Lys Gly Arg
```

-continued 130 135 140

His Arg Xaa Gly Pro Val Asp Glu Pro Asp Arg Arg Leu Pro Val Arg
145 150 155 160

Asp Arg Arg

<210> SEQ ID NO 70
<211> LENGTH: 344
<212> TYPE: PRT
<213> ORGANISM: Mycobacterium tuberculosis

<400> SEQUENCE: 70

Met Lys Phe Val Asn His Ile Glu Pro Val Ala Pro Arg Arg Ala Gly
1 5 10 15

Gly Ala Val Ala Glu Val Tyr Ala Glu Ala Arg Arg Glu Phe Gly Arg
20 25 30

Leu Pro Glu Pro Leu Ala Met Leu Ser Pro Asp Glu Gly Leu Leu Thr
35 40 45

Ala Gly Trp Ala Thr Leu Arg Glu Thr Leu Leu Val Gly Gln Val Pro
50 55 60

Arg Gly Arg Lys Glu Ala Val Ala Ala Ala Val Ala Ala Ser Leu Arg
65 70 75 80

Cys Pro Trp Cys Val Asp Ala His Thr Thr Met Leu Tyr Ala Ala Gly
85 90 95

Gln Thr Asp Thr Ala Ala Ala Ile Leu Ala Gly Thr Ala Pro Ala Ala
100 105 110

Gly Asp Pro Asn Ala Pro Tyr Val Ala Trp Ala Ala Gly Thr Gly Thr
115 120 125

Pro Ala Gly Pro Pro Ala Pro Phe Gly Pro Asp Val Ala Ala Glu Tyr
130 135 140

Leu Gly Thr Ala Val Gln Phe His Phe Ile Ala Arg Leu Val Leu Val
145 150 155 160

Leu Leu Asp Glu Thr Phe Leu Pro Gly Gly Pro Arg Ala Gln Gln Leu
165 170 175

Met Arg Arg Ala Gly Gly Leu Val Phe Ala Arg Lys Val Arg Ala Glu
180 185 190

His Arg Pro Gly Arg Ser Thr Arg Arg Leu Glu Pro Arg Thr Leu Pro
195 200 205

Asp Asp Leu Ala Trp Ala Thr Pro Ser Glu Pro Ile Ala Thr Ala Phe
210 215 220

Ala Ala Leu Ser His His Leu Asp Thr Ala Pro His Leu Pro Pro Pro
225 230 235 240

Thr Arg Gln Val Val Arg Arg Val Val Gly Ser Trp His Gly Glu Pro
245 250 255

Met Pro Met Ser Ser Arg Trp Thr Asn Glu His Thr Ala Glu Leu Pro
260 265 270

Ala Asp Leu His Ala Pro Thr Arg Leu Ala Leu Leu Thr Gly Leu Ala
275 280 285

Pro His Gln Val Thr Asp Asp Asp Val Ala Ala Ala Arg Ser Leu Leu
290 295 300

Asp Thr Asp Ala Ala Leu Val Gly Ala Leu Ala Trp Ala Ala Phe Thr
305 310 315 320

Ala Ala Arg Arg Ile Gly Thr Trp Ile Gly Ala Ala Ala Glu Gly Gln
325 330 335

Val Ser Arg Gln Asn Pro Thr Gly
340

<210> SEQ ID NO 71
<211> LENGTH: 485
<212> TYPE: PRT
<213> ORGANISM: Mycobacterium tuberculosis

<400> SEQUENCE: 71

```
Asp Asp Pro Asp Met Pro Gly Thr Val Ala Lys Ala Val Ala Asp Ala
  1               5                  10                  15

Leu Gly Arg Gly Ile Ala Pro Val Glu Asp Ile Gln Asp Cys Val Glu
             20                  25                  30

Ala Arg Leu Gly Glu Ala Gly Leu Asp Asp Val Ala Arg Val Tyr Ile
         35                  40                  45

Ile Tyr Arg Gln Arg Arg Ala Glu Leu Arg Thr Ala Lys Ala Leu Leu
     50                  55                  60

Gly Val Arg Asp Glu Leu Lys Leu Ser Leu Ala Ala Val Thr Val Leu
 65                  70                  75                  80

Arg Glu Arg Tyr Leu Leu His Asp Glu Gln Gly Arg Pro Ala Glu Ser
                 85                  90                  95

Thr Gly Glu Leu Met Asp Arg Ser Ala Arg Cys Val Ala Ala Ala Glu
            100                 105                 110

Asp Gln Tyr Glu Pro Gly Ser Ser Arg Arg Trp Ala Glu Arg Phe Ala
        115                 120                 125

Thr Leu Leu Arg Asn Leu Glu Phe Leu Pro Asn Ser Pro Thr Leu Met
    130                 135                 140

Asn Ser Gly Thr Asp Leu Gly Leu Leu Ala Gly Cys Phe Val Leu Pro
145                 150                 155                 160

Ile Glu Asp Ser Leu Gln Ser Ile Phe Ala Thr Leu Gly Gln Ala Ala
                165                 170                 175

Glu Leu Gln Arg Ala Gly Gly Gly Thr Gly Tyr Ala Phe Ser His Leu
            180                 185                 190

Arg Pro Ala Gly Asp Arg Val Ala Ser Thr Gly Gly Thr Ala Ser Gly
        195                 200                 205

Pro Val Ser Phe Leu Arg Leu Tyr Asp Ser Ala Ala Gly Val Val Ser
    210                 215                 220

Met Gly Gly Arg Arg Arg Gly Ala Cys Met Ala Val Leu Asp Val Ser
225                 230                 235                 240

His Pro Asp Ile Cys Asp Phe Val Thr Ala Lys Ala Glu Ser Pro Ser
                245                 250                 255

Glu Leu Pro His Phe Asn Leu Ser Val Gly Val Thr Asp Ala Phe Leu
            260                 265                 270

Arg Ala Val Glu Arg Asn Gly Leu His Arg Leu Val Asn Pro Arg Thr
        275                 280                 285

Gly Lys Ile Val Ala Arg Met Pro Ala Ala Glu Leu Phe Asp Ala Ile
    290                 295                 300

Cys Lys Ala Ala His Ala Gly Gly Asp Pro Gly Leu Val Phe Leu Asp
305                 310                 315                 320

Thr Ile Asn Arg Ala Asn Pro Val Pro Gly Arg Gly Arg Ile Glu Ala
                325                 330                 335

Thr Asn Pro Cys Gly Glu Val Pro Leu Leu Pro Tyr Glu Ser Cys Asn
            340                 345                 350

Leu Gly Ser Ile Asn Leu Ala Arg Met Leu Ala Asp Gly Arg Val Asp
        355                 360                 365

Trp Asp Arg Leu Glu Glu Val Ala Gly Val Ala Val Arg Phe Leu Asp
    370                 375                 380
```

```
Asp Val Ile Asp Val Ser Arg Tyr Pro Phe Pro Glu Leu Gly Glu Ala
385                 390                 395                 400

Ala Arg Ala Thr Arg Lys Ile Gly Leu Gly Val Met Gly Leu Ala Glu
                405                 410                 415

Leu Leu Ala Ala Leu Gly Ile Pro Tyr Asp Ser Glu Glu Ala Val Arg
            420                 425                 430

Leu Ala Thr Arg Leu Met Arg Arg Ile Gln Gln Ala Ala His Thr Ala
        435                 440                 445

Ser Arg Arg Leu Ala Glu Glu Arg Gly Ala Phe Pro Ala Phe Thr Asp
    450                 455                 460

Ser Arg Phe Ala Arg Ser Gly Pro Arg Arg Asn Ala Gln Val Thr Ser
465                 470                 475                 480

Val Ala Pro Thr Gly
                485


<210> SEQ ID NO 72
<211> LENGTH: 267
<212> TYPE: PRT
<213> ORGANISM: Mycobacterium tuberculosis

<400> SEQUENCE: 72

Gly Val Ile Val Leu Asp Leu Glu Pro Arg Gly Pro Leu Pro Thr Glu
  1               5                  10                  15

Ile Tyr Trp Arg Arg Arg Gly Leu Ala Leu Gly Ile Ala Val Val Val
             20                  25                  30

Val Gly Ile Ala Val Ala Ile Val Ile Ala Phe Val Asp Ser Ser Ala
         35                  40                  45

Gly Ala Lys Pro Val Ser Ala Asp Lys Pro Ala Ser Ala Gln Ser His
     50                  55                  60

Pro Gly Ser Pro Ala Pro Gln Ala Pro Gln Pro Ala Gly Gln Thr Glu
 65                  70                  75                  80

Gly Asn Ala Ala Ala Ala Pro Pro Gln Gly Gln Asn Pro Glu Thr Pro
                 85                  90                  95

Thr Pro Thr Ala Ala Val Gln Pro Pro Pro Val Leu Lys Glu Gly Asp
            100                 105                 110

Asp Cys Pro Asp Ser Thr Leu Ala Val Lys Gly Leu Thr Asn Ala Pro
        115                 120                 125

Gln Tyr Tyr Val Gly Asp Gln Pro Lys Phe Thr Met Val Val Thr Asn
    130                 135                 140

Ile Gly Leu Val Ser Cys Lys Arg Asp Val Gly Ala Ala Val Leu Ala
145                 150                 155                 160

Ala Tyr Val Tyr Ser Leu Asp Asn Lys Arg Leu Trp Ser Asn Leu Asp
                165                 170                 175

Cys Ala Pro Ser Asn Glu Thr Leu Val Lys Thr Phe Ser Pro Gly Glu
            180                 185                 190

Gln Val Thr Thr Ala Val Thr Trp Thr Gly Met Gly Ser Ala Pro Arg
        195                 200                 205

Cys Pro Leu Pro Arg Pro Ala Ile Gly Pro Gly Thr Tyr Asn Leu Val
    210                 215                 220

Val Gln Leu Gly Asn Leu Arg Ser Leu Pro Val Pro Phe Ile Leu Asn
225                 230                 235                 240

Gln Pro Pro Pro Pro Pro Gly Pro Val Pro Ala Pro Gly Pro Ala Gln
                245                 250                 255

Ala Pro Pro Pro Glu Ser Pro Ala Gln Gly Gly
            260                 265
```

<210> SEQ ID NO 73
<211> LENGTH: 97
<212> TYPE: PRT
<213> ORGANISM: Mycobacterium tuberculosis

<400> SEQUENCE: 73

Leu Ile Ser Thr Gly Lys Ala Ser His Ala Ser Leu Gly Val Gln Val
1 5 10 15

Thr Asn Asp Lys Asp Thr Pro Gly Ala Lys Ile Val Glu Val Val Ala
20 25 30

Gly Gly Ala Ala Ala Asn Ala Gly Val Pro Lys Gly Val Val Val Thr
35 40 45

Lys Val Asp Asp Arg Pro Ile Asn Ser Ala Asp Ala Leu Val Ala Ala
50 55 60

Val Arg Ser Lys Ala Pro Gly Ala Thr Val Ala Leu Thr Phe Gln Asp
65 70 75 80

Pro Ser Gly Gly Ser Arg Thr Val Gln Val Thr Leu Gly Lys Ala Glu
85 90 95

Gln

<210> SEQ ID NO 74
<211> LENGTH: 364
<212> TYPE: PRT
<213> ORGANISM: Mycobacterium tuberculosis

<400> SEQUENCE: 74

Gly Ala Ala Val Ser Leu Leu Ala Ala Gly Thr Leu Val Leu Thr Ala
1 5 10 15

Cys Gly Gly Gly Thr Asn Ser Ser Ser Ser Gly Ala Gly Gly Thr Ser
20 25 30

Gly Ser Val His Cys Gly Gly Lys Lys Glu Leu His Ser Ser Gly Ser
35 40 45

Thr Ala Gln Glu Asn Ala Met Glu Gln Phe Val Tyr Ala Tyr Val Arg
50 55 60

Ser Cys Pro Gly Tyr Thr Leu Asp Tyr Asn Ala Asn Gly Ser Gly Ala
65 70 75 80

Gly Val Thr Gln Phe Leu Asn Asn Glu Thr Asp Phe Ala Gly Ser Asp
85 90 95

Val Pro Leu Asn Pro Ser Thr Gly Gln Pro Asp Arg Ser Ala Glu Arg
100 105 110

Cys Gly Ser Pro Ala Trp Asp Leu Pro Thr Val Phe Gly Pro Ile Ala
115 120 125

Ile Thr Tyr Asn Ile Lys Gly Val Ser Thr Leu Asn Leu Asp Gly Pro
130 135 140

Thr Thr Ala Lys Ile Phe Asn Gly Thr Ile Thr Val Trp Asn Asp Pro
145 150 155 160

Gln Ile Gln Ala Leu Asn Ser Gly Thr Asp Leu Pro Pro Thr Pro Ile
165 170 175

Ser Val Ile Phe Arg Ser Asp Lys Ser Gly Thr Ser Asp Asn Phe Gln
180 185 190

Lys Tyr Leu Asp Gly Val Ser Asn Gly Ala Trp Gly Lys Gly Ala Ser
195 200 205

Glu Thr Phe Ser Gly Gly Val Gly Val Gly Ala Ser Gly Asn Asn Gly
210 215 220

Thr Ser Ala Leu Leu Gln Thr Thr Asp Gly Ser Ile Thr Tyr Asn Glu

```
225                 230                 235                 240

Trp Ser Phe Ala Val Gly Lys Gln Leu Asn Met Ala Gln Ile Ile Thr
                245                 250                 255

Ser Ala Gly Pro Asp Pro Val Ala Ile Thr Thr Glu Ser Val Gly Lys
            260                 265                 270

Thr Ile Ala Gly Ala Lys Ile Met Gly Gln Gly Asn Asp Leu Val Leu
        275                 280                 285

Asp Thr Ser Ser Phe Tyr Arg Pro Thr Gln Pro Gly Ser Tyr Pro Ile
    290                 295                 300

Val Leu Ala Thr Tyr Glu Ile Val Cys Ser Lys Tyr Pro Asp Ala Thr
305                 310                 315                 320

Thr Gly Thr Ala Val Arg Ala Phe Met Gln Ala Ala Ile Gly Pro Gly
                325                 330                 335

Gln Glu Gly Leu Asp Gln Tyr Gly Ser Ile Pro Leu Pro Lys Ser Phe
            340                 345                 350

Gln Ala Lys Leu Ala Ala Ala Val Asn Ala Ile Ser
        355                 360


<210> SEQ ID NO 75
<211> LENGTH: 309
<212> TYPE: PRT
<213> ORGANISM: Mycobacterium tuberculosis

<400> SEQUENCE: 75

Gln Ala Ala Ala Gly Arg Ala Val Arg Arg Thr Gly His Ala Glu Asp
  1               5                  10                  15

Gln Thr His Gln Asp Arg Leu His His Gly Cys Arg Arg Ala Ala Val
            20                  25                  30

Val Val Arg Gln Asp Arg Ala Ser Val Ser Ala Thr Ser Ala Arg Pro
        35                  40                  45

Pro Arg Arg His Pro Ala Gln Gly His Arg Arg Arg Val Ala Pro Ser
     50                  55                  60

Gly Gly Arg Arg Arg Pro His Pro His His Val Gln Pro Asp Asp Arg
 65                  70                  75                  80

Arg Asp Arg Pro Ala Leu Leu Asp Arg Thr Gln Pro Ala Glu His Pro
                85                  90                  95

Asp Pro His Arg Arg Gly Pro Ala Asp Pro Gly Arg Val Arg Gly Arg
            100                 105                 110

Gly Arg Leu Arg Arg Val Asp Asp Gly Arg Leu Gln Pro Asp Arg Asp
        115                 120                 125

Ala Asp His Gly Ala Pro Val Arg Gly Arg Gly Pro His Arg Gly Val
    130                 135                 140

Gln His Arg Gly Gly Pro Val Phe Val Arg Arg Val Pro Gly Val Arg
145                 150                 155                 160

Cys Ala His Arg Arg Gly His Arg Arg Val Ala Ala Pro Gly Gln Gly
                165                 170                 175

Asp Val Leu Arg Ala Gly Leu Arg Val Glu Arg Leu Arg Pro Val Ala
            180                 185                 190

Ala Val Glu Asn Leu His Arg Gly Ser Gln Arg Ala Asp Gly Arg Val
        195                 200                 205

Phe Arg Pro Ile Arg Arg Gly Ala Arg Leu Pro Ala Arg Arg Ser Arg
    210                 215                 220

Ala Gly Pro Gln Gly Arg Leu His Leu Asp Gly Ala Gly Pro Ser Pro
225                 230                 235                 240

Leu Pro Ala Arg Ala Gly Gln Gln Gln Pro Ser Ser Ala Gly Gly Arg
```

-continued 245 250 255

Arg Ala Gly Gly Ala Glu Arg Ala Asp Pro Gly Gln Arg Gly Arg His
260 265 270

His Gln Gly Gly His Asp Pro Gly Arg Gln Gly Ala Gln Arg Gly Thr
275 280 285

Ala Gly Val Ala His Ala Ala Ala Gly Pro Arg Arg Ala Ala Val Arg
290 295 300

Asn Arg Pro Arg Arg
305

<210> SEQ ID NO 76
<211> LENGTH: 580
<212> TYPE: PRT
<213> ORGANISM: Mycobacterium tuberculosis

<400> SEQUENCE: 76

Ser Ala Val Trp Cys Leu Asn Gly Phe Thr Gly Arg His Arg His Gly
1 5 10 15

Arg Cys Arg Val Arg Ala Ser Gly Trp Arg Ser Ser Asn Arg Trp Cys
20 25 30

Ser Thr Thr Ala Asp Cys Cys Ala Ser Lys Thr Pro Thr Gln Ala Ala
35 40 45

Ser Pro Leu Glu Arg Arg Phe Thr Cys Cys Ser Pro Ala Val Gly Cys
50 55 60

Arg Phe Arg Ser Phe Pro Val Arg Arg Leu Ala Leu Gly Ala Arg Thr
65 70 75 80

Ser Arg Thr Leu Gly Val Arg Arg Thr Leu Ser Gln Trp Asn Leu Ser
85 90 95

Pro Arg Ala Gln Pro Ser Cys Ala Val Thr Val Glu Ser His Thr His
100 105 110

Ala Ser Pro Arg Met Ala Lys Leu Ala Arg Val Val Gly Leu Val Gln
115 120 125

Glu Glu Gln Pro Ser Asp Met Thr Asn His Pro Arg Tyr Ser Pro Pro
130 135 140

Pro Gln Gln Pro Gly Thr Pro Gly Tyr Ala Gln Gly Gln Gln Gln Thr
145 150 155 160

Tyr Ser Gln Gln Phe Asp Trp Arg Tyr Pro Pro Ser Pro Pro Pro Gln
165 170 175

Pro Thr Gln Tyr Arg Gln Pro Tyr Glu Ala Leu Gly Gly Thr Arg Pro
180 185 190

Gly Leu Ile Pro Gly Val Ile Pro Thr Met Thr Pro Pro Pro Gly Met
195 200 205

Val Arg Gln Arg Pro Arg Ala Gly Met Leu Ala Ile Gly Ala Val Thr
210 215 220

Ile Ala Val Val Ser Ala Gly Ile Gly Gly Ala Ala Ala Ser Leu Val
225 230 235 240

Gly Phe Asn Arg Ala Pro Ala Gly Pro Ser Gly Gly Pro Val Ala Ala
245 250 255

Ser Ala Ala Pro Ser Ile Pro Ala Ala Asn Met Pro Pro Gly Ser Val
260 265 270

Glu Gln Val Ala Ala Lys Val Val Pro Ser Val Val Met Leu Glu Thr
275 280 285

Asp Leu Gly Arg Gln Ser Glu Glu Gly Ser Gly Ile Ile Leu Ser Ala
290 295 300

Glu Gly Leu Ile Leu Thr Asn Asn His Val Ile Ala Ala Ala Ala Lys

```
305                 310                 315                 320

Pro Pro Leu Gly Ser Pro Pro Pro Lys Thr Thr Val Thr Phe Ser Asp
                325                 330                 335

Gly Arg Thr Ala Pro Phe Thr Val Val Gly Ala Asp Pro Thr Ser Asp
            340                 345                 350

Ile Ala Val Val Arg Val Gln Gly Val Ser Gly Leu Thr Pro Ile Ser
        355                 360                 365

Leu Gly Ser Ser Ser Asp Leu Arg Val Gly Gln Pro Val Leu Ala Ile
    370                 375                 380

Gly Ser Pro Leu Gly Leu Glu Gly Thr Val Thr Thr Gly Ile Val Ser
385                 390                 395                 400

Ala Leu Asn Arg Pro Val Ser Thr Thr Gly Glu Ala Gly Asn Gln Asn
                405                 410                 415

Thr Val Leu Asp Ala Ile Gln Thr Asp Ala Ala Ile Asn Pro Gly Asn
            420                 425                 430

Ser Gly Gly Ala Leu Val Asn Met Asn Ala Gln Leu Val Gly Val Asn
        435                 440                 445

Ser Ala Ile Ala Thr Leu Gly Ala Asp Ser Ala Asp Ala Gln Ser Gly
    450                 455                 460

Ser Ile Gly Leu Gly Phe Ala Ile Pro Val Asp Gln Ala Lys Arg Ile
465                 470                 475                 480

Ala Asp Glu Leu Ile Ser Thr Gly Lys Ala Ser His Ala Ser Leu Gly
                485                 490                 495

Val Gln Val Thr Asn Asp Lys Asp Thr Pro Gly Ala Lys Ile Val Glu
            500                 505                 510

Val Val Ala Gly Gly Ala Ala Ala Asn Ala Gly Val Pro Lys Gly Val
        515                 520                 525

Val Val Thr Lys Val Asp Asp Arg Pro Ile Asn Ser Ala Asp Ala Leu
    530                 535                 540

Val Ala Ala Val Arg Ser Lys Ala Pro Gly Ala Thr Val Ala Leu Thr
545                 550                 555                 560

Phe Gln Asp Pro Ser Gly Gly Ser Arg Thr Val Gln Val Thr Leu Gly
                565                 570                 575

Lys Ala Glu Gln
            580


<210> SEQ ID NO 77
<211> LENGTH: 233
<212> TYPE: PRT
<213> ORGANISM: Mycobacterium tuberculosis

<400> SEQUENCE: 77

Met Asn Asp Gly Lys Arg Ala Val Thr Ser Ala Val Leu Val Val Leu
  1               5                  10                  15

Gly Ala Cys Leu Ala Leu Trp Leu Ser Gly Cys Ser Ser Pro Lys Pro
             20                  25                  30

Asp Ala Glu Glu Gln Gly Val Pro Val Ser Pro Thr Ala Ser Asp Pro
         35                  40                  45

Ala Leu Leu Ala Glu Ile Arg Gln Ser Leu Asp Ala Thr Lys Gly Leu
     50                  55                  60

Thr Ser Val His Val Ala Val Arg Thr Thr Gly Lys Val Asp Ser Leu
 65                  70                  75                  80

Leu Gly Ile Thr Ser Ala Asp Val Asp Val Arg Ala Asn Pro Leu Ala
                 85                  90                  95

Ala Lys Gly Val Cys Thr Tyr Asn Asp Glu Gln Gly Val Pro Phe Arg
```

```
            100                 105                 110

Val Gln Gly Asp Asn Ile Ser Val Lys Leu Phe Asp Asp Trp Ser Asn
        115                 120                 125

Leu Gly Ser Ile Ser Glu Leu Ser Thr Ser Arg Val Leu Asp Pro Ala
    130                 135                 140

Ala Gly Val Thr Gln Leu Leu Ser Gly Val Thr Asn Leu Gln Ala Gln
145                 150                 155                 160

Gly Thr Glu Val Ile Asp Gly Ile Ser Thr Thr Lys Ile Thr Gly Thr
                165                 170                 175

Ile Pro Ala Ser Ser Val Lys Met Leu Asp Pro Gly Ala Lys Ser Ala
            180                 185                 190

Arg Pro Ala Thr Val Trp Ile Ala Gln Asp Gly Ser His His Leu Val
        195                 200                 205

Arg Ala Ser Ile Asp Leu Gly Ser Gly Ser Ile Gln Leu Thr Gln Ser
    210                 215                 220

Lys Trp Asn Glu Pro Val Asn Val Asp
225                 230


<210> SEQ ID NO 78
<211> LENGTH: 66
<212> TYPE: PRT
<213> ORGANISM: Mycobacterium tuberculosis

<400> SEQUENCE: 78

Val Ile Asp Ile Ile Gly Thr Ser Pro Thr Ser Trp Glu Gln Ala Ala
  1               5                  10                  15

Ala Glu Ala Val Gln Arg Ala Arg Asp Ser Val Asp Asp Ile Arg Val
             20                  25                  30

Ala Arg Val Ile Glu Gln Asp Met Ala Val Asp Ser Ala Gly Lys Ile
         35                  40                  45

Thr Tyr Arg Ile Lys Leu Glu Val Ser Phe Lys Met Arg Pro Ala Gln
     50                  55                  60

Pro Arg
 65


<210> SEQ ID NO 79
<211> LENGTH: 69
<212> TYPE: PRT
<213> ORGANISM: Mycobacterium tuberculosis

<400> SEQUENCE: 79

Val Pro Pro Ala Pro Pro Leu Pro Pro Leu Pro Pro Ser Pro Ile Ser
  1               5                  10                  15

Cys Ala Ser Pro Pro Ser Pro Pro Leu Pro Pro Ala Pro Pro Val Ala
             20                  25                  30

Pro Gly Pro Pro Met Pro Pro Leu Asp Pro Trp Pro Pro Ala Pro Pro
         35                  40                  45

Leu Pro Tyr Ser Thr Pro Pro Gly Ala Pro Leu Pro Pro Ser Pro Pro
     50                  55                  60

Ser Pro Pro Leu Pro
 65


<210> SEQ ID NO 80
<211> LENGTH: 355
<212> TYPE: PRT
<213> ORGANISM: Mycobacterium tuberculosis

<400> SEQUENCE: 80
```

Met Ser Asn Ser Arg Arg Arg Ser Leu Arg Trp Ser Trp Leu Leu Ser
1 5 10 15

Val Leu Ala Ala Val Gly Leu Gly Leu Ala Thr Ala Pro Ala Gln Ala
20 25 30

Ala Pro Pro Ala Leu Ser Gln Asp Arg Phe Ala Asp Phe Pro Ala Leu
35 40 45

Pro Leu Asp Pro Ser Ala Met Val Ala Gln Val Ala Pro Gln Val Val
50 55 60

Asn Ile Asn Thr Lys Leu Gly Tyr Asn Asn Ala Val Gly Ala Gly Thr
65 70 75 80

Gly Ile Val Ile Asp Pro Asn Gly Val Val Leu Thr Asn Asn His Val
85 90 95

Ile Ala Gly Ala Thr Asp Ile Asn Ala Phe Ser Val Gly Ser Gly Gln
100 105 110

Thr Tyr Gly Val Asp Val Val Gly Tyr Asp Arg Thr Gln Asp Val Ala
115 120 125

Val Leu Gln Leu Arg Gly Ala Gly Gly Leu Pro Ser Ala Ala Ile Gly
130 135 140

Gly Gly Val Ala Val Gly Glu Pro Val Val Ala Met Gly Asn Ser Gly
145 150 155 160

Gly Gln Gly Gly Thr Pro Arg Ala Val Pro Gly Arg Val Val Ala Leu
165 170 175

Gly Gln Thr Val Gln Ala Ser Asp Ser Leu Thr Gly Ala Glu Glu Thr
180 185 190

Leu Asn Gly Leu Ile Gln Phe Asp Ala Ala Ile Gln Pro Gly Asp Ser
195 200 205

Gly Gly Pro Val Val Asn Gly Leu Gly Gln Val Val Gly Met Asn Thr
210 215 220

Ala Ala Ser Asp Asn Phe Gln Leu Ser Gln Gly Gly Gln Gly Phe Ala
225 230 235 240

Ile Pro Ile Gly Gln Ala Met Ala Ile Ala Gly Gln Ile Arg Ser Gly
245 250 255

Gly Gly Ser Pro Thr Val His Ile Gly Pro Thr Ala Phe Leu Gly Leu
260 265 270

Gly Val Val Asp Asn Asn Gly Asn Gly Ala Arg Val Gln Arg Val Val
275 280 285

Gly Ser Ala Pro Ala Ala Ser Leu Gly Ile Ser Thr Gly Asp Val Ile
290 295 300

Thr Ala Val Asp Gly Ala Pro Ile Asn Ser Ala Thr Ala Met Ala Asp
305 310 315 320

Ala Leu Asn Gly His His Pro Gly Asp Val Ile Ser Val Asn Trp Gln
325 330 335

Thr Lys Ser Gly Gly Thr Arg Thr Gly Asn Val Thr Leu Ala Glu Gly
340 345 350

Pro Pro Ala
355

<210> SEQ ID NO 81
<211> LENGTH: 205
<212> TYPE: PRT
<213> ORGANISM: Mycobacterium tuberculosis

<400> SEQUENCE: 81

Ser Pro Lys Pro Asp Ala Glu Glu Gln Gly Val Pro Val Ser Pro Thr
1 5 10 15

```
Ala Ser Asp Pro Ala Leu Leu Ala Glu Ile Arg Gln Ser Leu Asp Ala
            20                  25                  30

Thr Lys Gly Leu Thr Ser Val His Val Ala Val Arg Thr Thr Gly Lys
        35                  40                  45

Val Asp Ser Leu Leu Gly Ile Thr Ser Ala Asp Val Asp Val Arg Ala
    50                  55                  60

Asn Pro Leu Ala Ala Lys Gly Val Cys Thr Tyr Asn Asp Glu Gln Gly
65                  70                  75                  80

Val Pro Phe Arg Val Gln Gly Asp Asn Ile Ser Val Lys Leu Phe Asp
                85                  90                  95

Asp Trp Ser Asn Leu Gly Ser Ile Ser Glu Leu Ser Thr Ser Arg Val
            100                 105                 110

Leu Asp Pro Ala Ala Gly Val Thr Gln Leu Leu Ser Gly Val Thr Asn
        115                 120                 125

Leu Gln Ala Gln Gly Thr Glu Val Ile Asp Gly Ile Ser Thr Thr Lys
    130                 135                 140

Ile Thr Gly Thr Ile Pro Ala Ser Ser Val Lys Met Leu Asp Pro Gly
145                 150                 155                 160

Ala Lys Ser Ala Arg Pro Ala Thr Val Trp Ile Ala Gln Asp Gly Ser
                165                 170                 175

His His Leu Val Arg Ala Ser Ile Asp Leu Gly Ser Gly Ser Ile Gln
            180                 185                 190

Leu Thr Gln Ser Lys Trp Asn Glu Pro Val Asn Val Asp
        195                 200                 205


<210> SEQ ID NO 82
<211> LENGTH: 286
<212> TYPE: PRT
<213> ORGANISM: Mycobacterium tuberculosis
<220> FEATURE:
<221> NAME/KEY: MOD_RES
<222> LOCATION: (1)..(286)
<223> OTHER INFORMATION: Xaa = any amino acid

<400> SEQUENCE: 82

Gly Asp Ser Phe Trp Ala Ala Ala Asp Gln Met Ala Arg Gly Phe Val
1               5                   10                  15

Leu Gly Ala Thr Ala Gly Arg Thr Thr Leu Thr Gly Glu Gly Leu Gln
            20                  25                  30

His Ala Asp Gly His Ser Leu Leu Leu Asp Ala Thr Asn Pro Ala Val
        35                  40                  45

Val Ala Tyr Asp Pro Ala Phe Ala Tyr Glu Ile Gly Tyr Ile Xaa Glu
    50                  55                  60

Ser Gly Leu Ala Arg Met Cys Gly Glu Asn Pro Glu Asn Ile Phe Phe
65                  70                  75                  80

Tyr Ile Thr Val Tyr Asn Glu Pro Tyr Val Gln Pro Pro Glu Pro Glu
                85                  90                  95

Asn Phe Asp Pro Glu Gly Val Leu Gly Gly Ile Tyr Arg Tyr His Ala
            100                 105                 110

Ala Thr Glu Gln Arg Thr Asn Lys Xaa Gln Ile Leu Ala Ser Gly Val
        115                 120                 125

Ala Met Pro Ala Ala Leu Arg Ala Ala Gln Met Leu Ala Ala Glu Trp
    130                 135                 140

Asp Val Ala Ala Asp Val Trp Ser Val Thr Ser Trp Gly Glu Leu Asn
145                 150                 155                 160

Arg Asp Gly Val Val Ile Glu Thr Glu Lys Leu Arg His Pro Asp Arg
                165                 170                 175
```

```
Pro Ala Gly Val Pro Tyr Val Thr Arg Ala Leu Glu Asn Ala Arg Gly
            180                 185                 190

Pro Val Ile Ala Val Ser Asp Trp Met Arg Ala Val Pro Glu Gln Ile
        195                 200                 205

Arg Pro Trp Val Pro Gly Thr Tyr Leu Thr Leu Gly Thr Asp Gly Phe
    210                 215                 220

Gly Phe Ser Asp Thr Arg Pro Ala Gly Arg Arg Tyr Phe Asn Thr Asp
225                 230                 235                 240

Ala Glu Ser Gln Val Gly Arg Gly Phe Gly Arg Gly Trp Pro Gly Arg
                245                 250                 255

Arg Val Asn Ile Asp Pro Phe Gly Ala Gly Arg Gly Pro Pro Ala Gln
            260                 265                 270

Leu Pro Gly Phe Asp Glu Gly Gly Gly Leu Arg Pro Xaa Lys
        275                 280                 285


<210> SEQ ID NO 83
<211> LENGTH: 173
<212> TYPE: PRT
<213> ORGANISM: Mycobacterium tuberculosis

<400> SEQUENCE: 83

Thr Lys Phe His Ala Leu Met Gln Glu Gln Ile His Asn Glu Phe Thr
  1               5                  10                  15

Ala Ala Gln Gln Tyr Val Ala Ile Ala Val Tyr Phe Asp Ser Glu Asp
             20                  25                  30

Leu Pro Gln Leu Ala Lys His Phe Tyr Ser Gln Ala Val Glu Glu Arg
         35                  40                  45

Asn His Ala Met Met Leu Val Gln His Leu Leu Asp Arg Asp Leu Arg
     50                  55                  60

Val Glu Ile Pro Gly Val Asp Thr Val Arg Asn Gln Phe Asp Arg Pro
 65                  70                  75                  80

Arg Glu Ala Leu Ala Leu Ala Leu Asp Gln Glu Arg Thr Val Thr Asp
                 85                  90                  95

Gln Val Gly Arg Leu Thr Ala Val Ala Arg Asp Glu Gly Asp Phe Leu
            100                 105                 110

Gly Glu Gln Phe Met Gln Trp Phe Leu Gln Glu Gln Ile Glu Glu Val
        115                 120                 125

Ala Leu Met Ala Thr Leu Val Arg Val Ala Asp Arg Ala Gly Ala Asn
    130                 135                 140

Leu Phe Glu Leu Glu Asn Phe Val Ala Arg Glu Val Asp Val Ala Pro
145                 150                 155                 160

Ala Ala Ser Gly Ala Pro His Ala Ala Gly Gly Arg Leu
                165                 170


<210> SEQ ID NO 84
<211> LENGTH: 107
<212> TYPE: PRT
<213> ORGANISM: Mycobacterium tuberculosis
<220> FEATURE:
<221> NAME/KEY: MOD_RES
<222> LOCATION: (1)..(107)
<223> OTHER INFORMATION: Xaa = any amino acid

<400> SEQUENCE: 84

Arg Ala Asp Glu Arg Lys Asn Thr Thr Met Lys Met Val Lys Ser Ile
  1               5                  10                  15

Ala Ala Gly Leu Thr Ala Ala Ala Ala Ile Gly Ala Ala Ala Ala Gly
             20                  25                  30
```

Val Thr Ser Ile Met Ala Gly Gly Pro Val Val Tyr Gln Met Gln Pro
35 40 45

Val Val Phe Gly Ala Pro Leu Pro Leu Asp Pro Xaa Ser Ala Pro Xaa
50 55 60

Val Pro Thr Ala Ala Gln Trp Thr Xaa Leu Leu Asn Xaa Leu Xaa Asp
65 70 75 80

Pro Asn Val Ser Phe Xaa Asn Lys Gly Ser Leu Val Glu Gly Gly Ile
85 90 95

Gly Gly Xaa Glu Gly Xaa Xaa Arg Arg Xaa Gln
100 105

<210> SEQ ID NO 85
<211> LENGTH: 125
<212> TYPE: PRT
<213> ORGANISM: Mycobacterium tuberculosis
<220> FEATURE:
<221> NAME/KEY: MOD_RES
<222> LOCATION: (1)..(125)
<223> OTHER INFORMATION: Xaa = any amino acid

<400> SEQUENCE: 85

Val Leu Ser Val Pro Val Gly Asp Gly Phe Trp Xaa Arg Val Val Asn
1 5 10 15

Pro Leu Gly Gln Pro Ile Asp Gly Arg Gly Asp Val Asp Ser Asp Thr
20 25 30

Arg Arg Ala Leu Glu Leu Gln Ala Pro Ser Val Val Xaa Arg Gln Gly
35 40 45

Val Lys Glu Pro Leu Xaa Thr Gly Ile Lys Ala Ile Asp Ala Met Thr
50 55 60

Pro Ile Gly Arg Gly Gln Arg Gln Leu Ile Ile Gly Asp Arg Lys Thr
65 70 75 80

Gly Lys Asn Arg Arg Leu Cys Arg Thr Pro Ser Ser Asn Gln Arg Glu
85 90 95

Glu Leu Gly Val Arg Trp Ile Pro Arg Ser Arg Cys Ala Cys Val Tyr
100 105 110

Val Gly His Arg Ala Arg Arg Gly Thr Tyr His Arg Arg
115 120 125

<210> SEQ ID NO 86
<211> LENGTH: 117
<212> TYPE: PRT
<213> ORGANISM: Mycobacterium tuberculosis
<220> FEATURE:
<221> NAME/KEY: MOD_RES
<222> LOCATION: (1)..(117)
<223> OTHER INFORMATION: Xaa = any amino acid

<400> SEQUENCE: 86

Cys Asp Ala Val Met Gly Phe Leu Gly Gly Ala Gly Pro Leu Ala Val
1 5 10 15

Val Asp Gln Gln Leu Val Thr Arg Val Pro Gln Gly Trp Ser Phe Ala
20 25 30

Gln Ala Ala Ala Val Pro Val Val Phe Leu Thr Ala Trp Tyr Gly Leu
35 40 45

Ala Asp Leu Ala Glu Ile Lys Ala Gly Glu Ser Val Leu Ile His Ala
50 55 60

Gly Thr Gly Gly Val Gly Met Ala Ala Val Gln Leu Ala Arg Gln Trp
65 70 75 80

Gly Val Glu Val Phe Val Thr Ala Ser Arg Gly Lys Trp Asp Thr Leu

```
                85                  90                  95

Arg Ala Xaa Xaa Phe Asp Asp Xaa Pro Tyr Arg Xaa Phe Pro His Xaa
            100                 105                 110

Arg Ser Ser Xaa Gly
        115


<210> SEQ ID NO 87
<211> LENGTH: 103
<212> TYPE: PRT
<213> ORGANISM: Mycobacterium tuberculosis

<400> SEQUENCE: 87

Met Tyr Arg Phe Ala Cys Arg Thr Leu Met Leu Ala Ala Cys Ile Leu
  1               5                  10                  15

Ala Thr Gly Val Ala Gly Leu Gly Val Gly Ala Gln Ser Ala Ala Gln
            20                  25                  30

Thr Ala Pro Val Pro Asp Tyr Tyr Trp Cys Pro Gly Gln Pro Phe Asp
        35                  40                  45

Pro Ala Trp Gly Pro Asn Trp Asp Pro Tyr Thr Cys His Asp Asp Phe
    50                  55                  60

His Arg Asp Ser Asp Gly Pro Asp His Ser Arg Asp Tyr Pro Gly Pro
 65                  70                  75                  80

Ile Leu Glu Gly Pro Val Leu Asp Asp Pro Gly Ala Ala Pro Pro Pro
                85                  90                  95

Pro Ala Ala Gly Gly Gly Ala
            100


<210> SEQ ID NO 88
<211> LENGTH: 88
<212> TYPE: PRT
<213> ORGANISM: Mycobacterium tuberculosis

<400> SEQUENCE: 88

Val Gln Cys Arg Val Trp Leu Glu Ile Gln Trp Arg Gly Met Leu Gly
  1               5                  10                  15

Ala Asp Gln Ala Arg Ala Gly Gly Pro Ala Arg Ile Trp Arg Glu His
            20                  25                  30

Ser Met Ala Ala Met Lys Pro Arg Thr Gly Asp Gly Pro Leu Glu Ala
        35                  40                  45

Thr Lys Glu Gly Arg Gly Ile Val Met Arg Val Pro Leu Glu Gly Gly
    50                  55                  60

Gly Arg Leu Val Val Glu Leu Thr Pro Asp Glu Ala Ala Ala Leu Gly
 65                  70                  75                  80

Asp Glu Leu Lys Gly Val Thr Ser
                85


<210> SEQ ID NO 89
<211> LENGTH: 95
<212> TYPE: PRT
<213> ORGANISM: Mycobacterium tuberculosis

<400> SEQUENCE: 89

Thr Asp Ala Ala Thr Leu Ala Gln Glu Ala Gly Asn Phe Glu Arg Ile
  1               5                  10                  15

Ser Gly Asp Leu Lys Thr Gln Ile Asp Gln Val Glu Ser Thr Ala Gly
            20                  25                  30

Ser Leu Gln Gly Gln Trp Arg Gly Ala Ala Gly Thr Ala Ala Gln Ala
        35                  40                  45
```

Ala Val Val Arg Phe Gln Glu Ala Ala Asn Lys Gln Lys Gln Glu Leu
50 55 60

Asp Glu Ile Ser Thr Asn Ile Arg Gln Ala Gly Val Gln Tyr Ser Arg
65 70 75 80

Ala Asp Glu Glu Gln Gln Gln Ala Leu Ser Ser Gln Met Gly Phe
85 90 95

<210> SEQ ID NO 90
<211> LENGTH: 166
<212> TYPE: PRT
<213> ORGANISM: Mycobacterium tuberculosis
<220> FEATURE:
<221> NAME/KEY: MOD_RES
<222> LOCATION: (1)..(166)
<223> OTHER INFORMATION: Xaa = any amino acid

<400> SEQUENCE: 90

Met Thr Gln Ser Gln Thr Val Thr Val Asp Gln Gln Glu Ile Leu Asn
1 5 10 15

Arg Ala Asn Glu Val Glu Ala Pro Met Ala Asp Pro Pro Thr Asp Val
20 25 30

Pro Ile Thr Pro Cys Glu Leu Thr Xaa Xaa Lys Asn Ala Ala Gln Gln
35 40 45

Xaa Val Leu Ser Ala Asp Asn Met Arg Glu Tyr Leu Ala Ala Gly Ala
50 55 60

Lys Glu Arg Gln Arg Leu Ala Thr Ser Leu Arg Asn Ala Ala Lys Xaa
65 70 75 80

Tyr Gly Glu Val Asp Glu Glu Ala Ala Thr Ala Leu Asp Asn Asp Gly
85 90 95

Glu Gly Thr Val Gln Ala Glu Ser Ala Gly Ala Val Gly Gly Asp Ser
100 105 110

Ser Ala Glu Leu Thr Asp Thr Pro Arg Val Ala Thr Ala Gly Glu Pro
115 120 125

Asn Phe Met Asp Leu Lys Glu Ala Ala Arg Lys Leu Glu Thr Gly Asp
130 135 140

Gln Gly Ala Ser Leu Ala His Xaa Gly Asp Gly Trp Asn Thr Xaa Thr
145 150 155 160

Leu Thr Leu Gln Gly Asp
165

<210> SEQ ID NO 91
<211> LENGTH: 5
<212> TYPE: PRT
<213> ORGANISM: Mycobacterium tuberculosis

<400> SEQUENCE: 91

Arg Ala Glu Arg Met
1 5

<210> SEQ ID NO 92
<211> LENGTH: 263
<212> TYPE: PRT
<213> ORGANISM: Mycobacterium tuberculosis
<220> FEATURE:
<221> NAME/KEY: MOD_RES
<222> LOCATION: (254)
<223> OTHER INFORMATION: Xaa = any amino acid

<400> SEQUENCE: 92

Val Ala Trp Met Ser Val Thr Ala Gly Gln Ala Glu Leu Thr Ala Ala
1 5 10 15

```
Gln Val Arg Val Ala Ala Ala Ala Tyr Glu Thr Ala Tyr Gly Leu Thr
            20                  25                  30

Val Pro Pro Pro Val Ile Ala Glu Asn Arg Ala Glu Leu Met Ile Leu
        35                  40                  45

Ile Ala Thr Asn Leu Leu Gly Gln Asn Thr Pro Ala Ile Ala Val Asn
    50                  55                  60

Glu Ala Glu Tyr Gly Glu Met Trp Ala Gln Asp Ala Ala Ala Met Phe
65                  70                  75                  80

Gly Tyr Ala Ala Ala Thr Ala Thr Ala Thr Ala Thr Leu Leu Pro Phe
                85                  90                  95

Glu Glu Ala Pro Glu Met Thr Ser Ala Gly Gly Leu Leu Glu Gln Ala
            100                 105                 110

Ala Ala Val Glu Glu Ala Ser Asp Thr Ala Ala Ala Asn Gln Leu Met
        115                 120                 125

Asn Asn Val Pro Gln Ala Leu Lys Gln Leu Ala Gln Pro Thr Gln Gly
    130                 135                 140

Thr Thr Pro Ser Ser Lys Leu Gly Gly Leu Trp Lys Thr Val Ser Pro
145                 150                 155                 160

His Arg Ser Pro Ile Ser Asn Met Val Ser Met Ala Asn Asn His Met
                165                 170                 175

Ser Met Thr Asn Ser Gly Val Ser Met Thr Asn Thr Leu Ser Ser Met
            180                 185                 190

Leu Lys Gly Phe Ala Pro Ala Ala Ala Ala Gln Ala Val Gln Thr Ala
        195                 200                 205

Ala Gln Asn Gly Val Arg Ala Met Ser Ser Leu Gly Ser Ser Leu Gly
    210                 215                 220

Ser Ser Gly Leu Gly Gly Gly Val Ala Ala Asn Leu Gly Arg Ala Ala
225                 230                 235                 240

Ser Val Arg Tyr Gly His Arg Asp Gly Gly Lys Tyr Ala Xaa Ser Gly
                245                 250                 255

Arg Arg Asn Gly Gly Pro Ala
            260
```

<210> SEQ ID NO 93
<211> LENGTH: 303
<212> TYPE: PRT
<213> ORGANISM: Mycobacterium tuberculosis

<400> SEQUENCE: 93

```
Met Thr Tyr Ser Pro Gly Asn Pro Gly Tyr Pro Gln Ala Gln Pro Ala
1               5                   10                  15

Gly Ser Tyr Gly Gly Val Thr Pro Ser Phe Ala His Ala Asp Glu Gly
            20                  25                  30

Ala Ser Lys Leu Pro Met Tyr Leu Asn Ile Ala Val Ala Val Leu Gly
        35                  40                  45

Leu Ala Ala Tyr Phe Ala Ser Phe Gly Pro Met Phe Thr Leu Ser Thr
    50                  55                  60

Glu Leu Gly Gly Gly Asp Gly Ala Val Ser Gly Asp Thr Gly Leu Pro
65                  70                  75                  80

Val Gly Val Ala Leu Leu Ala Ala Leu Leu Ala Gly Val Val Leu Val
                85                  90                  95

Pro Lys Ala Lys Ser His Val Thr Val Val Ala Val Leu Gly Val Leu
            100                 105                 110

Gly Val Phe Leu Met Val Ser Ala Thr Phe Asn Lys Pro Ser Ala Tyr
        115                 120                 125
```

-continued

```
Ser Thr Gly Trp Ala Leu Trp Val Val Leu Ala Phe Ile Val Phe Gln
    130                 135                 140

Ala Val Ala Ala Val Leu Ala Leu Leu Val Glu Thr Gly Ala Ile Thr
145                 150                 155                 160

Ala Pro Ala Pro Arg Pro Lys Phe Asp Pro Tyr Gly Gln Tyr Gly Arg
                165                 170                 175

Tyr Gly Gln Tyr Gly Gln Tyr Gly Val Gln Pro Gly Gly Tyr Tyr Gly
            180                 185                 190

Gln Gln Gly Ala Gln Gln Ala Ala Gly Leu Gln Ser Pro Gly Pro Gln
        195                 200                 205

Gln Ser Pro Gln Pro Pro Gly Tyr Gly Ser Gln Tyr Gly Gly Tyr Ser
    210                 215                 220

Ser Ser Pro Ser Gln Ser Gly Ser Gly Tyr Thr Ala Gln Pro Pro Ala
225                 230                 235                 240

Gln Pro Pro Ala Gln Ser Gly Ser Gln Gln Ser His Gln Gly Pro Ser
                245                 250                 255

Thr Pro Pro Thr Gly Phe Pro Ser Phe Ser Pro Pro Pro Pro Val Ser
            260                 265                 270

Ala Gly Thr Gly Ser Gln Ala Gly Ser Ala Pro Val Asn Tyr Ser Asn
        275                 280                 285

Pro Ser Gly Gly Glu Gln Ser Ser Ser Pro Gly Gly Ala Pro Val
    290                 295                 300


<210> SEQ ID NO 94
<211> LENGTH: 507
<212> TYPE: DNA
<213> ORGANISM: Mycobacterium tuberculosis

<400> SEQUENCE: 94

atgaagatgg tgaaatcgat cgccgcaggt ctgaccgccg cggctgcaat cggcgccgct      60

gcggccggtg tgacttcgat catggctggc ggcccggtcg tataccagat gcagccggtc     120

gtcttcggcg cgccactgcc gttggacccg gcatccgccc ctgacgtccc gaccgccgcc     180

cagttgacca gcctgctcaa cagcctcgcc gatcccaacg tgtcgtttgc gaacaagggc     240

agtctggtcg agggcggcat cgggggcacc gaggcgcgca tcgccgacca caagctgaag     300

aaggccgccg agcacgggga tctgccgctg tcgttcagcg tgacgaacat ccagccggcg     360

gccgccggtt cggccaccgc cgacgtttcc gtctcgggtc cgaagctctc gtcgccggtc     420

acgcagaacg tcacgttcgt gaatcaaggc ggctggatgc tgtcacgcgc atcggcgatg     480

gagttgctgc aggccgcagg gaactga                                         507


<210> SEQ ID NO 95
<211> LENGTH: 168
<212> TYPE: PRT
<213> ORGANISM: Mycobacterium tuberculosis

<400> SEQUENCE: 95

Met Lys Met Val Lys Ser Ile Ala Ala Gly Leu Thr Ala Ala Ala Ala
  1               5                  10                  15

Ile Gly Ala Ala Ala Ala Gly Val Thr Ser Ile Met Ala Gly Gly Pro
             20                  25                  30

Val Val Tyr Gln Met Gln Pro Val Val Phe Gly Ala Pro Leu Pro Leu
         35                  40                  45

Asp Pro Ala Ser Ala Pro Asp Val Pro Thr Ala Ala Gln Leu Thr Ser
     50                  55                  60

Leu Leu Asn Ser Leu Ala Asp Pro Asn Val Ser Phe Ala Asn Lys Gly
```

```
 65                  70                  75                  80

Ser Leu Val Glu Gly Gly Ile Gly Gly Thr Glu Ala Arg Ile Ala Asp
                85                  90                  95

His Lys Leu Lys Lys Ala Ala Glu His Gly Asp Leu Pro Leu Ser Phe
            100                 105                 110

Ser Val Thr Asn Ile Gln Pro Ala Ala Ala Gly Ser Ala Thr Ala Asp
        115                 120                 125

Val Ser Val Ser Gly Pro Lys Leu Ser Ser Pro Val Thr Gln Asn Val
    130                 135                 140

Thr Phe Val Asn Gln Gly Gly Trp Met Leu Ser Arg Ala Ser Ala Met
145                 150                 155                 160

Glu Leu Leu Gln Ala Ala Gly Asn
                165


<210> SEQ ID NO 96
<211> LENGTH: 500
<212> TYPE: DNA
<213> ORGANISM: Mycobacterium tuberculosis

<400> SEQUENCE: 96

cgtggcaatg tcgttgaccg tcggggccgg ggtcgcctcc gcagatcccg tggacgcggt      60

cattaacacc acctgcaatt acgggcaggt agtagctgcg ctcaacgcga cggatccggg     120

ggctgccgca cagttcaacg cctcaccggt ggcgcagtcc tatttgcgca atttcctcgc     180

cgcaccgcca cctcagcgcg ctgccatggc cgcgcaattg caagctgtgc cgggggcggc     240

acagtacatc ggccttgtcg agtcggttgc cggctcctgc aacaactatt aagcccatgc     300

gggccccatc ccgcgacccg gcatcgtcgc cggggctagg ccagattgcc ccgctcctca     360

acgggccgca tcccgcgacc cggcatcgtc gccggggcta ggccagattg ccccgctcct     420

caacgggccg catctcgtgc cgaattcctg cagcccgggg gatccactag ttctagagcg     480

gccgccaccg cggtggagct                                                 500


<210> SEQ ID NO 97
<211> LENGTH: 96
<212> TYPE: PRT
<213> ORGANISM: Mycobacterium tuberculosis

<400> SEQUENCE: 97

Val Ala Met Ser Leu Thr Val Gly Ala Gly Val Ala Ser Ala Asp Pro
  1               5                  10                  15

Val Asp Ala Val Ile Asn Thr Thr Cys Asn Tyr Gly Gln Val Val Ala
             20                  25                  30

Ala Leu Asn Ala Thr Asp Pro Gly Ala Ala Ala Gln Phe Asn Ala Ser
         35                  40                  45

Pro Val Ala Gln Ser Tyr Leu Arg Asn Phe Leu Ala Ala Pro Pro Pro
     50                  55                  60

Gln Arg Ala Ala Met Ala Ala Gln Leu Gln Ala Val Pro Gly Ala Ala
 65                  70                  75                  80

Gln Tyr Ile Gly Leu Val Glu Ser Val Ala Gly Ser Cys Asn Asn Tyr
                85                  90                  95


<210> SEQ ID NO 98
<211> LENGTH: 154
<212> TYPE: DNA
<213> ORGANISM: Mycobacterium tuberculosis

<400> SEQUENCE: 98
```

-continued

```
atgacagagc agcagtggaa tttcgcgggt atcgaggccg cggcaagcgc aatccaggga     60

aatgtcacgt ccattcattc cctccttgac gaggggaagc agtccctgac caagctcgca    120

gcggcctggg gcggtagcgg ttcggaagcg tacc                                154
```

<210> SEQ ID NO 99
<211> LENGTH: 51
<212> TYPE: PRT
<213> ORGANISM: Mycobacterium tuberculosis

<400> SEQUENCE: 99

```
Met Thr Glu Gln Gln Trp Asn Phe Ala Gly Ile Glu Ala Ala Ala Ser
  1               5                  10                  15

Ala Ile Gln Gly Asn Val Thr Ser Ile His Ser Leu Leu Asp Glu Gly
             20                  25                  30

Lys Gln Ser Leu Thr Lys Leu Ala Ala Ala Trp Gly Gly Ser Gly Ser
         35                  40                  45

Glu Ala Tyr
     50
```

<210> SEQ ID NO 100
<211> LENGTH: 282
<212> TYPE: DNA
<213> ORGANISM: Mycobacterium tuberculosis
<220> FEATURE:
<221> NAME/KEY: modified_base
<222> LOCATION: (1)..(282)
<223> OTHER INFORMATION: n = g, a, c or t

<400> SEQUENCE: 100

```
cggtcgcgca cttccaggtg actatgaaag tcggcttccg nctggaggat tcctgaacct     60

tcaagcgcgg ccgataactg aggtgcatca ttaagcgact tttccagaac atcctgacgc    120

gctcgaaacg cggcacagcc gacggtggct ccgncgaggc gctgnctcca aaatccctga    180

gacaattcgn cgggggcgcc tacaaggaag tcggtgctga attcgncgng tatctggtcg    240

acctgtgtgg tctgnagccg gacgaagcgg tgctcgacgt cg                        282
```

<210> SEQ ID NO 101
<211> LENGTH: 3058
<212> TYPE: DNA
<213> ORGANISM: Mycobacterium tuberculosis

<400> SEQUENCE: 101

```
gatcgtaccc gtgcgagtgc tcgggccgtt tgaggatgga gtgcacgtgt ctttcgtgat     60

ggcataccca gagatgttgg cggcggcggc tgacaccctg cagagcatcg gtgctaccac    120

tgtggctagc aatgccgctg cggcggcccc gacgactggg gtggtgcccc ccgctgccga    180

tgaggtgtcg gcgctgactg cggcgcactt cgccgcacat gcggcgatgt atcagtccgt    240

gagcgctcgg gctgctgcga ttcatgacca gttcgtggcc acccttgcca gcagcgccag    300

ctcgtatgcg gccactgaag tcgccaatgc ggcggcggcc agctaagcca ggaacagtcg    360

gcacgagaaa ccacgagaaa tagggacacg taatggtgga tttcggggcg ttaccaccgg    420

agatcaactc cgcgaggatg tacgccggcc cgggttcggc ctcgctggtg gccgcggctc    480

agatgtggga cagcgtggcg agtgacctgt tttcggccgc gtcggcgttt cagtcggtgg    540

tctggggtct gacggtgggg tcgtggatag gttcgtcggc gggtctgatg gtggcggcgg    600

cctcgccgta tgtggcgtgg atgagcgtca ccgcggggca ggccgagctg accgccgccc    660

aggtccgggt tgctgcggcg gcctacgaga cggcgtatgg gctgacggtg cccccgccgg    720
```

-continued

```
tgatcgccga gaaccgtgct gaactgatga ttctgatagc gaccaacctc ttggggcaaa    780

acaccccggc gatcgcggtc aacgaggccg aatacggcga gatgtgggcc caagacgccg    840

ccgcgatgtt tggctacgcc gcggcgacgg cgacggcgac ggcgacgttg ctgccgttcg    900

aggaggcgcc ggagatgacc agcgcgggtg ggctcctcga gcaggccgcc gcggtcgagg    960

aggcctccga caccgccgcg gcgaaccagt tgatgaacaa tgtgccccag gcgctgcaac   1020

agctggccca gcccacgcag ggcaccacgc cttcttccaa gctgggtggc ctgtggaaga   1080

cggtctcgcc gcatcggtcg ccgatcagca acatggtgtc gatggccaac aaccacatgt   1140

cgatgaccaa ctcgggtgtg tcgatgacca acaccttgag ctcgatgttg aagggctttg   1200

ctccggcggc ggccgcccag gccgtgcaaa ccgcggcgca aaacggggtc cgggcgatga   1260

gctcgctggg cagctcgctg ggttcttcgg gtctgggcgg tggggtggcc gccaacttgg   1320

gtcgggcggc ctcggtcggt tcgttgtcgg tgccgcaggc ctgggccgcg gccaaccagg   1380

cagtcacccc ggcggcgcgg gcgctgccgc tgaccagcct gaccagcgcc gcggaaagag   1440

ggcccgggca gatgctgggc gggctgccgg tggggcagat gggcgccagg gccggtggtg   1500

ggctcagtgg tgtgctgcgt gttccgccgc gaccctatgt gatgccgcat tctccggcgg   1560

ccggctagga gagggggcgc agactgtcgt tatttgacca gtgatcggcg gtctcggtgt   1620

ttccgcggcc ggctatgaca acagtcaatg tgcatgacaa gttacaggta ttaggtccag   1680

gttcaacaag gagacaggca acatggcctc acgttttatg acggatccgc acgcgatgcg   1740

ggacatggcg ggccgttttg aggtgcacgc ccagacggtg gaggacgagg ctcgccggat   1800

gtgggcgtcc gcgcaaaaca tttccggtgc gggctggagt ggcatggccg aggcgacctc   1860

gctagacacc atggcccaga tgaatcaggc gtttcgcaac atcgtgaaca tgctgcacgg   1920

ggtgcgtgac gggctggttc gcgacgccaa caactacgag cagcaagagc aggcctccca   1980

gcagatcctc agcagctaac gtcagccgct gcagcacaat acttttacaa gcgaaggaga   2040

acaggttcga tgaccatcaa ctatcaattc ggggatgtcg acgctcacgg cgccatgatc   2100

cgcgctcagg ccgggttgct ggaggccgag catcaggcca tcattcgtga tgtgttgacc   2160

gcgagtgact tttggggcgg cgccggttcg gcggcctgcc aggggttcat tacccagttg   2220

ggccgtaact tccaggtgat ctacgagcag gccaacgccc acgggcagaa ggtgcaggct   2280

gccggcaaca acatggcgca aaccgacagc gccgtcggct ccagctgggc ctgacaccag   2340

gccaaggcca gggacgtggt gtacgagtga agttcctcgc gtgatccttc gggtggcagt   2400

ctaagtggtc agtgctgggg tgttggtggt ttgctgcttg gcgggttctt cggtgctggt   2460

cagtgctgct cgggctcggg tgaggacctc gaggcccagg tagcgccgtc cttcgatcca   2520

ttcgtcgtgt tgttcggcga ggacggctcc gacgaggcgg atgatcgagg cgcggtcggg   2580

gaagatgccc acgacgtcgg ttcggcgtcg tacctctcgg ttgaggcgtt cctgggggtt   2640

gttggaccag atttggcgcc agatctgctt ggggaaggcg gtgaacgcca gcaggtcggt   2700

gcgggcggtg tcgaggtgct cggccaccgc ggggagtttg tcggtcagag cgtcgagtac   2760

ccgatcatat tgggcaacaa ctgattcggc gtcgggctgg tcgtagatgg agtgcagcag   2820

ggtgcgcacc cacggccagg agggcttcgg ggtggctgcc atcagattgg ctgcgtagtg   2880

ggttctgcag cgctgccagg ccgctgcggg cagggtggcg ccgatcgcgg ccaccaggcc   2940

ggcgtgggcg tcgctggtga ccagcgcgac cccggacagg ccgcgggcga ccaggtcgcg   3000

gaagaacgcc agccagccgg ccccgtcctc ggcggaggtg acctggatgc ccaggatc     3058
```

<210> SEQ ID NO 102

<211> LENGTH: 391
<212> TYPE: PRT
<213> ORGANISM: Mycobacterium tuberculosis

<400> SEQUENCE: 102

```
Met Val Asp Phe Gly Ala Leu Pro Pro Glu Ile Asn Ser Ala Arg Met
  1               5                  10                  15

Tyr Ala Gly Pro Gly Ser Ala Ser Leu Val Ala Ala Ala Gln Met Trp
             20                  25                  30

Asp Ser Val Ala Ser Asp Leu Phe Ser Ala Ala Ser Ala Phe Gln Ser
         35                  40                  45

Val Val Trp Gly Leu Thr Val Gly Ser Trp Ile Gly Ser Ser Ala Gly
     50                  55                  60

Leu Met Val Ala Ala Ala Ser Pro Tyr Val Ala Trp Met Ser Val Thr
 65                  70                  75                  80

Ala Gly Gln Ala Glu Leu Thr Ala Ala Gln Val Arg Val Ala Ala Ala
                 85                  90                  95

Ala Tyr Glu Thr Ala Tyr Gly Leu Thr Val Pro Pro Pro Val Ile Ala
            100                 105                 110

Glu Asn Arg Ala Glu Leu Met Ile Leu Ile Ala Thr Asn Leu Leu Gly
        115                 120                 125

Gln Asn Thr Pro Ala Ile Ala Val Asn Glu Ala Glu Tyr Gly Glu Met
    130                 135                 140

Trp Ala Gln Asp Ala Ala Ala Met Phe Gly Tyr Ala Ala Ala Thr Ala
145                 150                 155                 160

Thr Ala Thr Ala Thr Leu Leu Pro Phe Glu Glu Ala Pro Glu Met Thr
                165                 170                 175

Ser Ala Gly Gly Leu Leu Glu Gln Ala Ala Ala Val Glu Glu Ala Ser
            180                 185                 190

Asp Thr Ala Ala Ala Asn Gln Leu Met Asn Asn Val Pro Gln Ala Leu
        195                 200                 205

Gln Gln Leu Ala Gln Pro Thr Gln Gly Thr Thr Pro Ser Ser Lys Leu
    210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
            260                 265                 270

Ala Ala Ala Gln Ala Val Gln Thr Ala Ala Gln Asn Gly Val Arg Ala
        275                 280                 285

Met Ser Ser Leu Gly Ser Ser Leu Gly Ser Ser Gly Leu Gly Gly Gly
    290                 295                 300

Val Ala Ala Asn Leu Gly Arg Ala Ala Ser Val Gly Ser Leu Ser Val
305                 310                 315                 320

Pro Gln Ala Trp Ala Ala Ala Asn Gln Ala Val Thr Pro Ala Ala Arg
                325                 330                 335

Ala Leu Pro Leu Thr Ser Leu Thr Ser Ala Ala Glu Arg Gly Pro Gly
            340                 345                 350

Gln Met Leu Gly Gly Leu Pro Val Gly Gln Met Gly Ala Arg Ala Gly
        355                 360                 365

Gly Gly Leu Ser Gly Val Leu Arg Val Pro Pro Arg Pro Tyr Val Met
    370                 375                 380

Pro His Ser Pro Ala Ala Gly
385                 390
```

<210> SEQ ID NO 103
<211> LENGTH: 1725
<212> TYPE: DNA
<213> ORGANISM: Mycobacterium tuberculosis

<400> SEQUENCE: 103

```
gacgtcagca cccgccgtgc agggctggag cgtggtcggt tttgatctgc ggtcaaggtg      60
acgtccctcg gcgtgtcgcc ggcgtggatg cagactcgat gccgctcttt agtgcaacta     120
atttcgttga agtgcctgcg aggtatagga cttcacgatt ggttaatgta gcgttcaccc     180
cgtgttgggg tcgatttggc cggaccagtc gtcaccaacg cttggcgtgc cgccaggcg      240
ggcgatcaga tcgcttgact accaatcaat cttgagctcc cgggccgatg ctcgggctaa     300
atgaggagga gcacgcgtgt ctttcactgc gcaaccggag atgttggcgg ccgcggctgg     360
cgaacttcgt tccctggggg caacgctgaa ggctagcaat gccgccgcag ccgtgccgac     420
gactggggtg gtgcccccgg ctgccgacga ggtgtcgctg ctgcttgcca cacaattccg     480
tacgcatgcg gcgacgtatc agacggccag cgccaaggcc gcggtgatcc atgagcagtt     540
tgtgaccacg ctggccacca gcgctagttc atatgcggac accgaggccg ccaacgctgt     600
ggtcaccggc tagctgacct gacggtattc gagcggaagg attatcgaag tggtggattt     660
cggggcgtta ccaccggaga tcaactccgc gaggatgtac gccggcccgg gttcggcctc     720
gctggtggcc gccgcgaaga tgtgggacag cgtggcgagt gacctgtttt cggccgcgtc     780
ggcgtttcag tcggtggtct ggggtctgac ggtggggtcg tggataggtt cgtcggcggg     840
tctgatggcg gcggcggcct cgccgtatgt ggcgtggatg agcgtcaccg cggggcaggc     900
ccagctgacc gccgcccagg tccgggttgc tgcggcggcc tacgagacag cgtataggct     960
gacggtgccc ccgccggtga tcgccgagaa ccgtaccgaa ctgatgacgc tgaccgcgac    1020
caacctcttg gggcaaaaca cgccggcgat cgaggccaat caggccgcat acagccagat    1080
gtggggccaa gacgcggagg cgatgtatgg ctacgccgcc acggcggcga cggcgaccga    1140
ggcgttgctg ccgttcgagg acgccccact gatcaccaac cccggcgggc tccttgagca    1200
ggccgtcgcg gtcgaggagg ccatcgacac cgccgcggcg aaccagttga tgaacaatgt    1260
gccccaagcg ctgcaacagc tggcccagcc agcgcagggc gtcgtacctt cttccaagct    1320
gggtgggctg tggacggcgg tctcgccgca tctgtcgccg ctcagcaacg tcagttcgat    1380
agccaacaac cacatgtcga tgatgggcac gggtgtgtcg atgaccaaca ccttgcactc    1440
gatgttgaag ggcttagctc cggcggcggc tcaggccgtg gaaaccgcgg cggaaaacgg    1500
ggtctgggcg atgagctcgc tgggcagcca gctgggttcg tcgctgggtt cttcgggtct    1560
gggcgctggg gtggccgcca acttgggtcg ggcggcctcg gtcggttcgt tgtcggtgcc    1620
gccagcatgg gccgcggcca accaggcggt caccccggcg gcgcgggcgc tgccgctgac    1680
cagcctgacc agcgccgccc aaaccgcccc cggacacatg ctggg                    1725
```

<210> SEQ ID NO 104
<211> LENGTH: 359
<212> TYPE: PRT
<213> ORGANISM: Mycobacterium tuberculosis

<400> SEQUENCE: 104

Val Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Lys Met Trp
            20                  25                  30

Asp Ser Val Ala Ser Asp Leu Phe Ser Ala Ala Ser Ala Phe Gln Ser
35 40 45

Val Val Trp Gly Leu Thr Val Gly Ser Trp Ile Gly Ser Ser Ala Gly
50 55 60

Leu Met Ala Ala Ala Ala Ser Pro Tyr Val Ala Trp Met Ser Val Thr
65 70 75 80

Ala Gly Gln Ala Gln Leu Thr Ala Ala Gln Val Arg Val Ala Ala Ala
85 90 95

Ala Tyr Glu Thr Ala Tyr Arg Leu Thr Val Pro Pro Pro Val Ile Ala
100 105 110

Glu Asn Arg Thr Glu Leu Met Thr Leu Thr Ala Thr Asn Leu Leu Gly
115 120 125

Gln Asn Thr Pro Ala Ile Glu Ala Asn Gln Ala Ala Tyr Ser Gln Met
130 135 140

Trp Gly Gln Asp Ala Glu Ala Met Tyr Gly Tyr Ala Ala Thr Ala Ala
145 150 155 160

Thr Ala Thr Glu Ala Leu Leu Pro Phe Glu Asp Ala Pro Leu Ile Thr
165 170 175

Asn Pro Gly Gly Leu Leu Glu Gln Ala Val Ala Val Glu Glu Ala Ile
180 185 190

Asp Thr Ala Ala Ala Asn Gln Leu Met Asn Asn Val Pro Gln Ala Leu
195 200 205

Gln Gln Leu Ala Gln Pro Ala Gln Gly Val Val Pro Ser Ser Lys Leu
210 215 220

Gly Gly Leu Trp Thr Ala Val Ser Pro His Leu Ser Pro Leu Ser Asn
225 230 235 240

Val Ser Ser Ile Ala Asn Asn His Met Ser Met Met Gly Thr Gly Val
245 250 255

Ser Met Thr Asn Thr Leu His Ser Met Leu Lys Gly Leu Ala Pro Ala
260 265 270

Ala Ala Gln Ala Val Glu Thr Ala Ala Glu Asn Gly Val Trp Ala Met
275 280 285

Ser Ser Leu Gly Ser Gln Leu Gly Ser Ser Leu Gly Ser Ser Gly Leu
290 295 300

Gly Ala Gly Val Ala Ala Asn Leu Gly Arg Ala Ala Ser Val Gly Ser
305 310 315 320

Leu Ser Val Pro Pro Ala Trp Ala Ala Ala Asn Gln Ala Val Thr Pro
325 330 335

Ala Ala Arg Ala Leu Pro Leu Thr Ser Leu Thr Ser Ala Ala Gln Thr
340 345 350

Ala Pro Gly His Met Leu Gly
355

<210> SEQ ID NO 105
<211> LENGTH: 3027
<212> TYPE: DNA
<213> ORGANISM: Mycobacterium tuberculosis

<400> SEQUENCE: 105
agttcagtcg agaatgatac tgacgggctg tatccacgat ggctgagaca accgaaccac 60
cgtcggacgc ggggacatcg caagccgacg cgatggcgtt ggccgccgaa gccgaagccg 120
ccgaagccga agcgctggcc gccgcggcgc gggcccgtgc ccgtgccgcc cggttgaagc 180
gtgaggcgct ggcgatggcc ccagccgagg acgagaacgt ccccgaggat atgcagactg 240

-continued

```
ggaagacgcc gaagactatg acgactatga cgactatgag gccgcagacc aggaggccgc    300
acggtcggca tcctggcgac ggcggttgcg ggtgcggtta ccaagactgt ccacgattgc    360
catggcggcc gcagtcgtca tcatctgcgg cttcaccggg ctcagcggat acattgtgtg    420
gcaacaccat gaggccaccg aacgccagca gcgcgccgcg gcgttcgccg ccggagccaa    480
gcaaggtgtc atcaacatga cctcgctgga cttcaacaag gccaaagaag acgtcgcgcg    540
tgtgatcgac agctccaccg gcgaattcag ggatgacttc cagcagcggg cagccgattt    600
caccaaggtt gtcgaacagt ccaaagtggt caccgaaggc acggtgaacg cgacagccgt    660
cgaatccatg aacgagcatt ccgccgtggt gctcgtcgcg gcgacttcac gggtcaccaa    720
ttccgctggg gcgaaagacg aaccacgtgc gtggcggctc aaagtgaccg tgaccgaaga    780
ggggggacag tacaagatgt cgaaagttga gttcgtaccg tgaccgatga cgtacgcgac    840
gtcaacaccg aaaccactga cgccaccgaa gtcgctgaga tcgactcagc cgcaggcgaa    900
gccggtgatt cggcgaccga ggcatttgac accgactctg caacggaatc taccgcgcag    960
aagggtcagc ggcaccgtga cctgtggcga atgcaggtta ccttgaaacc cgttccggtg   1020
attctcatcc tgctcatgtt gatctctggg ggcgcgacgg gatggctata ccttgagcaa   1080
tacgacccga tcagcagacg gactccggcg ccgcccgtgc tgccgtcgcc gcggcgtctg   1140
acgggacaat cgcgctgttg tgtattcacc cgacacgtcg accaagactt cgctaccgcc   1200
aggtcgcacc tcgccggcga tttcctgtcc tatacgacca gttcacgcag cagatcgtgg   1260
ctccggcggc caaacagaag tcactgaaaa ccaccgccaa ggtggtgcgc gcggccgtgt   1320
cggagctaca tccggattcg gccgtcgttc tggtttttgt cgaccagagc actaccagta   1380
aggacagccc caatccgtcg atggcggcca gcagcgtgat ggtgacccta gccaaggtcg   1440
acggcaattg gctgatcacc aagttcaccc cggtttaggt tgccgtaggc ggtcgccaag   1500
tctgacgggg gcgcgggtgg ctgctcgtgc gagataccgg ccgttctccg gacaatcacg   1560
gcccgacctc aaacagatct cggccgctgt ctaatcggcc gggttattta agattagttg   1620
ccactgtatt tacctgatgt tcagattgtt cagctggatt tagcttcgcg gcagggcggc   1680
tggtgcactt tgcatctggg gttgtgacta cttgagagaa tttgacctgt tgccgacgtt   1740
gtttgctgtc catcattggt gctagttatg gccgagcgga aggattatcg aagtggtgga   1800
cttcggggcg ttaccaccgg agatcaactc cgcgaggatg tacgccggcc cgggttcggc   1860
ctcgctggtg gccgccgcga agatgtggga cagcgtggcg agtgacctgt tttcggccgc   1920
gtcggcgttt cagtcggtgg tctggggtct gacgacggga tcgtggatag gttcgtcggc   1980
gggtctgatg gtggcggcgg cctcgccgta tgtggcgtgg atgagcgtca ccgcggggca   2040
ggccgagctg accgccgccc aggtccgggt tgctgcggcg gcctacgaga cggcgtatgg   2100
gctgacggtg cccccgccgg tgatcgccga gaaccgtgct gaactgatga ttctgatagc   2160
gaccaacctc ttggggcaaa acaccccggc gatcgcggtc aacgaggccg aatacgggga   2220
gatgtgggcc caagacgccg ccgcgatgtt tggctacgcc gccacggcgg cgacggcgac   2280
cgaggcgttg ctgccgttcg aggacgcccc actgatcacc aaccccggcg ggctccttga   2340
gcaggccgtc gcggtcgagg aggccatcga caccgccgcg gcgaaccagt tgatgaacaa   2400
tgtgccccaa gcgctgcaac aactggccca gcccacgaaa agcatctggc cgttcgacca   2460
actgagtgaa ctctggaaag ccatctcgcc gcatctgtcg ccgctcagca acatcgtgtc   2520
gatgctcaac aaccacgtgt cgatgaccaa ctcgggtgtg tcgatggcca gcaccttgca   2580
ctcaatgttg aagggctttg ctccggcggc ggctcaggcc gtggaaaccg cggcgcaaaa   2640
```

-continued

```
cggggtccag gcgatgagct cgctgggcag ccagctgggt tcgtcgctgg gttcttcggg   2700

tctgggcgct ggggtggccg ccaacttggg tcgggcggcc tcggtcggtt cgttgtcggt   2760

gccgcaggcc tgggccgcgg ccaaccaggc ggtcaccccg gcggcgcggg cgctgccgct   2820

gaccagcctg accagcgccg cccaaaccgc ccccggacac atgctgggcg ggctaccgct   2880

ggggcaactg accaatagcg gcggcgggtt cggcggggtt agcaatgcgt tgcggatgcc   2940

gccgcgggcg tacgtaatgc cccgtgtgcc cgccgccggg taacgccgat ccgcacgcaa   3000

tgcgggccct ctatgcgggc agcgatc                                      3027
```

```
<210> SEQ ID NO 106
<211> LENGTH: 396
<212> TYPE: PRT
<213> ORGANISM: Mycobacterium tuberculosis

<400> SEQUENCE: 106

Val Val Asp Phe Gly Ala Leu Pro Pro Glu Ile Asn Ser Ala Arg Met
  1               5                  10                  15

Tyr Ala Gly Pro Gly Ser Ala Ser Leu Val Ala Ala Ala Lys Met Trp
             20                  25                  30

Asp Ser Val Ala Ser Asp Leu Phe Ser Ala Ala Ser Ala Phe Gln Ser
         35                  40                  45

Val Val Trp Gly Leu Thr Thr Gly Ser Trp Ile Gly Ser Ser Ala Gly
     50                  55                  60

Leu Met Val Ala Ala Ala Ser Pro Tyr Val Ala Trp Met Ser Val Thr
 65                  70                  75                  80

Ala Gly Gln Ala Glu Leu Thr Ala Ala Gln Val Arg Val Ala Ala Ala
                 85                  90                  95

Ala Tyr Glu Thr Ala Tyr Gly Leu Thr Val Pro Pro Pro Val Ile Ala
            100                 105                 110

Glu Asn Arg Ala Glu Leu Met Ile Leu Ile Ala Thr Asn Leu Leu Gly
        115                 120                 125

Gln Asn Thr Pro Ala Ile Ala Val Asn Glu Ala Glu Tyr Gly Glu Met
    130                 135                 140

Trp Ala Gln Asp Ala Ala Ala Met Phe Gly Tyr Ala Ala Thr Ala Ala
145                 150                 155                 160

Thr Ala Thr Glu Ala Leu Leu Pro Phe Glu Asp Ala Pro Leu Ile Thr
                165                 170                 175

Asn Pro Gly Gly Leu Leu Glu Gln Ala Val Ala Val Glu Glu Ala Ile
            180                 185                 190

Asp Thr Ala Ala Ala Asn Gln Leu Met Asn Asn Val Pro Gln Ala Leu
        195                 200                 205

Gln Gln Leu Ala Gln Pro Thr Lys Ser Ile Trp Pro Phe Asp Gln Leu
    210                 215                 220

Ser Glu Leu Trp Lys Ala Ile Ser Pro His Leu Ser Pro Leu Ser Asn
225                 230                 235                 240

Ile Val Ser Met Leu Asn Asn His Val Ser Met Thr Asn Ser Gly Val
                245                 250                 255

Ser Met Ala Ser Thr Leu His Ser Met Leu Lys Gly Phe Ala Pro Ala
            260                 265                 270

Ala Ala Gln Ala Val Glu Thr Ala Ala Gln Asn Gly Val Gln Ala Met
        275                 280                 285

Ser Ser Leu Gly Ser Gln Leu Gly Ser Ser Leu Gly Ser Ser Gly Leu
    290                 295                 300

Gly Ala Gly Val Ala Ala Asn Leu Gly Arg Ala Ala Ser Val Gly Ser
```

-continued

```
305                 310                 315                 320

Leu Ser Val Pro Gln Ala Trp Ala Ala Ala Asn Gln Ala Val Thr Pro
                325                 330                 335

Ala Ala Arg Ala Leu Pro Leu Thr Ser Leu Thr Ser Ala Ala Gln Thr
            340                 345                 350

Ala Pro Gly His Met Leu Gly Gly Leu Pro Leu Gly Gln Leu Thr Asn
        355                 360                 365

Ser Gly Gly Gly Phe Gly Gly Val Ser Asn Ala Leu Arg Met Pro Pro
    370                 375                 380

Arg Ala Tyr Val Met Pro Arg Val Pro Ala Ala Gly
385                 390                 395
```

<210> SEQ ID NO 107
<211> LENGTH: 1616
<212> TYPE: DNA
<213> ORGANISM: Mycobacterium tuberculosis

<400> SEQUENCE: 107

```
catcggaggg agtgatcacc atgctgtggc acgcaatgcc accggagtaa ataccgcacg     60

gctgatggcc ggcgcgggtc cggctccaat gcttgcggcg gccgcgggat ggcagacgct    120

ttcggcggct ctggacgctc aggccgtcga gttgaccgcg cgcctgaact ctctgggaga    180

agcctggact ggaggtggca gcgacaaggc gcttgcggct gcaacgccga tggtggtctg    240

gctacaaacc gcgtcaacac aggccaagac ccgtgcgatg caggcgacgg cgcaagccgc    300

ggcatacacc caggccatgg ccacgacgcc gtcgctgccg gagatcgccg ccaaccacat    360

cacccaggcc gtccttacgg ccaccaactt cttcggtatc aacacgatcc cgatcgcgtt    420

gaccgagatg gattatttca tccgtatgtg gaaccaggca gccctggcaa tggaggtcta    480

ccaggccgag accgcggtta acacgctttt cgagaagctc gagccgatgg cgtcgatcct    540

tgatcccggc gcgagccaga gcacgacgaa cccgatcttc ggaatgccct cccctggcag    600

ctcaacaccg gttggccagt tgccgccggc ggctacccag accctcggcc aactgggtga    660

gatgagcggc ccgatgcagc agctgaccca gccgctgcag caggtgacgt cgttgttcag    720

ccaggtgggc ggcaccggcg gcggcaaccc agccgacgag gaagccgcgc agatgggcct    780

gctcggcacc agtccgctgt cgaaccatcc gctggctggt ggatcaggcc ccagcgcggg    840

cgcgggcctg ctgcgcgcgg agtcgctacc tggcgcaggt gggtcgttga cccgcacgcc    900

gctgatgtct cagctgatcg aaaagccggt tgccccctcg gtgatgccgg cggctgctgc    960

cggatcgtcg gcgacgggtg gcgccgctcc ggtgggtgcg ggagcgatgg gccagggtgc   1020

gcaatccggc ggctccacca ggccgggtct ggtcgcgccg gcaccgctcg cgcaggagcg   1080

tgaagaagac gacgaggacg actgggacga agaggacgac tggtgagctc ccgtaatgac   1140

aacagacttc ccggccaccc gggccggaag acttgccaac attttggcga ggaaggtaaa   1200

gagagaaagt agtccagcat ggcagagatg aagaccgatg ccgctaccct cgcgcaggag   1260

gcaggtaatt tcgagcggat ctccggcgac ctgaaaaccc agatcgacca ggtggagtcg   1320

acggcaggtt cgttgcaggg ccagtggcgc ggcgcggcgg ggacggccgc ccaggccgcg   1380

gtggtgcgct tccaagaagc agccaataag cagaagcagg aactcgacga gatctcgacg   1440

aatattcgtc aggccggcgt ccaatactcg agggccgacg aggagcagca gcaggcgctg   1500

tcctcgcaaa tgggcttctg acccgctaat acgaaaagaa acggagcaaa aacatgacag   1560

agcagcagtg gaatttcgcg ggtatcgagg ccgcggcaag cgcaatccag ggaaat       1616
```

<210> SEQ ID NO 108
<211> LENGTH: 432
<212> TYPE: DNA
<213> ORGANISM: Mycobacterium tuberculosis

<400> SEQUENCE: 108
ctagtggatg ggaccatggc cattttctgc agtctcactg ccttctgtgt tgacattttg 60
gcacgccggc ggaaacgaag cactggggtc gaagaacggc tgcgctgcca tatcgtccgg 120
agcttccata ccttcgtgcg gccggaagag cttgtcgtag tcggccgcca tgacaacctc 180
tcagagtgcg ctcaaacgta taaacacgag aaagggcgag accgacggaa ggtcgaactc 240
gcccgatccc gtgtttcgct attctacgcg aactcggcgt tgccctatgc gaacatccca 300
gtgacgttgc cttcggtcga agccattgcc tgaccggctt cgctgatcgt ccgcgccagg 360
ttctgcagcg cgttgttcag ctcggtagcc gtggcgtccc atttttgctg gacaccctgg 420
tacgcctccg aa 432

<210> SEQ ID NO 109
<211> LENGTH: 368
<212> TYPE: PRT
<213> ORGANISM: Mycobacterium tuberculosis
<220> FEATURE:
<221> NAME/KEY: MOD_RES
<222> LOCATION: (10)
<223> OTHER INFORMATION: Xaa = any amino acid

<400> SEQUENCE: 109

Met Leu Trp His Ala Met Pro Pro Glu Xaa Asn Thr Ala Arg Leu Met
1 5 10 15

Ala Gly Ala Gly Pro Ala Pro Met Leu Ala Ala Ala Ala Gly Trp Gln
20 25 30

Thr Leu Ser Ala Ala Leu Asp Ala Gln Ala Val Glu Leu Thr Ala Arg
35 40 45

Leu Asn Ser Leu Gly Glu Ala Trp Thr Gly Gly Gly Ser Asp Lys Ala
50 55 60

Leu Ala Ala Ala Thr Pro Met Val Val Trp Leu Gln Thr Ala Ser Thr
65 70 75 80

Gln Ala Lys Thr Arg Ala Met Gln Ala Thr Ala Gln Ala Ala Ala Tyr
85 90 95

Thr Gln Ala Met Ala Thr Thr Pro Ser Leu Pro Glu Ile Ala Ala Asn
100 105 110

His Ile Thr Gln Ala Val Leu Thr Ala Thr Asn Phe Phe Gly Ile Asn
115 120 125

Thr Ile Pro Ile Ala Leu Thr Glu Met Asp Tyr Phe Ile Arg Met Trp
130 135 140

Asn Gln Ala Ala Leu Ala Met Glu Val Tyr Gln Ala Glu Thr Ala Val
145 150 155 160

Asn Thr Leu Phe Glu Lys Leu Glu Pro Met Ala Ser Ile Leu Asp Pro
165 170 175

Gly Ala Ser Gln Ser Thr Thr Asn Pro Ile Phe Gly Met Pro Ser Pro
180 185 190

Gly Ser Ser Thr Pro Val Gly Gln Leu Pro Pro Ala Ala Thr Gln Thr
195 200 205

Leu Gly Gln Leu Gly Glu Met Ser Gly Pro Met Gln Gln Leu Thr Gln
210 215 220

Pro Leu Gln Gln Val Thr Ser Leu Phe Ser Gln Val Gly Gly Thr Gly
225 230 235 240

-continued

```
Gly Gly Asn Pro Ala Asp Glu Glu Ala Ala Gln Met Gly Leu Leu Gly
                245                 250                 255

Thr Ser Pro Leu Ser Asn His Pro Leu Ala Gly Gly Ser Gly Pro Ser
            260                 265                 270

Ala Gly Ala Gly Leu Leu Arg Ala Glu Ser Leu Pro Gly Ala Gly Gly
        275                 280                 285

Ser Leu Thr Arg Thr Pro Leu Met Ser Gln Leu Ile Glu Lys Pro Val
    290                 295                 300

Ala Pro Ser Val Met Pro Ala Ala Ala Ala Gly Ser Ser Ala Thr Gly
305                 310                 315                 320

Gly Ala Ala Pro Val Gly Ala Gly Ala Met Gly Gln Gly Ala Gln Ser
                325                 330                 335

Gly Gly Ser Thr Arg Pro Gly Leu Val Ala Pro Ala Pro Leu Ala Gln
            340                 345                 350

Glu Arg Glu Glu Asp Asp Glu Asp Asp Trp Asp Glu Glu Asp Asp Trp
        355                 360                 365
```

<210> SEQ ID NO 110
<211> LENGTH: 100
<212> TYPE: PRT
<213> ORGANISM: Mycobacterium tuberculosis

<400> SEQUENCE: 110

```
Met Ala Glu Met Lys Thr Asp Ala Ala Thr Leu Ala Gln Glu Ala Gly
  1               5                  10                  15

Asn Phe Glu Arg Ile Ser Gly Asp Leu Lys Thr Gln Ile Asp Gln Val
             20                  25                  30

Glu Ser Thr Ala Gly Ser Leu Gln Gly Gln Trp Arg Gly Ala Ala Gly
         35                  40                  45

Thr Ala Ala Gln Ala Ala Val Val Arg Phe Gln Glu Ala Ala Asn Lys
     50                  55                  60

Gln Lys Gln Glu Leu Asp Glu Ile Ser Thr Asn Ile Arg Gln Ala Gly
 65                  70                  75                  80

Val Gln Tyr Ser Arg Ala Asp Glu Glu Gln Gln Gln Ala Leu Ser Ser
                 85                  90                  95

Gln Met Gly Phe
            100
```

<210> SEQ ID NO 111
<211> LENGTH: 396
<212> TYPE: DNA
<213> ORGANISM: Mycobacterium tuberculosis

<400> SEQUENCE: 111

```
gatctccggc gacctgaaaa cccagatcga ccaggtggag tcgacggcag gttcgttgca      60

gggccagtgg cgcggcgcgg cggggacggc cgcccaggcc gcggtggtgc gcttccaaga     120

agcagccaat aagcagaagc aggaactcga cgagatctcg acgaatattc gtcaggccgg     180

cgtccaatac tcgagggccg acgaggagca gcagcaggcg ctgtcctcgc aaatgggctt     240

ctgacccgct aatacgaaaa gaaacggagc aaaaacatga cagagcagca gtggaatttc     300

gcgggtatcg aggccgcggc aagcgcaatc cagggaaatg tcacgtccat tcattccctc     360

cttgacgagg ggaagcagtc cctgaccaag ctcgca                               396
```

<210> SEQ ID NO 112
<211> LENGTH: 80
<212> TYPE: PRT
<213> ORGANISM: Mycobacterium tuberculosis

<400> SEQUENCE: 112

Ile Ser Gly Asp Leu Lys Thr Gln Ile Asp Gln Val Glu Ser Thr Ala
1 5 10 15

Gly Ser Leu Gln Gly Gln Trp Arg Gly Ala Ala Gly Thr Ala Ala Gln
20 25 30

Ala Ala Val Val Arg Phe Gln Glu Ala Ala Asn Lys Gln Lys Gln Glu
35 40 45

Leu Asp Glu Ile Ser Thr Asn Ile Arg Gln Ala Gly Val Gln Tyr Ser
50 55 60

Arg Ala Asp Glu Glu Gln Gln Gln Ala Leu Ser Ser Gln Met Gly Phe
65 70 75 80

<210> SEQ ID NO 113
<211> LENGTH: 387
<212> TYPE: DNA
<213> ORGANISM: Mycobacterium tuberculosis

<400> SEQUENCE: 113
gtggatcccg atcccgtgtt tcgctattct acgcgaactc ggcgttgccc tatgcgaaca 60
tcccagtgac gttgccttcg gtcgaagcca ttgcctgacc ggcttcgctg atcgtccgcg 120
ccaggttctg cagcgcgttg ttcagctcgg tagccgtggc gtcccatttt tgctggacac 180
cctggtacgc ctccgaaccg ctaccgcccc aggccgctgc gagcttggtc agggactgct 240
tcccctcgtc aaggagggaa tgaatggacg tgacatttcc ctggattgcg cttgccgcgg 300
cctcgatacc cgcgaaattc cactgctgct ctgtcatgtt tttgctccgt ttcttttcgt 360
attagcgggt cagaagccca tttgcga 387

<210> SEQ ID NO 114
<211> LENGTH: 272
<212> TYPE: DNA
<213> ORGANISM: Mycobacterium tuberculosis

<400> SEQUENCE: 114
cggcacgagg atctcggttg gcccaacggc gctggcgagg gctccgttcc gggggcgagc 60
tgcgcgccgg atgcttcctc tgcccgcagc cgcgcctgga tggatggacc agttgctacc 120
ttcccgacgt ttcgttcggt gtctgtgcga tagcggtgac cccggcgcgc acgtcgggag 180
tgttgggggg caggccgggt cggtggttcg gccggggacg cagacggtct ggacggaacg 240
ggcgggggtt cgccgattgg catctttgcc ca 272

<210> SEQ ID NO 115
<211> LENGTH: 20
<212> TYPE: PRT
<213> ORGANISM: Mycobacterium tuberculosis

<400> SEQUENCE: 115

Asp Pro Val Asp Ala Val Ile Asn Thr Thr Cys Asn Tyr Gly Gln Val
1 5 10 15

Val Ala Ala Leu
20

<210> SEQ ID NO 116
<211> LENGTH: 15
<212> TYPE: PRT
<213> ORGANISM: Mycobacterium tuberculosis

<400> SEQUENCE: 116

Ala Val Glu Ser Gly Met Leu Ala Leu Gly Thr Pro Ala Pro Ser
1 5 10 15

<210> SEQ ID NO 117
<211> LENGTH: 19
<212> TYPE: PRT
<213> ORGANISM: Mycobacterium tuberculosis

<400> SEQUENCE: 117

Ala Ala Met Lys Pro Arg Thr Gly Asp Gly Pro Leu Glu Ala Ala Lys
1 5 10 15

Glu Gly Arg

<210> SEQ ID NO 118
<211> LENGTH: 15
<212> TYPE: PRT
<213> ORGANISM: Mycobacterium tuberculosis

<400> SEQUENCE: 118

Tyr Tyr Trp Cys Pro Gly Gln Pro Phe Asp Pro Ala Trp Gly Pro
1 5 10 15

<210> SEQ ID NO 119
<211> LENGTH: 14
<212> TYPE: PRT
<213> ORGANISM: Mycobacterium tuberculosis
<220> FEATURE:
<221> NAME/KEY: MOD_RES
<222> LOCATION: (12)
<223> OTHER INFORMATION: Xaa = any amino acid

<400> SEQUENCE: 119

Asp Ile Gly Ser Glu Ser Thr Glu Asp Gln Gln Xaa Ala Val
1 5 10

<210> SEQ ID NO 120
<211> LENGTH: 13
<212> TYPE: PRT
<213> ORGANISM: Mycobacterium tuberculosis
<220> FEATURE:
<221> NAME/KEY: MOD_RES
<222> LOCATION: (1)..(13)
<223> OTHER INFORMATION: Xaa = any amino acid

<400> SEQUENCE: 120

Ala Glu Glu Ser Ile Ser Thr Xaa Glu Xaa Ile Val Pro
1 5 10

<210> SEQ ID NO 121
<211> LENGTH: 17
<212> TYPE: PRT
<213> ORGANISM: Mycobacterium tuberculosis

<400> SEQUENCE: 121

Asp Pro Glu Pro Ala Pro Pro Val Pro Thr Thr Ala Ala Ser Pro Pro
1 5 10 15

Ser

<210> SEQ ID NO 122
<211> LENGTH: 15
<212> TYPE: PRT
<213> ORGANISM: Mycobacterium tuberculosis
<220> FEATURE:
<221> NAME/KEY: MOD_RES
<222> LOCATION: (6)
<223> OTHER INFORMATION: Xaa = any amino acid

<400> SEQUENCE: 122

Ala Pro Lys Thr Tyr Xaa Glu Glu Leu Lys Gly Thr Asp Thr Gly
1 5 10 15

<210> SEQ ID NO 123
<211> LENGTH: 30
<212> TYPE: PRT
<213> ORGANISM: Mycobacterium tuberculosis

<400> SEQUENCE: 123

Asp Pro Ala Ser Ala Pro Asp Val Pro Thr Ala Ala Gln Leu Thr Ser
1 5 10 15

Leu Leu Asn Ser Leu Ala Asp Pro Asn Val Ser Phe Ala Asn
20 25 30

<210> SEQ ID NO 124
<211> LENGTH: 22
<212> TYPE: PRT
<213> ORGANISM: Mycobacterium tuberculosis
<220> FEATURE:
<221> NAME/KEY: MOD_RES
<222> LOCATION: (1)..(22)
<223> OTHER INFORMATION: Xaa = any amino acid

<400> SEQUENCE: 124

Asp Pro Pro Asp Pro His Gln Xaa Asp Met Thr Lys Gly Tyr Tyr Pro
1 5 10 15

Gly Gly Arg Arg Xaa Phe
20

<210> SEQ ID NO 125
<211> LENGTH: 7
<212> TYPE: PRT
<213> ORGANISM: Mycobacterium tuberculosis

<400> SEQUENCE: 125

Asp Pro Gly Tyr Thr Pro Gly
1 5

<210> SEQ ID NO 126
<211> LENGTH: 10
<212> TYPE: PRT
<213> ORGANISM: Mycobacterium tuberculosis
<220> FEATURE:
<221> NAME/KEY: MOD_RES
<222> LOCATION: (1)
<223> OTHER INFORMATION: Xaa = any amino acid
<220> FEATURE:
<221> NAME/KEY: MOD_RES
<222> LOCATION: (2)
<223> OTHER INFORMATION: Xaa = Pro or Thr

<400> SEQUENCE: 126

Xaa Xaa Gly Phe Thr Gly Pro Gln Phe Tyr
1 5 10

<210> SEQ ID NO 127
<211> LENGTH: 9
<212> TYPE: PRT
<213> ORGANISM: Mycobacterium tuberculosis
<220> FEATURE:
<221> NAME/KEY: MOD_RES
<222> LOCATION: (1)
<223> OTHER INFORMATION: Xaa = any amino acid
<220> FEATURE:
<221> NAME/KEY: MOD_RES
<222> LOCATION: (3)
<223> OTHER INFORMATION: Xaa = Gln or Leu

<400> SEQUENCE: 127

Xaa Pro Xaa Val Thr Ala Tyr Ala Gly
1 5

<210> SEQ ID NO 128
<211> LENGTH: 9
<212> TYPE: PRT
<213> ORGANISM: Mycobacterium tuberculosis
<220> FEATURE:
<221> NAME/KEY: MOD_RES
<222> LOCATION: (1)..(3)
<223> OTHER INFORMATION: Xaa = any amino acid

<400> SEQUENCE: 128

Xaa Xaa Xaa Glu Lys Pro Phe Leu Arg
1 5

<210> SEQ ID NO 129
<211> LENGTH: 15
<212> TYPE: PRT
<213> ORGANISM: Mycobacterium tuberculosis
<220> FEATURE:
<221> NAME/KEY: MOD_RES
<222> LOCATION: (1)
<223> OTHER INFORMATION: Xaa = any amino acid

<400> SEQUENCE: 129

Xaa Asp Ser Glu Lys Ser Ala Thr Ile Lys Val Thr Asp Ala Ser
1 5 10 15

<210> SEQ ID NO 130
<211> LENGTH: 15
<212> TYPE: PRT
<213> ORGANISM: Mycobacterium tuberculosis
<220> FEATURE:
<221> NAME/KEY: MOD_RES
<222> LOCATION: (5)
<223> OTHER INFORMATION: Xaa = any amino acid

<400> SEQUENCE: 130

Ala Gly Asp Thr Xaa Ile Tyr Ile Val Gly Asn Leu Thr Ala Asp
1 5 10 15

<210> SEQ ID NO 131
<211> LENGTH: 15
<212> TYPE: PRT
<213> ORGANISM: Mycobacterium tuberculosis

<400> SEQUENCE: 131

Ala Pro Glu Ser Gly Ala Gly Leu Gly Gly Thr Val Gln Ala Gly
1 5 10 15

<210> SEQ ID NO 132
<211> LENGTH: 21
<212> TYPE: PRT
<213> ORGANISM: Mycobacterium tuberculosis
<220> FEATURE:
<221> NAME/KEY: MOD_RES
<222> LOCATION: (1)..(21)
<223> OTHER INFORMATION: Xaa = any amino acid

<400> SEQUENCE: 132

Xaa Tyr Ile Ala Tyr Xaa Thr Thr Ala Gly Ile Val Pro Gly Lys Ile
1 5 10 15

Asn Val His Leu Val
20

<210> SEQ ID NO 133
<211> LENGTH: 882
<212> TYPE: DNA
<213> ORGANISM: Mycobacterium tuberculosis

<400> SEQUENCE: 133
gcaacgctgt cgtggccttt gcggtgatcg gtttcgcctc gctggcggtg gcggtggcgg 60
tcaccatccg accgaccgcg gcctcaaaac cggtagaggg acaccaaaac gcccagccag 120
ggaagttcat gccgttgttg ccgacgcaac agcaggcgcc ggtcccgccg cctccgcccg 180
atgatcccac cgctggattc cagggcggca ccattccggc tgtacagaac gtggtgccgc 240
ggccgggtac ctcacccggg gtgggtggga cgccggcttc gcctgcgccg gaagcgccgg 300
ccgtgcccgg tgttgtgcct gccccggtgc caatcccggt cccgatcatc attcccccgt 360
tcccgggttg gcagcctgga atgccgacca tccccaccgc accgccgacg acgccggtga 420
ccacgtcggc gacgacgccg ccgaccacgc cgccgaccac gccggtgacc acgccgccaa 480
cgacgccgcc gaccacgccg gtgaccacgc cgccaacgac gccgccgacc acgccggtga 540
ccacgccacc aacgaccgtc gccccgacga ccgtcgcccc gacgacggtc gctccgacca 600
ccgtcgcccc gaccacggtc gctccagcca ccgccacgcc gacgaccgtc gctccgcagc 660
cgacgcagca gcccacgcaa caaccaaccc aacagatgcc aacccagcag cagaccgtgg 720
ccccgcagac ggtggcgccg gctccgcagc cgccgtccgg tggccgcaac ggcagcggcg 780
ggggcgactt attcggcggg ttctgatcac ggtcgcggct tcactacggt cggaggacat 840
ggccggtgat gcggtgacgg tggtgctgcc ctgtctcaac ga 882

<210> SEQ ID NO 134
<211> LENGTH: 815
<212> TYPE: DNA
<213> ORGANISM: Mycobacterium tuberculosis
<220> FEATURE:
<221> NAME/KEY: modified_base
<222> LOCATION: (1)..(815)
<223> OTHER INFORMATION: n = g, a, c or t

<400> SEQUENCE: 134
ccatcaacca accgctcgcg ccgcccgcgc cgccggatcc gccgtcgccg ccacgcccgc 60
cggtgcctcc ggtgccccg ttgccgccgt cgccgccgtc gccgccgacc ggctgggtgc 120
ctagggcgct gttaccgccc tggttggcgg ggacgccgcc ggcaccaccg gtaccgccga 180
tggcgccgtt gccgccggcg gcaccgttgc caccgttgcc accgttgcca ccgttgccga 240
ccagccaccc gccgcgacca ccggcaccgc cggcgccgcc cgcaccgccg gcgtgcccgt 300
tcgtgcccgt accgccggca ccgccgttgc cgccgtcacc gccgacggaa ctaccggcgg 360
acgcggcctg cccgccggcg ccgcccgcac cgccattggc accgccgtca ccgccggctg 420
ggagtgccgc gattagggca ctgaccggcg caaccagcgc aagtactctc ggtcaccgag 480
cacttccaga cgacaccaca gcacggggtt gtcggcggac tgggtgaaat ggcagccgat 540
agcggctagc tgtcggctgc ggtcaacctc gatcatgatg tcgaggtgac cgtgaccgcg 600
ccccccgaag gaggcgctga actcggcgtt gagccgatcg gcgatcggtt ggggcagtgc 660
ccaggccaat acggggatac cgggtgtcna agccgccgcg agcgcagctt cggttgcgcg 720
acngtggtcg gggtggcctg ttacgccgtt gtcntcgaac acgagtagca ggtctgctcc 780
ggcgagggca tccaccacgc gttgcgtcag ctcgt 815

<210> SEQ ID NO 135

<211> LENGTH: 1152
<212> TYPE: DNA
<213> ORGANISM: Mycobacterium tuberculosis

<400> SEQUENCE: 135
accagccgcc ggctgaggtc tcagatcaga gagtctccgg actcaccggg gcggttcagc 60
cttctcccag aacaactgct gaagatcctc gcccgcgaaa caggcgctga tttgacgctc 120
tatgaccggt tgaacgacga gatcatccgg cagattgata tggcaccgct gggctaacag 180
gtgcgcaaga tggtgcagct gtatgtctcg gactccgtgt cgcggatcag ctttgccgac 240
ggccgggtga tcgtgtggag cgaggagctc ggcgagagcc agtatccgat cgagacgctg 300
gacggcatca cgctgtttgg gcggccgacg atgacaacgc ccttcatcgt tgagatgctc 360
aagcgtgagc gcgacatcca gctcttcacg accgacggcc actaccaggg ccggatctca 420
acacccgacg tgtcatacgc gccgcggctc cgtcagcaag ttcaccgcac cgacgatcct 480
gcgttctgcc tgtcgttaag caagcggatc gtgtcgagga agatcctgaa tcagcaggcc 540
ttgattcggg cacacacgtc ggggcaagac gttgctgaga gcatccgcac gatgaagcac 600
tcgctggcct gggtcgatcg atcgggctcc ctggcggagt tgaacgggtt cgagggaaat 660
gccgcaaagg catacttcac cgcgctgggg catctcgtcc cgcaggagtt cgcattccag 720
ggccgctcga ctcggccgcc gttggacgcc ttcaactcga tggtcagcct cggctattcg 780
ctgctgtaca agaacatcat aggggcgatc gagcgtcaca gcctgaacgc gtatatcggt 840
ttcctacacc aggattcacg agggcacgca acgtctcgtg ccgaattcgg cacgagctcc 900
gctgaaaccg ctggccggct gctcagtgcc cgtacgtaat ccgctgcgcc caggccggcc 960
cgccggccga ataccagcag atcggacagc gaattgccgc ccagccggtt ggagccgtgc 1020
ataccgccgg cacactcacc ggcagcgaac aggcctggca ccgtggcggc gccggtgtcc 1080
gcgtctactt cgacaccgcc catcacgtag tgacacgtcg gcccgacttc cattgcctgc 1140
gttcggcacg ag 1152

<210> SEQ ID NO 136
<211> LENGTH: 655
<212> TYPE: DNA
<213> ORGANISM: Mycobacterium tuberculosis
<220> FEATURE:
<221> NAME/KEY: modified_base
<222> LOCATION: (1)..(655)
<223> OTHER INFORMATION: n = g, a, c or t

<400> SEQUENCE: 136
ctcgtgccga ttcggcaggg tgtacttgcc ggtggtgtan gccgcatgag tgccgacgac 60
cagcaatgcg gcaacagcac ggatcccggt caacgacgcc acccggtcca cgtgggcgat 120
ccgctcgagt ccgccctggg cggctctttc cttgggcagg gtcatccgac gtgtttccgc 180
cgtggtttgc cgccattatg ccggcgcgcc gcgtcgggcg gccggtatgg ccgaangtcg 240
atcagcacac ccgagatacg ggtctgtgca agctttttga gcgtcgcgcg gggcagcttc 300
gccggcaatt ctactagcga gaagtctggc ccgatacgga tctgaccgaa gtcgctgcgg 360
tgcagcccac cctcattggc gatggcgccg acgatggcgc ctggaccgat cttgtgccgc 420
ttgccgacgg cgacgcggta ggtggtcaag tccggtctac gcttgggcct ttgcggacgg 480
tcccgacgct ggtcgcggtt gcgccgcgaa agcggcgggt cgggtgccat caggaatgcc 540
tcaccgccgc ggcactgcac ggccagtgcc gcggcgatgt cagccatcgg gacatcatgc 600
tcgcgttcat actcctcgac cagtcggcgg aacagctcga ttcccggacc gccca 655

<210> SEQ ID NO 137
<211> LENGTH: 267
<212> TYPE: PRT
<213> ORGANISM: Mycobacterium tuberculosis

<400> SEQUENCE: 137

```
Asn Ala Val Val Ala Phe Ala Val Ile Gly Phe Ala Ser Leu Ala Val
  1               5                  10                  15

Ala Val Ala Val Thr Ile Arg Pro Thr Ala Ala Ser Lys Pro Val Glu
             20                  25                  30

Gly His Gln Asn Ala Gln Pro Gly Lys Phe Met Pro Leu Leu Pro Thr
         35                  40                  45

Gln Gln Gln Ala Pro Val Pro Pro Pro Pro Pro Asp Asp Pro Thr Ala
     50                  55                  60

Gly Phe Gln Gly Gly Thr Ile Pro Ala Val Gln Asn Val Val Pro Arg
 65                  70                  75                  80

Pro Gly Thr Ser Pro Gly Val Gly Gly Thr Pro Ala Ser Pro Ala Pro
                 85                  90                  95

Glu Ala Pro Ala Val Pro Gly Val Val Pro Ala Pro Val Pro Ile Pro
            100                 105                 110

Val Pro Ile Ile Ile Pro Pro Phe Pro Gly Trp Gln Pro Gly Met Pro
        115                 120                 125

Thr Ile Pro Thr Ala Pro Pro Thr Thr Pro Val Thr Thr Ser Ala Thr
    130                 135                 140

Thr Pro Pro Thr Thr Pro Pro Thr Thr Pro Val Thr Thr Pro Pro Thr
145                 150                 155                 160

Thr Pro Pro Thr Thr Pro Val Thr Thr Pro Pro Thr Thr Pro Pro Thr
                165                 170                 175

Thr Pro Val Thr Thr Pro Pro Thr Thr Val Ala Pro Thr Thr Val Ala
            180                 185                 190

Pro Thr Thr Val Ala Pro Thr Thr Val Ala Pro Thr Thr Val Ala Pro
        195                 200                 205

Ala Thr Ala Thr Pro Thr Thr Val Ala Pro Gln Pro Thr Gln Gln Pro
    210                 215                 220

Thr Gln Gln Pro Thr Gln Gln Met Pro Thr Gln Gln Gln Thr Val Ala
225                 230                 235                 240

Pro Gln Thr Val Ala Pro Ala Pro Gln Pro Pro Ser Gly Gly Arg Asn
                245                 250                 255

Gly Ser Gly Gly Gly Asp Leu Phe Gly Gly Phe
            260                 265
```

<210> SEQ ID NO 138
<211> LENGTH: 174
<212> TYPE: PRT
<213> ORGANISM: Mycobacterium tuberculosis

<400> SEQUENCE: 138

```
Ile Asn Gln Pro Leu Ala Pro Pro Ala Pro Pro Asp Pro Pro Ser Pro
  1               5                  10                  15

Pro Arg Pro Pro Val Pro Pro Val Pro Pro Leu Pro Pro Ser Pro Pro
             20                  25                  30

Ser Pro Pro Thr Gly Trp Val Pro Arg Ala Leu Leu Pro Pro Trp Leu
         35                  40                  45

Ala Gly Thr Pro Pro Ala Pro Pro Val Pro Pro Met Ala Pro Leu Pro
     50                  55                  60

Pro Ala Ala Pro Leu Pro Pro Leu Pro Pro Leu Pro Pro Leu Pro Thr
```

-continued

```
 65                  70                  75                  80

Ser His Pro Pro Arg Pro Pro Ala Pro Pro Ala Pro Pro Ala Pro Pro
                85                  90                  95

Ala Cys Pro Phe Val Pro Val Pro Pro Ala Pro Pro Leu Pro Pro Ser
            100                 105                 110

Pro Pro Thr Glu Leu Pro Ala Asp Ala Ala Cys Pro Pro Ala Pro Pro
        115                 120                 125

Ala Pro Pro Leu Ala Pro Pro Ser Pro Pro Ala Gly Ser Ala Ala Ile
    130                 135                 140

Arg Ala Leu Thr Gly Ala Thr Ser Ala Ser Thr Leu Gly His Arg Ala
145                 150                 155                 160

Leu Pro Asp Asp Thr Thr Ala Arg Gly Cys Arg Arg Thr Gly
                165                 170


<210> SEQ ID NO 139
<211> LENGTH: 35
<212> TYPE: PRT
<213> ORGANISM: Mycobacterium tuberculosis

<400> SEQUENCE: 139

Gln Pro Pro Ala Glu Val Ser Asp Gln Arg Val Ser Gly Leu Thr Gly
  1               5                  10                  15

Ala Val Gln Pro Ser Pro Arg Thr Thr Ala Glu Asp Pro Arg Pro Arg
             20                  25                  30

Asn Arg Arg
         35


<210> SEQ ID NO 140
<211> LENGTH: 104
<212> TYPE: PRT
<213> ORGANISM: Mycobacterium tuberculosis
<220> FEATURE:
<221> NAME/KEY: MOD_RES
<222> LOCATION: (1)..(104)
<223> OTHER INFORMATION: Xaa = any amino acid

<400> SEQUENCE: 140

Arg Ala Asp Ser Ala Gly Cys Thr Cys Arg Trp Cys Xaa Pro His Glu
  1               5                  10                  15

Cys Arg Arg Pro Ala Met Arg Gln Gln His Gly Ser Arg Ser Thr Thr
             20                  25                  30

Pro Pro Gly Pro Arg Gly Arg Ser Ala Arg Val Arg Pro Gly Arg Leu
         35                  40                  45

Phe Pro Trp Ala Gly Ser Ser Asp Val Phe Pro Pro Trp Phe Ala Ala
     50                  55                  60

Ile Met Pro Ala Arg Arg Val Gly Arg Pro Val Trp Pro Xaa Val Asp
 65                  70                  75                  80

Gln His Thr Arg Asp Thr Gly Leu Cys Lys Leu Phe Glu Arg Arg Ala
                85                  90                  95

Gly Gln Leu Arg Arg Gln Phe Tyr
            100


<210> SEQ ID NO 141
<211> LENGTH: 53
<212> TYPE: DNA
<213> ORGANISM: Artificial Sequence
<220> FEATURE:
<223> OTHER INFORMATION: Description of Artificial Sequence:PCR primer
      PCM-64 used in preparation of fusion protein
      containing TbRa3, 38 kD and Tb38-1
```

<400> SEQUENCE: 141
ggatccatat gggccatcat catcatcatc acgtgatcga catcatcggg acc 53

<210> SEQ ID NO 142
<211> LENGTH: 42
<212> TYPE: DNA
<213> ORGANISM: Artificial Sequence
<220> FEATURE:
<223> OTHER INFORMATION: Description of Artificial Sequence:PCR primer PCM-65 used in preparation of fusion protein containing TbRa3, 38 kD and Tb38-1

<400> SEQUENCE: 142
cctgaattca ggcctcggtt gcgccggcct catcttgaac ga 42

<210> SEQ ID NO 143
<211> LENGTH: 31
<212> TYPE: DNA
<213> ORGANISM: Artificial Sequence
<220> FEATURE:
<223> OTHER INFORMATION: Description of Artificial Sequence:PCR primer PCM-57 used in preparation of fusion protein containing TbRa3, 38 kD and Tb38-1

<400> SEQUENCE: 143
ggatcctgca ggctcgaaac caccgagcgg t 31

<210> SEQ ID NO 144
<211> LENGTH: 31
<212> TYPE: DNA
<213> ORGANISM: Artificial Sequence
<220> FEATURE:
<223> OTHER INFORMATION: Description of Artificial Sequence:PCR primer PCM-58 used in preparation of fusion protein containing TbRa3, 38 kD and Tb38-1

<400> SEQUENCE: 144
ctctgaattc agcgctggaa atcgtcgcga t 31

<210> SEQ ID NO 145
<211> LENGTH: 33
<212> TYPE: DNA
<213> ORGANISM: Artificial Sequence
<220> FEATURE:
<223> OTHER INFORMATION: Description of Artificial Sequence:PCR primer PCM-69 used in preparation of fusion protein containing TbRa3, 38 kD and Tb38-1

<400> SEQUENCE: 145
ggatccagcg ctgagatgaa gaccgatgcc gct 33

<210> SEQ ID NO 146
<211> LENGTH: 33
<212> TYPE: DNA
<213> ORGANISM: Artificial Sequence
<220> FEATURE:
<223> OTHER INFORMATION: Description of Artificial Sequence:PCR primer PCM-60 used in preparation of fusion protein containing TbRa3, 38 kD and Tb38-1

<400> SEQUENCE: 146
gagagaattc tcagaagccc atttgcgagg aca 33

<210> SEQ ID NO 147
<211> LENGTH: 1993
<212> TYPE: DNA
<213> ORGANISM: Artificial Sequence
<220> FEATURE:

-continued

```
<223> OTHER INFORMATION: Description of Artificial Sequence:DNA
      sequence of fusion protein containing TbRa3, 38 kD and Tb38-1
<220> FEATURE:
<221> NAME/KEY: CDS
<222> LOCATION: (152)..(1276)

<400> SEQUENCE: 147

tgttcttcga cggcaggctg gtggaggaag ggcccaccga acagctgttc tcctcgccga      60

agcatgcgga aaccgcccga tacgtcgccg gactgtcggg ggacgtcaag gacgccaagc     120

gcggaaattg aagagcacag aaaggtatgg c gtg aaa att cgt ttg cat acg        172
                                   Val Lys Ile Arg Leu His Thr
                                    1               5

ctg ttg gcc gtg ttg acc gct gcg ccg ctg ctg cta gca gcg gcg ggc       220
Leu Leu Ala Val Leu Thr Ala Ala Pro Leu Leu Leu Ala Ala Ala Gly
         10                  15                  20

tgt ggc tcg aaa cca ccg agc ggt tcg cct gaa acg ggc gcc ggc gcc       268
Cys Gly Ser Lys Pro Pro Ser Gly Ser Pro Glu Thr Gly Ala Gly Ala
     25                  30                  35

ggt act gtc gcg act acc ccc gcg tcg tcg ccg gtg acg ttg gcg gag       316
Gly Thr Val Ala Thr Thr Pro Ala Ser Ser Pro Val Thr Leu Ala Glu
 40                  45                  50                  55

acc ggt agc acg ctg ctc tac ccg ctg ttc aac ctg tgg ggt ccg gcc       364
Thr Gly Ser Thr Leu Leu Tyr Pro Leu Phe Asn Leu Trp Gly Pro Ala
                 60                  65                  70

ttt cac gag agg tat ccg aac gtc acg atc acc gct cag ggc acc ggt       412
Phe His Glu Arg Tyr Pro Asn Val Thr Ile Thr Ala Gln Gly Thr Gly
             75                  80                  85

tct ggt gcc ggg atc gcg cag gcc gcc gcc ggg acg gtc aac att ggg       460
Ser Gly Ala Gly Ile Ala Gln Ala Ala Ala Gly Thr Val Asn Ile Gly
         90                  95                 100

gcc tcc gac gcc tat ctg tcg gaa ggt gat atg gcc gcg cac aag ggg       508
Ala Ser Asp Ala Tyr Leu Ser Glu Gly Asp Met Ala Ala His Lys Gly
    105                 110                 115

ctg atg aac atc gcg cta gcc atc tcc gct cag cag gtc aac tac aac       556
Leu Met Asn Ile Ala Leu Ala Ile Ser Ala Gln Gln Val Asn Tyr Asn
120                 125                 130                 135

ctg ccc gga gtg agc gag cac ctc aag ctg aac gga aaa gtc ctg gcg       604
Leu Pro Gly Val Ser Glu His Leu Lys Leu Asn Gly Lys Val Leu Ala
                140                 145                 150

gcc atg tac cag ggc acc atc aaa acc tgg gac gac ccg cag atc gct       652
Ala Met Tyr Gln Gly Thr Ile Lys Thr Trp Asp Asp Pro Gln Ile Ala
            155                 160                 165

gcg ctc aac ccc ggc gtg aac ctg ccc ggc acc gcg gta gtt ccg ctg       700
Ala Leu Asn Pro Gly Val Asn Leu Pro Gly Thr Ala Val Val Pro Leu
        170                 175                 180

cac cgc tcc gac ggg tcc ggt gac acc ttc ttg ttc acc cag tac ctg       748
His Arg Ser Asp Gly Ser Gly Asp Thr Phe Leu Phe Thr Gln Tyr Leu
    185                 190                 195

tcc aag caa gat ccc gag ggc tgg ggc aag tcg ccc ggc ttc ggc acc       796
Ser Lys Gln Asp Pro Glu Gly Trp Gly Lys Ser Pro Gly Phe Gly Thr
200                 205                 210                 215

acc gtc gac ttc ccg gcg gtg ccg ggt gcg ctg ggt gag aac ggc aac       844
Thr Val Asp Phe Pro Ala Val Pro Gly Ala Leu Gly Glu Asn Gly Asn
                220                 225                 230

ggc ggc atg gtg acc ggt tgc gcc gag aca ccg ggc tgc gtg gcc tat       892
Gly Gly Met Val Thr Gly Cys Ala Glu Thr Pro Gly Cys Val Ala Tyr
            235                 240                 245

atc ggc atc agc ttc ctc gac cag gcc agt caa cgg gga ctc ggc gag       940
Ile Gly Ile Ser Phe Leu Asp Gln Ala Ser Gln Arg Gly Leu Gly Glu
        250                 255                 260
```

-continued

```
gcc caa cta ggc aat agc tct ggc aat ttc ttg ttg ccc gac gcg caa      988
Ala Gln Leu Gly Asn Ser Ser Gly Asn Phe Leu Leu Pro Asp Ala Gln
    265                 270                 275

agc att cag gcc gcg gcg gct ggc ttc gca tcg aaa acc ccg gcg aac     1036
Ser Ile Gln Ala Ala Ala Ala Gly Phe Ala Ser Lys Thr Pro Ala Asn
280                 285                 290                 295

cag gcg att tcg atg atc gac ggg ccc gcc ccg gac ggc tac ccg atc     1084
Gln Ala Ile Ser Met Ile Asp Gly Pro Ala Pro Asp Gly Tyr Pro Ile
                300                 305                 310

atc aac tac gag tac gcc atc gtc aac aac cgg caa aag gac gcc gcc     1132
Ile Asn Tyr Glu Tyr Ala Ile Val Asn Asn Arg Gln Lys Asp Ala Ala
            315                 320                 325

acc gcg cag acc ttg cag gca ttt ctg cac tgg gcg atc acc gac ggc     1180
Thr Ala Gln Thr Leu Gln Ala Phe Leu His Trp Ala Ile Thr Asp Gly
        330                 335                 340

aac aag gcc tcg ttc ctc gac cag gtt cat ttc cag ccg ctg ccg ccc     1228
Asn Lys Ala Ser Phe Leu Asp Gln Val His Phe Gln Pro Leu Pro Pro
    345                 350                 355

gcg gtg gtg aag ttg tct gac gcg ttg atc gcg acg att tcc agc tag     1276
Ala Val Val Lys Leu Ser Asp Ala Leu Ile Ala Thr Ile Ser Ser
360                 365                 370

cctcgttgac caccacgcga cagcaacctc cgtcgggcca tcgggctgct ttgcggagca   1336

tgctggcccg tgccggtgaa gtcggccgcg ctggcccggc catccggtgg ttgggtggga   1396

taggtgcggt gatcccgctg cttgcgctgg tcttggtgct ggtggtgctg gtcatcgagg   1456

cgatgggtgc gatcaggctc aacgggttgc atttcttcac cgccaccgaa tggaatccag   1516

gcaacaccta cggcgaaacc gttgtcaccg acgcgtcgcc catccggtcg gcgcctacta   1576

cggggcgttg ccgctgatcg tcgggacgct ggcgacctcg gcaatcgccc tgatcatcgc   1636

ggtgccggtc tctgtaggag cggcgctggt gatcgtggaa cggctgccga aacggttggc   1696

cgaggctgtg ggaatagtcc tggaattgct cgccggaatc cccagcgtgg tcgtcggttt   1756

gtggggggca atgacgttcg ggccgttcat cgctcatcac atcgctccgg tgatcgctca   1816

caacgctccc gatgtgccgg tgctgaacta cttgcgcggc gacccgggca acggggaggg   1876

catgttggtg tccggtctgg tgttggcggt gatggtcgtt cccattatcg ccaccaccac   1936

tcatgacctg ttccggcagg tgccggtgtt gccccgggag ggcgcgatcg ggaattc      1993


<210> SEQ ID NO 148
<211> LENGTH: 374
<212> TYPE: PRT
<213> ORGANISM: Artificial Sequence
<220> FEATURE:
<223> OTHER INFORMATION: Description of Artificial Sequence:sequence of
      fusion protein containing TbRa3, 38 kD and Tb38-1

<400> SEQUENCE: 148

Val Lys Ile Arg Leu His Thr Leu Leu Ala Val Leu Thr Ala Ala Pro
  1               5                  10                  15

Leu Leu Leu Ala Ala Ala Gly Cys Gly Ser Lys Pro Pro Ser Gly Ser
            20                  25                  30

Pro Glu Thr Gly Ala Gly Ala Gly Thr Val Ala Thr Thr Pro Ala Ser
        35                  40                  45

Ser Pro Val Thr Leu Ala Glu Thr Gly Ser Thr Leu Leu Tyr Pro Leu
     50                  55                  60

Phe Asn Leu Trp Gly Pro Ala Phe His Glu Arg Tyr Pro Asn Val Thr
 65                  70                  75                  80

Ile Thr Ala Gln Gly Thr Gly Ser Gly Ala Gly Ile Ala Gln Ala Ala
                 85                  90                  95
```

```
Ala Gly Thr Val Asn Ile Gly Ala Ser Asp Ala Tyr Leu Ser Glu Gly
            100                 105                 110

Asp Met Ala Ala His Lys Gly Leu Met Asn Ile Ala Leu Ala Ile Ser
        115                 120                 125

Ala Gln Gln Val Asn Tyr Asn Leu Pro Gly Val Ser Glu His Leu Lys
    130                 135                 140

Leu Asn Gly Lys Val Leu Ala Ala Met Tyr Gln Gly Thr Ile Lys Thr
145                 150                 155                 160

Trp Asp Asp Pro Gln Ile Ala Ala Leu Asn Pro Gly Val Asn Leu Pro
                165                 170                 175

Gly Thr Ala Val Val Pro Leu His Arg Ser Asp Gly Ser Gly Asp Thr
            180                 185                 190

Phe Leu Phe Thr Gln Tyr Leu Ser Lys Gln Asp Pro Glu Gly Trp Gly
        195                 200                 205

Lys Ser Pro Gly Phe Gly Thr Thr Val Asp Phe Pro Ala Val Pro Gly
    210                 215                 220

Ala Leu Gly Glu Asn Gly Asn Gly Gly Met Val Thr Gly Cys Ala Glu
225                 230                 235                 240

Thr Pro Gly Cys Val Ala Tyr Ile Gly Ile Ser Phe Leu Asp Gln Ala
                245                 250                 255

Ser Gln Arg Gly Leu Gly Glu Ala Gln Leu Gly Asn Ser Ser Gly Asn
            260                 265                 270

Phe Leu Leu Pro Asp Ala Gln Ser Ile Gln Ala Ala Ala Ala Gly Phe
        275                 280                 285

Ala Ser Lys Thr Pro Ala Asn Gln Ala Ile Ser Met Ile Asp Gly Pro
    290                 295                 300

Ala Pro Asp Gly Tyr Pro Ile Ile Asn Tyr Glu Tyr Ala Ile Val Asn
305                 310                 315                 320

Asn Arg Gln Lys Asp Ala Ala Thr Ala Gln Thr Leu Gln Ala Phe Leu
                325                 330                 335

His Trp Ala Ile Thr Asp Gly Asn Lys Ala Ser Phe Leu Asp Gln Val
            340                 345                 350

His Phe Gln Pro Leu Pro Pro Ala Val Val Lys Leu Ser Asp Ala Leu
        355                 360                 365

Ile Ala Thr Ile Ser Ser
    370
```

<210> SEQ ID NO 149
<211> LENGTH: 1993
<212> TYPE: DNA
<213> ORGANISM: Mycobacterium tuberculosis

<400> SEQUENCE: 149

```
tgttcttcga cggcaggctg gtggaggaag ggcccaccga acagctgttc tcctcgccga      60

agcatgcgga aaccgcccga tacgtcgccg gactgtcggg ggacgtcaag gacgccaagc     120

gcggaaattg aagagcacag aaaggtatgg cgtgaaaatt cgtttgcata cgctgttggc     180

cgtgttgacc gctgcgccgc tgctgctagc agcggcgggc tgtggctcga aaccaccgag     240

cggttcgcct gaaacgggcg ccggcgccgg tactgtcgcg actacccccg cgtcgtcgcc     300

ggtgacgttg gcggagaccg gtagcacgct gctctacccg ctgttcaacc tgtggggtcc     360

ggcctttcac gagaggtatc cgaacgtcac gatcaccgct cagggcaccg gttctggtgc     420

cgggatcgcg caggccgccg ccgggacggt caacattggg gcctccgacg cctatctgtc     480

ggaaggtgat atggccgcgc acaaggggct gatgaacatc gcgctagcca tctccgctca     540
```

```
gcaggtcaac tacaacctgc ccggagtgag cgagcacctc aagctgaacg gaaaagtcct    600

ggcggccatg taccagggca ccatcaaaac ctgggacgac ccgcagatcg ctgcgctcaa    660

ccccggcgtg aacctgcccg gcaccgcggt agttccgctg caccgctccg acgggtccgg    720

tgacaccttc ttgttcaccc agtacctgtc caagcaagat cccgagggct ggggcaagtc    780

gcccggcttc ggcaccaccg tcgacttccc ggcggtgccg ggtgcgctgg gtgagaacgg    840

caacggcggc atggtgaccg gttgcgccga gacaccgggc tgcgtggcct atatcggcat    900

cagcttcctc gaccaggcca gtcaacgggg actcggcgag gcccaactag gcaatagctc    960

tggcaatttc ttgttgcccg acgcgcaaag cattcaggcc gcggcggctg gcttcgcatc   1020

gaaaaccccg gcgaaccagg cgatttcgat gatcgacggg cccgccccgg acggctaccc   1080

gatcatcaac tacgagtacg ccatcgtcaa caaccggcaa aaggacgccg ccaccgcgca   1140

gaccttgcag gcatttctgc actgggcgat caccgacggc aacaaggcct cgttcctcga   1200

ccaggttcat ttccagccgc tgccgcccgc ggtggtgaag ttgtctgacg cgttgatcgc   1260

gacgatttcc agctagcctc gttgaccacc acgcgacagc aacctccgtc gggccatcgg   1320

gctgctttgc ggagcatgct ggcccgtgcc ggtgaagtcg gccgcgctgg cccggccatc   1380

cggtggttgg gtgggatagg tgcggtgatc ccgctgcttg cgctggtctt ggtgctggtg   1440

gtgctggtca tcgaggcgat gggtgcgatc aggctcaacg ggttgcattt cttcaccgcc   1500

accgaatgga atccaggcaa cacctacggc gaaaccgttg tcaccgacgc gtcgcccatc   1560

cggtcggcgc ctactacggg gcgttgccgc tgatcgtcgg gacgctggcg acctcggcaa   1620

tcgccctgat catcgcggtg ccggtctctg taggagcggc gctggtgatc gtggaacggc   1680

tgccgaaacg gttggccgag gctgtgggaa tagtcctgga attgctcgcc ggaatcccca   1740

gcgtggtcgt cggtttgtgg ggggcaatga cgttcgggcc gttcatcgct catcacatcg   1800

ctccggtgat cgctcacaac gctcccgatg tgccggtgct gaactacttg cgcggcgacc   1860

cgggcaacgg ggagggcatg ttggtgtccg gtctggtgtt ggcggtgatg gtcgttccca   1920

ttatcgccac caccactcat gacctgttcc ggcaggtgcc ggtgttgccc cgggagggcg   1980

cgatcgggaa ttc                                                      1993
```

<210> SEQ ID NO 150
<211> LENGTH: 374
<212> TYPE: PRT
<213> ORGANISM: Mycobacterium tuberculosis

<400> SEQUENCE: 150

```
Met Lys Ile Arg Leu His Thr Leu Leu Ala Val Leu Thr Ala Ala Pro
  1               5                  10                  15

Leu Leu Leu Ala Ala Ala Gly Cys Gly Ser Lys Pro Pro Ser Gly Ser
             20                  25                  30

Pro Glu Thr Gly Ala Gly Ala Gly Thr Val Ala Thr Thr Pro Ala Ser
         35                  40                  45

Ser Pro Val Thr Leu Ala Glu Thr Gly Ser Thr Leu Leu Tyr Pro Leu
     50                  55                  60

Phe Asn Leu Trp Gly Pro Ala Phe His Glu Arg Tyr Pro Asn Val Thr
 65                  70                  75                  80

Ile Thr Ala Gln Gly Thr Gly Ser Gly Ala Gly Ile Ala Gln Ala Ala
                 85                  90                  95

Ala Gly Thr Val Asn Ile Gly Ala Ser Asp Ala Tyr Leu Ser Glu Gly
            100                 105                 110
```

-continued

Asp Met Ala Ala His Lys Gly Leu Met Asn Ile Ala Leu Ala Ile Ser
115 120 125

Ala Gln Gln Val Asn Tyr Asn Leu Pro Gly Val Ser Glu His Leu Lys
130 135 140

Leu Asn Gly Lys Val Leu Ala Ala Met Tyr Gln Gly Thr Ile Lys Thr
145 150 155 160

Trp Asp Asp Pro Gln Ile Ala Ala Leu Asn Pro Gly Val Asn Leu Pro
165 170 175

Gly Thr Ala Val Val Pro Leu His Arg Ser Asp Gly Ser Gly Asp Thr
180 185 190

Phe Leu Phe Thr Gln Tyr Leu Ser Lys Gln Asp Pro Glu Gly Trp Gly
195 200 205

Lys Ser Pro Gly Phe Gly Thr Thr Val Asp Phe Pro Ala Val Pro Gly
210 215 220

Ala Leu Gly Glu Asn Gly Asn Gly Gly Met Val Thr Gly Cys Ala Glu
225 230 235 240

Thr Pro Gly Cys Val Ala Tyr Ile Gly Ile Ser Phe Leu Asp Gln Ala
245 250 255

Ser Gln Arg Gly Leu Gly Glu Ala Gln Leu Gly Asn Ser Ser Gly Asn
260 265 270

Phe Leu Leu Pro Asp Ala Gln Ser Ile Gln Ala Ala Ala Ala Gly Phe
275 280 285

Ala Ser Lys Thr Pro Ala Asn Gln Ala Ile Ser Met Ile Asp Gly Pro
290 295 300

Ala Pro Asp Gly Tyr Pro Ile Ile Asn Tyr Glu Tyr Ala Ile Val Asn
305 310 315 320

Asn Arg Gln Lys Asp Ala Ala Thr Ala Gln Thr Leu Gln Ala Phe Leu
325 330 335

His Trp Ala Ile Thr Asp Gly Asn Lys Ala Ser Phe Leu Asp Gln Val
340 345 350

His Phe Gln Pro Leu Pro Pro Ala Val Val Lys Leu Ser Asp Ala Leu
355 360 365

Ile Ala Thr Ile Ser Ser
370

<210> SEQ ID NO 151
<211> LENGTH: 1777
<212> TYPE: DNA
<213> ORGANISM: Mycobacterium tuberculosis

<400> SEQUENCE: 151
ggtcttgacc accacctggg tgtcgaagtc ggtgcccgga ttgaagtcca ggtactcgtg 60
ggtggggcgg gcgaaacaat agcgacaagc atgcgagcag ccgcggtagc cgttgacggt 120
gtagcgaaac ggcaacgcgg ccgcgttggg caccttgttc agcgctgatt tgcacaacac 180
ctcgtggaag gtgatgccgt cgaattgtgg cgcgcgaacg ctgcggacca ggccgatccg 240
ctgcaacccg gcagcgcccg tcgtcaacgg gcatcccgtt caccgcgacg gcttgccggg 300
cccaacgcat accattattc gaacaaccgt tctatacttt gtcaacgctg gccgctaccg 360
agcgccgcac aggatgtgat atgccatctc tgcccgcaca gacaggagcc aggccttatg 420
acagcattcg gcgtcgagcc ctacgggcag ccgaagtacc tagaaatcgc cgggaagcgc 480
atggcgtata tcgacgaagg caagggtgac gccatcgtct ttcagcacgg caaccccacg 540
tcgtcttact tgtggcgcaa catcatgccg cacttggaag ggctgggccg gctggtggcc 600
tgcgatctga tcgggatggg cgcgtcggac aagctcagcc catcgggacc cgaccgctat 660
agctatggcg agcaacgaga ctttttgttc gcgctctggg atgcgctcga cctcggcgac 720
cacgtggtac tggtgctgca cgactggggc tcggcgctcg gcttcgactg ggctaaccag 780
catcgcgacc gagtgcaggg gatcgcgttc atggaagcga tcgtcacccc gatgacgtgg 840
gcggactggc cgccggccgt gcggggtgtg ttccagggtt tccgatcgcc tcaaggcgag 900
ccaatggcgt tggagcacaa catctttgtc gaacgggtgc tgcccggggc gatcctgcga 960
cagctcagcg acgaggaaat gaaccactat cggcggccat tcgtgaacgg cggcgaggac 1020
cgtcgcccca cgttgtcgtg gccacgaaac cttccaatcg acggtgagcc cgccgaggtc 1080
gtcgcgttgg tcaacgagta ccggagctgg ctcgaggaaa ccgacatgcc gaaactgttc 1140
atcaacgccg agcccggcgc gatcatcacc ggccgcatcc gtgactatgt caggagctgg 1200
cccaaccaga ccgaaatcac agtgcccggc gtgcatttcg ttcaggagga cagcgatggc 1260
gtcgtatcgt gggcgggcgc tcggcagcat cggcgacctg ggagcgctct catttcacga 1320
gaccaagaat gtgatttccg gcgaaggcgg cgccctgctt gtcaactcat aagacttcct 1380
gctccgggca gagattctca gggaaaaggg caccaatcgc agccgcttcc ttcgcaacga 1440
ggtcgacaaa tatacgtggc aggacaaagg tcttcctatt tgcccagcga attagtcgct 1500
gcctttctat gggctcagtt cgaggaagcc gagcggatca cgcgtatccg attggaccta 1560
tggaaccggt atcatgaaag cttcgaatca ttggaacagc gggggctcct gcgccgtccg 1620
atcatcccac agggctgctc tcacaacgcc cacatgtact acgtgttact agcgcccagc 1680
gccgatcggg aggaggtgct ggcgcgtctg acgagcgaag gtataggcgc ggtctttcat 1740
tacgtgccgc ttcacgattc gccggccggg cgtcgct 1777

<210> SEQ ID NO 152
<211> LENGTH: 324
<212> TYPE: DNA
<213> ORGANISM: Mycobacterium tuberculosis

<400> SEQUENCE: 152
gagattgaat cgtaccggtc tccttagcgg ctccgtcccg tgaatgccca tatcacgcac 60
ggccatgttc tggctgtcga ccttcgcccc atgcccggac gttggtaaac ccagggtttg 120
atcagtaatt ccgggggacg gttgcgggaa ggcggccagg atgtgcgtga gccgcggcgc 180
cgccgtcgcc caggcgaccg ctggatgctc agccccggtg cggcgacgta gccagcgttt 240
ggcgcgtgtc gtccacagtg gtactccggt gacgacgcgg cgcggtgcct gggtgaagac 300
cgtgaccgac gccgccgatt caga 324

<210> SEQ ID NO 153
<211> LENGTH: 1338
<212> TYPE: DNA
<213> ORGANISM: Mycobacterium tuberculosis

<400> SEQUENCE: 153
gcggtaccgc cgcgttgcgc tggcacggga cctgtacgac ctgaaccact tcgcctcgcg 60
aacgattgac gaaccgctcg tgcggcggct gtgggtgctc aaggtgtggg gtgatgtcgt 120
cgatgaccgg cgcggcaccc ggccactacg cgtcgaagac gtcctcgccg cccgcagcga 180
gcacgacttc cagcccgact cgatcggcgt gctgacccgt cctgtcgcta tggctgcctg 240
ggaagctcgc gttcggaagc gatttgcgtt cctcactgac ctcgacgccg acgagcagcg 300
gtgggccgcc tgcgacgaac ggcaccgccg cgaagtggag aacgcgctgg cggtgctgcg 360
gtcctgatca acctgccggc gatcgtgccg ttccgctggc acggttgcgg ctggacgcgg 420

-continued

```
ctgaatcgac tagatgagag cagttgggca cgaatccggc tgtggtggtg agcaagacac    480

gagtactgtc atcactattg gatgcactgg atgaccggcc tgattcagca ggaccaatgg    540

aactgcccgg ggcaaaacgt ctcggagatg atcggcgtcc cctcggaacc ctgcggtgct    600

ggcgtcattc ggacatcggt ccggctcgcg ggatcgtggt gacgccagcg ctgaaggagt    660

ggagcgcggc ggtgcacgcg ctgctggacg gccggcagac ggtgctgctg cgtaagggcg    720

ggatcggcga gaagcgcttc gaggtggcgg cccacgagtt cttgttgttc ccgacggtcg    780

cgcacagcca cgccgagcgg gttcgccccg agcaccgcga cctgctgggc ccggcggccg    840

ccgacagcac cgacgagtgt gtgctactgc gggccgcagc gaaagttgtt gccgcactgc    900

cggttaaccg gccagagggt ctggacgcca tcgaggatct gcacatctgg accgccgagt    960

cggtgcgcgc cgaccggctc gactttcggc ccaagcacaa actggccgtc ttggtggtct   1020

cggcgatccc gctggccgag ccggtccggc tggcgcgtag gcccgagtac ggcggttgca   1080

ccagctgggt gcagctgccg gtgacgccga cgttggcggc gccggtgcac gacgaggccg   1140

cgctggccga ggtcgccgcc cgggtccgcg aggccgtggg ttgactgggc ggcatcgctt   1200

gggtctgagc tgtacgccca gtcggcgctg cgagtgatct gctgtcggtt cggtccctgc   1260

tggcgtcaat tgacggcgcg ggcaacagca gcattggcgg cgccatcctc cgcgcggccg   1320

gcgcccaccg ctacaacc                                                 1338
```

<210> SEQ ID NO 154
<211> LENGTH: 321
<212> TYPE: DNA
<213> ORGANISM: Mycobacterium tuberculosis

<400> SEQUENCE: 154

```
ccggcggcac cggcggcacc ggcggtaccg gcggcaacgg cgctgacgcc gctgctgtgg     60

tgggcttcgg cgcgaacggc gaccctggct tcgctggcgg caaaggcggt aacggcggaa    120

taggtggggc cgcggtgaca ggcggggtcg ccggcgacgg cggcaccggc ggcaaaggtg    180

gcaccggcgg tgccggcggc gccggcaacg acgccggcag caccggcaat cccggcggta    240

agggcggcga cggcgggatc ggcggtgccg gcggggccgg cggcgcggcc ggcaccggca    300

acggcggcca tgccggcaac c                                              321
```

<210> SEQ ID NO 155
<211> LENGTH: 492
<212> TYPE: DNA
<213> ORGANISM: Mycobacterium tuberculosis

<400> SEQUENCE: 155

```
gaagacccgg ccccgccata tcgatcggct cgccgactac tttcgccgaa cgtgcacgcg     60

gcggcgtcgg gctgatcatc accggtggct acgcgcccaa ccgcaccgga tggctgctgc    120

cgttcgcctc cgaactcgtc acttcggcgc aagcccgacg gcaccgccga atcaccaggg    180

cggtccacga ttcgggtgca aagatcctgc tgcaaatcct gcacgccgga cgctacgcct    240

accacccact tgcggtcagc gcctcgccga tcaaggcgcc gatcaccccg tttcgtccgc    300

gagcactatc ggctcgcggg gtcgaagcga ccatcgcgga tttcgcccgc tgcgcgcagt    360

tggcccgcga tgccggctac gacggcgtcg aaatcatggg cagcgaaggg tatctgctca    420

atcagttcct ggcgccgcgc accaacaagc gcaccgactc gtggggcggc acaccggcca    480

accgtcgccg gt                                                        492
```

<210> SEQ ID NO 156
<211> LENGTH: 536
<212> TYPE: PRT
<213> ORGANISM: Mycobacterium tuberculosis

<400> SEQUENCE: 156

```
Phe Ala Gln His Leu Val Glu Gly Asp Ala Val Glu Leu Trp Arg Ala
  1               5                  10                  15

Asn Ala Ala Asp Gln Ala Asp Pro Leu Gln Pro Gly Ser Ala Arg Arg
             20                  25                  30

Gln Arg Ala Ser Arg Ser Pro Arg Arg Leu Ala Gly Pro Asn Ala Tyr
         35                  40                  45

His Tyr Ser Asn Asn Arg Ser Ile Leu Cys Gln Arg Trp Pro Leu Pro
     50                  55                  60

Ser Ala Ala Gln Asp Val Ile Cys His Leu Cys Pro His Arg Gln Glu
 65                  70                  75                  80

Pro Gly Leu Met Thr Ala Phe Gly Val Glu Pro Tyr Gly Gln Pro Lys
                 85                  90                  95

Tyr Leu Glu Ile Ala Gly Lys Arg Met Ala Tyr Ile Asp Glu Gly Lys
            100                 105                 110

Gly Asp Ala Ile Val Phe Gln His Gly Asn Pro Thr Ser Ser Tyr Leu
        115                 120                 125

Trp Arg Asn Ile Met Pro His Leu Glu Gly Leu Gly Arg Leu Val Ala
    130                 135                 140

Cys Asp Leu Ile Gly Met Gly Ala Ser Asp Lys Leu Ser Pro Ser Gly
145                 150                 155                 160

Pro Asp Arg Tyr Ser Tyr Gly Glu Gln Arg Asp Phe Leu Phe Ala Leu
                165                 170                 175

Trp Asp Ala Leu Asp Leu Gly Asp His Val Val Leu Val Leu His Asp
            180                 185                 190

Trp Gly Ser Ala Leu Gly Phe Asp Trp Ala Asn Gln His Arg Asp Arg
        195                 200                 205

Val Gln Gly Ile Ala Phe Met Glu Ala Ile Val Thr Pro Met Thr Trp
    210                 215                 220

Ala Asp Trp Pro Pro Ala Val Arg Gly Val Phe Gln Gly Phe Arg Ser
225                 230                 235                 240

Pro Gln Gly Glu Pro Met Ala Leu Glu His Asn Ile Phe Val Glu Arg
                245                 250                 255

Val Leu Pro Gly Ala Ile Leu Arg Gln Leu Ser Asp Glu Glu Met Asn
            260                 265                 270

His Tyr Arg Arg Pro Phe Val Asn Gly Gly Glu Asp Arg Arg Pro Thr
        275                 280                 285

Leu Ser Trp Pro Arg Asn Leu Pro Ile Asp Gly Glu Pro Ala Glu Val
    290                 295                 300

Val Ala Leu Val Asn Glu Tyr Arg Ser Trp Leu Glu Glu Thr Asp Met
305                 310                 315                 320

Pro Lys Leu Phe Ile Asn Ala Glu Pro Gly Ala Ile Ile Thr Gly Arg
                325                 330                 335

Ile Arg Asp Tyr Val Arg Ser Trp Pro Asn Gln Thr Glu Ile Thr Val
            340                 345                 350

Pro Gly Val His Phe Val Gln Glu Asp Ser Asp Gly Val Val Ser Trp
        355                 360                 365

Ala Gly Ala Arg Gln His Arg Arg Pro Gly Ser Ala Leu Ile Ser Arg
    370                 375                 380

Asp Gln Glu Cys Asp Phe Arg Arg Arg Arg Arg Pro Ala Cys Gln Leu
```

```
385                 390                 395                 400

Ile Arg Leu Pro Ala Pro Gly Arg Asp Ser Gln Gly Lys Gly His Gln
                405                 410                 415

Ser Gln Pro Leu Pro Ser Gln Arg Gly Arg Gln Ile Tyr Val Ala Gly
            420                 425                 430

Gln Arg Ser Ser Tyr Leu Pro Ser Glu Leu Val Ala Ala Phe Leu Trp
        435                 440                 445

Ala Gln Phe Glu Glu Ala Glu Arg Ile Thr Arg Ile Arg Leu Asp Leu
    450                 455                 460

Trp Asn Arg Tyr His Glu Ser Phe Glu Ser Leu Glu Gln Arg Gly Leu
465                 470                 475                 480

Leu Arg Arg Pro Ile Ile Pro Gln Gly Cys Ser His Asn Ala His Met
                485                 490                 495

Tyr Tyr Val Leu Leu Ala Pro Ser Ala Asp Arg Glu Glu Val Leu Ala
            500                 505                 510

Arg Leu Thr Ser Glu Gly Ile Gly Ala Val Phe His Tyr Val Pro Leu
        515                 520                 525

His Asp Ser Pro Ala Gly Arg Arg
    530                 535


<210> SEQ ID NO 157
<211> LENGTH: 284
<212> TYPE: PRT
<213> ORGANISM: Mycobacterium tuberculosis

<400> SEQUENCE: 157

Asn Glu Ser Ala Pro Arg Ser Pro Met Leu Pro Ser Ala Arg Pro Arg
  1               5                  10                  15

Tyr Asp Ala Ile Ala Val Leu Leu Asn Glu Met His Ala Gly His Cys
             20                  25                  30

Asp Phe Gly Leu Val Gly Pro Ala Pro Asp Ile Val Thr Asp Ala Ala
         35                  40                  45

Gly Asp Asp Arg Ala Gly Leu Gly Val Asp Glu Gln Phe Arg His Val
     50                  55                  60

Gly Phe Leu Glu Pro Ala Pro Val Leu Val Asp Gln Arg Asp Asp Leu
 65                  70                  75                  80

Gly Gly Leu Thr Val Asp Trp Lys Val Ser Trp Pro Arg Gln Arg Gly
                 85                  90                  95

Ala Thr Val Leu Ala Ala Val His Glu Trp Pro Pro Ile Val Val His
            100                 105                 110

Phe Leu Val Ala Glu Leu Ser Gln Asp Arg Pro Gly Gln His Pro Phe
        115                 120                 125

Asp Lys Asp Val Val Leu Gln Arg His Trp Leu Ala Leu Arg Arg Ser
    130                 135                 140

Glu Thr Leu Glu His Thr Pro His Gly Arg Arg Pro Val Arg Pro Arg
145                 150                 155                 160

His Arg Gly Asp Asp Arg Phe His Glu Arg Asp Pro Leu His Ser Val
                165                 170                 175

Ala Met Leu Val Ser Pro Val Glu Ala Glu Arg Arg Ala Pro Val Val
            180                 185                 190

Gln His Gln Tyr His Val Val Ala Glu Val Glu Arg Ile Pro Glu Arg
        195                 200                 205

Glu Gln Lys Val Ser Leu Leu Ala Ile Ala Ile Ala Val Gly Ser Arg
    210                 215                 220

Trp Ala Glu Leu Val Arg Arg Ala His Pro Asp Gln Ile Ala Gly His
```

-continued 225 230 235 240

Gln Pro Ala Gln Pro Phe Gln Val Arg His Asp Val Ala Pro Gln Val
245 250 255

Arg Arg Arg Gly Val Ala Val Leu Lys Asp Asp Gly Val Thr Leu Ala
260 265 270

Phe Val Asp Ile Arg His Ala Leu Pro Gly Asp Phe
275 280

<210> SEQ ID NO 158
<211> LENGTH: 264
<212> TYPE: DNA
<213> ORGANISM: Mycobacterium tuberculosis

<400> SEQUENCE: 158
atgaacatgt cgtcggtggt gggtcgcaag gcctttgcgc gattcgccgg ctactcctcc 60
gccatgcacg cgatcgccgg tttctccgat gcgttgcgcc aagagctgcg gggtagcgga 120
atcgccgtct cggtgatcca cccggcgctg acccagacac cgctgttggc caacgtcgac 180
cccgccgaca tgccgccgcc gtttcgcagc ctcacgccca ttcccgttca ctgggtcgcg 240
gcagcggtgc ttgacggtgt ggcg 264

<210> SEQ ID NO 159
<211> LENGTH: 1171
<212> TYPE: DNA
<213> ORGANISM: Mycobacterium tuberculosis

<400> SEQUENCE: 159
tagtcggcga cgatgacgtc gcggtccagg ccgaccgctt caagcaccag cgcgaccacg 60
aagccggtgc gatccttacc cgcgaagcag tgggtgagca ccgggcgtcc ggcggcaagc 120
agtgtgacga cacgatgtag cgcgcgctgt gctccattgc gcgttgggaa ttggcgatac 180
tcgtcggtca tgtagcgggt ggccgcgtca tttatcgact ggctggattc gccggactcg 240
ccgttggacc cgtcattggt tagcagcctc ttgaatgcgg tttcgtgcgg cgctgagtcg 300
tcggcgtcat catcggcgag gtcggggaac ggcagcaggt ggacgtcgat gccgtccgga 360
acccgtcctg gaccgcggcg ggcaacctcc cgggacgacc gcaggtcggc aacgtcggtg 420
atccccagcc ggcgcagcgt tgcccctcgt gccgaattcg gcacgaggct ggcgagccac 480
cgggcatcac caagcaacgc ttgcccagta cggatcgtca cttccgcatc cggcagacca 540
atctcctcgc cgcccatcgt cagatcccgc tcgtgcgttg acaagaacgg ccgcagatgt 600
gccagcgggt atcggagatt gaaccgcgca cgcagttctt caatcgctgc gcgctgccgc 660
actattggca ctttccggcg gtcgcggtat tcagcaagca tgcgagtctc gacgaactcg 720
ccccacgtaa cccacggcgt agctcccggc gtgacgcgga ggatcggcgg gtgatctttg 780
ccgccacgct cgtagccgtt gatccaccgc ttcgcggtgc cggcggggag gccgatcagc 840
ttatcgacct cggcgtatgc cgacggcaag ctgggcgcgt tcgtcgaggt caagaactcc 900
accatcggca ccggcaccaa ggtgccgcac ctgacctacg tcggcgacgc cgacatcggc 960
gagtacagca acatcggcgc ctccagcgtg ttcgtcaact acgacggtac gtccaaacgg 1020
cgcaccaccg tcggttcgca cgtacggacc gggtccgaca ccatgttcgt ggccccagta 1080
accatcggcg acggcgcgta taccggggcc ggcacagtgg tgcgggagga tgtcccgccg 1140
ggggcgctgg cagtgtcggc gggtccgcaa c 1171

<210> SEQ ID NO 160
<211> LENGTH: 227

<212> TYPE: DNA
<213> ORGANISM: Mycobacterium tuberculosis

<400> SEQUENCE: 160
gcaaaggcgg caccggcggg gccggcatga acagcctcga cccgctgcta gccgcccaag 60
acggcggcca aggcggcacc ggcggcaccg gcggcaacgc cggcgccggc ggcaccagct 120
tcacccaagg cgccgacggc aacgccggca acggcggtga cggcggggtc ggcggcaacg 180
gcggaaacgg cggaaacggc gcagacaaca ccaccaccgc cgccgcc 227

<210> SEQ ID NO 161
<211> LENGTH: 304
<212> TYPE: DNA
<213> ORGANISM: Mycobacterium tuberculosis

<400> SEQUENCE: 161
cctcgccacc atgggcgggc agggcggtag cggtggcgcc ggctctaccc caggcgccaa 60
gggcgcccac ggcttcactc caaccagcgg cggcgacggc ggcgacggcg gcaacggcgg 120
caactcccaa gtggtcggcg gcaacggcgg cgacggcggc aatggcggca acggcggcag 180
cgccggcacg ggcggcaacg gcggccgcgg cggcgacggc gcgtttggtg gcatgagtgc 240
caacgccacc aaccctggtg aaaacgggcc aaacggtaac cccggcggca acggtggcgc 300
cggc 304

<210> SEQ ID NO 162
<211> LENGTH: 1439
<212> TYPE: DNA
<213> ORGANISM: Mycobacterium tuberculosis

<400> SEQUENCE: 162
gtgggacgct gccgaggctg tataacaagg acaacatcga ccagcgccgg ctcggtgagc 60
tgatcgacct atttaacagt gcgcgcttca gccggcaggg cgagcaccgc gcccgggatc 120
tgatgggtga ggtctacgaa tacttcctcg gcaatttcgc tcgcgcggaa gggaagcggg 180
gtggcgagtt ctttaccccg cccagcgtgg tcaaggtgat cgtggaggtg ctggagccgt 240
cgagtgggcg ggtgtatgac ccgtgctgcg gttccggagg catgtttgtg cagaccgaga 300
agttcatcta cgaacacgac ggcgatccga aggatgtctc gatctatggc caggaaagca 360
ttgaggagac ctggcggatg gcgaagatga acctcgccat ccacggcatc gacaacaagg 420
ggctcggcgc ccgatggagt gataccttcg cccgcgacca gcacccggac gtgcagatgg 480
actacgtgat ggccaatccg ccgttcaaca tcaaagactg ggcccgcaac gaggaagacc 540
cacgctggcg cttcggtgtt ccgcccgcca ataacgccaa ctacgcatgg attcagcaca 600
tcctgtacaa cttggcgccg ggaggtcggg cgggcgtggt gatggccaac gggtcgatgt 660
cgtcgaactc caacggcaag gggatattc gcgcgcaaat cgtggaggcg gatttggttt 720
cctgcatggt cgcgttaccc acccagctgt tccgcagcac cggaatcccg gtgtgcctgt 780
ggtttttcgc caaaaacaag gcggcaggta agcaagggtc tatcaaccgg tgcgggcagg 840
tgctgttcat cgacgctcgt gaactgggcg acctagtgga ccgggccgag cgggcgctga 900
ccaacgagga gatcgtccgc atcggggata ccttccacgc gagcacgacc accggcaacg 960
ccggctccgg tggtgccggc ggtaatgggg gcactggcct caacggcgcg ggcggtgctg 1020
gcggggccgg cggcaacgcg ggtgtcgccg gcgtgtcctt cggcaacgct gtgggcggcg 1080
acggcggcaa cggcggcaac ggcggccacg gcggcgacgg cacgacgggc ggcgccggcg 1140
gcaagggcgg caacggcagc agcggtgccg ccagcggctc aggcgtcgtc aacgtcaccg 1200

-continued ccggccacgg cggcaacggc ggcaatggcg gcaacggcgg caacggctcc gcgggcgccg 1260
gcggccaggg cggtgccggc ggcagcgccg gcaacggcgg ccacggcggc ggtgccaccg 1320
gcggcgccag cggcaagggc ggcaacggca ccagcggtgc cgccagcggc tcaggcgtca 1380
tcaacgtcac cgccggccac ggcggcaacg gcggcaatgg ccgcaacggc ggcaacggc 1439

<210> SEQ ID NO 163
<211> LENGTH: 329
<212> TYPE: DNA
<213> ORGANISM: Mycobacterium tuberculosis

<400> SEQUENCE: 163
gggccggcgg ggccggattt tctcgtgcct tgattgtcgc tggggataac ggcggtgatg 60
gtggtaacgg cgggatgggc ggggctggcg gggctggcgg ccccggcggg gccggcggcc 120
tgatcagcct gctgggcggc caaggcgccg gcggggccgg cgggaccggc ggggccggcg 180
gtgttggcgg tgacggcggg gccggcggcc ccggcaacca ggccttcaac gcaggtgccg 240
gcggggccgg cggcctgatc agcctgctgg gcggccaagg cgccggcggg gccggcggga 300
ccggcggggc cggcggtgtt ggcggtgac 329

<210> SEQ ID NO 164
<211> LENGTH: 80
<212> TYPE: DNA
<213> ORGANISM: Mycobacterium tuberculosis

<400> SEQUENCE: 164
gcaacggtgg caacggcggc accagcacga ccgtggggat ggccggaggt aactgtggtg 60
ccgccgggct gatcggcaac 80

<210> SEQ ID NO 165
<211> LENGTH: 392
<212> TYPE: DNA
<213> ORGANISM: Mycobacterium tuberculosis

<400> SEQUENCE: 165
gggctgtgtc gcactcacac cgccgcattc ggcgacgttg gccgcccaat atccagctca 60
aggcctacta cttaccgtcg gaggaccgcc gcatcaaggt gcgggtcagc gcccaaggaa 120
tcaaggtcat cgaccgcgac gggcatcgag gccgtcgtcg cgcggctcgg gcaggatccg 180
ccccggcgca cttcgcgcgc caagcgggct catcgctccg aacggcggcg atcctgtgag 240
cacaactgat ggcgcgcaac gagattcgtc caattgtcaa gccgtgttcg accgcaggga 300
ccggttatac gtatgtcaac ctatgtcact cgcaagaacc ggcataacga tcccgtgatc 360
cgccgacagc ccacgagtgc aagaccgtta ca 392

<210> SEQ ID NO 166
<211> LENGTH: 535
<212> TYPE: DNA
<213> ORGANISM: Mycobacterium tuberculosis

<400> SEQUENCE: 166
accggcgcca ccggcggcac cgggttcgcc ggtggcgccg gcggggccgg cgggcagggc 60
ggtatcagcg gtgccggcgg caccaacggc tctggtggcg ctggcggcac cggcggacaa 120
ggcggcgccg gggcgctgg cggggccggc gccgataacc ccaccggcat cggcggcgcc 180
ggcggcaccg gcggcaccgg cggagcggcc ggagccggcg gggccggtgg cgccatcggt 240
accggcggca ccggcggcgc ggtgggcagc gtcggtaacg ccgggatcgg cggtaccggc 300
ggtacgggtg gtgtcggtgg tgctggtggt gcaggtgcgg ctgcggccgc tggcagcagc 360
gctaccggtg gcgccgggtt cgccggcggc gccggcggag aaggcggacc gggcggcaac 420
agcggtgtgg gcggcaccaa cggctccggc ggcgccggcg gtgcaggcgg caagggcggc 480
accggaggtg ccggcgggtc cggcgcggac aaccccaccg gtgctggttt cgccg 535

<210> SEQ ID NO 167
<211> LENGTH: 690
<212> TYPE: DNA
<213> ORGANISM: Mycobacterium tuberculosis

<400> SEQUENCE: 167
ccgacgtcgc cggggcgata cgggggtcac cgactactac atcatccgca ccgagaatcg 60
gccgctgctg caaccgctgc gggcggtgcc ggtcatcgga gatccgctgg ccgacctgat 120
ccagccgaac ctgaaggtga tcgtcaacct gggctacggc gacccgaact acggctactc 180
gacgagctac gccgatgtgc gaacgccgtt cgggctgtgg ccgaacgtgc cgcctcaggt 240
catcgccgat gccctggccg ccggaacaca agaaggcatc cttgacttca cggccgacct 300
gcaggcgctg tccgcgcaac cgctcacgct cccgcagatc cagctgccgc aacccgccga 360
tctggtggcc gcggtggccg ccgcaccgac gccggccgag gtggtgaaca cgctcgccag 420
gatcatctca accaactacg ccgtcctgct gcccaccgtg gacatcgccc tcgcctggtc 480
accaccctgc cgctgtacac cacccaactg ttcgtcaggc aactcgctgc gggcaatctg 540
atcaacgcga tcggctatcc cctggcggcc accgtaggtt taggcacgat cgatagcggg 600
cggcgtggaa ttgctcaccc tcctcgcggc ggcctcggac accgttcgaa acatcgaggg 660
cctcgtcacc taacggattc ccgacggcat 690

<210> SEQ ID NO 168
<211> LENGTH: 407
<212> TYPE: DNA
<213> ORGANISM: Mycobacterium tuberculosis

<400> SEQUENCE: 168
acggtgacgg cggtactggc ggcggccacg gcggcaacgg cgggaatccc gggtggctct 60
tgggcacagc cgggggtggc ggcaacggtg gcgccggcag caccggtact gcaggtggcg 120
gctctggggg caccggcggc gacggcggga ccggcgggcg tggcggcctg ttaatgggcg 180
ccggcgccgg cgggcacggt ggcactggcg gcgcgggcgg tgccggtgtc gacggtggcg 240
gcgccggcgg ggccggcggg gccggcggca acggcggcgc cgggggtcaa gccgccctgc 300
tgttcgggcg cggcggcacc ggcggagccg gcggctacgg cggcgatggc ggtggcggcg 360
gtgacggctt cgacggcacg atggccggcc tgggtggtac cggtggc 407

<210> SEQ ID NO 169
<211> LENGTH: 468
<212> TYPE: DNA
<213> ORGANISM: Mycobacterium tuberculosis

<400> SEQUENCE: 169
gatcggtcag cgcatcgccc tcggcggcaa gcgattccgc ggtctcaccg aagaacatcg 60
tgcacgcggc ggcgcggacc agcccgctgc gctgcggcgc gtcgaacgcc tccagcaggc 120
acagccagtc cttggcggcc tgcgaggcga acacgtcggt gtcaccggtg tagatcgccg 180
ggatgcccgc ctccgccaac gcattccggc acgcccgcgc gtctttgtga tgctcgacga 240
tcaccgcgat gtctgcggcc accacgggcc gcccggcgaa ggtggccccg ctggccagta 300
gcgccgcgac gtcggcggcc aggtcgtcgg ggatgtgccg gcgcagcgct ccggcgcgac 360
gcccgaaaaa cgacccctca cccagctggg tcccgctggc atatcccttg ccgtcctggg 420
cgatattgga cgcgcatgcc ccgaccgcgt acaggccggc caccaccg 468

<210> SEQ ID NO 170
<211> LENGTH: 219
<212> TYPE: DNA
<213> ORGANISM: Mycobacterium tuberculosis

<400> SEQUENCE: 170
ggtggtaacg gcggccaggg tggcatcggc ggcgccggcg agagaggcgc cgacggcgcc 60
ggccccaatg ctaacggcgc aaacggcgag aacggcggta gcggtggtaa cggtggcgac 120
ggcggcgccg gcggcaatgg cggcgcgggc ggcaacgcgc aggcggccgg gtacaccgac 180
ggcgccacgg gcaccggcgg cgacggcggc aacggcggc 219

<210> SEQ ID NO 171
<211> LENGTH: 494
<212> TYPE: DNA
<213> ORGANISM: Mycobacterium tuberculosis

<400> SEQUENCE: 171
tagctccggc gagggcggca agggcggcga cggtggccac ggcggtgacg gcgtcggcgg 60
caacagttcc gtcacccaag gcggcagcgg cggtggcggc ggcgccggcg gcgccggcgg 120
cagcggcttt ttcggcggca agggcggctt cggcggcgac ggcggtcagg gcggccccaa 180
cggcggcggt accgtcggca ccgtggccgg tggcggcggc aacggcggtg tcggcggccg 240
gggcggcgac ggcgtctttg ccggtgccgg cggccagggc ggcctcggtg ggcagggcgg 300
caatggcggc ggctccaccg gcggcaacgg cggccttggc ggcgcgggcg gtggcggagg 360
caacgccccg gctcgtgccg aatccgggct gaccatggac agcgcggcca agttcgctgc 420
catcgcatca ggcgcgtact gccccgaaca cctggaacat cacccgagtt agcggggcgc 480
atttcctgat cacc 494

<210> SEQ ID NO 172
<211> LENGTH: 220
<212> TYPE: DNA
<213> ORGANISM: Mycobacterium tuberculosis

<400> SEQUENCE: 172
gggccggtgg tgccgcgggc cagctcttca gcgccggagg cgcggcgggt gccgttgggg 60
ttggcggcac cggcggccag ggtggggctg gcggtgccgg agcggccggc gccgacgccc 120
ccgccagcac aggtctaacc ggtggtaccg ggttcgctgg cggggccggc ggcgtcggcg 180
gccagagcgg caacgccatt gccggcggca tcaacggctc 220

<210> SEQ ID NO 173
<211> LENGTH: 388
<212> TYPE: DNA
<213> ORGANISM: Mycobacterium tuberculosis

<400> SEQUENCE: 173
atggcggcaa cgggggcccc ggcggtgctg gcggggccgg cgactacaat ttccaacggc 60
gggcagggtg gtgccggcgg ccaaggcggc caaggcggcc tgggcggggc aagcaccacc 120
tgatcggcct agccgcaccc gggaaagccg atccaacagg cgacgatgcc gccttccttg 180
ccgcgttgga ccaggccggc atcacctacg ctgacccagg ccacgccata acggccgcca 240
aggcgatgtg tgggctgtgt gctaacggcg taacaggtct acagctggtc gcggacctgc 300
gggactacaa tcccgggctg accatggaca gcgcggccaa gttcgctgcc atcgcatcag 360
gcgcgtactg ccccgaacac ctggaaca 388

<210> SEQ ID NO 174
<211> LENGTH: 400
<212> TYPE: DNA
<213> ORGANISM: Mycobacterium tuberculosis

<400> SEQUENCE: 174
gcaaaggcgg caccggcggg gccggcatga acagcctcga cccgctgcta gccgcccaag 60
acggcggcca aggcggcacc ggcggcaccg gcggcaacgc cggcgccggc ggcaccagct 120
tcacccaagg cgccgacggc aacgccggca acggcggtga cggcggggtc ggcggcaacg 180
gcggaaacgg cggaaacggc gcagacaaca ccaccaccgc cgccgccggc accacaggcg 240
gcgacggcgg ggccggcggg gccggcggaa ccggcggaac cggcggagcc gccggcaccg 300
gcaccggcgg ccaacaaggc aacggcggca acggcggcac cggcggcaaa ggcggcaccg 360
gcggcgacgg tgcactctca ggcagcaccg gtggtgccgg 400

<210> SEQ ID NO 175
<211> LENGTH: 538
<212> TYPE: DNA
<213> ORGANISM: Mycobacterium tuberculosis

<400> SEQUENCE: 175
ggcaacggcg gcaacggcgg catcgccggc attgggcggc aacggcgttc cgggacgggc 60
agcggcaacg gcggccaacg gcggcagcgg cggcaacggc ggcaacgccg gcatgggcgg 120
caacagcggc accggcagcg gcgacggcgg tgccggcggg aacggcggcg cggcgggcac 180
gggcggcacc ggcggcgacg gcggcctcac cggtactggc ggcaccggcg gcagcggtgg 240
caccggcggt gacggcggta acggcggcaa cggagcagat aacaccgcaa acatgactgc 300
gcaggcgggc ggtgacggtg gcaacggcgg cgacggtggc ttcggcggcg gggccggggc 360
cggcggcggt ggcttgaccg ctggcgccaa cggcaccggc gggcaaggcg gcgccggcgg 420
cgatggcggc aacggggcca tcggcggcca cggcccactc actgacgacc ccggcggcaa 480
cgggggcacc ggcggcaacg gcggcaccgg cggcaccggc ggcgcgggca tcggcagc 538

<210> SEQ ID NO 176
<211> LENGTH: 239
<212> TYPE: DNA
<213> ORGANISM: Mycobacterium tuberculosis

<400> SEQUENCE: 176
gggccggtgg tgccgcgggc cagctcttca gcgccggagg cgcggcgggt gccgttgggg 60
ttggcggcac cggcggccag ggtggggctg gcggtgccgg agcggccggc gccgacgccc 120
ccgccagcac aggtctaacc ggtggtaccg ggttcgctgg cggggccggc ggcgtcggcg 180
gccacggcgg caacgccatt gccggcggca tcaacggctc cggtggtgcc ggcggcacc 239

<210> SEQ ID NO 177
<211> LENGTH: 985
<212> TYPE: DNA
<213> ORGANISM: Mycobacterium tuberculosis

<400> SEQUENCE: 177
agcagcgcta ccggtggcgc cgggttcgcc ggcggcgccg gcggagaagg cggagcgggc 60
ggcaacagcg gtgtgggcgg caccaacggc tccggcggcg ccggcggtgc aggcggcaag 120
ggcggcaccg gaggtgccgg cgggtccggc gcggacaacc ccaccggtgc tggtttcgcc 180
ggtggcgccg gcggcacagg tggcgcggcc ggcgccggcg gggccggcgg ggcgaccggt 240
accggcggca ccggcggcgt tgtcggcgcc accggtagtg caggcatcgg cggggccggc 300
ggccgcggcg gtgacggcgg cgatggggcc agcggtctcg gcctgggcct ctccggcttt 360
gacggcggcc aaggcggcca aggcggggcc ggcggcagcg ccggcgccgg cggcatcaac 420
ggggccggcg gggccggcgg caacggcggc gacggcgggg acggcgcaac cggtgccgca 480
ggtctcggcg acaacggcgg ggtcggcggt gacggtgggg ccggtggcgc cgccggcaac 540
ggcggcaacg cgggcgtcgg cctgacagcc aaggccggcg acggcggcgc cgcgggcaat 600
ggcggcaacg gggcgccgg cggtgctggc ggggccggcg acaacaattt caacggcggc 660
cagggtggtg ccggcggcca aggcggccaa ggcggcttgg gcggggcaag caccacctga 720
tcggcctagc cgcacccggg aaagccgatc caacaggcga cgatgccgcc ttccttgccg 780
cgttggacca ggccggcatc acctacgctg acccaggcca cgccataacg gccgccaagg 840
cgatgtgtgg gctgtgtgct aacggcgtaa caggtctaca gctggtcgcg gacctgcggg 900
aatacaatcc cgggctgacc atggacagcg cggccaagtt cgctgccatc gcatcaggcg 960
cgtactgccc cgaacacctg gaaca 985

<210> SEQ ID NO 178
<211> LENGTH: 2138
<212> TYPE: DNA
<213> ORGANISM: Mycobacterium tuberculosis

<400> SEQUENCE: 178
cggcacgagg atcggtaccc cgcggcatcg gcagctgccg attcgccggg tttccccacc 60
cgaggaaagc cgctaccaga tggcgctgcc gaagtagggc gatccgttcg cgatgccggc 120
atgaacgggc ggcatcaaat tagtgcagga acctttcagt ttagcgacga taatggctat 180
agcactaagg aggatgatcc gatatgacgc agtcgcagac cgtgacggtg gatcagcaag 240
agattttgaa cagggccaac gaggtggagg ccccgatggc ggacccaccg actgatgtcc 300
ccatcacacc gtgcgaactc acggcggcta aaaacgccgc ccaacagctg gtattgtccg 360
ccgacaacat gcgggaatac ctggcggccg gtgccaaaga gcggcagcgt ctggcgacct 420
cgctgcgcaa cgcggccaag gcgtatggcg aggttgatga ggaggctgcg accgcgctgg 480
acaacgacgg cgaaggaact gtgcaggcag aatcggccgg ggccgtcgga ggggacagtt 540
cggccgaact aaccgatacg ccgagggtgg ccacggccgg tgaacccaac ttcatggatc 600
tcaaagaagc ggcaaggaag ctcgaaacgg gcgaccaagg cgcatcgctc gcgcactttg 660
cggatgggtg gaacactttc aacctgacgc tgcaaggcga cgtcaagcgg ttccgggggt 720
ttgacaactg ggaaggcgat gcggctaccg cttgcgaggc ttcgctcgat caacaacggc 780
aatggatact ccacatggcc aaattgagcg ctgcgatggc caagcaggct caatatgtcg 840
cgcagctgca cgtgtgggct aggcgggaac atccgactta tgaagacata gtcgggctcg 900
aacggcttta cgcggaaaac ccttcggccc gcgaccaaat tctcccggtg tacgcggagt 960
atcagcagag gtcggagaag gtgctgaccg aatacaacaa caaggcagcc ctggaaccgg 1020
taaacccgcc gaagcctccc cccgccatca agatcgaccc gcccccgcct ccgcaagagc 1080
agggattgat ccctggcttc ctgatgccgc cgtctgacgg ctccggtgtg actcccggta 1140
ccgggatgcc agccgcaccg atggttccgc ctaccggatc gccgggtggt ggcctcccgg 1200

```
ctgacacggc ggcgcagctg acgtcggctg ggcgggaagc cgcagcgctg tcgggcgacg   1260

tggcggtcaa agcggcatcg ctcggtggcg gtggaggcgg cggggtgccg tcggcgccgt   1320

tgggatccgc gatcgggggc gccgaatcgg tgcggcccgc tggcgctggt gacattgccg   1380

gcttaggcca gggaagggcc ggcggcggcg ccgcgctggg cggcggtggc atgggaatgc   1440

cgatgggtgc cgcgcatcag ggacaagggg gcgccaagtc caagggttct cagcaggaag   1500

acgaggcgct ctacaccgag gatcgggcat ggaccgaggc cgtcattggt aaccgtcggc   1560

gccaggacag taaggagtcg aagtgagcat ggacgaattg gacccgcatg tcgcccgggc   1620

gttgacgctg gcggcgcggt ttcagtcggc cctagacggg acgctcaatc agatgaacaa   1680

cggatccttc cgcgccaccg acgaagccga gaccgtcgaa gtgacgatca atgggcacca   1740

gtggctcacc ggcctgcgca tcgaagatgg tttgctgaag aagctgggtg ccgaggcggt   1800

ggctcagcgg gtcaacgagg cgctgcacaa tgcgcaggcc gcggcgtccg cgtataacga   1860

cgcggcgggc gagcagctga ccgctgcgtt atcggccatg tcccgcgcga tgaacgaagg   1920

aatggcctaa gcccattgtt gcggtggtag cgactacgca ccgaatgagc gccgcaatgc   1980

ggtcattcag cgcgcccgac acggcgtgag tacgcattgt caatgttttg acatggatcg   2040

gccgggttcg gagggcgcca tagtcctggt cgccaatatt gccgcagcta gctggtctta   2100

ggttcggtta cgctggttaa ttatgacgtc cgttacca                           2138
```

```
<210> SEQ ID NO 179
<211> LENGTH: 460
<212> TYPE: PRT
<213> ORGANISM: Mycobacterium tuberculosis

<400> SEQUENCE: 179

Met Thr Gln Ser Gln Thr Val Thr Val Asp Gln Gln Glu Ile Leu Asn
1               5                   10                  15

Arg Ala Asn Glu Val Glu Ala Pro Met Ala Asp Pro Pro Thr Asp Val
            20                  25                  30

Pro Ile Thr Pro Cys Glu Leu Thr Ala Ala Lys Asn Ala Ala Gln Gln
        35                  40                  45

Leu Val Leu Ser Ala Asp Asn Met Arg Glu Tyr Leu Ala Ala Gly Ala
    50                  55                  60

Lys Glu Arg Gln Arg Leu Ala Thr Ser Leu Arg Asn Ala Ala Lys Ala
65                  70                  75                  80

Tyr Gly Glu Val Asp Glu Glu Ala Ala Thr Ala Leu Asp Asn Asp Gly
                85                  90                  95

Glu Gly Thr Val Gln Ala Glu Ser Ala Gly Ala Val Gly Gly Asp Ser
            100                 105                 110

Ser Ala Glu Leu Thr Asp Thr Pro Arg Val Ala Thr Ala Gly Glu Pro
        115                 120                 125

Asn Phe Met Asp Leu Lys Glu Ala Ala Arg Lys Leu Glu Thr Gly Asp
    130                 135                 140

Gln Gly Ala Ser Leu Ala His Phe Ala Asp Gly Trp Asn Thr Phe Asn
145                 150                 155                 160

Leu Thr Leu Gln Gly Asp Val Lys Arg Phe Arg Gly Phe Asp Asn Trp
                165                 170                 175

Glu Gly Asp Ala Ala Thr Ala Cys Glu Ala Ser Leu Asp Gln Gln Arg
            180                 185                 190

Gln Trp Ile Leu His Met Ala Lys Leu Ser Ala Ala Met Ala Lys Gln
        195                 200                 205
```

Ala Gln Tyr Val Ala Gln Leu His Val Trp Ala Arg Arg Glu His Pro
210 215 220

Thr Tyr Glu Asp Ile Val Gly Leu Glu Arg Leu Tyr Ala Glu Asn Pro
225 230 235 240

Ser Ala Arg Asp Gln Ile Leu Pro Val Tyr Ala Glu Tyr Gln Gln Arg
245 250 255

Ser Glu Lys Val Leu Thr Glu Tyr Asn Asn Lys Ala Ala Leu Glu Pro
260 265 270

Val Asn Pro Pro Lys Pro Pro Pro Ala Ile Lys Ile Asp Pro Pro Pro
275 280 285

Pro Pro Gln Glu Gln Gly Leu Ile Pro Gly Phe Leu Met Pro Pro Ser
290 295 300

Asp Gly Ser Gly Val Thr Pro Gly Thr Gly Met Pro Ala Ala Pro Met
305 310 315 320

Val Pro Pro Thr Gly Ser Pro Gly Gly Gly Leu Pro Ala Asp Thr Ala
325 330 335

Ala Gln Leu Thr Ser Ala Gly Arg Glu Ala Ala Ala Leu Ser Gly Asp
340 345 350

Val Ala Val Lys Ala Ala Ser Leu Gly Gly Gly Gly Gly Gly Gly Val
355 360 365

Pro Ser Ala Pro Leu Gly Ser Ala Ile Gly Gly Ala Glu Ser Val Arg
370 375 380

Pro Ala Gly Ala Gly Asp Ile Ala Gly Leu Gly Gln Gly Arg Ala Gly
385 390 395 400

Gly Gly Ala Ala Leu Gly Gly Gly Gly Met Gly Met Pro Met Gly Ala
405 410 415

Ala His Gln Gly Gln Gly Gly Ala Lys Ser Lys Gly Ser Gln Gln Glu
420 425 430

Asp Glu Ala Leu Tyr Thr Glu Asp Arg Ala Trp Thr Glu Ala Val Ile
435 440 445

Gly Asn Arg Arg Arg Gln Asp Ser Lys Glu Ser Lys
450 455 460

<210> SEQ ID NO 180
<211> LENGTH: 277
<212> TYPE: PRT
<213> ORGANISM: Mycobacterium tuberculosis

<400> SEQUENCE: 180

Ala Gly Asn Val Thr Ser Ala Ser Gly Pro His Arg Phe Gly Ala Pro
1 5 10 15

Asp Arg Gly Ser Gln Arg Arg Arg Arg His Pro Ala Ala Ser Thr Ala
20 25 30

Thr Glu Arg Cys Arg Phe Asp Arg His Val Ala Arg Gln Arg Cys Gly
35 40 45

Phe Pro Pro Ser Arg Arg Gln Leu Arg Arg Arg Val Ser Arg Glu Ala
50 55 60

Thr Thr Arg Arg Ser Gly Arg Arg Asn His Arg Cys Gly Trp His Pro
65 70 75 80

Gly Thr Gly Ser His Thr Gly Ala Val Arg Arg Arg His Gln Glu Ala
85 90 95

Arg Asp Gln Ser Leu Leu Leu Arg Arg Arg Gly Arg Val Asp Leu Asp
100 105 110

Gly Gly Gly Arg Leu Arg Arg Val Tyr Arg Phe Gln Gly Cys Leu Val
115 120 125

```
Val Val Phe Gly Gln His Leu Leu Arg Pro Leu Leu Ile Leu Arg Val
    130                 135                 140

His Arg Glu Asn Leu Val Ala Gly Arg Arg Val Phe Arg Val Lys Pro
145                 150                 155                 160

Phe Glu Pro Asp Tyr Val Phe Ile Ser Arg Met Phe Pro Pro Ser Pro
                165                 170                 175

His Val Gln Leu Arg Asp Ile Leu Ser Leu Leu Gly His Arg Ser Ala
            180                 185                 190

Gln Phe Gly His Val Glu Tyr Pro Leu Pro Leu Leu Ile Glu Arg Ser
        195                 200                 205

Leu Ala Ser Gly Ser Arg Ile Ala Phe Pro Val Val Lys Pro Pro Glu
    210                 215                 220

Pro Leu Asp Val Ala Leu Gln Arg Gln Val Glu Ser Val Pro Pro Ile
225                 230                 235                 240

Arg Lys Val Arg Glu Arg Cys Ala Leu Val Ala Arg Phe Glu Leu Pro
                245                 250                 255

Cys Arg Phe Phe Glu Ile His Glu Val Gly Phe Thr Gly Arg Gly His
            260                 265                 270

Pro Arg Arg Ile Gly
        275


<210> SEQ ID NO 181
<211> LENGTH: 192
<212> TYPE: PRT
<213> ORGANISM: Mycobacterium tuberculosis

<400> SEQUENCE: 181

Arg Val Ala Ala Ser Phe Ile Asp Trp Leu Asp Ser Pro Asp Ser Pro
  1               5                  10                  15

Leu Asp Pro Ser Leu Val Ser Ser Leu Leu Asn Ala Val Ser Cys Gly
            20                  25                  30

Ala Glu Ser Ser Ala Ser Ser Ser Ala Arg Ser Gly Asn Gly Ser Arg
        35                  40                  45

Trp Thr Ser Met Pro Ser Gly Thr Arg Pro Gly Pro Arg Arg Ala Thr
     50                  55                  60

Ser Arg Asp Asp Arg Arg Ser Ala Thr Ser Val Ile Pro Ser Arg Arg
 65                  70                  75                  80

Ser Val Ala Pro Arg Ala Glu Phe Gly Thr Arg Leu Ala Ser His Arg
                 85                  90                  95

Ala Ser Pro Ser Asn Ala Cys Pro Val Arg Ile Val Thr Ser Ala Ser
            100                 105                 110

Gly Arg Pro Ile Ser Ser Pro Pro Ile Val Arg Ser Arg Ser Cys Val
        115                 120                 125

Asp Lys Asn Gly Arg Arg Cys Ala Ser Gly Tyr Arg Arg Leu Asn Arg
    130                 135                 140

Ala Arg Ser Ser Ser Ile Ala Ala Arg Cys Arg Thr Ile Gly Thr Phe
145                 150                 155                 160

Arg Arg Ser Arg Tyr Ser Ala Ser Met Arg Val Ser Thr Asn Ser Pro
                165                 170                 175

His Val Thr His Gly Val Ala Pro Gly Val Thr Arg Arg Ile Gly Gly
            180                 185                 190


<210> SEQ ID NO 182
<211> LENGTH: 196
<212> TYPE: PRT
<213> ORGANISM: Mycobacterium tuberculosis
```

<400> SEQUENCE: 182

Gln Glu Arg Pro Gln Met Cys Gln Arg Val Ser Glu Ile Glu Pro Arg
1 5 10 15

Thr Gln Phe Phe Asn Arg Cys Ala Leu Pro His Tyr Trp His Phe Pro
20 25 30

Ala Val Ala Val Phe Ser Lys His Ala Ser Leu Asp Glu Leu Ala Pro
35 40 45

Arg Asn Pro Arg Arg Ser Ser Arg Arg Asp Ala Glu Asp Arg Arg Val
50 55 60

Ile Phe Ala Ala Thr Leu Val Ala Val Asp Pro Pro Leu Arg Gly Ala
65 70 75 80

Gly Gly Glu Ala Asp Gln Leu Ile Asp Leu Gly Val Cys Arg Arg Gln
85 90 95

Ala Gly Arg Val Arg Arg Gly Gln Glu Leu His His Arg His Arg His
100 105 110

Gln Gly Ala Ala Pro Asp Leu Arg Arg Arg Arg Arg His Arg Arg Val
115 120 125

Gln Gln His Arg Arg Leu Gln Arg Val Arg Gln Leu Arg Arg Tyr Val
130 135 140

Gln Thr Ala His His Arg Arg Phe Ala Arg Thr Asp Arg Val Arg His
145 150 155 160

His Val Arg Gly Pro Ser Asn His Arg Arg Arg Arg Val Tyr Arg Gly
165 170 175

Arg His Ser Gly Ala Gly Gly Cys Pro Ala Gly Gly Ala Gly Ser Val
180 185 190

Gly Gly Ser Ala
195

<210> SEQ ID NO 183
<211> LENGTH: 311
<212> TYPE: PRT
<213> ORGANISM: Mycobacterium tuberculosis

<400> SEQUENCE: 183

Val Arg Cys Gly Thr Leu Val Pro Val Pro Met Val Glu Phe Leu Thr
1 5 10 15

Ser Thr Asn Ala Pro Ser Leu Pro Ser Ala Tyr Ala Glu Val Asp Lys
20 25 30

Leu Ile Gly Leu Pro Ala Gly Thr Ala Lys Arg Trp Ile Asn Gly Tyr
35 40 45

Glu Arg Gly Gly Lys Asp His Pro Pro Ile Leu Arg Val Thr Pro Gly
50 55 60

Ala Thr Pro Trp Val Thr Trp Gly Glu Phe Val Glu Thr Arg Met Leu
65 70 75 80

Ala Glu Tyr Arg Asp Arg Arg Lys Val Pro Ile Val Arg Gln Arg Ala
85 90 95

Ala Ile Glu Glu Leu Arg Ala Arg Phe Asn Leu Arg Tyr Pro Leu Ala
100 105 110

His Leu Arg Pro Phe Leu Ser Thr His Glu Arg Asp Leu Thr Met Gly
115 120 125

Gly Glu Glu Ile Gly Leu Pro Asp Ala Glu Val Thr Ile Arg Thr Gly
130 135 140

Gln Ala Leu Leu Gly Asp Ala Arg Trp Leu Ala Ser Leu Val Pro Asn
145 150 155 160

Ser Ala Arg Gly Ala Thr Leu Arg Arg Leu Gly Ile Thr Asp Val Ala

-continued

```
                165                 170                 175

Asp Leu Arg Ser Ser Arg Glu Val Ala Arg Arg Gly Pro Gly Arg Val
            180                 185                 190

Pro Asp Gly Ile Asp Val His Leu Leu Pro Phe Pro Asp Leu Ala Asp
        195                 200                 205

Asp Asp Ala Asp Asp Ser Ala Pro His Glu Thr Ala Phe Lys Arg Leu
    210                 215                 220

Leu Thr Asn Asp Gly Ser Asn Gly Glu Ser Gly Glu Ser Ser Gln Ser
225                 230                 235                 240

Ile Asn Asp Ala Ala Thr Arg Tyr Met Thr Asp Glu Tyr Arg Gln Phe
                245                 250                 255

Pro Thr Arg Asn Gly Ala Gln Arg Ala Leu His Arg Val Val Thr Leu
            260                 265                 270

Leu Ala Ala Gly Arg Pro Val Leu Thr His Cys Phe Ala Gly Lys Asp
        275                 280                 285

Arg Thr Gly Phe Val Val Ala Leu Val Leu Glu Ala Val Gly Leu Asp
    290                 295                 300

Arg Asp Val Ile Val Ala Asp
305                 310
```

<210> SEQ ID NO 184
<211> LENGTH: 2072
<212> TYPE: DNA
<213> ORGANISM: Mycobacterium tuberculosis

<400> SEQUENCE: 184

```
ctcgtgccga ttcggcacga gctgagcagc ccaaggggcc gttcggcgaa gtcatcgagg     60
cattcgccga cgggctggcc ggcaagggta agcaaatcaa caccacgctg aacagcctgt    120
cgcaggcgtt gaacgccttg aatgagggcc gcggcgactt cttcgcggtg gtacgcagcc    180
tggcgctatt cgtcaacgcg ctacatcagg acgaccaaca gttcgtcgcg ttgaacaaga    240
accttgcgga gttcaccgac aggttgaccc actccgatgc ggacctgtcg aacgccatcc    300
agcaattcga cagcttgctc gccgtcgcgc gcccgttctt cgccaagaac cgcgaggtgc    360
tgacgcatga cgtcaataat ctcgcgaccg tgaccaccac gttgctgcag cccgatccgt    420
tggatgggtt ggagaccgtc ctgcacatct tcccgacgct ggcggcgaac attaaccagc    480
tttaccatcc gacacacggt ggcgtggtgt cgctttccgc gttcacgaat ttcgccaacc    540
cgatggagtt catctgcagc tcgattcagg cgggtagccg gctcggttat caagagtcgg    600
ccgaactctg tgcgcagtat ctggcgccag tcctcgatgc gatcaagttc aactactttc    660
cgttcggcct gaacgtggcc agcaccgcct cgacactgcc taaagagatc gcgtactccg    720
agccccgctt gcagccgccc aacgggtaca aggacaccac ggtgcccggc atctgggtgc    780
cggatacgcc gttgtcacac cgcaacacgc agcccggttg ggtggtggca cccgggatgc    840
aaggggttca ggtgggaccg atcacgcagg gtttgctgac gccggagtcc ctggccgaac    900
tcatgggtgg tcccgatatc gcccctccgt cgtcagggct gcaaaccccg cccggacccc    960
cgaatgcgta cgacgagtac cccgtgctgc cgccgatcgg tttacaggcc ccacaggtgc   1020
cgataccacc gccgcctcct gggcccgacg taatcccggg tccggtgcca ccggtcttgg   1080
cggcgatcgt gttcccaaga gatcgcccgg cagcgtcgga aaacttcgac tacatgggcc   1140
tcttgttgct gtcgccgggc ctggcgacct tcctgttcgg ggtgtcatct agccccgccc   1200
gtggaacgat ggccgatcgg cacgtgttga taccggcgat caccggcctg gcgttgatcg   1260
cggcattcgt cgcacattcg tggtaccgca cagaacatcc gctcatagac atgcgcttgt   1320
```

tccagaaccg agcggtcgcg caggccaaca tgacgatgac ggtgctctcc ctcgggctgt 1380
ttggctcctt cttgctgctc ccgagctacc tccagcaagt gttgcaccaa tcaccgatgc 1440
aatcgggggt gcatatcatc ccacagggcc tcggtgccat gctggcgatg ccgatcgccg 1500
gagcgatgat ggaccgacgg ggaccggcca agatcgtgct ggttgggatc atgctgatcg 1560
ctgcggggtt gggcaccttc gcctttggtg tcgcgcggca agcggactac ttacccattc 1620
tgccgaccgg gctggcaatc atgggcatgg gcatgggctg ctccatgatg ccactgtccg 1680
gggcggcagt gcagaccctg gccccacatc agatcgctcg cggttcgacg ctgatcagcg 1740
tcaaccagca ggtgggcggt tcgataggga ccgcactgat gtcggtgctg ctcacctacc 1800
agttcaatca cagcgaaatc atcgctactg caaagaaagt cgcactgacc ccagagagtg 1860
gcgccgggcg gggggcggcg gttgaccctt cctcgctacc gcgccaaacc aacttcgcgg 1920
cccaactgct gcatgacctt tcgcacgcct acgcggtggt attcgtgata gcgaccgcgc 1980
tagtggtctc gacgctgatc cccgcggcat tcctgccgaa acagcaggct agtcatcgaa 2040
gagcaccgtt gctatccgca tgacgtctgc tt 2072

<210> SEQ ID NO 185
<211> LENGTH: 1923
<212> TYPE: DNA
<213> ORGANISM: Mycobacterium tuberculosis

<400> SEQUENCE: 185
tcaccccgga gaagtcgttc gtcgacgacc tggacatcga ctcgctgtcg atggtcgaga 60
tcgccgtgca gaccgaggac aagtacggcg tcaagatccc cgacgaggac ctcgccggtc 120
tgcgtaccgt cggtgacgtt gtcgcctaca tccagaagct cgaggaagaa aacccggagg 180
cggctcaggc gttgcgcgcg aagattgagt cggagaaccc cgatgcggca cgagcagatc 240
ggtgcgtttc acccacatcg caagctcgag acgcccgtcg tcctcttgca cgctcagcca 300
ggttggcgtg tcgccgcctt ccagcaagtg ttcccaccac acgaagggac cctcgcgaaa 360
ggtgactgat ccgcggacca catagtcgat gccaccgtgg ctgacaattg cgccgggtcc 420
gagttggcgg gggccgaatt gcggcattgc gtcgaaggcc agcggatccc ggcgcccgcc 480
cggcgtggct ggtgttttgg gccgccggat ggccacgacg agaacgacga tggcggcgat 540
gaacagcgcc acggcaatca cgaccagcag atttcccacg cataccctct cgtaccgctg 600
cgccgcggtt ggtcgatcgg tcgcatatcg atggcgccgt ttaacgtaac agctttcgcg 660
ggaccggggg tcacaacggg cgagttgtcc ggccgggaac ccggcaggtc tcggccgcgg 720
tcaccccagc tcactggtgc accatccggg tgtcggtgag cgtgcaactc aaacacactc 780
aacggcaacg gtttctcagg tcaccagctc aacctcgacc cgcaatcgct cgtacgtttc 840
gaccgcgcgc aggtcgcgag tcagcagctt tgcgccggca gctttcgccg tgaagccgac 900
cagggcatcg taggttgcgc caccggtgac atcgtgctcg gcgaggtggt cggtcaagcc 960
gcgatatgag caggcatcca gtgccaggta gttgctggag gtgatgtccg ccaagtaggc 1020
gtggacggca acaggggcaa tacgatgcgg cggtggtagc cgggtcaaga ccgaataggt 1080
ttccacagcc gcgtgcgcga tcagatggac gccacggttg agcgcgcgca cggcggcctc 1140
gtgcccttcg tgccaggtcg cgaatccggc aaccagcacg ctggtgtctg gtgcgatcac 1200
cgccgtgtgc gatcgagcgt ttcccgaacg atttcgtcgg tcaacggggg caggggacgt 1260
tctggccgtg cgacgagaac cgagccttcc cgaacgagtt cgacaccggt cggggccggc 1320
tcaatctcga tgcgcccatc gcgctcggtg atctccacct ggtcgttccc gcgcaagcca 1380
aggcgctcgc gaatccgctt gggaatcacc agacgtcctg cgacatcgat ggttgttcgc 1440
atggtaggaa atttaccatc gcacgttcca taggcgtgtc ctgcgcggga tgtcgggacg 1500
atccgctagc gtatcgaacg attgtttcgg aaatggctga gggagcgtgc ggtgcgggtg 1560
atgggtgtcg atcccgggtt gacccgatgc gggctgtcgc tcatcgagag tgggcgtggt 1620
cggcagctca ccgcgctgga tgtcgacgtg gtgcgcacac cgtcggatgc ggccttggcg 1680
cagcgcctgt tggccatcag cgatgccgtc gagcactggc tggacaccca tcatccggag 1740
gtggtggcta tcgaacgggt gttctctcag ctcaacgtga ccacggtgat gggcaccgcg 1800
caggccggcg gcgtgatcgc cctggcggcg gccaaacgtg gtgtcgacgt gcatttccat 1860
acccccagcg aggtcaaggc ggcggtcact ggcaacggtt ccgcagacaa ggctcaggtc 1920
acc 1923

<210> SEQ ID NO 186
<211> LENGTH: 1055
<212> TYPE: DNA
<213> ORGANISM: Mycobacterium tuberculosis
<220> FEATURE:
<221> NAME/KEY: modified_base
<222> LOCATION: (1016)
<223> OTHER INFORMATION: n = g, a, c or t

<400> SEQUENCE: 186
ctggcgtgcc agtgtcaccg gcgatatgac gtcggcattc aatttcgcgg ccccgccgga 60
cccgtcgcca cccaatctgg accacccggt ccgtcaattg ccgaaggtcg ccaagtgcgt 120
gcccaatgtg gtgctgggtt tcttgaacga aggcctgccg tatcgggtgc cctacccccca 180 aacaacgcca gtccaggaat ccggtcccgc gcggccgatt cccagcggca tctgctagcc 240
ggggatggtt cagacgtaac ggttggctag gtcgaaaccc gcgccagggc cgctggacgg 300
gctcatggca gcgaaattag aaaacccggg atattgtccg cggattgtca tacgatgctg 360
agtgcttggt ggttcgtgtt tagccattga gtgtggatgt gttgagaccc tggcctggaa 420
ggggacaacg tgcttttgcc tcttggtccg cctttgccgc ccgacgcggt ggtggcgaaa 480
cgggctgagt cgggaatgct cggcgggttg tcggttccgc tcagctgggg agtggctgtg 540
ccacccgatg attatgacca ctgggcgcct gcgccggagg acggcgccga tgtcgatgtc 600
caggcggccg aaggggcgga cgcagaggcc gcggccatgg acgagtggga tgagtggcag 660
gcgtggaacg agtgggtggc ggagaacgct gaacccccgct ttgaggtgcc acggagtagc 720
agcagcgtga ttccgcattc tccggcggcc ggctaggaga gggggcgcag actgtcgtta 780
tttgaccagt gatcggcggt ctcggtgttc ccgcggccgg ctatgacaac agtcaatgtg 840
catgacaagt tacaggtatt aggtccaggt tcaacaagga gacaggcaac atggcaacac 900
gttttatgac ggatccgcac gcgatgcggg acatggcggg ccgttttgag gtgcacgccc 960
agacggtgga ggacgaggct cgccggatgt gggcgtccgc gcaaaacatc tcgggngcgg 1020
gctggagtgg catggccgag gcgacctcgc tagac 1055

<210> SEQ ID NO 187
<211> LENGTH: 359
<212> TYPE: DNA
<213> ORGANISM: Mycobacterium tuberculosis

<400> SEQUENCE: 187
ccgcctcgtt gttggcatac tccgccgcgg ccgcctcgac cgcactggcc gtggcgtgtg 60
tccgggctga ccaccgggat cgccgaacca tccgagatca cctcgcaatg atccacctcg 120

```
cgcagctggt cacccagcca ccgggcggtg tgcgacagcg cctgcatcac cttggtatag    180

ccgtcgcgcc ccagccgcag gaagttgtag tactggccca ccacctggtt accgggacgg    240

gagaagttca gggtgaaggt cggcatgtcg ccgccgaggt agttgacccg gaaaaccaga    300

tcctccggca ggtgctcggg cccgcgccac acgacaaacc cgacgccggg ataggtcag     359
```

<210> SEQ ID NO 188
<211> LENGTH: 350
<212> TYPE: DNA
<213> ORGANISM: Mycobacterium tuberculosis

<400> SEQUENCE: 188

```
aacgggcccg tgggcaccgc tcctctaagg gctctcgttg gtcgcatgaa gtgctggaag     60

gatgcatctt ggcagattcc cgccagagca aaacagccgc tagtcctagt ccgagtcgcc    120

cgcaaagttc ctcgaataac tccgtacccg gagcgccaaa ccgggtctcc ttcgctaagc    180

tgcgcgaacc acttgaggtt ccgggactcc ttgacgtcca gaccgattcg ttcgagtggc    240

tgatcggttc gccgcgctgg cgcgaatccg ccgccgagcg gggtgatgtc aacccagtgg    300

gtggcctgga agaggtgctc tacgagctgt ctccgatcga ggacttctcc               350
```

<210> SEQ ID NO 189
<211> LENGTH: 679
<212> TYPE: PRT
<213> ORGANISM: Mycobacterium tuberculosis

<400> SEQUENCE: 189

```
Glu Gln Pro Lys Gly Pro Phe Gly Glu Val Ile Glu Ala Phe Ala Asp
  1               5                  10                  15

Gly Leu Ala Gly Lys Gly Lys Gln Ile Asn Thr Thr Leu Asn Ser Leu
             20                  25                  30

Ser Gln Ala Leu Asn Ala Leu Asn Glu Gly Arg Gly Asp Phe Phe Ala
         35                  40                  45

Val Val Arg Ser Leu Ala Leu Phe Val Asn Ala Leu His Gln Asp Asp
     50                  55                  60

Gln Gln Phe Val Ala Leu Asn Lys Asn Leu Ala Glu Phe Thr Asp Arg
 65                  70                  75                  80

Leu Thr His Ser Asp Ala Asp Leu Ser Asn Ala Ile Gln Gln Phe Asp
                 85                  90                  95

Ser Leu Leu Ala Val Ala Arg Pro Phe Phe Ala Lys Asn Arg Glu Val
            100                 105                 110

Leu Thr His Asp Val Asn Asn Leu Ala Thr Val Thr Thr Thr Leu Leu
        115                 120                 125

Gln Pro Asp Pro Leu Asp Gly Leu Glu Thr Val Leu His Ile Phe Pro
    130                 135                 140

Thr Leu Ala Ala Asn Ile Asn Gln Leu Tyr His Pro Thr His Gly Gly
145                 150                 155                 160

Val Val Ser Leu Ser Ala Phe Thr Asn Phe Ala Asn Pro Met Glu Phe
                165                 170                 175

Ile Cys Ser Ser Ile Gln Ala Gly Ser Arg Leu Gly Tyr Gln Glu Ser
            180                 185                 190

Ala Glu Leu Cys Ala Gln Tyr Leu Ala Pro Val Leu Asp Ala Ile Lys
        195                 200                 205

Phe Asn Tyr Phe Pro Phe Gly Leu Asn Val Ala Ser Thr Ala Ser Thr
    210                 215                 220

Leu Pro Lys Glu Ile Ala Tyr Ser Glu Pro Arg Leu Gln Pro Pro Asn
```

-continued

```
225                 230                 235                 240

Gly Tyr Lys Asp Thr Thr Val Pro Gly Ile Trp Val Pro Asp Thr Pro
                245                 250                 255

Leu Ser His Arg Asn Thr Gln Pro Gly Trp Val Val Ala Pro Gly Met
            260                 265                 270

Gln Gly Val Gln Val Gly Pro Ile Thr Gln Gly Leu Leu Thr Pro Glu
        275                 280                 285

Ser Leu Ala Glu Leu Met Gly Gly Pro Asp Ile Ala Pro Pro Ser Ser
    290                 295                 300

Gly Leu Gln Thr Pro Pro Gly Pro Pro Asn Ala Tyr Asp Glu Tyr Pro
305                 310                 315                 320

Val Leu Pro Pro Ile Gly Leu Gln Ala Pro Gln Val Pro Ile Pro Pro
                325                 330                 335

Pro Pro Pro Gly Pro Asp Val Ile Pro Gly Pro Val Pro Pro Val Leu
            340                 345                 350

Ala Ala Ile Val Phe Pro Arg Asp Arg Pro Ala Ala Ser Glu Asn Phe
        355                 360                 365

Asp Tyr Met Gly Leu Leu Leu Leu Ser Pro Gly Leu Ala Thr Phe Leu
    370                 375                 380

Phe Gly Val Ser Ser Ser Pro Ala Arg Gly Thr Met Ala Asp Arg His
385                 390                 395                 400

Val Leu Ile Pro Ala Ile Thr Gly Leu Ala Leu Ile Ala Ala Phe Val
                405                 410                 415

Ala His Ser Trp Tyr Arg Thr Glu His Pro Leu Ile Asp Met Arg Leu
            420                 425                 430

Phe Gln Asn Arg Ala Val Ala Gln Ala Asn Met Thr Met Thr Val Leu
        435                 440                 445

Ser Leu Gly Leu Phe Gly Ser Phe Leu Leu Leu Pro Ser Tyr Leu Gln
    450                 455                 460

Gln Val Leu His Gln Ser Pro Met Gln Ser Gly Val His Ile Ile Pro
465                 470                 475                 480

Gln Gly Leu Gly Ala Met Leu Ala Met Pro Ile Ala Gly Ala Met Met
                485                 490                 495

Asp Arg Arg Gly Pro Ala Lys Ile Val Leu Val Gly Ile Met Leu Ile
            500                 505                 510

Ala Ala Gly Leu Gly Thr Phe Ala Phe Gly Val Ala Arg Gln Ala Asp
        515                 520                 525

Tyr Leu Pro Ile Leu Pro Thr Gly Leu Ala Ile Met Gly Met Gly Met
    530                 535                 540

Gly Cys Ser Met Met Pro Leu Ser Gly Ala Ala Val Gln Thr Leu Ala
545                 550                 555                 560

Pro His Gln Ile Ala Arg Gly Ser Thr Leu Ile Ser Val Asn Gln Gln
                565                 570                 575

Val Gly Gly Ser Ile Gly Thr Ala Leu Met Ser Val Leu Leu Thr Tyr
            580                 585                 590

Gln Phe Asn His Ser Glu Ile Ile Ala Thr Ala Lys Lys Val Ala Leu
        595                 600                 605

Thr Pro Glu Ser Gly Ala Gly Arg Gly Ala Ala Val Asp Pro Ser Ser
    610                 615                 620

Leu Pro Arg Gln Thr Asn Phe Ala Ala Gln Leu Leu His Asp Leu Ser
625                 630                 635                 640

His Ala Tyr Ala Val Val Phe Val Ile Ala Thr Ala Leu Val Val Ser
                645                 650                 655
```

Thr Leu Ile Pro Ala Ala Phe Leu Pro Lys Gln Gln Ala Ser His Arg
660 665 670

Arg Ala Pro Leu Leu Ser Ala
675

<210> SEQ ID NO 190
<211> LENGTH: 120
<212> TYPE: PRT
<213> ORGANISM: Mycobacterium tuberculosis

<400> SEQUENCE: 190

Thr Pro Glu Lys Ser Phe Val Asp Asp Leu Asp Ile Asp Ser Leu Ser
1 5 10 15

Met Val Glu Ile Ala Val Gln Thr Glu Asp Lys Tyr Gly Val Lys Ile
20 25 30

Pro Asp Glu Asp Leu Ala Gly Leu Arg Thr Val Gly Asp Val Val Ala
35 40 45

Tyr Ile Gln Lys Leu Glu Glu Glu Asn Pro Glu Ala Ala Gln Ala Leu
50 55 60

Arg Ala Lys Ile Glu Ser Glu Asn Pro Asp Ala Ala Arg Ala Asp Arg
65 70 75 80

Cys Val Ser Pro Thr Ser Gln Ala Arg Asp Ala Arg Arg Pro Leu Ala
85 90 95

Arg Ser Ala Arg Leu Ala Cys Arg Arg Leu Pro Ala Ser Val Pro Thr
100 105 110

Thr Arg Arg Asp Pro Arg Glu Arg
115 120

<210> SEQ ID NO 191
<211> LENGTH: 89
<212> TYPE: PRT
<213> ORGANISM: Mycobacterium tuberculosis

<400> SEQUENCE: 191

Leu Ala Cys Gln Cys His Arg Arg Tyr Asp Val Gly Ile Gln Phe Arg
1 5 10 15

Gly Pro Ala Gly Pro Val Ala Thr Gln Ser Gly Pro Pro Gly Pro Ser
20 25 30

Ile Ala Glu Gly Arg Gln Val Arg Ala Gln Cys Gly Ala Gly Phe Leu
35 40 45

Glu Arg Arg Pro Ala Val Ser Gly Ala Leu Pro Pro Asn Asn Ala Ser
50 55 60

Pro Gly Ile Arg Ser Arg Ala Ala Asp Ser Gln Arg His Leu Leu Ala
65 70 75 80

Gly Asp Gly Ser Asp Val Thr Val Gly
85

<210> SEQ ID NO 192
<211> LENGTH: 119
<212> TYPE: PRT
<213> ORGANISM: Mycobacterium tuberculosis

<400> SEQUENCE: 192

Ala Ser Leu Leu Ala Tyr Ser Ala Ala Ala Ala Ser Thr Ala Leu Ala
1 5 10 15

Val Ala Cys Val Arg Ala Asp His Arg Asp Arg Arg Thr Ile Arg Asp
20 25 30

His Leu Ala Met Ile His Leu Ala Gln Leu Val Thr Gln Pro Pro Gly
35 40 45

```
Gly Val Arg Gln Arg Leu His His Leu Gly Ile Ala Val Ala Pro Gln
     50                  55                  60

Pro Gln Glu Val Val Val Leu Ala His His Leu Val Thr Gly Thr Gly
 65                  70                  75                  80

Glu Val Gln Gly Glu Gly Arg His Val Ala Ala Glu Val Val Asp Pro
                 85                  90                  95

Glu Asn Gln Ile Leu Arg Gln Val Leu Gly Pro Ala Pro His Asp Lys
            100                 105                 110

Pro Asp Ala Gly Ile Gly Gln
        115
```

<210> SEQ ID NO 193
<211> LENGTH: 116
<212> TYPE: PRT
<213> ORGANISM: Mycobacterium tuberculosis

<400> SEQUENCE: 193

```
Arg Ala Arg Gly His Arg Ser Ser Lys Gly Ser Arg Trp Ser His Glu
  1               5                  10                  15

Val Leu Glu Gly Cys Ile Leu Ala Asp Ser Arg Gln Ser Lys Thr Ala
            20                  25                  30

Ala Ser Pro Ser Pro Ser Arg Pro Gln Ser Ser Ser Asn Asn Ser Val
        35                  40                  45

Pro Gly Ala Pro Asn Arg Val Ser Phe Ala Lys Leu Arg Glu Pro Leu
     50                  55                  60

Glu Val Pro Gly Leu Leu Asp Val Gln Thr Asp Ser Phe Glu Trp Leu
 65                  70                  75                  80

Ile Gly Ser Pro Arg Trp Arg Glu Ser Ala Ala Glu Arg Gly Asp Val
                 85                  90                  95

Asn Pro Val Gly Gly Leu Glu Glu Val Leu Tyr Glu Leu Ser Pro Ile
            100                 105                 110

Glu Asp Phe Ser
        115
```

<210> SEQ ID NO 194
<211> LENGTH: 811
<212> TYPE: DNA
<213> ORGANISM: Mycobacterium tuberculosis

<400> SEQUENCE: 194

```
tgctacgcag caatcgcttt ggtgacagat gtggatgccg gcgtcgctgc tggcgatggc      60

gtgaaagccg ccgacgtgtt cgccgcattc ggggagaaca tcgaactgct caaaaggctg     120

gtgcgggccg ccatcgatcg ggtcgccgac gagcgcacgt gcacgcactg tcaacaccac     180

gccggtgttc cgttgccgtt cgagctgcca tgagggtgct gctgaccggc gcggccggct     240

tcatcgggtc gcgcgtggat gcggcgttac gggctgcggg tcacgacgtg gtgggcgtcg     300

acgcgctgct gcccgccgcg cacgggccaa acccggtgct gccaccgggc tgccagcggg     360

tcgacgtgcg cgacgccagc gcgctggccc cgttgttggc cggtgtcgat ctggtgtgtc     420

accaggccgc catggtgggt gccggcgtca acgccgccga cgcacccgcc tatggcggcc     480

acaacgattt cgccaccacg gtgctgctgg cgcagatgtt cgccgccggg gtccgccgtt     540

tggtgctggc gtcgtcgatg gtggtttacg ggcaggggcg ctatgactgt ccccagcatg     600

gaccggtcga cccgctgccg cggcggcgag ccgacctgga caatggggtc ttcgagcacc     660

gttgcccggg gtgcggcgag ccagtcatct ggcaattggt cgacgaagat gccccgttgc     720
```

gcccgcgcag cctgtacgcg gcagcaagac cgcgcaggag cactacgcgc tggcgtggtc 780
ggaaacgaat ggcggttccg tggtggcgtt g 811

<210> SEQ ID NO 195
<211> LENGTH: 966
<212> TYPE: DNA
<213> ORGANISM: Mycobacterium tuberculosis

<400> SEQUENCE: 195
gtcccgcgat gtggccgagc atgactttcg gcaacaccgg cgtagtagtc gaagatatcg 60
gactttgtgg tcccggtggc gggatagagc acctgtcggc gttggtcagc gtcacccgtt 120
gctcggacgc cgaacccatg ctttcaacgt agcctgtcgg tcacacaagt cgcgagcgta 180
acgtcacggt caaatatcgc gtggaatttc gccgtgacgt tccgctcgcg gacaatcaag 240
gcatactcac ttacatgcga gccatttgga cgggttcgat cgccttcggg ctggtgaacg 300
tgccggtcaa ggtgtacagc gctaccgcag accacgacat caggttccac caggtgcacg 360
ccaaggacaa cggacgcatc cggtacaagc gcgtctgcga ggcgtgtggc gaggtggtcg 420
actaccgcga tcttgcccgg gcctacgagt ccggcgacgg ccaaatggtg gcgatcaccg 480
acgacgacat cgccagcttg cctgaagaac gcagccggga gatcgaggtg ttggagttcg 540
tccccgccgc cgacgtggac ccgatgatgt tcgaccgcag ctactttttg gagcctgatt 600
cgaagtcgtc gaaatcgtat gtgctgctgg ctaagacact cgccgagacc gaccggatgg 660
cgatcgtgga tcgccccacc ggccgtgaat gcaggaaaaa taagagccgc tatccacaat 720
tcggcgtcga gctcggctac cacaaacggt agaacgatcg agacattccc gagctgaagt 780
gcggcgctat agaagccgct ctgcgcgatt atcaaacgca aaatacgctt actcatgcca 840
tcggcgctgc tcacccgatg cgacgttttt gccacgctcc accgcctgcc gcgcgacctc 900
aagtgggcat gcatcccacc cgttcccgga aaccggttcc ggcgggtcgg ctcatcgctt 960
catcct 966

<210> SEQ ID NO 196
<211> LENGTH: 2367
<212> TYPE: DNA
<213> ORGANISM: Mycobacterium tuberculosis

<400> SEQUENCE: 196
ccgcaccgcc ggcaataccg ccagcgccac cgttaccgcc gtttgcgccg ttgcccccgt 60
tgccgcccgt cccgccggcc ccgccgatgg agttctcatc gccaaaagta ctggcgttgc 120
caccggagcc gccgttgccg ccgtcaccgc cagccccgcc gactccaccg gccccaccga 180
ctccgccgct gccaccgttg ccgccgttgc cgatcaacat gccgctggcg ccacccttgc 240
cacccacgcc accggctccg cccaccccgc cgacaccaag cgagctgccg ccggagccac 300
catcaccacc tacgccaccg accgcccaga caccagcgac cgggtcttcg tgaaacgtcg 360
cggtgccacc accgccgccg ttaccgccaa ccccaccggc aacgccggcg ccgccatccc 420
cgccggcccc ggcgttgccg ccgttgccgc cgttgccgaa caacaacccg ccggcgccgc 480
cgttgccgcc cgcgccgccg gtcccgccgg cgccgccgac gccaaggccg ctgccgccct 540
tgccgccatc accacccttg ccgccgacca catcgggttc tgcctcgggg tctgggctgt 600
caaacctcgc gatgccagcg ttgccgccgc ttcccccggg cccccccgtg gcgccgtcac 660
caccgatacc acccgcgcca ccggcgccac cgttgccgcc atcaccgaat agcaacccgc 720
cggcgccacc attgccgcca gctccccctg cgccaccgtc ggcgccggag gcggcactgg 780

-continued

```
cagccccgtt accaccgaaa ccgccgctac caccggtaga ggtggcagtg gcgatgtgta    840

cgaaagcgcc gcctccggcg ccgccgctac cacccccact gccggcggct acaccgtcgg    900

acccgttgcc accatcaccg ccaaaggcgc tcgcaatgtc gccctgcgcg actccgccgt    960

cgccgccgtt gccgccgccg ccaccggcag cggcggtacc gccgtcacca ccggcaccgc   1020

cggtggcctt gcccgagcct gccgtcgcgg tggcaccgtc gccgccggtg ccaccggtcg   1080

gcgtgccggc agtgccatgg ccgcccgtgc cgccgtcgcc gccggtttga tcaccgatgc   1140

cggacacatc tgccgggctg tccccggtgc tggccgcggg gccgggcgtg ggattgaccc   1200

cgtttgcccc ggcgaggccg gcgccgccgg taccaccggc gccgccatgg ccgaacagcc   1260

cggcgttgcc gccgttaccg cccgcacccc cgatgcctgc ggccacgctg gtgccgccga   1320

caccgccgtt gccgccgttg ccccacaacc accccccgtt cccaccggca ccgccggccg   1380

cgccggtacc accggccccg ccgttgccgc cgttgccgat caacccggcc gcgcctccgc   1440

tgccgccggt ttgaccgaac ccgccagccg cgccgttgcc accgttgcca aacagcaacc   1500

cgccggccgc gccaggctgc ccgggtgccg tcccgtcggc gccgtttccg atcaacgggc   1560

gccccaaaag cgcctcggtg ggcgcattca ccgcacccag cagactccgc tcaacagcgg   1620

cttcagtgct ggcataccga cccgcggccg cagtcaacgc ctgcacaaac tgctcgtgaa   1680

acgctgccac ctgtacgctg agcgcctgat actgccgagc atgggccccg aacaaccccg   1740

caatcgccgc cgacacttca tcggcagccg cagccaccac ttccgtcgtc gggatcgccg   1800

cggccgcatt agccgcgctc acctgcgaac caatagtcga taaatccaaa gccgcagttg   1860

ccagcagctg cggcgtcgcg atcaccaagg acacctcgca cctccggata ccccatatcg   1920

ccgcaccgtg tccccagcgg ccacgtgacc tttggtcgct ggctggcggc cctgactatg   1980

gccgcgacgg ccctcgttct gattcgcccc ggcgcgcagc ttgttgcgcg agttgaagac   2040

gggaggacag gccgagcttg gtgtagacgt gggtcaagtg ggaatgcacg gtccgcggcg   2100

agatgaatag gcggacgccg atctccttgt tgctgagtcc ctcaccgacc agtagagcca   2160

cctcaagctc tgtcggtgtc aacgcgcccc agccacttgt cgggcgtttc cgtgcaccgc   2220

ggcctcgttg cgcgtacgcg atcgcctcat cgatcgataa cgcagttcct tcggcccagg   2280

catcgtcgaa ctcgctgtca cccatggatt ttcgaagggt ggctagcgac gagttacagc   2340

ccgcctggta gatcccgaag cggaccg                                       2367
```

<210> SEQ ID NO 197
<211> LENGTH: 376
<212> TYPE: PRT
<213> ORGANISM: Mycobacterium tuberculosis

<400> SEQUENCE: 197

```
Gln Pro Ala Gly Ala Thr Ile Ala Ala Ser Ser Pro Cys Ala Thr Val
  1               5                  10                  15

Gly Ala Gly Gly Gly Thr Gly Ser Pro Val Thr Thr Glu Thr Ala Ala
             20                  25                  30

Thr Thr Gly Arg Gly Gly Ser Gly Asp Val Tyr Glu Ser Ala Ala Ser
         35                  40                  45

Gly Ala Ala Ala Thr Thr Pro Thr Ala Gly Gly Tyr Thr Val Gly Pro
     50                  55                  60

Val Ala Thr Ile Thr Ala Lys Gly Ala Arg Asn Val Ala Leu Arg Asp
 65                  70                  75                  80

Ser Ala Val Ala Ala Val Ala Ala Ala Ala Thr Gly Ser Gly Gly Thr
                 85                  90                  95
```

-continued

```
Ala Val Thr Thr Gly Thr Ala Gly Gly Leu Ala Arg Ala Cys Arg Arg
            100                 105                 110

Gly Gly Thr Val Ala Ala Gly Ala Thr Gly Arg Arg Ala Gly Ser Ala
        115                 120                 125

Met Ala Ala Arg Ala Ala Val Ala Ala Gly Leu Ile Thr Asp Ala Gly
    130                 135                 140

His Ile Cys Arg Ala Val Pro Gly Ala Gly Arg Gly Ala Gly Arg Gly
145                 150                 155                 160

Ile Asp Pro Val Cys Pro Gly Glu Ala Gly Ala Ala Gly Thr Thr Gly
                165                 170                 175

Ala Ala Met Ala Glu Gln Pro Gly Val Ala Ala Val Thr Ala Arg Thr
            180                 185                 190

Pro Asp Ala Cys Gly His Ala Gly Ala Ala Asp Thr Ala Val Ala Ala
        195                 200                 205

Val Ala Pro Gln Pro Pro Pro Val Pro Thr Gly Thr Ala Gly Arg Ala
    210                 215                 220

Gly Thr Thr Gly Pro Ala Val Ala Ala Val Ala Asp Gln Pro Gly Arg
225                 230                 235                 240

Ala Ser Ala Ala Ala Gly Leu Thr Glu Pro Ala Ser Arg Ala Val Ala
                245                 250                 255

Thr Val Ala Lys Gln Gln Pro Ala Gly Arg Ala Arg Leu Pro Gly Cys
            260                 265                 270

Arg Pro Val Gly Ala Val Ser Asp Gln Arg Ala Pro Gln Lys Arg Leu
        275                 280                 285

Gly Gly Arg Ile His Arg Thr Gln Gln Thr Pro Leu Asn Ser Gly Phe
    290                 295                 300

Ser Ala Gly Ile Pro Thr Arg Gly Arg Ser Gln Arg Leu His Lys Leu
305                 310                 315                 320

Leu Val Lys Arg Cys His Leu Tyr Ala Glu Arg Leu Ile Leu Pro Ser
                325                 330                 335

Met Gly Pro Glu Gln Pro Arg Asn Arg Arg Arg His Phe Ile Gly Ser
            340                 345                 350

Arg Ser His His Phe Arg Arg Arg Asp Arg Arg Gly Arg Ile Ser Arg
        355                 360                 365

Ala His Leu Arg Thr Asn Ser Arg
    370                 375
```

<210> SEQ ID NO 198
<211> LENGTH: 2852
<212> TYPE: DNA
<213> ORGANISM: Mycobacterium tuberculosis

<400> SEQUENCE: 198

```
ggccaaaacg ccccggcgat cgcggccacc gaggccgcct acgaccagat gtgggcccag      60

gacgtggcgg cgatgtttgg ctaccatgcc ggggcttcgg cggccgtctc ggcgttgaca     120

ccgttcggcc aggcgctgcc gaccgtggcg ggcggcggtg cgctggtcag cgcggccgcg     180

gctcaggtga ccacgcgggt cttccgcaac ctgggcttgg cgaacgtccg cgagggcaac     240

gtccgcaacg gtaatgtccg gaacttcaat ctcggctcgg ccaacatcgg caacggcaac     300

atcggcagcg gcaacatcgg cagctccaac atcgggtttg gcaacgtggg tcctgggttg     360

accgcagcgc tgaacaacat cggtttcggc aacaccggca gcaacaacat cgggtttggc     420

aacaccggca gcaacaacat cgggttcggc aataccggag acggcaaccg aggtatcggg     480

ctcacgggta gcggtttgtt ggggttcggc ggcctgaact cgggcaccgg caacatcggt     540
```

-continued

```
ctgttcaact cgggcaccgg aaacgtcggc atcggcaact cgggtaccgg gaactggggc    600
attggcaact cgggcaacag ctacaacacc ggttttggca actccggcga cgccaacacg    660
ggcttcttca actccggaat agccaacacc ggcgtcggca acgccggcaa ctacaacacc    720
ggtagctaca acccgggcaa cagcaatacc ggcggcttca acatgggcca gtacaacacg    780
ggctacctga acagcggcaa ctacaacacc ggcttggcaa actccggcaa tgtcaacacc    840
ggcgccttca ttactggcaa cttcaacaac ggcttcttgt ggcgcggcga ccaccaaggc    900
ctgattttcg ggagccccgg cttcttcaac tcgaccagtg cgccgtcgtc gggattcttc    960
aacagcggtg ccggtagcgc gtccggcttc ctgaactccg gtgccaacaa ttctggcttc   1020
ttcaactctt cgtcgggggc catcggtaac tccggcctgg caaacgcggg cgtgctggta   1080
tcgggcgtga tcaactcggg caacaccgta tcgggtttgt tcaacatgag cctggtggcc   1140
atcacaacgc cggccttgat ctcgggcttc ttcaacaccg gaagcaacat gtcgggattt   1200
ttcggtggcc caccggtctt caatctcggc ctggcaaacc ggggcgtcgt gaacattctc   1260
ggcaacgcca acatcggcaa ttacaacatt ctcggcagcg gaaacgtcgg tgacttcaac   1320
atccttggca gcggcaacct cggcagccaa aacatcttgg gcagcggcaa cgtcggcagc   1380
ttcaatatcg gcagtggaaa catcggagta ttcaatgtcg gttccggaag cctgggaaac   1440
tacaacatcg gatccggaaa cctcgggatc tacaacatcg gttttggaaa cgtcggcgac   1500
tacaacgtcg gcttcgggaa cgcgggcgac ttcaaccaag gctttgccaa caccggcaac   1560
aacaacatcg ggttcgccaa caccggcaac aacaacatcg gcatcgggct gtccggcgac   1620
aaccagcagg gcttcaatat tgctagcggc tggaactcgg gcaccggcaa cagcggcctg   1680
ttcaattcgg gcaccaataa cgttggcatc ttcaacgcgg gcaccggaaa cgtcggcatc   1740
gcaaactcgg gcaccgggaa ctggggtatc gggaacccgg gtaccgacaa taccggcatc   1800
ctcaatgctg gcagctacaa cacgggcatc ctcaacgccg gcgacttcaa cacgggcttc   1860
tacaacacgg gcagctacaa caccggcggc ttcaacgtcg gtaacaccaa caccggcaac   1920
ttcaacgtgg gtgacaccaa taccggcagc tataacccgg gtgacaccaa caccggcttc   1980
ttcaatcccg gcaacgtcaa taccggcgct ttcgacacgg gcgacttcaa caatggcttc   2040
ttggtggcgg gcgataacca gggccagatt gccatcgatc tctcggtcac cactccattc   2100
atccccataa acgagcagat ggtcattgac gtacacaacg taatgacctt cggcggcaac   2160
atgatcacgg tcaccgaggc ctcgaccgtt ttcccccaaa ccttctatct gagcggtttg   2220
ttcttcttcg gcccggtcaa tctcagcgca tccacgctga ccgttccgac gatcaccctc   2280
accatcggcg gaccgacggt gaccgtcccc atcagcattg tcggtgctct ggagagccgc   2340
acgattacct tcctcaagat cgatccggcg ccgggcatcg gaaattcgac caccaacccc   2400
tcgtccggct tcttcaactc gggcaccggt ggcacatctg gcttccaaaa cgtcggcggc   2460
ggcagttcag gcgtctggaa cagtggtttg agcagcgcga tagggaattc gggtttccag   2520
aacctcggct cgctgcagtc aggctgggcg aacctgggca actccgtatc gggctttttc   2580
aacaccagta cggtgaacct ctccacgccg gccaatgtct cgggcctgaa caacatcggc   2640
accaacctgt ccggcgtgtt ccgcggtccg accgggacga ttttcaacgc gggccttgcc   2700
aacctgggcc agttgaacat cggcagcgcc tcgtgccgaa ttcggcacga gttagatacg   2760
gtttcaacaa tcatatccgc gttttgcggc agtgcatcag acgaatcgaa cccgggaagc   2820
gtaagcgaat aaaccgaatg gcggcctgtc at                                 2852
```

<210> SEQ ID NO 199

<211> LENGTH: 943
<212> TYPE: PRT
<213> ORGANISM: Mycobacterium tuberculosis

<400> SEQUENCE: 199

```
Gly Gln Asn Ala Pro Ala Ile Ala Ala Thr Glu Ala Ala Tyr Asp Gln
  1               5                  10                  15

Met Trp Ala Gln Asp Val Ala Ala Met Phe Gly Tyr His Ala Gly Ala
             20                  25                  30

Ser Ala Ala Val Ser Ala Leu Thr Pro Phe Gly Gln Ala Leu Pro Thr
         35                  40                  45

Val Ala Gly Gly Gly Ala Leu Val Ser Ala Ala Ala Ala Gln Val Thr
     50                  55                  60

Thr Arg Val Phe Arg Asn Leu Gly Leu Ala Asn Val Arg Glu Gly Asn
 65                  70                  75                  80

Val Arg Asn Gly Asn Val Arg Asn Phe Asn Leu Gly Ser Ala Asn Ile
                 85                  90                  95

Gly Asn Gly Asn Ile Gly Ser Gly Asn Ile Gly Ser Ser Asn Ile Gly
            100                 105                 110

Phe Gly Asn Val Gly Pro Gly Leu Thr Ala Ala Leu Asn Asn Ile Gly
        115                 120                 125

Phe Gly Asn Thr Gly Ser Asn Asn Ile Gly Phe Gly Asn Thr Gly Ser
    130                 135                 140

Asn Asn Ile Gly Phe Gly Asn Thr Gly Asp Gly Asn Arg Gly Ile Gly
145                 150                 155                 160

Leu Thr Gly Ser Gly Leu Leu Gly Phe Gly Gly Leu Asn Ser Gly Thr
                165                 170                 175

Gly Asn Ile Gly Leu Phe Asn Ser Gly Thr Gly Asn Val Gly Ile Gly
            180                 185                 190

Asn Ser Gly Thr Gly Asn Trp Gly Ile Gly Asn Ser Gly Asn Ser Tyr
        195                 200                 205

Asn Thr Gly Phe Gly Asn Ser Gly Asp Ala Asn Thr Gly Phe Phe Asn
    210                 215                 220

Ser Gly Ile Ala Asn Thr Gly Val Gly Asn Ala Gly Asn Tyr Asn Thr
225                 230                 235                 240

Gly Ser Tyr Asn Pro Gly Asn Ser Asn Thr Gly Gly Phe Asn Met Gly
                245                 250                 255

Gln Tyr Asn Thr Gly Tyr Leu Asn Ser Gly Asn Tyr Asn Thr Gly Leu
            260                 265                 270

Ala Asn Ser Gly Asn Val Asn Thr Gly Ala Phe Ile Thr Gly Asn Phe
        275                 280                 285

Asn Asn Gly Phe Leu Trp Arg Gly Asp His Gln Gly Leu Ile Phe Gly
    290                 295                 300

Ser Pro Gly Phe Phe Asn Ser Thr Ser Ala Pro Ser Ser Gly Phe Phe
305                 310                 315                 320

Asn Ser Gly Ala Gly Ser Ala Ser Gly Phe Leu Asn Ser Gly Ala Asn
                325                 330                 335

Asn Ser Gly Phe Phe Asn Ser Ser Ser Gly Ala Ile Gly Asn Ser Gly
            340                 345                 350

Leu Ala Asn Ala Gly Val Leu Val Ser Gly Val Ile Asn Ser Gly Asn
        355                 360                 365

Thr Val Ser Gly Leu Phe Asn Met Ser Leu Val Ala Ile Thr Thr Pro
    370                 375                 380

Ala Leu Ile Ser Gly Phe Phe Asn Thr Gly Ser Asn Met Ser Gly Phe
385                 390                 395                 400
```

-continued

```
Phe Gly Gly Pro Pro Val Phe Asn Leu Gly Leu Ala Asn Arg Gly Val
                405                 410                 415

Val Asn Ile Leu Gly Asn Ala Asn Ile Gly Asn Tyr Asn Ile Leu Gly
            420                 425                 430

Ser Gly Asn Val Gly Asp Phe Asn Ile Leu Gly Ser Gly Asn Leu Gly
        435                 440                 445

Ser Gln Asn Ile Leu Gly Ser Gly Asn Val Gly Ser Phe Asn Ile Gly
    450                 455                 460

Ser Gly Asn Ile Gly Val Phe Asn Val Gly Ser Gly Ser Leu Gly Asn
465                 470                 475                 480

Tyr Asn Ile Gly Ser Gly Asn Leu Gly Ile Tyr Asn Ile Gly Phe Gly
                485                 490                 495

Asn Val Gly Asp Tyr Asn Val Gly Phe Gly Asn Ala Gly Asp Phe Asn
            500                 505                 510

Gln Gly Phe Ala Asn Thr Gly Asn Asn Asn Ile Gly Phe Ala Asn Thr
        515                 520                 525

Gly Asn Asn Asn Ile Gly Ile Gly Leu Ser Gly Asp Asn Gln Gln Gly
    530                 535                 540

Phe Asn Ile Ala Ser Gly Trp Asn Ser Gly Thr Gly Asn Ser Gly Leu
545                 550                 555                 560

Phe Asn Ser Gly Thr Asn Asn Val Gly Ile Phe Asn Ala Gly Thr Gly
                565                 570                 575

Asn Val Gly Ile Ala Asn Ser Gly Thr Gly Asn Trp Gly Ile Gly Asn
            580                 585                 590

Pro Gly Thr Asp Asn Thr Gly Ile Leu Asn Ala Gly Ser Tyr Asn Thr
        595                 600                 605

Gly Ile Leu Asn Ala Gly Asp Phe Asn Thr Gly Phe Tyr Asn Thr Gly
    610                 615                 620

Ser Tyr Asn Thr Gly Gly Phe Asn Val Gly Asn Thr Asn Thr Gly Asn
625                 630                 635                 640

Phe Asn Val Gly Asp Thr Asn Thr Gly Ser Tyr Asn Pro Gly Asp Thr
                645                 650                 655

Asn Thr Gly Phe Phe Asn Pro Gly Asn Val Asn Thr Gly Ala Phe Asp
            660                 665                 670

Thr Gly Asp Phe Asn Asn Gly Phe Leu Val Ala Gly Asp Asn Gln Gly
        675                 680                 685

Gln Ile Ala Ile Asp Leu Ser Val Thr Thr Pro Phe Ile Pro Ile Asn
    690                 695                 700

Glu Gln Met Val Ile Asp Val His Asn Val Met Thr Phe Gly Gly Asn
705                 710                 715                 720

Met Ile Thr Val Thr Glu Ala Ser Thr Val Phe Pro Gln Thr Phe Tyr
                725                 730                 735

Leu Ser Gly Leu Phe Phe Phe Gly Pro Val Asn Leu Ser Ala Ser Thr
            740                 745                 750

Leu Thr Val Pro Thr Ile Thr Leu Thr Ile Gly Gly Pro Thr Val Thr
        755                 760                 765

Val Pro Ile Ser Ile Val Gly Ala Leu Glu Ser Arg Thr Ile Thr Phe
    770                 775                 780

Leu Lys Ile Asp Pro Ala Pro Gly Ile Gly Asn Ser Thr Thr Asn Pro
785                 790                 795                 800

Ser Ser Gly Phe Phe Asn Ser Gly Thr Gly Gly Thr Ser Gly Phe Gln
                805                 810                 815

Asn Val Gly Gly Gly Ser Ser Gly Val Trp Asn Ser Gly Leu Ser Ser
```

-continued

```
            820                 825                 830

Ala Ile Gly Asn Ser Gly Phe Gln Asn Leu Gly Ser Leu Gln Ser Gly
        835                 840                 845

Trp Ala Asn Leu Gly Asn Ser Val Ser Gly Phe Phe Asn Thr Ser Thr
    850                 855                 860

Val Asn Leu Ser Thr Pro Ala Asn Val Ser Gly Leu Asn Asn Ile Gly
865                 870                 875                 880

Thr Asn Leu Ser Gly Val Phe Arg Gly Pro Thr Gly Thr Ile Phe Asn
                885                 890                 895

Ala Gly Leu Ala Asn Leu Gly Gln Leu Asn Ile Gly Ser Ala Ser Cys
            900                 905                 910

Arg Ile Arg His Glu Leu Asp Thr Val Ser Thr Ile Ile Ser Ala Phe
        915                 920                 925

Cys Gly Ser Ala Ser Asp Glu Ser Asn Pro Gly Ser Val Ser Glu
    930                 935                 940


<210> SEQ ID NO 200
<211> LENGTH: 53
<212> TYPE: DNA
<213> ORGANISM: Artificial Sequence
<220> FEATURE:
<223> OTHER INFORMATION: Description of Artificial Sequence:PCR primer
      PDM-83 used in preparation of fusion protein
      containing TbRa3, 38 kD, Tb38-1 and DPEP (TbF-2)

<400> SEQUENCE: 200

ggatccatat gggccatcat catcatcatc acgtgatcga catcatcggg acc           53


<210> SEQ ID NO 201
<211> LENGTH: 42
<212> TYPE: DNA
<213> ORGANISM: Artificial Sequence
<220> FEATURE:
<223> OTHER INFORMATION: Description of Artificial Sequence:PCR primer
      PDM-84 used in preparation of fusion protein
      containing TbRa3, 38 kD, Tb38-1 and DPEP (TbF-2)

<400> SEQUENCE: 201

cctgaattca ggcctcggtt gcgccggcct catcttgaac ga                       42


<210> SEQ ID NO 202
<211> LENGTH: 31
<212> TYPE: DNA
<213> ORGANISM: Artificial Sequence
<220> FEATURE:
<223> OTHER INFORMATION: Description of Artificial Sequence:PCR primer
      PDM-85 used in preparation of fusion protein
      containing TbRa3, 38 kD, Tb38-1 and DPEP (TbF-2)

<400> SEQUENCE: 202

ggatcctgca ggctcgaaac caccgagcgg t                                   31


<210> SEQ ID NO 203
<211> LENGTH: 31
<212> TYPE: DNA
<213> ORGANISM: Artificial Sequence
<220> FEATURE:
<223> OTHER INFORMATION: Description of Artificial Sequence:PCR primer
      used in preparation of fusion protein containing TbRa3, 38 kD,
      Tb38-1 and DPEP (TbF-2)

<400> SEQUENCE: 203

ctctgaattc agcgctggaa atcgtcgcga t                                   31
```

<210> SEQ ID NO 204
<211> LENGTH: 33
<212> TYPE: DNA
<213> ORGANISM: Artificial Sequence
<220> FEATURE:
<223> OTHER INFORMATION: Description of Artificial Sequence:PCR primer used in preparation of fusion protein containing TbRa3, 38 kD, Tb38-1 and DPEP (TbF-2)

<400> SEQUENCE: 204
ggatccagcg ctgagatgaa gaccgatgcc gct 33

<210> SEQ ID NO 205
<211> LENGTH: 38
<212> TYPE: DNA
<213> ORGANISM: Artificial Sequence
<220> FEATURE:
<223> OTHER INFORMATION: Description of Artificial Sequence:PCR primer used in preparation of fusion protein containing TbRa3, 38 kD, Tb38-1 and DPEP (TbF-2)

<400> SEQUENCE: 205
ggatatctgc agaattcagg tttaaagccc atttgcga 38

<210> SEQ ID NO 206
<211> LENGTH: 30
<212> TYPE: DNA
<213> ORGANISM: Artificial Sequence
<220> FEATURE:
<223> OTHER INFORMATION: Description of Artificial Sequence:PCR primer used in preparation of fusion protein containing TbRa3, 38 kD, Tb38-1 and DPEP (TbF-2)

<400> SEQUENCE: 206
ccgcatgcga gccacgtgcc cacaacggcc 30

<210> SEQ ID NO 207
<211> LENGTH: 37
<212> TYPE: DNA
<213> ORGANISM: Artificial Sequence
<220> FEATURE:
<223> OTHER INFORMATION: Description of Artificial Sequence:PCR primer used in preparation of fusion protein containing TbRa3, 38 kD, Tb38-1 and DPEP (TbF-2)

<400> SEQUENCE: 207
cttcatggaa ttctcaggcc ggtaaggtcc gctgcgg 37

<210> SEQ ID NO 208
<211> LENGTH: 7676
<212> TYPE: DNA
<213> ORGANISM: Artificial Sequence
<220> FEATURE:
<223> OTHER INFORMATION: Description of Artificial Sequence:DNA sequence of fusion protein TbF-2

<400> SEQUENCE: 208
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420

-continued

```
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
```

-continued

```
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatgggccat catcatcatc atcacgtgat   5100
cgacatcatc gggaccagcc ccacatcctg ggaacaggcg gcggcggagg cggtccagcg   5160
ggcgcgggat agcgtcgatg acatccgcgt cgctcgggtc attgagcagg acatggccgt   5220
```

-continued

```
ggacagcgcc ggcaagatca cctaccgcat caagctcgaa gtgtcgttca agatgaggcc   5280
ggcgcaaccg aggggctcga aaccaccgag cggttcgcct gaaacgggcg ccggcgccgg   5340
tactgtcgcg actacccccg cgtcgtcgcc ggtgacgttg gcggagaccg gtagcacgct   5400
gctctacccg ctgttcaacc tgtggggtcc ggcctttcac gagaggtatc cgaacgtcac   5460
gatcaccgct cagggcaccg gttctggtgc cgggatcgcg caggccgccg ccgggacggt   5520
caacattggg gcctccgacg cctatctgtc ggaaggtgat atggccgcgc acaaggggct   5580
gatgaacatc gcgctagcca tctccgctca gcaggtcaac tacaacctgc ccggagtgag   5640
cgagcacctc aagctgaacg gaaaagtcct ggcggccatg taccagggca ccatcaaaac   5700
ctgggacgac ccgcagatcg ctgcgctcaa ccccggcgtg aacctgcccg gcaccgcggt   5760
agttccgctg caccgctccg acgggtccgg tgacaccttc ttgttcaccc agtacctgtc   5820
caagcaagat cccgagggct ggggcaagtc gcccggcttc ggcaccaccg tcgacttccc   5880
ggcggtgccg ggtgcgctgg gtgagaacgg caacggcggc atggtgaccg gttgcgccga   5940
gacaccgggc tgcgtggcct atatcggcat cagcttcctc gaccaggcca gtcaacgggg   6000
actcggcgag gcccaactag gcaatagctc tggcaatttc ttgttgcccg acgcgcaaag   6060
cattcaggcc gcggcggctg gcttcgcatc gaaaaccccg gcgaaccagg cgatttcgat   6120
gatcgacggg cccgccccgg acggctaccc gatcatcaac tacgagtacg ccatcgtcaa   6180
caaccggcaa aaggacgccg ccaccgcgca gaccttgcag gcatttctgc actgggcgat   6240
caccgacggc aacaaggcct cgttcctcga ccaggttcat ttccagccgc tgccgcccgc   6300
ggtggtgaag ttgtctgacg cgttgatcgc gacgatttcc agcgctgaga tgaagaccga   6360
tgccgctacc ctcgcgcagg aggcaggtaa tttcgagcgg atctccggcg acctgaaaac   6420
ccagatcgac caggtggagt cgacggcagg ttcgttgcag ggccagtggc gcggcgcggc   6480
ggggacggcc gcccaggccg cggtggtgcg cttccaagaa gcagccaata agcagaagca   6540
ggaactcgac gagatctcga cgaatattcg tcaggccggc gtccaatact cgagggccga   6600
cgaggagcag cagcaggcgc tgtcctcgca aatgggcttt gtgcccacaa cggccgcctc   6660
gccgccgtcg accgctgcag cgccacccgc accggcgaca cctgttgccc ccccaccacc   6720
ggccgccgcc aacacgccga atgcccagcc gggcgatccc aacgcagcac ctccgccggc   6780
cgacccgaac gcaccgccgc cacctgtcat tgccccaaac gcaccccaac ctgtccggat   6840
cgacaacccg gttggaggat tcagcttcgc gctgcctgct ggctgggtgg agtctgacgc   6900
cgcccacttc gactacggtt cagcactcct cagcaaaacc accgggggacc cgccatttcc   6960
cggacagccg ccgccggtgg ccaatgacac ccgtatcgtg ctcggccggc tagaccaaaa   7020
gctttacgcc agcgccgaag ccaccgactc caaggccgcg gcccggttgg gctcggacat   7080
gggtgagttc tatatgccct acccgggcac ccggatcaac caggaaaccg tctcgcttga   7140
cgccaacggg gtgtctggaa gcgcgtcgta ttacgaagtc aagttcagcg atccgagtaa   7200
gccgaacggc cagatctgga cgggcgtaat cggctcgccc gcggcgaacg caccggacgc   7260
cgggcccccct cagcgctggt ttgtggtatg gctcgggacc gccaacaacc cggtggacaa   7320
gggcgcggcc aaggcgctgg ccgaatcgat ccggcctttg gtcgccccgc cgccggcgcc   7380
ggcaccggct cctgcagagc ccgctccggc gccggcgccg gccggggaag tcgctcctac   7440
cccgacgaca ccgacaccgc agcggacctt accggcctga gaattctgca gatatccatc   7500
acactggcgg ccgctcgagc accaccacca ccaccactga gatccggctg ctaacaaagc   7560
ccgaaaggaa gctgagttgg ctgctgccac cgctgagcaa taactagcat aacccccttgg   7620
```

```
ggcctctaaa cgggtcttga ggggtttttt gctgaaagga ggaactatat ccggat       7676


<210> SEQ ID NO 209
<211> LENGTH: 802
<212> TYPE: PRT
<213> ORGANISM: Artificial Sequence
<220> FEATURE:
<223> OTHER INFORMATION: Description of Artificial Sequence:amino acid
      sequence of fusion protein TbF-2

<400> SEQUENCE: 209

Met Gly His His His His His His Val Ile Asp Ile Ile Gly Thr Ser
  1               5                  10                  15

Pro Thr Ser Trp Glu Gln Ala Ala Ala Glu Ala Val Gln Arg Ala Arg
             20                  25                  30

Asp Ser Val Asp Asp Ile Arg Val Ala Arg Val Ile Glu Gln Asp Met
         35                  40                  45

Ala Val Asp Ser Ala Gly Lys Ile Thr Tyr Arg Ile Lys Leu Glu Val
     50                  55                  60

Ser Phe Lys Met Arg Pro Ala Gln Pro Arg Gly Ser Lys Pro Pro Ser
 65                  70                  75                  80

Gly Ser Pro Glu Thr Gly Ala Gly Ala Gly Thr Val Ala Thr Thr Pro
                 85                  90                  95

Ala Ser Ser Pro Val Thr Leu Ala Glu Thr Gly Ser Thr Leu Leu Tyr
            100                 105                 110

Pro Leu Phe Asn Leu Trp Gly Pro Ala Phe His Glu Arg Tyr Pro Asn
        115                 120                 125

Val Thr Ile Thr Ala Gln Gly Thr Gly Ser Gly Ala Gly Ile Ala Gln
    130                 135                 140

Ala Ala Ala Gly Thr Val Asn Ile Gly Ala Ser Asp Ala Tyr Leu Ser
145                 150                 155                 160

Glu Gly Asp Met Ala Ala His Lys Gly Leu Met Asn Ile Ala Leu Ala
                165                 170                 175

Ile Ser Ala Gln Gln Val Asn Tyr Asn Leu Pro Gly Val Ser Glu His
            180                 185                 190

Leu Lys Leu Asn Gly Lys Val Leu Ala Ala Met Tyr Gln Gly Thr Ile
        195                 200                 205

Lys Thr Trp Asp Asp Pro Gln Ile Ala Ala Leu Asn Pro Gly Val Asn
    210                 215                 220

Leu Pro Gly Thr Ala Val Val Pro Leu His Arg Ser Asp Gly Ser Gly
225                 230                 235                 240

Asp Thr Phe Leu Phe Thr Gln Tyr Leu Ser Lys Gln Asp Pro Glu Gly
                245                 250                 255

Trp Gly Lys Ser Pro Gly Phe Gly Thr Thr Val Asp Phe Pro Ala Val
            260                 265                 270

Pro Gly Ala Leu Gly Glu Asn Gly Asn Gly Gly Met Val Thr Gly Cys
        275                 280                 285

Ala Glu Thr Pro Gly Cys Val Ala Tyr Ile Gly Ile Ser Phe Leu Asp
    290                 295                 300

Gln Ala Ser Gln Arg Gly Leu Gly Glu Ala Gln Leu Gly Asn Ser Ser
305                 310                 315                 320

Gly Asn Phe Leu Leu Pro Asp Ala Gln Ser Ile Gln Ala Ala Ala Ala
                325                 330                 335

Gly Phe Ala Ser Lys Thr Pro Ala Asn Gln Ala Ile Ser Met Ile Asp
            340                 345                 350

Gly Pro Ala Pro Asp Gly Tyr Pro Ile Ile Asn Tyr Glu Tyr Ala Ile
```

```
        355                 360                 365

Val Asn Asn Arg Gln Lys Asp Ala Ala Thr Ala Gln Thr Leu Gln Ala
    370                 375                 380

Phe Leu His Trp Ala Ile Thr Asp Gly Asn Lys Ala Ser Phe Leu Asp
385                 390                 395                 400

Gln Val His Phe Gln Pro Leu Pro Pro Ala Val Val Lys Leu Ser Asp
                405                 410                 415

Ala Leu Ile Ala Thr Ile Ser Ser Ala Glu Met Lys Thr Asp Ala Ala
            420                 425                 430

Thr Leu Ala Gln Glu Ala Gly Asn Phe Glu Arg Ile Ser Gly Asp Leu
        435                 440                 445

Lys Thr Gln Ile Asp Gln Val Glu Ser Thr Ala Gly Ser Leu Gln Gly
    450                 455                 460

Gln Trp Arg Gly Ala Ala Gly Thr Ala Ala Gln Ala Ala Val Val Arg
465                 470                 475                 480

Phe Gln Glu Ala Ala Asn Lys Gln Lys Gln Glu Leu Asp Glu Ile Ser
                485                 490                 495

Thr Asn Ile Arg Gln Ala Gly Val Gln Tyr Ser Arg Ala Asp Glu Glu
            500                 505                 510

Gln Gln Gln Ala Leu Ser Ser Gln Met Gly Phe Val Pro Thr Thr Ala
        515                 520                 525

Ala Ser Pro Pro Ser Thr Ala Ala Ala Pro Pro Ala Pro Ala Thr Pro
    530                 535                 540

Val Ala Pro Pro Pro Pro Ala Ala Ala Asn Thr Pro Asn Ala Gln Pro
545                 550                 555                 560

Gly Asp Pro Asn Ala Ala Pro Pro Pro Ala Asp Pro Asn Ala Pro Pro
                565                 570                 575

Pro Pro Val Ile Ala Pro Asn Ala Pro Gln Pro Val Arg Ile Asp Asn
            580                 585                 590

Pro Val Gly Gly Phe Ser Phe Ala Leu Pro Ala Gly Trp Val Glu Ser
        595                 600                 605

Asp Ala Ala His Phe Asp Tyr Gly Ser Ala Leu Leu Ser Lys Thr Thr
    610                 615                 620

Gly Asp Pro Pro Phe Pro Gly Gln Pro Pro Pro Val Ala Asn Asp Thr
625                 630                 635                 640

Arg Ile Val Leu Gly Arg Leu Asp Gln Lys Leu Tyr Ala Ser Ala Glu
                645                 650                 655

Ala Thr Asp Ser Lys Ala Ala Ala Arg Leu Gly Ser Asp Met Gly Glu
            660                 665                 670

Phe Tyr Met Pro Tyr Pro Gly Thr Arg Ile Asn Gln Glu Thr Val Ser
        675                 680                 685

Leu Asp Ala Asn Gly Val Ser Gly Ser Ala Ser Tyr Tyr Glu Val Lys
    690                 695                 700

Phe Ser Asp Pro Ser Lys Pro Asn Gly Gln Ile Trp Thr Gly Val Ile
705                 710                 715                 720

Gly Ser Pro Ala Ala Asn Ala Pro Asp Ala Gly Pro Pro Gln Arg Trp
                725                 730                 735

Phe Val Val Trp Leu Gly Thr Ala Asn Asn Pro Val Asp Lys Gly Ala
            740                 745                 750

Ala Lys Ala Leu Ala Glu Ser Ile Arg Pro Leu Val Ala Pro Pro Pro
        755                 760                 765

Ala Pro Ala Pro Ala Pro Ala Glu Pro Ala Pro Ala Pro Ala Pro Ala
    770                 775                 780
```

Gly Glu Val Ala Pro Thr Pro Thr Thr Pro Thr Pro Gln Arg Thr Leu
785 790 795 800

Pro Ala

<210> SEQ ID NO 210
<211> LENGTH: 454
<212> TYPE: DNA
<213> ORGANISM: Mycobacterium tuberculosis

<400> SEQUENCE: 210
gtggcggcgc tgcggccggc cagcagagcg atgtgcatcc gttcgcgaac ctgatcgcgg 60
tcgacgatga gcgcgccgaa cgccgcgacg acgaagaacg tcaggaagcc gtccagcagc 120
gcggtccgcg cggtgacgaa gctgaccccg tcgcagatca gcagcacccc ggcgatggcg 180
ccgaccaatg tcgaccggct gatccgccgc acgatccgca ccaccagcgc caccaggacc 240
acacccagca gggcgccggt gaaccgccag ccgaatccgt tgtgaccgaa gatggcctcc 300
ccgatcgcga tcagctgctt accgaccggc gggtgaacca ccaggccgta cccggggttg 360
tcttccaccc catggttgtt cagcacctgc caggcctggc ggtgcgtaat gcttctcgtc 420
gaagatgggg gtgccggcat ccgtcaccga gccc 454

<210> SEQ ID NO 211
<211> LENGTH: 470
<212> TYPE: DNA
<213> ORGANISM: Mycobacterium tuberculosis

<400> SEQUENCE: 211
tgcagaagta cggcggatcc tcggtggccg acgccgaacg gattcgccgc gtcgccgaac 60
gcatcgtcgc caccaagaag caaggcaatg acgtcgtcgt cgtcgtctct gccatggggg 120
ataccaccga cgacctgctg gatctggctc agcaggtgtg cccggcgccg ccgcctcggg 180
agctggacat gctgcttacc gccggtgaac gcatctcgaa tgcgttggtg gccatggcca 240
tcgagtcgct cggcgcgcat gcccggtcgt tcaccggttc gcaggccggg gtgatcacca 300
ccggcaccca cggcaacgcc aagatcatcg acgtcacgcc ggggcggctg caaaccgccc 360
ttgaggaagg gcgggtcgtc ttggtggccg gattccaagg ggtcagccag gacaccaagg 420
atgtcacgac gttgggccgc ggcggctcgg acaccaccgc cgtcgccatg 470

<210> SEQ ID NO 212
<211> LENGTH: 279
<212> TYPE: DNA
<213> ORGANISM: Mycobacterium tuberculosis

<400> SEQUENCE: 212
ggccggcgta cccggccggg acaaacaacg atcgattgat atcgatgaga gacggaggaa 60
tcgtggccct tccccagttg accgacgagc agcgcgcggc cgcgttggag aaggctgctg 120
ccgcacgtcg agcgcgagca gagctcaagg atcggctcaa gcgtggcggc accaacctca 180
cccaggtcct caaggacgcg gagagcgatg aagtcttggg caaaatgaag gtgtctgcgc 240
tgcttgaggc cttgccaaag gtgggcaagg tccaggcgc 279

<210> SEQ ID NO 213
<211> LENGTH: 219
<212> TYPE: DNA
<213> ORGANISM: Mycobacterium tuberculosis

<400> SEQUENCE: 213
acacggtcga actcgacgag cccctcgtgg aggtgtcgac cgacaaggtc gacaccgaaa 60

-continued tccctcgccg gccgcgggtg tgctgaccaa gatcatcgcc caagaagatg acacggtcga 120
ggtcggcggc gagctctctg tcattggcga cgcccatgat gccggcgagg ccgcggtccc 180
ggcaccccag aaagtctctg ccggcccaac ccgaatcca 219

<210> SEQ ID NO 214
<211> LENGTH: 342
<212> TYPE: DNA
<213> ORGANISM: Mycobacterium tuberculosis

<400> SEQUENCE: 214
tcgctgccga catcggcgcc gcgcccgccc ccaagcccgc acccaagccc gtccccgagc 60
cagcgccgac gccgaaggcc gaacccgcac catcgccgcc ggcggcccag ccagccggtg 120
cggccgaggg cgcaccgtac gtgacgccgc tggtgcgaaa gctggcgtcg gaaaacaaca 180
tcgacctcgc cggggtgacc ggcaccggag tgggtggtcg catccgcaaa caggatgtgc 240
tggccgcggc tgaacaaaag aagcgggcga aagcaccggc gccggccgcc caggccgccg 300
ccgcgccggc cccgaaagcg ccgcctgaag atccgatgcc gc 342

<210> SEQ ID NO 215
<211> LENGTH: 515
<212> TYPE: DNA
<213> ORGANISM: Mycobacterium tuberculosis

<400> SEQUENCE: 215
gggtcttggt cagtatcagc gccgacgagg acgccacggt gcccgtcggc ggcgagttgg 60
cccggatcgg tgtcgctgcc gacatcggcg ccgcgcccgc ccccaagccc gcacccaagc 120
ccgtccccga gccagcgccg acgccgaagg ccgaacccgc accatcgccg ccggcggccc 180
agccagccgg tgcggccgag ggcgcaccgt acgtgacgcc gctggtgcga aagctggcgt 240
cggaaaacaa catcgacctc gccggggtga ccggcaccgg agtgggtggt cgcatccgca 300
aacaggatgt gctggccgcg gctgaacaaa agaagcgggc gaaagcaccg gcgccctgag 360
cgcttcatca cccggttaac cagcttgccc cagaagccgg cttcgacctc ttcgcgggtc 420
ttggtccgct gcaggcggtc ggcgagccag ttcaggttag gcggccgaaa tcttccagtt 480
cgccaggaag ggcacccgga acagggtccg caccc 515

<210> SEQ ID NO 216
<211> LENGTH: 557
<212> TYPE: DNA
<213> ORGANISM: Mycobacterium tuberculosis

<400> SEQUENCE: 216
ccgaccccaa ggtgcagatt caacaggcca ttgaggaagc acagcgcacc caccaagcgc 60
tgactcaaca ggcggcgcaa gtgatcggta accagcgtca attggagatg cgactcaacc 120
gacagctggc ggacatcgaa aagcttcagg tcaatgtgcg ccaagccctg acgctggccg 180
accaggccac cgccgccgga gacgctgcca aggccaccga atacaacaac gccgccgagg 240
cgttcgcagc ccagctggtg accgccgagc agagcgtcga agacctcaag acgctgcatg 300
accaggcgct tagcgccgca gctcaggcca agaaggccgt cgaacgaaat gcgatggtgc 360
tgcagcagaa gatcgccgag cgaaccaagc tgctcagcca gctcgagcag gcgaagatgc 420
aggagcaggt cagcgcatcg ttgcggtcga tgagtgagct cgccgcgcca ggcaacacgc 480
cgagcctcga cgaggtgcgc gacaagatcg agcgtcgcta cgccaacgcg atcggttcgg 540
ctgaacttgc cgagagt 557

-continued

<210> SEQ ID NO 217
<211> LENGTH: 223
<212> TYPE: DNA
<213> ORGANISM: Mycobacterium tuberculosis

<400> SEQUENCE: 217
caggataggt ttcgacatcc acctgggttc cgcacccggt gcgcgaccgt gtgataggcc 60
agaggtggac ctgcgccgac cgacgatcga tcgaggagtc aacagaaatg gccttctccg 120
tccagatgcc ggcactcggt gagagcgtca ccgaggggac ggttacccgc tggctcaaac 180
aggaaggcga cacggtcgaa ctcgacgagc ccctcgtgga ggt 223

<210> SEQ ID NO 218
<211> LENGTH: 578
<212> TYPE: DNA
<213> ORGANISM: Mycobacterium tuberculosis

<400> SEQUENCE: 218
aagaagtaca tctgccggtc gatgtcggcg aaccacggca gccaaccggc gcagtagccg 60
accaggacca ccgcataacg ccagtcccgg cgcacaaaca tacgccaccc cgcgtatgcc 120
aggactggca ccgccagcca ccacatcgcg ggcgtgccga ccagcatctc ggccttgacg 180
cacgactgtg cgccgcagcc tgcaacgtct tgctggtcga tggcgtacag caccggccgc 240
aacgacatgg gccaggtcca cggtttggat tcccaagggt ggtagttgcc tgcggaattc 300
gtcaggcccg cgtggaagtg gaacgctttg gcggtgtatt gccagagcga gcgcacggcg 360
tcgggcagcg gaacaaccga gttgcgaccg accgcttgac cgaccgcatg ccgatcgatc 420
gcggtctcgg acgcgaacca cggagcgtag gtggccagat agaccgcgaa cgggatcaac 480
cccagcgcat acccgctggg aagcacgtca cgccgcactg ttcccagcca cggtctttgc 540
acttggtatg aacgtcgcgc cgccacgtca acgccagc 578

<210> SEQ ID NO 219
<211> LENGTH: 484
<212> TYPE: DNA
<213> ORGANISM: Mycobacterium tuberculosis

<400> SEQUENCE: 219
acaacgatcg attgatatcg atgagagacg gaggaatcgt ggcccttccc cagttgaccg 60
acgagcagcg cgcggccgcg ttggagaagg ctgctgccgc acgtcgagcg cgagcagagc 120
tcaaggatcg gctcaagcgt ggcggcacca acctcaccca ggtcctcaag gacgcggaga 180
gcgatgaagt cttgggcaaa atgaaggtgt ctgcgctgct tgaggccttg ccaaaggtgg 240
gcaaggtcaa ggcgcaggag atcatgaccg agctggaaat tgcgccccac cccgccgcct 300
tcgtggcctc ggtgaccgtc agcgcaaggc cctgctggaa aagttcggct ccgcctaacc 360
ccgccggccg acgatgcggg ccggaaggcc tgtggtgggc gtacccccgc atacggggga 420
gaagcggcct gacagggcca gctcacaatt caggccgaac gccccggtgg gggggaaccc 480
gccc 484

<210> SEQ ID NO 220
<211> LENGTH: 537
<212> TYPE: DNA
<213> ORGANISM: Mycobacterium tuberculosis

<400> SEQUENCE: 220
aggactggca ccgccagcca ccacatcgcg ggcgtgccga ccagcatctc ggccttgacg 60

```
cacgactgtg cgccgcagcc tgcaacgtct tgctggtcga tggcgtacag caccggccgc    120

aacgacatgg gccaggtcca cggtttggat tcccaagggt ggtagttgcc tgcggaattc    180

gtcaggcccg cgtggaagtg gaacgctttg gcggtgtagt gccagagcga gcgcacggcg    240

tcgggcagcg gaacaaccga gttgcgaccg accgcttgac cgaccgcatg ccgatcgatc    300

gcggtctcgg acgcgaacca cggagcgtag gtggccagat agaccgcgaa cgggatcaac    360

cccagcgcat acccgctggg aagcacgtca cgccgcactg tccccagcca cggtctttgc    420

acttggtact gacgtcgcgc cgccacgtcg aacgccagcg ccatcgcgcc gaagaacagc    480

acgaagtaca cgccggacca cttggtggcg caagccaatc ccaagcagca ccccggc       537
```

<210> SEQ ID NO 221
<211> LENGTH: 135
<212> TYPE: PRT
<213> ORGANISM: Mycobacterium tuberculosis

<400> SEQUENCE: 221

```
Gly Gly Ala Ala Ala Gly Gln Gln Ser Asp Val His Pro Phe Ala Asn
  1               5                  10                  15

Leu Ile Ala Val Asp Asp Glu Arg Ala Glu Arg Arg Asp Asp Glu Glu
             20                  25                  30

Arg Gln Glu Ala Val Gln Gln Arg Gly Pro Arg Gly Asp Glu Ala Asp
         35                  40                  45

Pro Val Ala Asp Gln Gln His Pro Gly Asp Gly Ala Asp Gln Cys Arg
     50                  55                  60

Pro Ala Asp Pro Pro His Asp Pro His His Gln Arg His Gln Asp His
 65                  70                  75                  80

Thr Gln Gln Gly Ala Gly Glu Pro Pro Ala Glu Ser Val Val Thr Glu
                 85                  90                  95

Asp Gly Leu Pro Asp Arg Asp Gln Leu Leu Thr Asp Arg Arg Val Asn
            100                 105                 110

His Gln Ala Val Pro Gly Val Val Phe His Pro Met Val Val Gln His
        115                 120                 125

Leu Pro Gly Leu Ala Val Arg
    130                 135
```

<210> SEQ ID NO 222
<211> LENGTH: 156
<212> TYPE: PRT
<213> ORGANISM: Mycobacterium tuberculosis

<400> SEQUENCE: 222

```
Gln Lys Tyr Gly Gly Ser Ser Val Ala Asp Ala Glu Arg Ile Arg Arg
  1               5                  10                  15

Val Ala Glu Arg Ile Val Ala Thr Lys Lys Gln Gly Asn Asp Val Val
             20                  25                  30

Val Val Val Ser Ala Met Gly Asp Thr Thr Asp Asp Leu Leu Asp Leu
         35                  40                  45

Ala Gln Gln Val Cys Pro Ala Pro Pro Pro Arg Glu Leu Asp Met Leu
     50                  55                  60

Leu Thr Ala Gly Glu Arg Ile Ser Asn Ala Leu Val Ala Met Ala Ile
 65                  70                  75                  80

Glu Ser Leu Gly Ala His Ala Arg Ser Phe Thr Gly Ser Gln Ala Gly
                 85                  90                  95

Val Ile Thr Thr Gly Thr His Gly Asn Ala Lys Ile Ile Asp Val Thr
            100                 105                 110
```

Pro Gly Arg Leu Gln Thr Ala Leu Glu Glu Gly Arg Val Val Leu Val
115 120 125

Ala Gly Phe Gln Gly Val Ser Gln Asp Thr Lys Asp Val Thr Thr Leu
130 135 140

Gly Arg Gly Gly Ser Asp Thr Thr Ala Val Ala Met
145 150 155

<210> SEQ ID NO 223
<211> LENGTH: 92
<212> TYPE: PRT
<213> ORGANISM: Mycobacterium tuberculosis

<400> SEQUENCE: 223

Pro Ala Tyr Pro Ala Gly Thr Asn Asn Asp Arg Leu Ile Ser Met Arg
1 5 10 15

Asp Gly Gly Ile Val Ala Leu Pro Gln Leu Thr Asp Glu Gln Arg Ala
20 25 30

Ala Ala Leu Glu Lys Ala Ala Ala Ala Arg Arg Ala Arg Ala Glu Leu
35 40 45

Lys Asp Arg Leu Lys Arg Gly Gly Thr Asn Leu Thr Gln Val Leu Lys
50 55 60

Asp Ala Glu Ser Asp Glu Val Leu Gly Lys Met Lys Val Ser Ala Leu
65 70 75 80

Leu Glu Ala Leu Pro Lys Val Gly Lys Val Gln Ala
85 90

<210> SEQ ID NO 224
<211> LENGTH: 72
<212> TYPE: PRT
<213> ORGANISM: Mycobacterium tuberculosis

<400> SEQUENCE: 224

Thr Val Glu Leu Asp Glu Pro Leu Val Glu Val Ser Thr Asp Lys Val
1 5 10 15

Asp Thr Glu Ile Pro Ser Pro Ala Ala Gly Val Leu Thr Lys Ile Ile
20 25 30

Ala Gln Glu Asp Asp Thr Val Glu Val Gly Gly Glu Leu Ser Val Ile
35 40 45

Gly Asp Ala His Asp Ala Gly Glu Ala Ala Val Pro Ala Pro Gln Lys
50 55 60

Val Ser Ala Gly Pro Thr Arg Ile
65 70

<210> SEQ ID NO 225
<211> LENGTH: 113
<212> TYPE: PRT
<213> ORGANISM: Mycobacterium tuberculosis

<400> SEQUENCE: 225

Ala Ala Asp Ile Gly Ala Ala Pro Ala Pro Lys Pro Ala Pro Lys Pro
1 5 10 15

Val Pro Glu Pro Ala Pro Thr Pro Lys Ala Glu Pro Ala Pro Ser Pro
20 25 30

Pro Ala Ala Gln Pro Ala Gly Ala Ala Glu Gly Ala Pro Tyr Val Thr
35 40 45

Pro Leu Val Arg Lys Leu Ala Ser Glu Asn Asn Ile Asp Leu Ala Gly
50 55 60

Val Thr Gly Thr Gly Val Gly Gly Arg Ile Arg Lys Gln Asp Val Leu 65 70 75 80

Ala Ala Ala Glu Gln Lys Lys Arg Ala Lys Ala Pro Ala Pro Ala Ala
85 90 95

Gln Ala Ala Ala Ala Pro Ala Pro Lys Ala Pro Pro Glu Asp Pro Met
100 105 110

Pro

<210> SEQ ID NO 226
<211> LENGTH: 118
<212> TYPE: PRT
<213> ORGANISM: Mycobacterium tuberculosis

<400> SEQUENCE: 226

Val Leu Val Ser Ile Ser Ala Asp Glu Asp Ala Thr Val Pro Val Gly
1 5 10 15

Gly Glu Leu Ala Arg Ile Gly Val Ala Ala Asp Ile Gly Ala Ala Pro
20 25 30

Ala Pro Lys Pro Ala Pro Lys Pro Val Pro Glu Pro Ala Pro Thr Pro
35 40 45

Lys Ala Glu Pro Ala Pro Ser Pro Pro Ala Ala Gln Pro Ala Gly Ala
50 55 60

Ala Glu Gly Ala Pro Tyr Val Thr Pro Leu Val Arg Lys Leu Ala Ser
65 70 75 80

Glu Asn Asn Ile Asp Leu Ala Gly Val Thr Gly Thr Gly Val Gly Gly
85 90 95

Arg Ile Arg Lys Gln Asp Val Leu Ala Ala Ala Glu Gln Lys Lys Arg
100 105 110

Ala Lys Ala Pro Ala Pro
115

<210> SEQ ID NO 227
<211> LENGTH: 185
<212> TYPE: PRT
<213> ORGANISM: Mycobacterium tuberculosis

<400> SEQUENCE: 227

Asp Pro Lys Val Gln Ile Gln Gln Ala Ile Glu Glu Ala Gln Arg Thr
1 5 10 15

His Gln Ala Leu Thr Gln Gln Ala Ala Gln Val Ile Gly Asn Gln Arg
20 25 30

Gln Leu Glu Met Arg Leu Asn Arg Gln Leu Ala Asp Ile Glu Lys Leu
35 40 45

Gln Val Asn Val Arg Gln Ala Leu Thr Leu Ala Asp Gln Ala Thr Ala
50 55 60

Ala Gly Asp Ala Ala Lys Ala Thr Glu Tyr Asn Asn Ala Ala Glu Ala
65 70 75 80

Phe Ala Ala Gln Leu Val Thr Ala Glu Gln Ser Val Glu Asp Leu Lys
85 90 95

Thr Leu His Asp Gln Ala Leu Ser Ala Ala Ala Gln Ala Lys Lys Ala
100 105 110

Val Glu Arg Asn Ala Met Val Leu Gln Gln Lys Ile Ala Glu Arg Thr
115 120 125

Lys Leu Leu Ser Gln Leu Glu Gln Ala Lys Met Gln Glu Gln Val Ser
130 135 140

Ala Ser Leu Arg Ser Met Ser Glu Leu Ala Ala Pro Gly Asn Thr Pro
145 150 155 160

```
Ser Leu Asp Glu Val Arg Asp Lys Ile Glu Arg Arg Tyr Ala Asn Ala
                165                 170                 175

Ile Gly Ser Ala Glu Leu Ala Glu Ser
            180                 185


<210> SEQ ID NO 228
<211> LENGTH: 71
<212> TYPE: PRT
<213> ORGANISM: Mycobacterium tuberculosis

<400> SEQUENCE: 228

Val Ser Thr Ser Thr Trp Val Pro His Pro Val Arg Asp Arg Val Ile
  1               5                  10                  15

Gly Gln Arg Trp Thr Cys Ala Asp Arg Arg Ser Ile Glu Glu Ser Thr
             20                  25                  30

Glu Met Ala Phe Ser Val Gln Met Pro Ala Leu Gly Glu Ser Val Thr
         35                  40                  45

Glu Gly Thr Val Thr Arg Trp Leu Lys Gln Glu Gly Asp Thr Val Glu
     50                  55                  60

Leu Asp Glu Pro Leu Val Glu
 65                  70


<210> SEQ ID NO 229
<211> LENGTH: 182
<212> TYPE: PRT
<213> ORGANISM: Mycobacterium tuberculosis

<400> SEQUENCE: 229

Glu Val His Leu Pro Val Asp Val Gly Glu Pro Arg Gln Pro Thr Gly
  1               5                  10                  15

Ala Val Ala Asp Gln Asp His Arg Ile Thr Pro Val Pro Ala His Lys
             20                  25                  30

His Thr Pro Pro Arg Val Cys Gln Asp Trp His Arg Gln Pro Pro His
         35                  40                  45

Arg Gly Arg Ala Asp Gln His Leu Gly Leu Asp Ala Arg Leu Cys Ala
     50                  55                  60

Ala Ala Cys Asn Val Leu Leu Val Asp Gly Val Gln His Arg Pro Gln
 65                  70                  75                  80

Arg His Gly Pro Gly Pro Arg Phe Gly Phe Pro Arg Val Val Val Ala
                 85                  90                  95

Cys Gly Ile Arg Gln Ala Arg Val Glu Val Glu Arg Phe Gly Gly Val
            100                 105                 110

Leu Pro Glu Arg Ala His Gly Val Gly Gln Arg Asn Asn Arg Val Ala
        115                 120                 125

Thr Asp Arg Leu Thr Asp Arg Met Pro Ile Asp Arg Gly Leu Gly Arg
    130                 135                 140

Glu Pro Arg Ser Val Gly Gly Gln Ile Asp Arg Glu Arg Asp Gln Pro
145                 150                 155                 160

Gln Arg Ile Pro Ala Gly Lys His Val Thr Pro His Cys Ser Gln Pro
                165                 170                 175

Arg Ser Leu His Leu Val
            180


<210> SEQ ID NO 230
<211> LENGTH: 160
<212> TYPE: PRT
<213> ORGANISM: Mycobacterium tuberculosis

<400> SEQUENCE: 230
```

```
Asn Asp Arg Leu Ile Ser Met Arg Asp Gly Gly Ile Val Ala Leu Pro
  1               5                  10                  15

Gln Leu Thr Asp Glu Gln Arg Ala Ala Ala Leu Glu Lys Ala Ala Ala
             20                  25                  30

Ala Arg Arg Ala Arg Ala Glu Leu Lys Asp Arg Leu Lys Arg Gly Gly
         35                  40                  45

Thr Asn Leu Thr Gln Val Leu Lys Asp Ala Glu Ser Asp Glu Val Leu
     50                  55                  60

Gly Lys Met Lys Val Ser Ala Leu Leu Glu Ala Leu Pro Lys Val Gly
 65                  70                  75                  80

Lys Val Lys Ala Gln Glu Ile Met Thr Glu Leu Glu Ile Ala Pro His
                 85                  90                  95

Pro Ala Ala Phe Val Ala Ser Val Thr Val Ser Ala Arg Pro Cys Trp
            100                 105                 110

Lys Ser Ser Ala Pro Pro Asn Pro Ala Gly Arg Arg Cys Gly Pro Glu
        115                 120                 125

Gly Leu Trp Trp Ala Tyr Pro Arg Ile Arg Gly Arg Ser Gly Leu Thr
    130                 135                 140

Gly Pro Ala His Asn Ser Gly Arg Thr Pro Arg Trp Gly Gly Thr Arg
145                 150                 155                 160


<210> SEQ ID NO 231
<211> LENGTH: 178
<212> TYPE: PRT
<213> ORGANISM: Mycobacterium tuberculosis

<400> SEQUENCE: 231

Asp Trp His Arg Gln Pro Pro His Arg Gly Arg Ala Asp Gln His Leu
  1               5                  10                  15

Gly Leu Asp Ala Arg Leu Cys Ala Ala Ala Cys Asn Val Leu Leu Val
             20                  25                  30

Asp Gly Val Gln His Arg Pro Gln Arg His Gly Pro Gly Pro Arg Phe
         35                  40                  45

Gly Phe Pro Arg Val Val Val Ala Cys Gly Ile Arg Gln Ala Arg Val
     50                  55                  60

Glu Val Glu Arg Phe Gly Gly Val Val Pro Glu Arg Ala His Gly Val
 65                  70                  75                  80

Gly Gln Arg Asn Asn Arg Val Ala Thr Asp Arg Leu Thr Asp Arg Met
                 85                  90                  95

Pro Ile Asp Arg Gly Leu Gly Arg Glu Pro Arg Ser Val Gly Gly Gln
            100                 105                 110

Ile Asp Arg Glu Arg Asp Gln Pro Gln Arg Ile Pro Ala Gly Lys His
        115                 120                 125

Val Thr Pro His Cys Pro Gln Pro Arg Ser Leu His Leu Val Leu Thr
    130                 135                 140

Ser Arg Arg His Val Glu Arg Gln Arg His Arg Ala Glu Glu Gln His
145                 150                 155                 160

Glu Val His Ala Gly Pro Leu Gly Gly Ala Ser Gln Ser Gln Ala Ala
                165                 170                 175

Pro Arg


<210> SEQ ID NO 232
<211> LENGTH: 271
<212> TYPE: DNA
<213> ORGANISM: Mycobacterium tuberculosis
```

<400> SEQUENCE: 232
atgccaagcc ggtgctgatg cccgagctcg gcgaatcggt gaccgagggg accgtcattc 60
gttggctgaa gaagatcggg gattcggttc aggttgacga gccactcgtg gaggtgtcca 120
ccgacaaggt ggacaccgag atcccgtccc cggtggctgg ggtcttggtc agtatcagcg 180
ccgacgagga cgccacggtg cccgtcggcg gcgagttggc ccggatcggt gtcgctgccg 240
agatcggcgc cgcgcccgcc cccaagcccc c 271

<210> SEQ ID NO 233
<211> LENGTH: 89
<212> TYPE: PRT
<213> ORGANISM: Mycobacterium tuberculosis

<400> SEQUENCE: 233

Ala Lys Pro Val Leu Met Pro Glu Leu Gly Glu Ser Val Thr Glu Gly
1 5 10 15

Thr Val Ile Arg Trp Leu Lys Lys Ile Gly Asp Ser Val Gln Val Asp
20 25 30

Glu Pro Leu Val Glu Val Ser Thr Asp Lys Val Asp Thr Glu Ile Pro
35 40 45

Ser Pro Val Ala Gly Val Leu Val Ser Ile Ser Ala Asp Glu Asp Ala
50 55 60

Thr Val Pro Val Gly Gly Glu Leu Ala Arg Ile Gly Val Ala Ala Glu
65 70 75 80

Ile Gly Ala Ala Pro Ala Pro Lys Pro
85

<210> SEQ ID NO 234
<211> LENGTH: 107
<212> TYPE: DNA
<213> ORGANISM: Mycobacterium tuberculosis

<400> SEQUENCE: 234
gaggtagcgg atggccggag gagcacccca ggaccgcgcc cgaaccgcgg gtgccggtca 60
tcgatatgtg ggcaccgttc gttccgtccg ccgaggtcat tgacgat 107

<210> SEQ ID NO 235
<211> LENGTH: 339
<212> TYPE: DNA
<213> ORGANISM: Mycobacterium tuberculosis

<400> SEQUENCE: 235
atgaagttga agtttgctcg cctgagtact gcgatactgg gttgtgcagc ggcgcttgtg 60
tttcctgcct cggttgccag cgcagatcca cctgacccgc atcagccgga catgacgaaa 120
ggctattgcc cgggtggccg atggggtttt ggcgacttgg ccgtgtgcga cggcgagaag 180
taccccgacg gctcgttttg gcaccagtgg atgcaaacgt ggtttaccgg cccacagttt 240
tacttcgatt gtgtcagcgg cggtgagccc ctccccggcc cgccgccacc gggtggttgc 300
ggtggggcaa ttccgtccga gcagcccaac gctccctga 339

<210> SEQ ID NO 236
<211> LENGTH: 112
<212> TYPE: PRT
<213> ORGANISM: Mycobacterium tuberculosis

<400> SEQUENCE: 236

Met Lys Leu Lys Phe Ala Arg Leu Ser Thr Ala Ile Leu Gly Cys Ala
1 5 10 15

-continued

```
Ala Ala Leu Val Phe Pro Ala Ser Val Ala Ser Ala Asp Pro Pro Asp
            20                  25                  30

Pro His Gln Pro Asp Met Thr Lys Gly Tyr Cys Pro Gly Gly Arg Trp
        35                  40                  45

Gly Phe Gly Asp Leu Ala Val Cys Asp Gly Glu Lys Tyr Pro Asp Gly
    50                  55                  60

Ser Phe Trp His Gln Trp Met Gln Thr Trp Phe Thr Gly Pro Gln Phe
65                  70                  75                  80

Tyr Phe Asp Cys Val Ser Gly Gly Glu Pro Leu Pro Gly Pro Pro Pro
                85                  90                  95

Pro Gly Gly Cys Gly Gly Ala Ile Pro Ser Glu Gln Pro Asn Ala Pro
            100                 105                 110
```

<210> SEQ ID NO 237
<211> LENGTH: 371
<212> TYPE: DNA
<213> ORGANISM: Mycobacterium tuberculosis

<400> SEQUENCE: 237

```
gtgaccacgg tgggcctgcc accaacccgg gcagcggcag ccgcggcggc gccggcggct     60

ccggcggcaa cggtggcgcc gggggtaacg ccaccggctc aggcggcaag ggcggcgccg    120

gtggcaatgg cggtgatggg agcttcggcg ctaccagcgg ccccgcctcc atcggggtca    180

cgggcgcccc cggcggcaac ggcggcaagg gcggcgccgg tggcagcaac cccaacggct    240

caggtggcga cggcggcaaa ggcggcaacg gcggtgccgg cggcaacggg ggctcgatcg    300

gcgccaacag cggcatcgtc ggcggttccg gtggggccgg tggcgctggc ggcgccggcg    360

gaaacggcag c                                                         371
```

<210> SEQ ID NO 238
<211> LENGTH: 424
<212> TYPE: DNA
<213> ORGANISM: Mycobacterium tuberculosis

<400> SEQUENCE: 238

```
gtccgggtcc caccaccgcg ccggcgcgcc cctagcggcc gggcgcacca gccccttttc     60

ttgactcgtt caagaaaagg gccttctgtt tggtcggcca tgttggcatg atcgtgaccc    120

atgggcaaca tcgacgtcga catctcggcc aaggtctagc tccatgcgaa tcgccgccgc    180

ggtggtgagc atcggtctag ccgtcatagc agggttcgcg gtacctgttg ccgacgcaca    240

cccgtcggag cccggggttg tgtcctacgc ggtgctcgga aaggggtcgg tcggcaacat    300

cgtcggcgcc ccaatggggt gggaggcggt gttcaccaag ccgttccagg cgttttgggt    360

cgaactaccg gcgtgcaaca actgggtgga catcgggctg cccgaggtgt acgacgatcc    420

cgac                                                                 424
```

<210> SEQ ID NO 239
<211> LENGTH: 317
<212> TYPE: DNA
<213> ORGANISM: Mycobacterium tuberculosis

<400> SEQUENCE: 239

```
gcgatggcgg ccgcgggtac caccgccaat gtggaacggt ttcccaaccc caacgatcct     60

ttgcatctgg cgtcaattga cttcagcccg gccgatttcg tcaccgaggg ccaccgtcta    120

agggcggatg cgatcctact gcgccgtacc gaccggctgc ctttcgccga gccgccggat    180

tgggacttgg tggagtcgca gttgcgcacg accgtcaccg ccgacacggt gcgcatcgac    240
```

gtcatcgccg acgatatgcg tcccgaactg gcggcggcgt ccaaactcac cgaatcgctg 300
cggctctacg attcgtc 317

<210> SEQ ID NO 240
<211> LENGTH: 422
<212> TYPE: DNA
<213> ORGANISM: Mycobacterium tuberculosis

<400> SEQUENCE: 240
tggcgtatgc gcttcgcagc cggtgccgcg tcaacgcgcc ggaggcaatc gcttcgctgc 60
cgaggaatgg ttcgatcacg atcgcagtgt gccgtcgtgc accgacaccg ccgtccaacg 120
tgaactgagg gcggaaaatc ggccgaaatc tcgccctcag ttcacgctcg gcgcctaacg 180
gttctggaag ttgggtgcgc gcttctcggc gaacgcgcgc gggccttcct tggcgtcgtc 240
ggacaggaag accttgatgc cgatctgggt gtcgatcttg aacgcctcgt tttcgggcat 300
gcactcggtc tcgcggatgg accgcaagat ggcctgcacg gccaggggtc cgttagccga 360
gatggcgtcg gcaagttcta gaaccttggt caacgcctgg ccgtcgggca cacgtggccg 420
at 422

<210> SEQ ID NO 241
<211> LENGTH: 426
<212> TYPE: DNA
<213> ORGANISM: Mycobacterium tuberculosis

<400> SEQUENCE: 241
gcgtgccgct gaacaccagc ccgcggctgc cagatctccc ggactcggta gtgccgccgg 60
tggcgtcgtt gctctcctga cggggcgcgg cgaccataag gtcgctaatg cccaggtagc 120
ggcccaggtg catggagtcg atgatgatgc gactctccag ctcgccgacc gggagcttgg 180
catcgggcct gatcagccag gacgcgtagg acaagtcgat cgaatgcata gtggcctcca 240
gagtggccgt gccacttccg gcgtgctcca cggcaaatgc cttgatttct agctccgcgt 300
agtgttcccg catcgcctgc gggatgaatg ggaaccgcag gatggcgaca aacgggtctg 360
acctcaggtt tgccgctttg cgcacagtgg tcgacagccg gtactcggca taaatgctgg 420
ccccga 426

<210> SEQ ID NO 242
<211> LENGTH: 327
<212> TYPE: DNA
<213> ORGANISM: Mycobacterium tuberculosis

<400> SEQUENCE: 242
agaccggcga gggtgtggtc gctgcccgcg gcattgtcga taatctgcgc tgggtcgacg 60
cgccgatcaa ctagtgaggc gcaacgctag gctttgggat acccacagct aaaaagttta 120
tcaaagaaac gaagaaggtt gccatgagca ctgttgccgc ctacgccgcc atgtcggcga 180
ccgaacccct gaccaagacc acgatcaccc gtcgcgaccc gggcccgcac gacatggcga 240
tcgacatcaa attcgccgga atctgtcgct cggacatcca taccgtccaa accgaatggg 300
ggcaaccgaa tttacctgtg gtccctg 327

<210> SEQ ID NO 243
<211> LENGTH: 123
<212> TYPE: PRT
<213> ORGANISM: Mycobacterium tuberculosis

<400> SEQUENCE: 243

-continued

```
Asp His Gly Gly Pro Ala Thr Asn Pro Gly Ser Gly Ser Arg Gly Gly
  1               5                  10                  15

Ala Gly Gly Ser Gly Gly Asn Gly Gly Ala Gly Gly Asn Ala Thr Gly
             20                  25                  30

Ser Gly Gly Lys Gly Gly Ala Gly Gly Asn Gly Gly Asp Gly Ser Phe
         35                  40                  45

Gly Ala Thr Ser Gly Pro Ala Ser Ile Gly Val Thr Gly Ala Pro Gly
     50                  55                  60

Gly Asn Gly Gly Lys Gly Gly Ala Gly Gly Ser Asn Pro Asn Gly Ser
 65                  70                  75                  80

Gly Gly Asp Gly Gly Lys Gly Gly Asn Gly Gly Ala Gly Gly Asn Gly
                 85                  90                  95

Gly Ser Ile Gly Ala Asn Ser Gly Ile Val Gly Gly Ser Gly Gly Ala
            100                 105                 110

Gly Gly Ala Gly Gly Ala Gly Gly Asn Gly Ser
        115                 120


<210> SEQ ID NO 244
<211> LENGTH: 104
<212> TYPE: PRT
<213> ORGANISM: Mycobacterium tuberculosis

<400> SEQUENCE: 244

Met Ala Ala Ala Gly Thr Thr Ala Asn Val Glu Arg Phe Pro Asn Pro
  1               5                  10                  15

Asn Asp Pro Leu His Leu Ala Ser Ile Asp Phe Ser Pro Ala Asp Phe
             20                  25                  30

Val Thr Glu Gly His Arg Leu Arg Ala Asp Ala Ile Leu Leu Arg Arg
         35                  40                  45

Thr Asp Arg Leu Pro Phe Ala Glu Pro Pro Asp Trp Asp Leu Val Glu
     50                  55                  60

Ser Gln Leu Arg Thr Thr Val Thr Ala Asp Thr Val Arg Ile Asp Val
 65                  70                  75                  80

Ile Ala Asp Asp Met Arg Pro Glu Leu Ala Ala Ala Ser Lys Leu Thr
                 85                  90                  95

Glu Ser Leu Arg Leu Tyr Asp Ser
            100


<210> SEQ ID NO 245
<211> LENGTH: 41
<212> TYPE: PRT
<213> ORGANISM: Mycobacterium tuberculosis

<400> SEQUENCE: 245

Ala Tyr Ala Leu Arg Ser Arg Cys Arg Val Asn Ala Pro Glu Ala Ile
  1               5                  10                  15

Ala Ser Leu Pro Arg Asn Gly Ser Ile Thr Ile Ala Val Cys Arg Arg
             20                  25                  30

Ala Pro Thr Pro Pro Ser Asn Val Asn
         35                  40


<210> SEQ ID NO 246
<211> LENGTH: 25
<212> TYPE: PRT
<213> ORGANISM: Mycobacterium tuberculosis

<400> SEQUENCE: 246

Val Pro Leu Asn Thr Ser Pro Arg Leu Pro Asp Leu Pro Asp Ser Val
```

1 5 10 15

Val Pro Pro Val Ala Ser Leu Leu Ser
20 25

<210> SEQ ID NO 247
<211> LENGTH: 61
<212> TYPE: PRT
<213> ORGANISM: Mycobacterium tuberculosis

<400> SEQUENCE: 247

Met Ser Thr Val Ala Ala Tyr Ala Ala Met Ser Ala Thr Glu Pro Leu
1 5 10 15

Thr Lys Thr Thr Ile Thr Arg Arg Asp Pro Gly Pro His Asp Met Ala
20 25 30

Ile Asp Ile Lys Phe Ala Gly Ile Cys Arg Ser Asp Ile His Thr Val
35 40 45

Gln Thr Glu Trp Gly Gln Pro Asn Leu Pro Val Val Pro
50 55 60

<210> SEQ ID NO 248
<211> LENGTH: 213
<212> TYPE: DNA
<213> ORGANISM: Mycobacterium tuberculosis

<400> SEQUENCE: 248
gcttggagcc ctggagcgac ggtgtgggtc tgggggtcga ttcgttctcg gcgaaagtca 60
actaaagacc acgttgacac ccaaccggcg gcccggcatg ggccgtcgcg gcgtagaagc 120
tttgaccgcg gcgcgaaacg ttcgctgctg cggcccatgc agatcgcaca cgcttgcttg 180
aacatcgggt ggagccggtg gtaacgccag gct 213

<210> SEQ ID NO 249
<211> LENGTH: 367
<212> TYPE: DNA
<213> ORGANISM: Mycobacterium tuberculosis

<400> SEQUENCE: 249
ccgagctgct gttcggcgcc ggcggtgcgg gcggcgcggg tggggcgggc accgacggcg 60
ggcccggtgc taccggcggg accggcggac acggcggagt cggcggcgac ggcggatggc 120
tggcacccgg cggggccggc ggggccggcg ggcaaggcgg ggcaggtggt gcccgcagcg 180
atggtggcgc gttgggtggt accggcggga cgggcggtac cggcggcgcc ggtggcgccg 240
gcggtcgcgg cacactgctg ctgggcgctg gcggacaggg cggcctcggc ggcgccggcg 300
gacaaggcgg caccggcggg ggccggcgga gatggcgttc tggggggtgt cagtggcact 360
ggtggta 367

<210> SEQ ID NO 250
<211> LENGTH: 420
<212> TYPE: DNA
<213> ORGANISM: Mycobacterium tuberculosis

<400> SEQUENCE: 250
aaggcgtgat tggcaaggcg accgcgcagc ggcccgtagc cgcgggacgg cccaggcccc 60
gaccgcagcg gccggtgtct gaccgggtca gcgaccagcg gcgctgaccg tgccgctcgt 120
ctacttcgac gccagcgcct tcgtcaaact tctcaccacc gagacaggga gctcgctggc 180
gtccgctcta tgggacggct gcgacgccgc attgtccaac cgcctggcct accccgaagt 240
ccgcgccgca ctcgctgcaa cgggccgcaa tcacgaccta accgaatccg agctcgccga 300
cgccgagcgt gactgggagg acttctgggc cgcacccgcc cagtcgaact caccgcgacg 360
gttgaacagc acgccgggca cctcgcccga acacatgcct tacgcggagc cgacaccgtt 420

<210> SEQ ID NO 251
<211> LENGTH: 299
<212> TYPE: DNA
<213> ORGANISM: Mycobacterium tuberculosis

<400> SEQUENCE: 251
ctcttgtcgg tggcatcggc ggtaccggcg gaaccggcgg caacgccggt atgctcgccg 60
gcgccgccgg ggccggcggt gccggcgggt tcagcttcag cactgccggt ggggctggcg 120
gcgccggcgg ggccggtggg ctgttcacca ccggcggtgt cggcggcgcc ggtgggcagg 180
gtcacacggg cggggcgggc ggcgccggcg gggccggcgg gttgtttggt gccggcggca 240
tgggcggggc gggcggattc ggggatcacg gaacgctcgg caccggcggg gccggcggg 299

<210> SEQ ID NO 252
<211> LENGTH: 20
<212> TYPE: PRT
<213> ORGANISM: Mycobacterium tuberculosis

<400> SEQUENCE: 252

Leu Glu Pro Trp Ser Asp Gly Val Gly Leu Gly Val Asp Ser Phe Ser
1 5 10 15

Ala Lys Val Asn
20

<210> SEQ ID NO 253
<211> LENGTH: 121
<212> TYPE: PRT
<213> ORGANISM: Mycobacterium tuberculosis

<400> SEQUENCE: 253

Glu Leu Leu Phe Gly Ala Gly Gly Ala Gly Gly Ala Gly Gly Ala Gly
1 5 10 15

Thr Asp Gly Gly Pro Gly Ala Thr Gly Gly Thr Gly Gly His Gly Gly
20 25 30

Val Gly Gly Asp Gly Gly Trp Leu Ala Pro Gly Gly Ala Gly Gly Ala
35 40 45

Gly Gly Gln Gly Gly Ala Gly Gly Ala Arg Ser Asp Gly Gly Ala Leu
50 55 60

Gly Gly Thr Gly Gly Thr Gly Gly Thr Gly Gly Ala Gly Gly Ala Gly
65 70 75 80

Gly Arg Gly Thr Leu Leu Leu Gly Ala Gly Gly Gln Gly Gly Leu Gly
85 90 95

Gly Ala Gly Gly Gln Gly Gly Thr Gly Gly Gly Arg Arg Arg Trp Arg
100 105 110

Ser Gly Gly Cys Gln Trp His Trp Trp
115 120

<210> SEQ ID NO 254
<211> LENGTH: 34
<212> TYPE: PRT
<213> ORGANISM: Mycobacterium tuberculosis

<400> SEQUENCE: 254

Gly Val Ile Gly Lys Ala Thr Ala Gln Arg Pro Val Ala Ala Gly Arg
1 5 10 15

-continued

Pro Arg Pro Arg Pro Gln Arg Pro Val Ser Asp Arg Val Ser Asp Gln
20 25 30

Arg Arg

<210> SEQ ID NO 255
<211> LENGTH: 99
<212> TYPE: PRT
<213> ORGANISM: Mycobacterium tuberculosis

<400> SEQUENCE: 255

Leu Val Gly Gly Ile Gly Gly Thr Gly Gly Thr Gly Gly Asn Ala Gly
1 5 10 15

Met Leu Ala Gly Ala Ala Gly Ala Gly Gly Ala Gly Gly Phe Ser Phe
20 25 30

Ser Thr Ala Gly Gly Ala Gly Gly Ala Gly Gly Ala Gly Gly Leu Phe
35 40 45

Thr Thr Gly Gly Val Gly Gly Ala Gly Gly Gln Gly His Thr Gly Gly
50 55 60

Ala Gly Gly Ala Gly Gly Ala Gly Gly Leu Phe Gly Ala Gly Gly Met
65 70 75 80

Gly Gly Ala Gly Gly Phe Gly Asp His Gly Thr Leu Gly Thr Gly Gly
85 90 95

Ala Gly Gly

<210> SEQ ID NO 256
<211> LENGTH: 282
<212> TYPE: DNA
<213> ORGANISM: Mycobacterium tuberculosis

<400> SEQUENCE: 256
tcctgttcgg cgccggcggg gtgggcggtg ttggcggtga cggtgtggca ttcctgggca 60
ccgcccccgg cgggcccggt ggtgccggcg gggccggtgg gctgttcagc gtcggtgggg 120
ccggcggcgc cggcggaatc ggattggtcg ggaacagcgg tgccgggggg tccggcgggt 180
ccgccctgct ctggggcgac ggcggtgccg gcggcgcggg tggggtcggg tccactaccg 240
gcggtgccgg cggggcgggc ggcaacgcca gcctgctggt aa 282

<210> SEQ ID NO 257
<211> LENGTH: 415
<212> TYPE: DNA
<213> ORGANISM: Mycobacterium tuberculosis

<400> SEQUENCE: 257
cggcacgagc cgtgctactg gtcaactgat gccctgattg tgaccttccc ggcgccggat 60
cagtgcttct caggaccgac gtaatattcg aaaaccaatc cggccgccga ggcgaggatg 120
aatgccacac cggcggcgat cagccacggg agccacaacg cgatgccgac cgctgccacc 180
gagccggaca acgcgaccat gatcggccac cagctatgcg gactgaagaa tccaagttct 240
cctgcgccgt cgctgatttc agcgccttcg tagtcctcgg gccgggaatc taaccggcgg 300
gccacaaacc ggaagaaggt ggcgacgatc aacgccatgc cgccggtgag cgccaacgca 360
atggtgccag cccactcgac accaccggtg gcgaacatcg aggtcaacac gccgt 415

<210> SEQ ID NO 258
<211> LENGTH: 373
<212> TYPE: DNA
<213> ORGANISM: Mycobacterium tuberculosis

<400> SEQUENCE: 258

```
tcaccgcgtg aacggttcgt aacactgata cgtatgcttg tcagcgagca gatcaagtcc     60

agtccgacca atgccaggag atcatcggct aggctcacgg tttcgcctgg gacgagacgg    120

tattgagttc tggcgttgga cggtccgtgg cgtggtggga agtctgacgc ggcatcagaa    180

cggttgtcaa taccagtctt tgggggatat ggcctatttg gtgtcgtcgg gccgctccac    240

cggatccctt ttcgaacgtt gcgcaagcgc ggtccagtta cggcctgttc actgcgcgct    300

ggcgtagctg cgcggcctcg atcggtttga acgtcatcgc aattcccgca atgggtgagt    360

acctgacgct cct                                                       373
```

<210> SEQ ID NO 259
<211> LENGTH: 423
<212> TYPE: DNA
<213> ORGANISM: Mycobacterium tuberculosis

<400> SEQUENCE: 259

```
ccaaaccgga caggccggca gcgacggtcg gaagttgcac cacggtgcgc gctccatgta     60

gccaaccggt gaccacggcg tagacagcag atccgtggat cgcgcgttcg gtgtcgtccg    120

ggccgagtac ccgcgggccg aaccgcagcg accaaagcaa cgcgatcgat acggggatcg    180

ccactcgtgc cgaattcgag ctccgtcgac aagcttgcgg ccgcactcga acccgggtga    240

atgattgagt ttaaaccgct tagcaataac tagcataacc ccttggggcc tctaaacggg    300

tcttgagggg ttttttgctg aaaggaggaa ctatatccgg ataacctggc gtagtagcga    360

agaggcccgc accgatcgcc cttcccaaca gttgcgcagc ctgaatggcg aatggacgcg    420

ccc                                                                  423
```

<210> SEQ ID NO 260
<211> LENGTH: 404
<212> TYPE: DNA
<213> ORGANISM: Mycobacterium tuberculosis

<400> SEQUENCE: 260

```
agtggccagc cggtcggcca atgcatccag ctcccggtac gtcagctgac catccgccca     60

actgaccgcc accgagtcag gctgtgccgc agcgatttcg gcgaaccggg tatgcaccgc    120

gggtgccgac gtcgtcacat ccggcaggcc gggtgcggtc ggatcgtgct cgccgtccag    180

cagaatgtcg acgtcgcgca gcggccgatc ccaccggctg accaagcgct gtaacacagc    240

cagcacccgc ctgccgaggc tttcgggcgc catcgtgccc agcgcaccgt cgagcacctc    300

cactagcagc gtgagctcac cggtgctgcg gtgcgcggcg acggtcaccg gaaagtgcga    360

caaactctct agcgccaccg gacggaacgt caccccgttt gcga                     404
```

<210> SEQ ID NO 261
<211> LENGTH: 421
<212> TYPE: DNA
<213> ORGANISM: Mycobacterium tuberculosis

<400> SEQUENCE: 261

```
gtcctggtcg caggctgttc ttcgaacccg ctggctaact tcgcacccgg gtatccgccc     60

accatcgaac ccgcccaacc ggcggtgtca ccgcctactt cgcaagaccc ggccggtgca    120

gtgcgaccac tgagcggcca cccccgggcg gcactattcg acaacggcac ccgccaattg    180

gtggctctgc gcccgggcgc cgattcggcg gcacccgcca gcatcatggt cttcgatgac    240

atgcacgttg caccgcgcgt catttttctg ccgggcccgg cagccgcgtt gaccagcgac    300

gaccacggca cggccttcct tgccgcccgc ggcggctact tcgtggccga cctgtcctcc    360
```

ggtcacaccg cacgagtgaa tgtcgctgac gcagcgcaca ccgatttcac cgcgatcgcc 420
c 421

<210> SEQ ID NO 262
<211> LENGTH: 426
<212> TYPE: DNA
<213> ORGANISM: Mycobacterium tuberculosis

<400> SEQUENCE: 262
atgcatatca cgctcaacgc catcctgcgt gcgatcttcg gggccggcgg cagtgaacta 60
gacgagctgc gccgcctcat tccgccgtgg gtcacgctgg gctcgcgcct ggcggcgcta 120
ccgaaaccca aacgcgacta tggccgcctt agcccgtggg gccggctggc cgagtggcgg 180
cgccagtacg acactgtcat cgacgagctc atcgaagccg agcgggccga cccgaacttc 240
gccgatcgga ccgacgtttt ggcgttgatg ctgcgcagca cttacgacga cggttccatc 300
atgtcgcgca aggacattgg cgacgaactg ctcacgctgc ttgccgccgg gcacgaaacc 360
acggcggcga catgggctgg gcgttcgaac ggctcaaccg gcaccccgac gtgctcgcgg 420
ctctgg 426

<210> SEQ ID NO 263
<211> LENGTH: 522
<212> TYPE: DNA
<213> ORGANISM: Mycobacterium tuberculosis

<400> SEQUENCE: 263
gtcctggtcg caggctgttc ttcgaacccg ctggctaact tcgcacccgg gtatccgccc 60
accatcgaac ccgcccaacc ggcggtgtca ccgcctactt cgcaagaccc ggccggtgca 120
gtgcgaccac tgagcggcca cccccgggcg gcactattcg acaacggcac ccgccaattg 180
gtggctctgc gcccgggcgc cgattcggcg gcacccgcca gcatcatggt cttcgatgac 240
gtgcacgttg caccgcgcgt catttttctg ccgggcccgg cagccgcgtt gaccagcgac 300
gaccacggca cggccttcct tgccgcccgc ggcggctact tcgtggccga cctgtcctcc 360
ggtcacaccg cacgagtgaa tgtcgctgac gcagcgcaca ccgatttcac cgcgatcgcc 420
cgccgctccg acggcaagct ggtgctgggc agcgcagatg gcgccgtcta cacgcttgcc 480
aagaacccgc agttgaccgg cgtcggcgcc gccaccgtag cc 522

<210> SEQ ID NO 264
<211> LENGTH: 739
<212> TYPE: DNA
<213> ORGANISM: Mycobacterium tuberculosis

<400> SEQUENCE: 264
gctggggcgc accgccgtcc ggcggcccca gcccctgggc ccagaccccg cgcaaaacca 60
acccgtggcc cttagtggcc ggcgccgccg ccgtcgtgct cgtcctcgtg ttgggcgcca 120
tcggcatctg gatcgccatc cggcccaagc cggtacagcc gcctcagccg gttgcggagg 180
agcgccttag cgccctactg ctgaactcct cagaagtcaa cgccgtgatg ggctcgtcgt 240
ccatgcagcc gggcaaaccg atcacatcga tggactcttc gccggtgacg gtgtccctgc 300
cggactgcca gggcgcgctg tataccagcc aggatccggt gtatgccggc accggctaca 360
ccgccatcaa cggcttgatt tcatccgagc cgggcgacaa ctacgaacat tgggtgaacc 420
aagccgtcgt cgcctttccg accgccgaca aagcccgcgc gttcgtgcag acttcggccg 480
acaaatggaa gaactgcgca ggcaagacgg tcaccgtcac gaataaggcc aagacctacc 540
ggtggacgtt tgccgacgtc aaaggcagcc cgccgacgat cacggtgata gacacccaag 600
aaggcgctga gggctgggaa tgccaacgcg cgatgagcgt ggccaacaat gtggttgtcg 660
acgtcaacgc atgcgggtac cagatcacca atcaagcagg ccagatcgcc gccaagatct 720
gttgacaaag tcaacaagg 739

<210> SEQ ID NO 265
<211> LENGTH: 69
<212> TYPE: DNA
<213> ORGANISM: Mycobacterium tuberculosis

<400> SEQUENCE: 265
agacgtcgtc gaggccgcca tcgcccgcgc cgaagccgtt aacccggcac tgaacgcgtt 60
ggcgtatgc 69

<210> SEQ ID NO 266
<211> LENGTH: 523
<212> TYPE: DNA
<213> ORGANISM: Mycobacterium tuberculosis

<400> SEQUENCE: 266
actgcacccg gcaggcgcga ccaacggatc gggtcaacta gcactgccgg tggaggcgcc 60
cccgcggtct gtgccttccc acggggaacc cttgggcagc gcggctccag aagggttgga 120
gggagagttc gacgaccgta tcgacgagcg gttcccggtc ttcagctcgg ccagtctcgc 180
cgaagcgctg ccgggtccgc tgaccccgat gacgctggat gtccagttga gtggactgcg 240
cgcggccggt cgggcgatgg gtcgggtact ggcgcttggc ggtgtcgttg ccgatgagtg 300
ggagagaaga gccatcgcgg tgttcggtca ccgcccgtat atcggagtgt cggccaatat 360
tgtggccgcc gcccaactgc cggggtggga cgcgcaggcc gtaacccggc gggcactggg 420
cgagcaaccg caggtcactg agctgcttcc gtttggtcga ccgcaacttg cgggcggacc 480
gctcggctcg gtcgcgaagg tggtcgtgac ggcacggtcg ctg 523

<210> SEQ ID NO 267
<211> LENGTH: 224
<212> TYPE: DNA
<213> ORGANISM: Mycobacterium tuberculosis

<400> SEQUENCE: 267
gtgtcggtgt cgtcggggta ggagcgactt ccccggccgg cgccggcgcc ggagcgggct 60
ctgcaggaac cggtgccggc gccggcggcg gggcgaccaa aggccggatc gattcggcca 120
gcgccttggc cgcgcccttg tccaccgggt tgttggcggt cccgagccat accacaaacc 180
aacgctgaag ggcccggcg tccggtgcgt tcgccgcggg cgac 224

<210> SEQ ID NO 268
<211> LENGTH: 521
<212> TYPE: DNA
<213> ORGANISM: Mycobacterium tuberculosis

<400> SEQUENCE: 268
tgaactgact gccccgctcg atcggcggcg gcggcgtgtc atagctgcgc cgccaggcca 60
tgaactgctc ttcgccatag cgggccttgg tctcggcctt gtccaaaccc tgcagcgcgc 120
cgtagtggcg ttcgttgagc cgccagctac gccgcacggg aatccagagc cgatcggcgc 180
tgtccaacgc cagatgcgcg gtggtgatcg cgcgccgcag caacgaggtg tagagcacgt 240
cgggcaatag gtcgtgttcc gcgatcagct cgccgcttcg aaccgcctct gcctggccct 300
tgtccgtcag gccgacatcg acccagccgg tgaacaggtt gagggcattc cagtcgctct 360
cgccgtggcg cagcaacacc aggctgccag tgtttgccat accggcaagt ctctcacgca 420
ctcccgcact cctcatcgtg gaccaaaatg cccgaattct cctcggtccg ctgcgcagcg 480
cgttcatacc gccgaggtgg tcggcaccgt aacggccggt t 521

<210> SEQ ID NO 269
<211> LENGTH: 426
<212> TYPE: DNA
<213> ORGANISM: Mycobacterium tuberculosis

<400> SEQUENCE: 269
ctccaggctc attcgctcga acaaagccac ccggccgtac agcggacgcc cccattcgtt 60
gtcgtgatag tcgcggtaca gctgggcatc gggccctgga cgaacctccg cccaggggca 120
gcgaaccagc ccgtcgccgc tcacgcgggg tcagaacggt agtgcacgac agtctcgccg 180
cgcgaagggt ttgacgcgtc agactcggcc tcggcgtctt ccgacgaggc gtggatcgcc 240
ccgagctgag agcgtagcgc ctcgagctca cggccgagcc gttccagcac ccagtccacc 300
tcgctggtct tgttcccgcg cagcacctgc gtgaacttga ccgcgtcgac atcggcgcgg 360
gtgaccccga acgccggcag cgtcgtcgcc gtcgtcgccc gcggcagggg cggcaactgc 420
tcgcca 426

<210> SEQ ID NO 270
<211> LENGTH: 219
<212> TYPE: DNA
<213> ORGANISM: Mycobacterium tuberculosis

<400> SEQUENCE: 270
gcggacacgg cggacaaagc gcaatcggcc tcggcggcgg cgccggcggc gacgggggcc 60
agggcggcgc cggccgcgga ctgtggggta ctggcggcgc cggcggacac ggcggggcaa 120
ggcggtggta ccgggggccc accgctgccc ggtcaggcag gcatgggcgc cgcgggtggc 180
gccggtgggc tgatcggcaa cggcggggcc ggcggcgac 219

<210> SEQ ID NO 271
<211> LENGTH: 571
<212> TYPE: DNA
<213> ORGANISM: Mycobacterium tuberculosis

<400> SEQUENCE: 271
aagatcatcg gcgccgctcc ttagcatcgc tgcgctctgc atcgtcgccg gcgcggatca 60
cggaggtccg gccttgtacc ccactcctcg aacggtcagc accacagtcg ggttctcggg 120
atccttttcg accttggccc gcagacgctg gacatgcacg ttcaccagcc tggtatcggc 180
tgggtgccgg taaccccata cctgttcgag cagcacatca cgagtaaaca cctggcgcgg 240
cttgcgcgcc aatgcgacca acaggtcgaa ttccagcggt gtcaacgaga tctgctcacc 300
gttgcgagtg accttgtgcg ccggtacgtc gatttctacg tcggcgatgg acagcatctc 360
ggcgggttcg tcgtcgttgc ggcgcagccg cgcccgcacc cgcgcaacca gctccttggg 420
cttgaacggc ttcatgatgt agtcgtcggc gcccgactcc agacccagca ccacatccac 480
ggtgtcggtc tttgcggtga gcatcacgat cggaacaccg gaatcggcgc gcaacacccg 540
gcacacgtcg atgccgttca taccggggca a 571

<210> SEQ ID NO 272
<211> LENGTH: 93

<212> TYPE: PRT
<213> ORGANISM: Mycobacterium tuberculosis

<400> SEQUENCE: 272

```
Leu Phe Gly Ala Gly Gly Val Gly Gly Val Gly Gly Asp Gly Val Ala
  1               5                  10                  15

Phe Leu Gly Thr Ala Pro Gly Gly Pro Gly Gly Ala Gly Gly Ala Gly
             20                  25                  30

Gly Leu Phe Ser Val Gly Gly Ala Gly Gly Ala Gly Gly Ile Gly Leu
         35                  40                  45

Val Gly Asn Ser Gly Ala Gly Gly Ser Gly Gly Ser Ala Leu Leu Trp
     50                  55                  60

Gly Asp Gly Gly Ala Gly Gly Ala Gly Gly Val Gly Ser Thr Thr Gly
 65                  70                  75                  80

Gly Ala Gly Gly Ala Gly Gly Asn Ala Ser Leu Leu Val
                 85                  90
```

<210> SEQ ID NO 273
<211> LENGTH: 26
<212> TYPE: PRT
<213> ORGANISM: Mycobacterium tuberculosis

<400> SEQUENCE: 273

```
Met Pro Pro Val Ser Ala Asn Ala Met Val Pro Ala His Ser Thr Pro
  1               5                  10                  15

Pro Val Ala Asn Ile Glu Val Asn Thr Pro
             20                  25
```

<210> SEQ ID NO 274
<211> LENGTH: 26
<212> TYPE: PRT
<213> ORGANISM: Mycobacterium tuberculosis

<400> SEQUENCE: 274

```
Lys Pro Asp Arg Pro Ala Ala Thr Val Gly Ser Cys Thr Thr Val Arg
  1               5                  10                  15

Ala Pro Cys Ser Gln Pro Val Thr Thr Ala
             20                  25
```

<210> SEQ ID NO 275
<211> LENGTH: 20
<212> TYPE: PRT
<213> ORGANISM: Mycobacterium tuberculosis

<400> SEQUENCE: 275

```
Trp Pro Ala Gly Arg Pro Met His Pro Ala Pro Gly Thr Ser Ala Asp
  1               5                  10                  15

His Pro Pro Asn
             20
```

<210> SEQ ID NO 276
<211> LENGTH: 140
<212> TYPE: PRT
<213> ORGANISM: Mycobacterium tuberculosis

<400> SEQUENCE: 276

```
Val Leu Val Ala Gly Cys Ser Ser Asn Pro Leu Ala Asn Phe Ala Pro
  1               5                  10                  15

Gly Tyr Pro Pro Thr Ile Glu Pro Ala Gln Pro Ala Val Ser Pro Pro
             20                  25                  30

Thr Ser Gln Asp Pro Ala Gly Ala Val Arg Pro Leu Ser Gly His Pro
```

```
        35                  40                  45

Arg Ala Ala Leu Phe Asp Asn Gly Thr Arg Gln Leu Val Ala Leu Arg
     50                  55                  60

Pro Gly Ala Asp Ser Ala Ala Pro Ala Ser Ile Met Val Phe Asp Asp
 65                  70                  75                  80

Met His Val Ala Pro Arg Val Ile Phe Leu Pro Gly Pro Ala Ala Ala
                 85                  90                  95

Leu Thr Ser Asp Asp His Gly Thr Ala Phe Leu Ala Ala Arg Gly Gly
            100                 105                 110

Tyr Phe Val Ala Asp Leu Ser Ser Gly His Thr Ala Arg Val Asn Val
        115                 120                 125

Ala Asp Ala Ala His Thr Asp Phe Thr Ala Ile Ala
    130                 135                 140


<210> SEQ ID NO 277
<211> LENGTH: 142
<212> TYPE: PRT
<213> ORGANISM: Mycobacterium tuberculosis

<400> SEQUENCE: 277

Met His Ile Thr Leu Asn Ala Ile Leu Arg Ala Ile Phe Gly Ala Gly
  1               5                  10                  15

Gly Ser Glu Leu Asp Glu Leu Arg Arg Leu Ile Pro Pro Trp Val Thr
             20                  25                  30

Leu Gly Ser Arg Leu Ala Ala Leu Pro Lys Pro Lys Arg Asp Tyr Gly
        35                  40                  45

Arg Leu Ser Pro Trp Gly Arg Leu Ala Glu Trp Arg Arg Gln Tyr Asp
     50                  55                  60

Thr Val Ile Asp Glu Leu Ile Glu Ala Glu Arg Ala Asp Pro Asn Phe
 65                  70                  75                  80

Ala Asp Arg Thr Asp Val Leu Ala Leu Met Leu Arg Ser Thr Tyr Asp
                 85                  90                  95

Asp Gly Ser Ile Met Ser Arg Lys Asp Ile Gly Asp Glu Leu Leu Thr
            100                 105                 110

Leu Leu Ala Ala Gly His Glu Thr Thr Ala Ala Thr Trp Ala Gly Arg
        115                 120                 125

Ser Asn Gly Ser Thr Gly Thr Pro Thr Cys Ser Arg Leu Trp
    130                 135                 140


<210> SEQ ID NO 278
<211> LENGTH: 163
<212> TYPE: PRT
<213> ORGANISM: Mycobacterium tuberculosis

<400> SEQUENCE: 278

Val Leu Val Ala Gly Cys Ser Ser Asn Pro Leu Ala Asn Phe Ala Pro
  1               5                  10                  15

Gly Tyr Pro Pro Thr Ile Glu Pro Ala Gln Pro Ala Val Ser Pro Pro
             20                  25                  30

Thr Ser Gln Asp Pro Ala Gly Ala Val Arg Pro Leu Ser Gly His Pro
        35                  40                  45

Arg Ala Ala Leu Phe Asp Asn Gly Thr Arg Gln Leu Val Ala Leu Arg
     50                  55                  60

Pro Gly Ala Asp Ser Ala Ala Pro Ala Ser Ile Met Val Phe Asp Asp
 65                  70                  75                  80

Val His Val Ala Pro Arg Val Ile Phe Leu Pro Gly Pro Ala Ala Ala
                 85                  90                  95
```

```
Leu Thr Ser Asp Asp His Gly Thr Ala Phe Leu Ala Ala Arg Gly Gly
            100                 105                 110

Tyr Phe Val Ala Asp Leu Ser Ser Gly His Thr Ala Arg Val Asn Val
        115                 120                 125

Ala Asp Ala Ala His Thr Asp Phe Thr Ala Ile Ala Arg Arg Ser Asp
    130                 135                 140

Gly Lys Leu Val Leu Gly Ser Ala Asp Gly Ala Val Tyr Thr Leu Ala
145                 150                 155                 160

Lys Asn Pro


<210> SEQ ID NO 279
<211> LENGTH: 240
<212> TYPE: PRT
<213> ORGANISM: Mycobacterium tuberculosis

<400> SEQUENCE: 279

Trp Gly Ala Pro Pro Ser Gly Gly Pro Ser Pro Trp Ala Gln Thr Pro
  1               5                  10                  15

Arg Lys Thr Asn Pro Trp Pro Leu Val Ala Gly Ala Ala Ala Val Val
            20                  25                  30

Leu Val Leu Val Leu Gly Ala Ile Gly Ile Trp Ile Ala Ile Arg Pro
        35                  40                  45

Lys Pro Val Gln Pro Pro Gln Pro Val Ala Glu Glu Arg Leu Ser Ala
     50                  55                  60

Leu Leu Leu Asn Ser Ser Glu Val Asn Ala Val Met Gly Ser Ser Ser
 65                  70                  75                  80

Met Gln Pro Gly Lys Pro Ile Thr Ser Met Asp Ser Ser Pro Val Thr
                 85                  90                  95

Val Ser Leu Pro Asp Cys Gln Gly Ala Leu Tyr Thr Ser Gln Asp Pro
            100                 105                 110

Val Tyr Ala Gly Thr Gly Tyr Thr Ala Ile Asn Gly Leu Ile Ser Ser
        115                 120                 125

Glu Pro Gly Asp Asn Tyr Glu His Trp Val Asn Gln Ala Val Val Ala
    130                 135                 140

Phe Pro Thr Ala Asp Lys Ala Arg Ala Phe Val Gln Thr Ser Ala Asp
145                 150                 155                 160

Lys Trp Lys Asn Cys Ala Gly Lys Thr Val Thr Val Thr Asn Lys Ala
                165                 170                 175

Lys Thr Tyr Arg Trp Thr Phe Ala Asp Val Lys Gly Ser Pro Pro Thr
            180                 185                 190

Ile Thr Val Ile Asp Thr Gln Glu Gly Ala Glu Gly Trp Glu Cys Gln
        195                 200                 205

Arg Ala Met Ser Val Ala Asn Asn Val Val Val Asp Val Asn Ala Cys
    210                 215                 220

Gly Tyr Gln Ile Thr Asn Gln Ala Gly Gln Ile Ala Ala Lys Ile Cys
225                 230                 235                 240


<210> SEQ ID NO 280
<211> LENGTH: 22
<212> TYPE: PRT
<213> ORGANISM: Mycobacterium tuberculosis

<400> SEQUENCE: 280

Asp Val Val Glu Ala Ala Ile Ala Arg Ala Glu Ala Val Asn Pro Ala
  1               5                  10                  15

Leu Asn Ala Leu Ala Tyr
```

20

<210> SEQ ID NO 281
<211> LENGTH: 174
<212> TYPE: PRT
<213> ORGANISM: Mycobacterium tuberculosis

<400> SEQUENCE: 281

Leu His Pro Ala Gly Ala Thr Asn Gly Ser Gly Gln Leu Ala Leu Pro
1 5 10 15

Val Glu Ala Pro Pro Arg Ser Val Pro Ser His Gly Glu Pro Leu Gly
20 25 30

Ser Ala Ala Pro Glu Gly Leu Glu Gly Glu Phe Asp Asp Arg Ile Asp
35 40 45

Glu Arg Phe Pro Val Phe Ser Ser Ala Ser Leu Ala Glu Ala Leu Pro
50 55 60

Gly Pro Leu Thr Pro Met Thr Leu Asp Val Gln Leu Ser Gly Leu Arg
65 70 75 80

Ala Ala Gly Arg Ala Met Gly Arg Val Leu Ala Leu Gly Gly Val Val
85 90 95

Ala Asp Glu Trp Glu Arg Arg Ala Ile Ala Val Phe Gly His Arg Pro
100 105 110

Tyr Ile Gly Val Ser Ala Asn Ile Val Ala Ala Ala Gln Leu Pro Gly
115 120 125

Trp Asp Ala Gln Ala Val Thr Arg Arg Ala Leu Gly Glu Gln Pro Gln
130 135 140

Val Thr Glu Leu Leu Pro Phe Gly Arg Pro Gln Leu Ala Gly Gly Pro
145 150 155 160

Leu Gly Ser Val Ala Lys Val Val Val Thr Ala Arg Ser Leu
165 170

<210> SEQ ID NO 282
<211> LENGTH: 61
<212> TYPE: PRT
<213> ORGANISM: Mycobacterium tuberculosis

<400> SEQUENCE: 282

Val Gly Val Val Gly Val Gly Ala Thr Ser Pro Ala Gly Ala Gly Ala
1 5 10 15

Gly Ala Gly Ser Ala Gly Thr Gly Ala Gly Ala Gly Gly Gly Ala Thr
20 25 30

Lys Gly Arg Ile Asp Ser Ala Ser Ala Leu Ala Ala Pro Leu Ser Thr
35 40 45

Gly Leu Leu Ala Val Pro Ser His Thr Thr Asn Gln Arg
50 55 60

<210> SEQ ID NO 283
<211> LENGTH: 133
<212> TYPE: PRT
<213> ORGANISM: Mycobacterium tuberculosis

<400> SEQUENCE: 283

Met Ala Asn Thr Gly Ser Leu Val Leu Leu Arg His Gly Glu Ser Asp
1 5 10 15

Trp Asn Ala Leu Asn Leu Phe Thr Gly Trp Val Asp Val Gly Leu Thr
20 25 30

Asp Lys Gly Gln Ala Glu Ala Val Arg Ser Gly Glu Leu Ile Ala Glu
35 40 45

```
His Asp Leu Leu Pro Asp Val Leu Tyr Thr Ser Leu Leu Arg Arg Ala
     50                  55                  60

Ile Thr Thr Ala His Leu Ala Leu Asp Ser Ala Asp Arg Leu Trp Ile
 65                  70                  75                  80

Pro Val Arg Arg Ser Trp Arg Leu Asn Glu Arg His Tyr Gly Ala Leu
                 85                  90                  95

Gln Gly Leu Asp Lys Ala Glu Thr Lys Ala Arg Tyr Gly Glu Glu Gln
            100                 105                 110

Phe Met Ala Trp Arg Arg Ser Tyr Asp Thr Pro Pro Pro Pro Ile Glu
        115                 120                 125

Arg Gly Ser Gln Phe
    130


<210> SEQ ID NO 284
<211> LENGTH: 63
<212> TYPE: PRT
<213> ORGANISM: Mycobacterium tuberculosis

<400> SEQUENCE: 284

Pro Gly Ser Phe Ala Arg Thr Lys Pro Pro Gly Arg Thr Ala Asp Ala
  1               5                  10                  15

Pro Ile Arg Cys Arg Asp Ser Arg Gly Thr Ala Gly His Arg Ala Leu
             20                  25                  30

Asp Glu Pro Pro Pro Arg Gly Ser Glu Pro Ala Arg Arg Arg Ser Arg
         35                  40                  45

Gly Val Arg Thr Val Val His Asp Ser Leu Ala Ala Arg Arg Val
     50                  55                  60


<210> SEQ ID NO 285
<211> LENGTH: 72
<212> TYPE: PRT
<213> ORGANISM: Mycobacterium tuberculosis

<400> SEQUENCE: 285

Gly His Gly Gly Gln Ser Ala Ile Gly Leu Gly Gly Gly Ala Gly Gly
  1               5                  10                  15

Asp Gly Gly Gln Gly Gly Ala Gly Arg Gly Leu Trp Gly Thr Gly Gly
             20                  25                  30

Ala Gly Gly His Gly Gly Ala Arg Arg Trp Tyr Arg Gly Pro Thr Ala
         35                  40                  45

Ala Arg Ser Gly Arg His Gly Arg Arg Gly Trp Arg Arg Trp Ala Asp
     50                  55                  60

Arg Gln Arg Arg Gly Arg Arg Arg
 65                  70


<210> SEQ ID NO 286
<211> LENGTH: 74
<212> TYPE: PRT
<213> ORGANISM: Mycobacterium tuberculosis

<400> SEQUENCE: 286

Asp His Arg Arg Arg Ser Leu Ala Ser Leu Arg Ser Ala Ser Ser Pro
  1               5                  10                  15

Ala Arg Ile Thr Glu Val Arg Pro Cys Thr Pro Leu Leu Glu Arg Ser
             20                  25                  30

Ala Pro Gln Ser Gly Ser Arg Asp Pro Phe Arg Pro Trp Pro Ala Asp
         35                  40                  45

Ala Gly His Ala Arg Ser Pro Ala Trp Tyr Arg Leu Gly Ala Gly Asn
     50                  55                  60
```

```
Pro Ile Pro Val Arg Ala Ala His His Glu
 65                  70


<210> SEQ ID NO 287
<211> LENGTH: 174
<212> TYPE: DNA
<213> ORGANISM: Mycobacterium tuberculosis

<400> SEQUENCE: 287

ccgcacgtaa caccgtgaat tgaagggagc cgctggtcat gggccgattc tatccgtggg     60

cgaacggtta ttgacggccc ggaggccact ccgctgccac caagtggtga ctcagcgcgt    120

tttcacggca acgaacggcg gacacaccac ttgacattcg acagcacggc cgcg          174


<210> SEQ ID NO 288
<211> LENGTH: 404
<212> TYPE: DNA
<213> ORGANISM: Mycobacterium tuberculosis

<400> SEQUENCE: 288

tcgcaaacgg ggtgacgttc cgtccggtgg cgctagagag tttgtcgcac tttccggtga     60

ccgtcgccgc gcaccgcagc accggtgagc tcacgctgct agtggaggtg ctcgacggtg    120

cgctgggcac gatggcgccc gaaagcctcg gcaggcgggt gctggctgtg ttacagcgct    180

tggtcagccg gtgggatcgg ccgctgcgcg acgtcgacat tctgctggac ggcgagcacg    240

atccgaccgc acccggcctg ccggatgtga cgacgtcggc acccgcggtg catacccggt    300

tcgccgaaat cgctgcggca cagcctgact cggtggcggt cagttgggcg gatggtcagc    360

tgacgtaccg ggagctggat gcattggccg accggctggc cact                     404


<210> SEQ ID NO 289
<211> LENGTH: 134
<212> TYPE: PRT
<213> ORGANISM: Mycobacterium tuberculosis

<400> SEQUENCE: 289

Ala Asn Gly Val Thr Phe Arg Pro Val Ala Leu Glu Ser Leu Ser His
  1               5                  10                  15

Phe Pro Val Thr Val Ala Ala His Arg Ser Thr Gly Glu Leu Thr Leu
            20                  25                  30

Leu Val Glu Val Leu Asp Gly Ala Leu Gly Thr Met Ala Pro Glu Ser
        35                  40                  45

Leu Gly Arg Arg Val Leu Ala Val Leu Gln Arg Leu Val Ser Arg Trp
    50                  55                  60

Asp Arg Pro Leu Arg Asp Val Asp Ile Leu Leu Asp Gly Glu His Asp
 65                  70                  75                  80

Pro Thr Ala Pro Gly Leu Pro Asp Val Thr Thr Ser Ala Pro Ala Val
                85                  90                  95

His Thr Arg Phe Ala Glu Ile Ala Ala Ala Gln Pro Asp Ser Val Ala
            100                 105                 110

Val Ser Trp Ala Asp Gly Gln Leu Thr Tyr Arg Glu Leu Asp Ala Leu
        115                 120                 125

Ala Asp Arg Leu Ala Thr
    130


<210> SEQ ID NO 290
<211> LENGTH: 526
<212> TYPE: DNA
<213> ORGANISM: Mycobacterium tuberculosis
```

<400> SEQUENCE: 290
gcttcgacgg ctacgagtac ctgttctggg tgggttgtgc gggcgcctac gacgacaagg 60
ccaagaagac caccaaggcc gtcgccgagc tgttcgccgt cgccggggtg aaatacttgg 120
tgctgggcgc tggggaaacc tgcaacggcg actcggcgcg ccgctccggc aacgagttcc 180
tcttccagca gctggcacaa caggccgtcg agaccctgga cggtttgttc gagggtgtgg 240
agaccgtcga ccgcaagatc gttgtcacct gcccgcactg cttcaacacc atcggcaagg 300
aatatcggca gctgggcgcc aactacaccg tgctgcacca cacccagctg ctcaatcggt 360
tggtgcgcga caagaggctg gtccctgtca ctccggtttc tcaggacatc acctaccacg 420
acccgtgcta cctgggtcgg cacaacaagg tctacgaggc accacgggag ctgatcggtg 480
ccgcgggggc cacctgagcc gagatgccgc gccatgccga ccgcag 526

<210> SEQ ID NO 291
<211> LENGTH: 487
<212> TYPE: DNA
<213> ORGANISM: Mycobacterium tuberculosis

<400> SEQUENCE: 291
ctcgccgccg tgatctggcc ggcgaacttc gtcagtgcat ccagacccca acgatcatcg 60
atcaggccga tgcccatgat caccgcaccg gccaccagca ccgcgggcat gccggtggaa 120
tagacgaacc cccgggtgag tgccggaagc tgggaggcaa gaaagacggc gccgacaatg 180
cccaggaaca tcgccaaccc acccatccga ggggtaggcg tgacgtgcac atctcgctcc 240
cgcgggtagg cgacggctcc caggcgactg gccagcatcc gcaccggacc ggtcgcaaaa 300
taggtgatga tcgccgcggt cagcccgacc agcgcaagct cacgcagcgg gacaccggcg 360
ccgcgatagg acagggcgag caagccaccg gcaacgccgg ccacatcgct ggacacctcg 420
agaccgtact gcaccaacct gaagagctga acactcgccg aacgtgcaac agctgcgaac 480
aattggg 487

<210> SEQ ID NO 292
<211> LENGTH: 528
<212> TYPE: DNA
<213> ORGANISM: Mycobacterium tuberculosis

<400> SEQUENCE: 292
acgaagcgcg agaatatgag ccggggcaac ccggcatgta cgagcttgag ttcccggcgc 60
ctcagctgtc gtcgtccgac ggccgtggtc cggtgttggt gcacgctttg gaaggtttct 120
ccgacgccgg ccatgcgatc cggctggccg ccgcccacct caaggcggcc ctggacacag 180
agctggtcgc gtccttcgcg atcgatgaac tactggacta ccgctcgcgg cggccattaa 240
tgactttcaa gaccgatcat ttcacccact ccgatgatcc tgagctaagc ctgtatgcgc 300
tgcgcgacag catcggcacc ccatttctgc tgctggcggg tttggagccg gacctgaagt 360
gggagcggtt catcaccgcc gtccgattgc tggccgagcg cctgggtgta cggcagaacc 420
atcggcctgg gcaccgtccc gatggccgtt ccgcacacac gaccgatcac gatgaccgct 480
cattccaaca accgggagct atctccgatt ttcaaccgtt cgatctcc 528

<210> SEQ ID NO 293
<211> LENGTH: 610
<212> TYPE: DNA
<213> ORGANISM: Mycobacterium tuberculosis

<400> SEQUENCE: 293

-continued

```
ccaagcccgt caaggagccg gtgccggcct tgcctccggt gccgccgacg ccggcgttgc     60

cgccgttgcc gccgttgccg ccggtaccgg ggtttcctac ggtgccgccg cccggcagca    120

tggccccgct gtttaggccg ttttcgccgg ccccgccgtc accggctttg ccgccatcgc    180

cgccgttgcc gccgctggtg ggggtggcgg cctggttgac gtattgttcc accggcccgg    240

cccttgaccc tttggcggtg tcgatcgcgg cgtcgatgga tccgccgacc acgacgtgcg    300

aagcctcgcc tgccgccgca gccgcccaac tgtgtcgcgg ctcctgcgat ttggccccgg    360

ccgacgagat gatgggcacc accggagcct gcggccgtct gggggaggcc agcgcgggtt    420

cgcggtcacg ccatacgcga cggtgcgccg ccgcttcgga gatttgcagg ctgcgttgca    480

ccagatcgag cagcggtgtg cccagggact gggttagccc gttggcgccg ccgttgtagc    540

ggcgagcgca atatcggtgc ccactcgacc caaccgcgac tccataagcg acaccattcg    600

cggttgatgc                                                           610
```

<210> SEQ ID NO 294
<211> LENGTH: 164
<212> TYPE: PRT
<213> ORGANISM: Mycobacterium tuberculosis

<400> SEQUENCE: 294

```
Phe Asp Gly Tyr Glu Tyr Leu Phe Trp Val Gly Cys Ala Gly Ala Tyr
  1               5                  10                  15

Asp Asp Lys Ala Lys Lys Thr Thr Lys Ala Val Ala Glu Leu Phe Ala
             20                  25                  30

Val Ala Gly Val Lys Tyr Leu Val Leu Gly Ala Gly Glu Thr Cys Asn
         35                  40                  45

Gly Asp Ser Ala Arg Arg Ser Gly Asn Glu Phe Leu Phe Gln Gln Leu
     50                  55                  60

Ala Gln Gln Ala Val Glu Thr Leu Asp Gly Leu Phe Glu Gly Val Glu
 65                  70                  75                  80

Thr Val Asp Arg Lys Ile Val Val Thr Cys Pro His Cys Phe Asn Thr
                 85                  90                  95

Ile Gly Lys Glu Tyr Arg Gln Leu Gly Ala Asn Tyr Thr Val Leu His
            100                 105                 110

His Thr Gln Leu Leu Asn Arg Leu Val Arg Asp Lys Arg Leu Val Pro
        115                 120                 125

Val Thr Pro Val Ser Gln Asp Ile Thr Tyr His Asp Pro Cys Tyr Leu
    130                 135                 140

Gly Arg His Asn Lys Val Tyr Glu Ala Pro Arg Glu Leu Ile Gly Ala
145                 150                 155                 160

Ala Gly Ala Thr
```

<210> SEQ ID NO 295
<211> LENGTH: 161
<212> TYPE: PRT
<213> ORGANISM: Mycobacterium tuberculosis

<400> SEQUENCE: 295

```
Arg Arg Arg Asp Leu Ala Gly Glu Leu Arg Gln Cys Ile Gln Thr Pro
  1               5                  10                  15

Thr Ile Ile Asp Gln Ala Asp Ala His Asp His Arg Thr Gly His Gln
             20                  25                  30

His Arg Gly His Ala Gly Gly Ile Asp Glu Pro Pro Gly Glu Cys Arg
         35                  40                  45
```

```
Lys Leu Gly Gly Lys Lys Asp Gly Ala Asp Asn Ala Gln Glu His Arg
     50                  55                  60

Gln Pro Thr His Pro Arg Gly Arg Arg Asp Val His Ile Ser Leu Pro
 65                  70                  75                  80

Arg Val Gly Asp Gly Ser Gln Ala Thr Gly Gln His Pro His Arg Thr
                 85                  90                  95

Gly Arg Lys Ile Gly Asp Asp Arg Arg Gly Gln Pro Asp Gln Arg Lys
            100                 105                 110

Leu Thr Gln Arg Asp Thr Gly Ala Ala Ile Gly Gln Gly Glu Gln Ala
        115                 120                 125

Thr Gly Asn Ala Gly His Ile Ala Gly His Leu Glu Thr Val Leu His
    130                 135                 140

Gln Pro Glu Glu Leu Asn Thr Arg Arg Thr Cys Asn Ser Cys Glu Gln
145                 150                 155                 160

Leu


<210> SEQ ID NO 296
<211> LENGTH: 175
<212> TYPE: PRT
<213> ORGANISM: Mycobacterium tuberculosis

<400> SEQUENCE: 296

Glu Ala Arg Glu Tyr Glu Pro Gly Gln Pro Gly Met Tyr Glu Leu Glu
  1               5                  10                  15

Phe Pro Ala Pro Gln Leu Ser Ser Ser Asp Gly Arg Gly Pro Val Leu
             20                  25                  30

Val His Ala Leu Glu Gly Phe Ser Asp Ala Gly His Ala Ile Arg Leu
         35                  40                  45

Ala Ala Ala His Leu Lys Ala Ala Leu Asp Thr Glu Leu Val Ala Ser
     50                  55                  60

Phe Ala Ile Asp Glu Leu Leu Asp Tyr Arg Ser Arg Arg Pro Leu Met
 65                  70                  75                  80

Thr Phe Lys Thr Asp His Phe Thr His Ser Asp Asp Pro Glu Leu Ser
                 85                  90                  95

Leu Tyr Ala Leu Arg Asp Ser Ile Gly Thr Pro Phe Leu Leu Leu Ala
            100                 105                 110

Gly Leu Glu Pro Asp Leu Lys Trp Glu Arg Phe Ile Thr Ala Val Arg
        115                 120                 125

Leu Leu Ala Glu Arg Leu Gly Val Arg Gln Asn His Arg Pro Gly His
    130                 135                 140

Arg Pro Asp Gly Arg Ser Ala His Thr Thr Asp His Asp Asp Arg Ser
145                 150                 155                 160

Phe Gln Gln Pro Gly Ala Ile Ser Asp Phe Gln Pro Phe Asp Leu
                165                 170                 175


<210> SEQ ID NO 297
<211> LENGTH: 178
<212> TYPE: PRT
<213> ORGANISM: Mycobacterium tuberculosis

<400> SEQUENCE: 297

Lys Pro Val Lys Glu Pro Val Pro Ala Leu Pro Pro Val Pro Pro Thr
  1               5                  10                  15

Pro Ala Leu Pro Pro Leu Pro Pro Leu Pro Pro Val Pro Gly Phe Pro
             20                  25                  30

Thr Val Pro Pro Pro Gly Ser Met Ala Pro Leu Phe Arg Pro Phe Ser
         35                  40                  45
```

```
Pro Ala Pro Pro Ser Pro Ala Leu Pro Pro Ser Pro Pro Leu Pro Pro
     50                  55                  60

Leu Val Gly Val Ala Ala Trp Leu Thr Tyr Cys Ser Thr Gly Pro Ala
 65                  70                  75                  80

Leu Asp Pro Leu Ala Val Ser Ile Ala Ala Ser Met Asp Pro Pro Thr
                 85                  90                  95

Thr Thr Cys Glu Ala Ser Pro Ala Ala Ala Ala Ala Gln Leu Cys Arg
            100                 105                 110

Gly Ser Cys Asp Leu Ala Pro Ala Asp Glu Met Met Gly Thr Thr Gly
        115                 120                 125

Ala Cys Gly Arg Leu Gly Glu Ala Ser Ala Gly Ser Arg Ser Arg His
    130                 135                 140

Thr Arg Arg Cys Ala Ala Ala Ser Glu Ile Cys Arg Leu Arg Cys Thr
145                 150                 155                 160

Arg Ser Ser Ser Gly Val Pro Arg Asp Trp Val Ser Pro Leu Ala Pro
                165                 170                 175

Pro Leu
```

<210> SEQ ID NO 298
<211> LENGTH: 921
<212> TYPE: DNA
<213> ORGANISM: Mycobacterium tuberculosis
<220> FEATURE:
<221> NAME/KEY: modified_base
<222> LOCATION: (1)..(921)
<223> OTHER INFORMATION: n = g, a, c or t

<400> SEQUENCE: 298

```
aattcggcac garcagcacc aacaccggct tcttcaactc cggcgacgtc aataccggta     60

tcggcaacac cggcagcttc aacaccggca gcttcaatcc gggcgattcc aacaccgggg    120

atttcaaccc angcagctac cacacgggga ctcggaaaca ccggcgattt tacaccggcs    180

ccttcatctc cggcagctac agcaacgggt cttgtggagt ggaaattatc agggctcatt    240

ggntgcaccc ggscttrcga atccctcgkg ccaattcaac tcctcnacaa gcttgcggcc    300

gcactcsagc ccgggtgaat gattgagttt aaccgctnan caataactag cataacccct    360

tkgggcctct aaacgggtct tgaagggttt tttgctgaaa ggangaacta tatccggata    420

actggcgtan tacgaaaagc cgcaccgatc gccttcccaa cagttgcgca cckgaatggc    480

aatggaccnc cctkttaccg gscattaacn cgggggtgtn ggkgttaccc ccacgtnacc    540

gctaccttgc cannsscctn rsgccgtctt tcstttcttc cttccttctc ccmcttcgcc    600

ggttcccntc agctctaaat cggggnnccc tttmgggttc caattattgc ttacngsccc    660

ccaccccaaa aaytnattng ggttaatgtc ccttmttggg cntcccccta wtnanngttt    720

tccccttna ctttgrstcc cttcyttatw ntgamnctnt ttccacygga aaamnctcca    780

ccnttyssgs tttcctttga wttatmrggr aattscaaty ccgcyttkgg ttmaanttaa    840

cytatttcna attttcccgm ttttmmnatr ttnsnckcgm knctccnrka ssgntttcct    900

cccccyttss gktyccccrn g                                              921
```

<210> SEQ ID NO 299
<211> LENGTH: 1082
<212> TYPE: DNA
<213> ORGANISM: Mycobacterium tuberculosis
<220> FEATURE:
<221> NAME/KEY: modified_base
<222> LOCATION: (1)..(1082)
<223> OTHER INFORMATION: n = g, a, c or t

<400> SEQUENCE: 299
aattcggcac gagatanggg cgcaccgggg tccgcagccg gcgggaccgt cgccagcacc 60
accggggtca acagcaccac ggtggcgtcc angcagagcg ccgcggtgat ggcggccgag 120
acggcraaca cctgccgtag cagtcggtgc gactccgcgc tcgctcganc catggccgcg 180
ccggctgcct cgaacangcc ttcgtcgtcc acagcttagc cagcanccaa accgcaccca 240
gaaacccaca cgcccgccgc cccgganacc tgcgccatcg kctgctgggg cganatcccc 300
cgatcgctna cangatgacc gctgccggaa cgccgccgct gcctccgggc agccgcgtgg 360
gcsgggcaac cgcgaaccca ngaacacggc aagcagtatc ancgcaacag caattgtcaa 420
gggctaaacg cttcacatcc agggatctcg cggcgccaca ccgtcggmtc tgcagsgcga 480
ccccntcctn gggcggncac tcntcaaaga tgcngatcna cagkctaggt cttcggccga 540
tatgsaaggn cccaacggnt ttaaagcggc saaaaaastc tcccantgga taaaatcagc 600 cggggancc cccgtgscmm ngtcycggkc attnttcaac mggtttnacg gcggktgcng 660
gccaactkgc caaamttaag ktnggggnty cggggcggta accggcnntk ngccccttaa 720
aaaaccggnc ytttctkgat tammaccggn cccccawtgg cggktgktcc cangntyaac 780
amccycccss mngggktggs saacccttcc cgnggggttc ntkgttscyt awmcccccgg 840
aaaccsgkyg ggktggcrtn wassamnccc cmngyytctt taaaggccan knraawgkyt 900
ccttgggaaw cctncaatyc gaaaayyctc ctymmgsscn cttkcwrtyn nrngggaacs 960
amwtnyccnc gwttcawtcg ggtccgasmn aaackcttty ttttycgssc stccmggsnc 1020
sggtknanan aaasatttmc yycnnnankk yyycssgctt cykmgrrnrr gmgaacccgr 1080 gs 1082

<210> SEQ ID NO 300
<211> LENGTH: 990
<212> TYPE: DNA
<213> ORGANISM: Mycobacterium tuberculosis
<220> FEATURE:
<221> NAME/KEY: modified_base
<222> LOCATION: (1)..(990)
<223> OTHER INFORMATION: n = g, a, c or t

<400> SEQUENCE: 300
aattggcacg agtgatcgcg ctgaagccgg tagcgcgggt ggctcgggtg gtttgcgaac 60
raaatccgct cgangtggtc tcggtaggcg gtgtccanaa cggtggcgcg gtgccggcgg 120
atctgatcgg cgcggccgta gtgcacgtcg gcgggcgtgt gcagtccgat gccggaatgc 180
ttgtgttcgt ggttgtacca gccgaagaac cggtcgcagt gcacccgggc cgcctcgatc 240
gactcgaacc gtttcgggaa atcgggccgg tacttgaagg tctygaactg ggcctcagac 300
aacgggttgt cttgctggtg tgcgggcgtg agtgcgactt ggtgacaccg aagtcggcca 360
ncancaatgc caccggtttg gaactcatcc acaacccccg tccgcgtcma ggtcacttgt 420
ncggcgctaa tttnytgggc ggcaagggtt tgccgaycan kccgctcggc caaaacttcg 480
antcncscca aggccnccat ccncccaaac amgttacggg anaaaanaty caaagaycac 540
cytccggktn ttatanctyc ccytttgsty gggccccccn cyytgkknat acccctncca 600
awtcccaacn ccckccaana rcykggggcc cccnccaacc cgggkgaaka wtaatttaaa 660
cccyaacmaw actwmmnacc cnngggsccy aamcgtyynr aggttttsct naaagaaasa 720
antcggaamc cggntstacc aaaaasccck ccnwtccctc crasattgsc nccsaawksa 780
akgcccccny tcsgcnwnnc csgcggkkkt kkgttnccct wmrcwmwyts ggccnasccn 840
ckyyssmycc cccctccccm ctccgnktcc ccamccyanc mggccccytm gkkcccwknt 900
ykgccccccc ammnnngggg wgaccctngg ccccmkrrgm tcccnantga mcctcwgnra 960
mkcyccnrar anmccscncc ngcncrcknn 990

<210> SEQ ID NO 301
<211> LENGTH: 223
<212> TYPE: DNA
<213> ORGANISM: Mycobacterium tuberculosis
<220> FEATURE:
<221> NAME/KEY: modified_base
<222> LOCATION: (136)
<223> OTHER INFORMATION: n = g, a, c or t

<400> SEQUENCE: 301
aattcgggtg gcaacgcggg cctgttcggc aacggcggcg ccggtggtgc cggtggggct 60
ggtggtggcg ccggcggcgc gggcggtaac gcggggtggt ttggtcatgg gggcgctggc 120
ggcgtgggtg gtgtangtgc ggccggggcc aacggtgcta cgcccggtca ggatggggcg 180
gctggtgttg ccgggtcgga cracrctcgt gccgctcgtg ccg 223

<210> SEQ ID NO 302
<211> LENGTH: 418
<212> TYPE: DNA
<213> ORGANISM: Mycobacterium tuberculosis
<220> FEATURE:
<221> NAME/KEY: modified_base
<222> LOCATION: (1)..(418)
<223> OTHER INFORMATION: n = g, a, c or t

<400> SEQUENCE: 302
aattcggcac gangcggcaa cggtggcagc ggcggcacgt cngttgccac cggggggggcc 60 gggaacggcg gtgccggcgg cgccggcggc ggggccgggc tgatcggcaa cggcsgcaac 120
ggcggcagtg gcggaatggg cgatgccccg ggcggcaccg gcgtcngcgg catcrgtggg 180
ctgttgttgg gtttggacrg cgccaacgcc ccggccagca ccaacccgct gcacaccgcg 240
cagcacaggc gttggccgca gtcaacgcgc ccatccaggc cgtgaccggg cgcccctgat 300
cggcaacgcg ccaacggcgc cccgggcaac ggggcccccg gcrggcacgg cgggtggttg 360
ttcggcggcg gaaggaacgg cgggtccggc gtcancrgcg gggcgggcgg aaatgccg 418

<210> SEQ ID NO 303
<211> LENGTH: 1049
<212> TYPE: DNA
<213> ORGANISM: Mycobacterium tuberculosis
<220> FEATURE:
<221> NAME/KEY: modified_base
<222> LOCATION: (1)..(1049)
<223> OTHER INFORMATION: n = g, a, c or t

<400> SEQUENCE: 303
aattcggcac gaggggcacg atcgcataca gcgctcgcgg cagacccgcc cgatacagca 60
gctcggcaca cgcgagcgca caatacggcg tctggctgtc cggcttgarc accaccgcgt 120
taccggccac cagcgcgggc accgagtccg acaccgtaag cgtcatgggg tagttccacg 180
gcgagatcac ccccaccacg cccttcggtt gatagcacac cgtggtcttg cctatcccgg 240
gcagcagcgg ctgtgcctta cggggcttca gcaggtccac acagactcgt gcsttataat 300
tncgcsttcc gcgatcagat cgacaatttc ctcttgcgcc gcccatcggg ccttgcccgc 360
ctcggcttgc aggaagtcca tgaagaactc gcggttctcg atnaacaggt cgcgatagcg 420
gcsgatgact gcagctcgct cgatnacggg accttcgcca gtcggtctgc gccgcgcgan 480

-continued

```
cttccgcgaa tgccgcttcg acttccgcgg ncgtgccaac ggaatcntat cacgggttgc    540

cggttaaaac tcctcaatst ncyggtcgaa attcggcaac ttcttatccc ggcaggtrcc    600

aacsanncaa acctcggcaa ggttaggmtt tcccccnctt ycaaaaatnc ggkttttggn    660

cmaatttcgc ckcnatgktg mcaaggmtct ckaanaakcs gggtcytctn ntcngkggak    720

ccaaamggkt ttggggmagc gknmnccaan cctwaccctg ktkaanggnw ttcccccggg    780

gggakkgnga atycyccsna ncccrggggg gnmcarattc tyccggmctc ctckggawtc    840

wgmgstttcc caaaaaacsc cccaaattmm tttttccrcn trttganacw cttttkarca    900

mmcssaarns anmcnctcyc ckctktgktk aaaaagnayw ccccmaaatt tytawttssc    960

ccscgcgggn cccnctnttt tscnmtwctm wnytncrmcc mmmsncksng kkggnrccnn   1020

crccsncccm aawyntkgyn kntatmagc                                     1049
```

<210> SEQ ID NO 304
<211> LENGTH: 1036
<212> TYPE: DNA
<213> ORGANISM: Mycobacterium tuberculosis
<220> FEATURE:
<221> NAME/KEY: modified_base
<222> LOCATION: (1)..(1036)
<223> OTHER INFORMATION: n = g, a, c or t

<400> SEQUENCE: 304

```
aattcggcac gagggaatcg agaatcccgg aatggtgaag cctcggtgcc tgccgttacg     60

ccaagaktca gggtgagcgg ccccccggtg ggaatgctga sgccaaccgg gaaaagggtg    120

agggctgggg tggaataact gaangttact gggatggaaa acccggtatt gatatgtatt    180

gggccgatca angttgtggg aatgggggaa ggctgagggc gacctgttgg atttggggaa    240

ttgtyrtgga crakacwggc cagccmgcgt gatggtttgg ttsaantttt gtgccgscca    300

canggtgatg ggattgattt tgatggggcc satcgaaata ttgggtatgc cnacgccsaa    360

cgagatygcc gggacgttca tgggcgggac aaccmasggt ccsangtaak ggtttccttn    420

atnttgatcg ggattccgga actmtstcga tgsgctcsay mtsatsgccc nacnccwccg    480

yttatttcms gctnayggga atbamrggaa caayntccct cccmggaaaa accaacmsgc    540

cctggtnsyc cncccrccnc akaacccrtt kctgtrstmc ccsmaaatna cscccsctts    600

nactccncsg aantnscccc cccscknntt atstycccgk gttcccccmc cccttnaamc    660

tccccggtta acccccwtnt sncncccccs ytaakmncrg gcttsttnct cccccytrmk    720

cnccccctck samcwnccnc ctckaacnac ccckcykgsm tncccaatnt wcmwckccns    780

kttntmctkc ccaaytncrc ccncrctccc cckststcam wtataaaacc wcwyawynnk    840

kcncwmawta mgacwctcny nccccncnck nttktamwcc ckmccckcsw twcyckcscc    900

ccmtctmnac ycccccckkty nkwmcccttc ccccccctccc mcnmbmktct ycsgktwcwc    960

ncynttmtcn cynanmckck ktctcttccn crntctcccc ccwcccccccv kkctctskcc   1020

cncnctccsc mmkgsc                                                   1036
```

<210> SEQ ID NO 305
<211> LENGTH: 1036
<212> TYPE: DNA
<213> ORGANISM: Mycobacterium tuberculosis
<220> FEATURE:
<221> NAME/KEY: modified_base
<222> LOCATION: (1)..(1036)
<223> OTHER INFORMATION: n = g, a, c or t

<400> SEQUENCE: 305
aattcggcac gagatcatga atagcgggct ggtcagcacc gaagtggtcg gcgatctcgc 60
gagcaagtct cgtctgctcg cccagcagga ggtcggcatc gatgcggaca cctgcgatgt 120
cttggatggt gttcagttgc aggtaaggcc gacgccgcag ctttgctagc agggtgtctt 180
ggctcttcgc acgtgaggta accaataact ccgacgcaga ccaactccgg ccctcgatcc 240
gggtaccagg ctccgccgga gccagccgtt gtgccccctg ggccgaaggt cagctgctgt 300
gcgatcgaag taagaaaccg cgccatgccc gtcgccaagt acgactgacc gagcaaacga 360
acgatcgtcg tcctttccgt gggggtaatc gancccagca accgcacgag ccaccaatca 420
ttgggattcg gccactgacc gaccaaccgc ctgtgcgaca ccccagcgga attggtggtc 480
ttccgcgggg ccgcnaacgg aatcancgsg acgcgctcgc cgaascancc gcatanccnt 540
acatancaac ggnntctgcg cccacatttc gggsttmtgc ccctcngcaa cssnaayncc 600
cccaattcyg aacnaaaaaa ttggyccaty arngtyctcm ccaaaaaccn awtccccкta 660 tcccccgggg gggrccccyy nmnaaaacgg cccwwaancc ccsgggcscc cgggttrwtn 720
ccccttgtcg gcccnccsgg tttggtcmcm ggscmmtnwn gggntgcscc cccncnaaaa 780
aaaaayckng ncaaatyaaa ccckycmaaa asktgggssc cccmarccgg ggkaakkwwa 840
anttaanccn kaaaaaaaww ncannmcccc ngggncctaa ggkyttaggg gttsttnang 900
araaaatmtc canatmnssk ttnnaaaaaa asccswakcc cccnnnkknn ccaawkaarr 960
srccttcggg tnwnsggggg kkkkktncms kmnmmttwgr cccnccgccn nntwkccttn 1020
tccnyggngc rncagn 1036

<210> SEQ ID NO 306
<211> LENGTH: 1060
<212> TYPE: DNA
<213> ORGANISM: Mycobacterium tuberculosis
<220> FEATURE:
<221> NAME/KEY: modified_base
<222> LOCATION: (1)..(1060)
<223> OTHER INFORMATION: n = g, a, c or t

<400> SEQUENCE: 306
aattcggcac gagtcgattc gatcgaacac gcccgcacct ggccaggcca catgggcgcg 60
gccatggcca acgcctactc ggccaacccg aatccattcg gcgtctcacc gcaacccccg 120
aaaccggcga ccgcggcatg gatcaacccg cccaccccag atccgaaata gcgtccacat 180
aatgagacac tggcgcaaag agcttgacag gcgccgcacc acgcaagctg ttagacgtgt 240
cggtcttgca agaagcgggt tggccaccca agatcacgcc gcccaagggc atcgagtcaa 300
cgttgcggtg gtatcgcgct aacgtcggcg ccgccaagaa atgacggtgc gcattaccat 360
ggccctgctg atcacctttg gccacctgcg caccanaact atgancagcc ttatgccgag 420
tctcgtggac atcggcagcc gcttcaaaaa ctccttgtcg acaatsgtat tgctganccg 480
ccgaattctt ntrcttgcaa saacactnca tgttncsggt naacaaccyt ggttngaaaa 540
acanccaata ttgaantccc antcgggcam gaaccngttm cggaagktgk tgggaacgaa 600
tgktgcccaa aaatcccggg nggtraaaww cccnsnatgg msaattttsc ctngaacaam 660
aaaaggtcca agkycaaagg ngcccccccc sgnaaattgg tgaacscaka wyanrttccc 720
wwwtncaaat mttngggtcc knntccccwt aaangggscn ccccnccrgg gmgtytcccc 780
nwnmgggmgn cyycscccca aaaaaaammm mtttcsgkgg smggkkcccc ccsggtywgg 840
gkkyttaaac ccggkgggtn caaaaaanan accccccams ngggggggaaa atttgnaawt 900 aaggkkktkc scmaccccaa aaanmmnncn awnccccgmgk sarggggrny ttmkagggmg 960
gnyccccccw ycgggggggna naayaaaagk ngsngrgaat nttnttttgk rsssrnkttt 1020
tyntcctycn ccnmgnrwwg sramntgkts nssgggsggc 1060

<210> SEQ ID NO 307
<211> LENGTH: 1040
<212> TYPE: DNA
<213> ORGANISM: Mycobacterium tuberculosis
<220> FEATURE:
<221> NAME/KEY: modified_base
<222> LOCATION: (1)..(1040)
<223> OTHER INFORMATION: n = g, a, c or t

<400> SEQUENCE: 307
aattcggcac gagcttcacc aaagagctga catgccgggt gatgcgacat cgcatcgagg 60
gcaatacggg catggatgan ccgaanggan tctggcgttc gctcaactgg attacggttc 120
ccaaggtgaa acgctttgcg gcgaaagatg cgacgcttaa cttgcgcttc caccgtgcaa 180
tgttngtatg gatgctggaa ccgcgctgac ngataangaa ttcgctggtc gccgggcacn 240
atggatggtc ckstttttcnc tccgcsgtta aattgcstgt gcatcatctg gcaggctatg 300
ttcccgctac rctgcagccc atcatggatg tgcggctaac gaanaagtta tgacatggcg 360
caagcgamtc gggcatscnc gcggcamttt cgcaacctgc tgtgtntgaa gcgtmtcaac 420
cgaatgcggc gctyaaaagc nggcttgcgt tgattmmaac cnaacccntn cnatyctttg 480
ccgngnmntg cgttctctcc aactccgkkg sytgccnccg tgaaacccma ctnccccccc 540
gttggactta mrtnttcaaa aamcggmtna accsgaatnn saacctnccr tcaaantamm 600
saantcgggc ttygggnrcc ccccngaayw ttcknengggg gmnntyctcn ggttynggcg 660
saaacntttg ccrtncymnn tttacamggc ncmtnmttgm gggscsnnas gwcccgggkk 720
tntttncaaw tcncnskttt ttkgggggggg ggcygrtrmc ncgggccccc ggccckkmaa 780
aaaaamcmsa rrccncyggg kkcccccccm nnatngggcg ykcraaacaa accccaanra 840
tngngmgggc smaccsgngn gynaaakggt tsnsctmanm mkgmannnct sgmsccmnsn 900
nctgmgggkt ttkgnngarn aanamkmggm rcggncgcnn gaaagggsms gsckscnngn 960
ngasngwmgn crnnganrcc ncngygnmrn nngnnngnnn gggrknnacn nmkmcawsmc 1020
nsnmmgnnns cgymtnkcgc 1040

<210> SEQ ID NO 308
<211> LENGTH: 348
<212> TYPE: DNA
<213> ORGANISM: Mycobacterium tuberculosis
<220> FEATURE:
<221> NAME/KEY: modified_base
<222> LOCATION: (1)..(348)
<223> OTHER INFORMATION: n = g, a, c or t

<400> SEQUENCE: 308
aattcggcac gagacaangg cgtgaaatgg gatccggccg agctggggcc cgtcgtcagc 60
gacctgttgg ccaagtcgcg gccgccggtt ccggtctatg gggcctagtt atctgcgccg 120
agcgtgaact cagggcgaga tttcggccgt tttctcgccc tggcttcacg ttcggcgaag 180
tkgggaacgg tcagggttcg caaaccacga tcgggatcgt gcggtcggtc caggactggt 240
antcctgata cttkggtaca tcgtgaccaa ctgtggncaa tattcggcgc gctcctcgtc 300
ngtcgcgtcc cgcgcggtaa ggtccancac ttcctttttc tcgtgccg 348

<210> SEQ ID NO 309
<211> LENGTH: 332

-continued

<212> TYPE: DNA
<213> ORGANISM: Mycobacterium tuberculosis

<400> SEQUENCE: 309
aattcggcac gagagaccgg gtcgttgacc aacggacgct tgggcgcggg ccccttgcgt 60
ggcatcagcc cttctccttc ttagcgccgt aacggctgcg tgcctgtttg cggttcttga 120
caccctgcgt atccagcgaa ccgcggatga tcttgtagcg cacaccaggc aggtccttca 180
cccggccgcc gcgcaccagc accatcgagt gctcctgcag gttgtggccc tcgccgggaa 240
tgtacgccgt gacctcgaac tgactcgtca cttcacgcgg gcaaccttcc gaagcgccga 300
gttcggcttc ttcggagtgg tggctcgtgc cg 332

<210> SEQ ID NO 310
<211> LENGTH: 962
<212> TYPE: DNA
<213> ORGANISM: Mycobacterium tuberculosis
<220> FEATURE:
<221> NAME/KEY: modified_base
<222> LOCATION: (1)..(962)
<223> OTHER INFORMATION: n = g, a, c or t

<400> SEQUENCE: 310
aattcggcac ragtcggtct agacggattc aatgctcccg cgagcacctc gccactgcac 60
accctgcagc aaaatgtgct caatgtggtg aacgagccct tccagacgct caccggccgc 120
ccgctgatcg gcaacggcgc caacgggact cctggaaccg gggctgacgc ggggccggcg 180
ggtggctgtt cggcaacggc ggcaacggcg ggtccggggc gaacggaacc aacggcgggg 240
acgtggggac gcgcccggcg ggatttcttc gcaccggsgc accggcgggg ccggcggcgt 300
cgcacaacgg caccggcggg gacgcngcgc ccgtngggcg gcttctkgat gggctccggc 360
ggtnacgcgg cacggcggcg cccggctcac cgccngttgg gacgcgggga cgcgtnaccc 420
cgatcttctt ccgcnccccg gaaaccgcgg ggccggcccc acattakacc cggcggnacc 480
gcggmcccgg cggaacggng ggyntttttcc aacggcgggg ccgcggaacc gnmggstgtt 540
ccttnggsga aggnccaakt cccgkctanc yyaatccccg anggktgamc ctsatgsnca 600
myttmaggaa cytnccccant kttsgraccw crccnggaaa asrawnkngt kggcaaacna 660
nntncyttkn nattkggnna aaaanccccty ccwcsgract ncccccccngm grgmcnntnn 720 ntttygncnn cccggsnaam rnttkatttc ngggggntcn gggtkmnnna aaccccaaam 780
mnrnnkcsca angggksngc nknnmmnsgt tttycknmra mrnwtyknkn ntcngarsrn 840
naamcnnsnk ngkkknnkaa arnnttwktn knscnnncnn grrngvrggc ckmkgsnmng 900
mcwhnawrng nngsncnckc nnkmnaaaaa aasggvncks nsmknkkkkg nrgggggggg 960
gg 962

<210> SEQ ID NO 311
<211> LENGTH: 323
<212> TYPE: DNA
<213> ORGANISM: Mycobacterium tuberculosis
<220> FEATURE:
<221> NAME/KEY: modified_base
<222> LOCATION: (1)..(323)
<223> OTHER INFORMATION: n = g, a, c or t

<400> SEQUENCE: 311
aattcggcac ragaagacgc ccgaangttt gcgctggctc tacaacttca tcaargcgca 60
gggggaacgc aacttcggca agatctacgt tcgcttcccc gaagcggtct cgatgcgcca 120
gtacctcggc gcaccgcacg gcgagctgac ccaggatccg gccgcgaaac ggcttgcgtt 180
gcagaagatg tcgttcgagg tggcctggag gattttgcan gcgacgccng tgaccgcgac 240
gggtttkgtg tccgcactgc tgctcaccac ccgcggcacc gcgttgacct cgaccagctg 300
caccactcgt gccgctcgtg ccg 323

<210> SEQ ID NO 312
<211> LENGTH: 1034
<212> TYPE: DNA
<213> ORGANISM: Mycobacterium tuberculosis
<220> FEATURE:
<221> NAME/KEY: modified_base
<222> LOCATION: (1)..(1034)
<223> OTHER INFORMATION: n = g, a, c or t

<400> SEQUENCE: 312
aattcgcagt gtgtgtggcg gcgtccagaa gaagatgatc gcgaacatcg ccagcgccgg 60
ccaggctatg gtgccggtga tggccgacca gccgatcatc accggcatac agccggccgc 120
cccaccccac accacgttct gtgacgtgcg tcgcttgagc caaagcgtgt agacraacac 180
ataaaacgcg acggtgacca gggccagcac ccccgccagc aggttcgtgg cgcaccatag 240
ccagaagaac gagatcaccg tcnacgtcac ccgagtgcca acgcgtttcg ggtcggcacc 300
gcttcccgcg ccaagggccg gcgcgcggtt cgcttcatca ccttgtcgat atcggcgtcg 360
gcnaccagtt gagcgtgttg gcgccggcgg csgccatcat cccgccgacn ancgtgttga 420
gcatgancag cggatgaatg gcgccgcggc tcgtgccgct cgtgccgaat tcaactccgt 480
cnacaacttg cggncgcact cgaacccggg tgaatgawtg aatttaaacc gstsaacant 540
aactacataa cccttggggg ctcttaaccg gtyytgaang ggttttttgc ttaaaggaag 600
aacyatttcc ggatanctgg csttnwtarc gaaaaggccc crcccatngc cctccacagt 660
ttscccctga atggsaatgg mncnccyknr cngggncttt aacrcsggcg ggnttttgkt 720
mcccnnctka cnttmmmtgc arnncnggcc skcccttcck tntyccctcc ntcccccnst 780
tncngktccc cnnamnytnw acggggggcc ytngggkcrm twtkktttgg gccccmcccc 840
maaanasaan ggggkrngty cstttggcnc cccamaargg nycccccccam ytnrrkmcsy 900 cnntnkggnn ctgtnckncg gaaramamcc kccccgnsts sttngtywag gnrwkgnsrg 960 ccscccccggy mnnnaayawn wmnatncnns stnanmakkn nnnnnnnscn wngngnntcn 1020
scnsnggkbc cscc 1034

<210> SEQ ID NO 313
<211> LENGTH: 331
<212> TYPE: DNA
<213> ORGANISM: Mycobacterium tuberculosis
<220> FEATURE:
<221> NAME/KEY: modified_base
<222> LOCATION: (292)
<223> OTHER INFORMATION: n = g, a, c or t

<400> SEQUENCE: 313
aattcggcac gagcccacat ccggggccgc tcgttgcatg actcgttcgt catcgtcgac 60
raggcacagt cgctggagcg caatgtgttg ctgaccgtgc tgtcccggtt ggggaccggt 120
tcccgggtgg tgttgaccca cgacatcgcc cagcgcgaca acctgcgggt cggccgccac 180
gacgggtcgc cgcggtgatc gagaagctca aaggtcatcc gttgttcgcc cacatcacct 240
tgctgcgcag tgagcgctcg ccgatcgccg cgctggtcac gagatgctcg angagatcac 300
cgggccgcgc tgagtgcgcc tcccgcgagc a 331

<210> SEQ ID NO 314
<211> LENGTH: 1026
<212> TYPE: DNA
<213> ORGANISM: Mycobacterium tuberculosis
<220> FEATURE:
<221> NAME/KEY: modified_base
<222> LOCATION: (1)..(1026)
<223> OTHER INFORMATION: n = g, a, c or t

<400> SEQUENCE: 314
aattcggcac gagatcgtca ccctggcgac cagtgcaccc aggccacgcc accagttacg 60
gctgatgggc cagaagatgg accaggtgct gcccatcccg cccaccgcac tgcagctgag 120
caccgggatc gcggtcctca gctacggcga tragctggtg ttcggcatca ccgctgacta 180
tgacgccgcg tccgaaatgc agcagctggt caacggtatc gaactgggtg tggcgcgtct 240
ggtggcgctc ancgacaatt ccgtgctgct gtttacaagg atcggcstaa gcgttcatcc 300
cgcgcactcc ccancgccgc gcggcsgggg cggccctctg tgccgaccgc ccgagcgcgt 360
cactgacgcc atctccgtcg gcgttaaccc cgtgagaagg tgggtcgtgc gcaagttggg 420
cccggtcacc atcnatccgc gccgccatga cgcngtgctg ttccacacca cntsngacnc 480
cccccaggaa ctggtccggc amtncaggaa ntycgtgtgg gcaccngctt cttccgktrt 540
ggcytaaact tccnatsttn csgcsggcct ctggcgttnc gnccgggccg ntcttnccaa 600
atcggsmmaa atccccanmc aaaccccccg ggtcttgsgg gcsgggnggc ggccnawncc 660 aaacccccccc nttaaantct ttgktnccnn cncsggcncc ncnaanscan ccctttkggc 720
ncttcccccc cccawtttaa ccgakcgscn aaycccaagy tmmgkccycy knaaaaaaaa 780
aatttgscsg ccccaantaa attcccnggc ccyttggggg cgrancnynt tttmccsnss 840
tkgnnnaamc ngganccsgg kaaytmmtkg naaycgccsn aambnttttc taannccccn 900
yncccsgaaa attnnamaam cmnnktgsng ggggkttsnc sgkkgraggm aaaaaanrsn 960
skttnmcnnn sanmncnsnn sggnsnnnnn nnncncgykc csnaanmccc cgcggggggg 1020 ccmmcc 1026

<210> SEQ ID NO 315
<211> LENGTH: 324
<212> TYPE: DNA
<213> ORGANISM: Mycobacterium tuberculosis
<220> FEATURE:
<221> NAME/KEY: modified_base
<222> LOCATION: (1)..(324)
<223> OTHER INFORMATION: n = g, a, c or t

<400> SEQUENCE: 315
aattcggcac gagaagacgc ccgarngtst gcgctggctc tacaacttca tcaargcgca 60
nggggaacgc aacttcggca agatctacgt tcgcttcccc gaagcggtct cgatgcgcca 120
gtacctcggc gcaccgcacg gcgagctgac ccaggatccg gccgcgaaac ggcttgcgtt 180
gcagaagatg tcgttcgagg tggcctggan gattttgcan gcgacgccng tnaccgcgac 240
gggtttkgtg tccgcactgc tgctcaccac ccgcsgcacc gcgttgacgc tcgaccagct 300
gcaccactcg tgccgctcgt gccg 324

<210> SEQ ID NO 316
<211> LENGTH: 1010
<212> TYPE: DNA
<213> ORGANISM: Mycobacterium tuberculosis
<220> FEATURE:
<221> NAME/KEY: modified_base
<222> LOCATION: (1)..(1010)
<223> OTHER INFORMATION: n = g, a, c or t

<400> SEQUENCE: 316
aattcggcac gangcgtgcc gctnaacacc agcccgcggc tgccagatat cccggactcg 60
gtagtgccgc cggtggcgtc gttgctctcc tgacggggcg cggcgaccat aaggtcgctm 120
atgcccaggt agcggcccag gtgcatggag tcgatgatga tgcgactctc cagctcgccg 180
accgggagct tggcatcggg cctgatcagc caggacgcgt aggacaagtc gatcgaatgc 240
atagtggcct ccagagtggc cgtgcamttc cngcgtgctc cacggcaaat gccttgattt 300
ctactccgcg tantgttccc gcatcgcctg cgggatgaat gggaaccgca sgatggcgac 360
gaacgggtct ganctcaggt ttgccgcttt gcgcacagtg gtcnacancc ggtactcggc 420
atanatctgg cccnaaatcg gcgccgacgg cgcccacnat aanaacgggc acnacaatcg 480
ccgccccggt cacccnaaca acancttgsc atcggatttt gtccccancg ctcaanccgt 540
cccgaacgcc tcntccggcg nacttttctt nnawtaactg ccgcttccgk ccctggngca 600
wtaaatggga aacccttncc ccaccttgaa ggggttgttg natttttact gstaaccccg 660
aattnttccg gantcggtcn kccgggsttt ystnttcccc accttngnan gggccggcca 720
agsttttctt sytgaagggg gaaacccaac tttntytyyn aaccscmnaa mymtttycsg 780
mnaasccnkt cccctttaac camggsggtn aaccgktmng nggktaaaaa gggsknnktg 840
nccccymang gggggraaaa tstktcnncg gggcckaaaw accmmmmygn gtgkkknkss 900
gcsaaatttt nmmraactkn ggggccssga nntttnaaag msccccсsnn gstgkcccnn 960
ntttccnnaa wmkkgknwnm snmnscsngg gkynsggsnn nnaagmgggg 1010

<210> SEQ ID NO 317
<211> LENGTH: 1010
<212> TYPE: DNA
<213> ORGANISM: Mycobacterium tuberculosis
<220> FEATURE:
<221> NAME/KEY: modified_base
<222> LOCATION: (1)..(1010)
<223> OTHER INFORMATION: n = g, a, c or t

<400> SEQUENCE: 317
aattcggcac gangcgtgcc gctnaacacc agcccgcggc tgccagatat cccggactcg 60
gtagtgccgc cggtggcgtc gttgctctcc tgacggggcg cggcgaccat aaggtcgctm 120
atgcccaggt agcggcccag gtgcatggag tcgatgatga tgcgactctc cagctcgccg 180
accgggagct tggcatcggg cctgatcagc caggacgcgt aggacaagtc gatcgaatgc 240
atagtggcct ccagagtggc cgtgcamttc cngcgtgctc cacggcaaat gccttgattt 300
ctactccgcg tantgttccc gcatcgcctg cgggatgaat gggaaccgca sgatggcgac 360
gaacgggtct ganctcaggt ttgccgcttt gcgcacagtg gtcnacancc ggtactcggc 420
atanatctgg cccnaaatcg gcgccgacgg cgcccacnat aanaacgggc acnacaatcg 480
ccgccccggt cacccnaaca acancttgsc atcggatttt gtccccancg ctcaanccgt 540
cccgaacgcc tcntccggcg nacttttctt nnawtaactg ccgcttccgk ccctggngca 600
wtaaatggga aacccttncc ccaccttgaa ggggttgttg natttttact gstaaccccg 660
aattnttccg gantcggtcn kccgggsttt ystnttcccc accttngnan gggccggcca 720
agsttttctt sytgaagggg gaaacccaac tttntytyyn aaccscmnaa mymtttycsg 780
mnaasccnkt cccctttaac camggsggtn aaccgktmng nggktaaaaa gggsknnktg 840
nccccymang gggggraaaa tstktcnncg gggcckaaaw accmmmmygn gtgkkknkss 900
gcsaaatttt nmmraactkn ggggccssga nntttnaaag msccccсsnn gstgkcccnn 960 ntttccnnaa wmkkgknwnm snmnscsngg gkynsggsnn nnaagmgggg 1010

<210> SEQ ID NO 318
<211> LENGTH: 1092
<212> TYPE: DNA
<213> ORGANISM: Mycobacterium tuberculosis
<220> FEATURE:
<221> NAME/KEY: modified_base
<222> LOCATION: (1)..(1092)
<223> OTHER INFORMATION: n = g, a, c or t

<400> SEQUENCE: 318
ngnggggwns ntcaycayca ycacsgggyw cwattgcggc cgcawcttgt maasagatct 60
cgaaytcggc amgagggamt ckctmgcncc gctgtgcaan ccaatraggc ctrataatty 120
ccactccaca aaaaaccgtt gtgtgtayyt sccgraaatr aaggcgccgg tntcaacwyc 180
gccggtktty ccratycccg tkttgtamct gcckgggtsr aaayccccgg tgttggaycc 240
ccggattgaa actgccggkt tgaaactgcc gktttsgcsa tccggkwatt gamstcrcgg 300
attaaaaaac cggkkttggn gctgsncgtg ccaaatncgr ayccratayc ccatggcctg 360
kyctyctcck ycggtaccca aayctgggta tcctatactg gyccctaaak gcaawyckgg 420
gctgycmmtk ttgckggsgt ccnaatttas caccascggt tccttccata ccnaaacncg 480
cktgggcwcc agmccgraaa aaakaataat rakaakggtg catnyccaaa accnccgccn 540
cccnantncn atccgntncc mscnccccca gcggtnaagk tksggaaytt ctmmaacccc 600 caaanccccca taacntncgr gaasaaaccc ctycncgggg gycnwncaaa acascnttat 660
ttgctksttt cgggmwccgt gccgccnaaa ycccaaasta ctttytgggt ccnagakaaa 720
accncgggcn ccmcccsnaa nwtatytctt kggcaanccc csaaaccttr tcmnaccnck 780
atrmtccctt ccccvscaat tggycggrat ncgsnccyty tcaaakkksc cakwwnngng 840
grrnnaccma accccaagty ccmnaaaatn gkccccgctc cnaacacgnk tyytccsaaa 900
ascccwcccc cccccccraa aaccccccna rkantnccca aaaacnyngk ggcccccccc 960
caaacmaaaa amcccccsgm rmacsggggn nmccccgkkk kktttttcttt tkccmrsccc 1020 aamgcamwsy ksktnmaaaa ggaagrancn tyccsananm tcccnywrsw ccgswgmgna 1080
gaasmccccc cs 1092

<210> SEQ ID NO 319
<211> LENGTH: 1251
<212> TYPE: DNA
<213> ORGANISM: Mycobacterium tuberculosis
<220> FEATURE:
<221> NAME/KEY: modified_base
<222> LOCATION: (1)..(1251)
<223> OTHER INFORMATION: n = g, a, c or t

<400> SEQUENCE: 319
gggggggnnn natacatcwt cygtgyaccg gggmtctakt ggcgggccgc aatctngtca 60
asagatctct namttcgggc acaaaaactw gacaaasymt cgngcnmtcc gtgtcctnka 120
tcgcaaaacg ngtracasac asacacrtat gtgtgcccac cascaaytck ttgggacctc 180
gctraccggy tgcccrnacg ccacgytgcs cwtctatccc racgccggcc acgggygggg 240
atattccagg caccacgccc agtttggtgg acaatgccct ggcaktttcc tcraanttcg 300
tgaaaccgaa ttcnsmttga accnccaarg ccccsnccnr aacarttggg wtccgcggtt 360
ctccccaccg ktttccgggg gtntcggcan aancgcaccc wtggwttctm tcnccgcacc 420
gggcggacaa ntcgggttgc aattttgcra aycggggccg ggattccsca aacgggtgcc 480
gaaactgtty ycraamaccg ggakccgcaa tttccgggcr anaaatttcn ycncaccact 540
gcttrtactt ccccgaccgt aacmantttc atcgtcntnn cctctgccct tggggcaggg 600
ckaaayaccg cmttkggttt cgcaacctgc ggcccaantc ccnamccrca ctttcnattt 660
ggntcgaatt sccccccggt ranaaccscc ntggccnnyt cggassaaaa ngggccctnt 720
kggcnscccc agtaanaccc taccnnayts cawtctttgc caaasttkgg acgaansktg 780
ggnttccggk atttyyttgs ggncnccctn tatnggsntn gggcckcync ncstktgkca 840
nasskayccs ngnkgggggt accccccctmg gggggttttt nssgcccccc awaygnkstg 900
gcccccnngg ggaakaatwt mwwtmcnsgg gggaawtttt ntstggamcs sggacycccr 960
gggggktttt tccccncsa nnawangggg gggggganayt ntgnsgnggg kwntttattt 1020
ytyycycctm tkacmsgggg gtttkkakng gggggagaaa anaaaaaaaa rakggykntt 1080
tskncacnct gkwnwnwanr nagagktcct ckckccncsg sntttctttt mgnsgsyggg 1140
gnngnnnaaa acnksrmmac kcsytycccg cgyctcctcc ncnggggygs ngscgnstyn 1200
gnnkgrkwta tntmgncgtn scctccnccc gcknkntgtc tmtcnmygsg c 1251

<210> SEQ ID NO 320
<211> LENGTH: 1099
<212> TYPE: DNA
<213> ORGANISM: Mycobacterium tuberculosis
<220> FEATURE:
<221> NAME/KEY: modified_base
<222> LOCATION: (1)..(1099)
<223> OTHER INFORMATION: n = g, a, c or t

<400> SEQUENCE: 320
aaytcggcac mgagtatcac caakctgygt ggcccagcaa agtggagcta ttactacctg 60
tatgtgatcc tcracatcty ctcccgctac ktggtcgggt ggatggtggc ctcgcktgak 120
tcraaggtct tggccraacg gctgatcgcg caaacccttg cgcccagcac atcakcgccg 180
aacagctgac ctgcmcgccg accgggggyc gncaataact ccaaaccggt ggcmctgctg 240
ctggccnacy ccgtgtccca antcgaactc asccsgcnma ccakmaacka naaccgttgt 300
ctgaagccca gttcaaaaac ctcaagtwcc ggcccractt cccgaaacgg tncgagtcka 360
tcrsaggsgg ccgggtgcmc tgcaaccggt tcttcggntg gtrcamcccn aaamcaagca 420
ttccgggmtc cgmmtgccca cgccgccaas tttmctacgg gcsgsccnat caaattcgcc 480
gggaacsgsn ccmccktcnk ggamacgccc twccaaaacc cycgaacggk atccttckgy 540
naacncccga rcncccckskt tccgggcttc nmsgcgaata cccknscmnt ccgaatccaa 600
ttcccmkygg cttttyyycc ccccggcccc aaayngggyc cctassnmkc knccamnant 660
ccnwatctgg nggtcccnan kyyggcgttc nmaatsamna nmnrgggtyt tscyaccmmn 720
aaccgknnkg kccccmkctk manaaaakatt ratcamkwng ggnkckcncn naamaccscn 780
cncyncwytc tmycsskwgc gcsmynanca snggggaggw ggsgrmkmct ctmtctcnct 840 mgcgccckntn tycksgakat acasmnktcc gcgcngcgcn maamanraka ctakccgygn 900
ccsnstmtyn ctsnnmkmnn tccwmwnatc ntyygkkcnn kctmkatnwc csctskcnck 960
mramtcktyg snmtcctcca tcnctckksc snmskntckc kscnccncwn cnkcnmkcwn 1020
ggnstcrccy tctmnnntcs agckcgsknc wacncacack ngwctyttcc wknnmkcnkm 1080
tckckcacrg mtmtcwccs 1099

<210> SEQ ID NO 321
<211> LENGTH: 296

-continued

<212> TYPE: DNA
<213> ORGANISM: Mycobacterium tuberculosis
<220> FEATURE:
<221> NAME/KEY: modified_base
<222> LOCATION: (1)..(296)
<223> OTHER INFORMATION: n = g, a, c or t

<400> SEQUENCE: 321
gngntataca tcwctgtgya ccsaggatcw antgcggccg maakctwstm casagatctc 60
aaaytctgca mgagcggcac akakystcgt ccmracccgg cayacwccwg cncgccccwt 120
cttrgaccgg ggckatasmc accgttggcc ccggcncgca cctacaccac ccacgccgcc 180
agcgcccccw tramcaaacc accccgcktt taccgcccgc gccgccgggg ccaccaccag 240
ccccaccggc accaccggcg ccgccgttgc caaaacaggc ccgckttttgc caccra 296

<210> SEQ ID NO 322
<211> LENGTH: 1073
<212> TYPE: DNA
<213> ORGANISM: Mycobacterium tuberculosis
<220> FEATURE:
<221> NAME/KEY: modified_base
<222> LOCATION: (1)..(1073)
<223> OTHER INFORMATION: n = g, a, c or t

<400> SEQUENCE: 322
ngngsgnkmy atcatcwttc tgcaccsngg mtcwattgcg gccgcaatct tstmnasaga 60
tctcgaaytc ggcamgarca tctgcgcggn gaatgtccaa awgtcwktaa cggcmatcgg 120
tttgccgyca accackctrt scakatgcgg gccamwtyca aaccrattat ttgggycgag 180
aaaatttmcg cktgtrasca acctgcagcg ggtcaascaa cagcctctra accgtaaaty 240
cktaggtnkt yccggcaaca ascycrataa tscggcccgc amccacaaaa cctgantngt 300
tnttcncraa nccggtyccc gragggtsa actgcsgtar gcttntcwyc nccttracat 360
taaacccccc cggntcwtcg ccgcgcccaa atycytgccc wtkgcnacca ycccancctg 420
csgtatggts raancastsg gcraacggtm mccstacckc tggctgatyc ktcggntccs 480
snaattcggg gatttacggs camggttaay ccaggycccc tntgcytcky cnacaaccsg 540
atcmwcnccg tacctkttaa aattctttgt ggtggaaccc awyckaaaaa nmtntycccn 600
tccammgggg cycggaakkt cnacntggkt nacccctncc yttgaasttt tcytgncccc 660
ggccckaaas anaccsgakc cccggaaycs wtaggcytcn tgccccstta aattkgncyc 720
aatcckccaa cgctccccgg ggtcssccmt taaamttccc ccckscasng gaatycyksg 780
gcwgtmattw ccncccnttt cyygknaaac scccccwkgn gsctycccn snttssgccs 840 ggttsgamyc aaaawtnggg mmcnragncg sgnamccscn gkkgggsatw tkaayycygg 900
gggggtcnyc ccccrcsnaa aagygtkggc kccsssccyc ccmartttyt cnggmrcmam 960
accangggng ctcccgtncw wggctcccsn snsmamaaan nkckcckggs ckgarrnmna 1020
mctcsngngg wtcccknktc nscnsgncgs yggnsaswcc ynycnccaca anc 1073

<210> SEQ ID NO 323
<211> LENGTH: 1166
<212> TYPE: DNA
<213> ORGANISM: Mycobacterium tuberculosis
<220> FEATURE:
<221> NAME/KEY: modified_base
<222> LOCATION: (1)..(1166)
<223> OTHER INFORMATION: n = g, a, c or t

<400> SEQUENCE: 323
cgccccgttc ttmmmttcay tcattcaccg ggmtctagtg cggccgcaak cttgtckaca 60

```
gatctcgaay tcggcamgas acaatstcgg gtkgggcaat gtcnggtggg gcaactttgg    120
gctcggraat ycggggttaa cgccgggtct ratgggtstg ggtaatatcg ggtttggtaa    180
tgccggcagc tacaatttcg gtttggcaaa atatgggtgt gggcaatatn gggtycgcta    240
acaccgscas tggraattyc ggtattsggt naccggtray aayctgaccg ggtncggtgg    300
ttycaatacc ggtaacggga atgtsggtts yyyacyccgs gsaacggnww yttngktcct    360
tmmcnctssm ccksaamtsm kmggtstyct mtycnnggas tamtynmccc ccgwayckss    420
waycccctcgt catyccmcmc sgsgycctca mnccaccytg ngyyccctcc mkmtcycayt    480
cmntccggtw cctntmmncc cscncryctc amcnctksgk caccnatmyc csackchtct    540
mcymcscakn mttcccctcn cctytnncca mcmcsctctm tcmaactckc ccggyckcnc    600
myctctckcc aynmaacckk tycywcnwyc ymyckckcag wyknmctccw actctmyntt    660
tctctcnkcc cmkacckntt ctcwcscccc ccacakaymc yawcmtmtcc mctckacscc    720
cyycnnyccm nmcwcmtcwc twnakcancn ttcttctctc mmymtmackc wcnntcncck    780
sgaccytctc actkmkcckm tctccttmck ccymwcntcc mkyncccctcc nmtcmtckyt    840
cctcncnmry cyyyakcakc nmctccccan kmcakctkct cccccakmks acnckcccwc    900
cctcctatcc wctctcwcty atctckctcw cnycmymkmc acnckcyayt cnactmnmwn    960
ccancnctct ctnyctcwck acgtyckcck ctmckcnymc nrwctyrcct ckkccnccrn   1020
cknmcmkctm ctctccwmkm tcccwcccat ctmmkstctc wcncmtccct cnkccynynt   1080
kcytyccmyg cttckntcmt mccwccyatc tctmkcctct cwcacymcac wmttacwncc   1140
actctctrcw ckcckcmccr mtctcb                                        1166
```

```
<210> SEQ ID NO 324
<211> LENGTH: 1230
<212> TYPE: DNA
<213> ORGANISM: Mycobacterium tuberculosis
<220> FEATURE:
<221> NAME/KEY: modified_base
<222> LOCATION: (1)..(1230)
<223> OTHER INFORMATION: n = g, a, c or t

<400> SEQUENCE: 324
```

```
ngnggnnnnt cwtacatcwn tctncaccsg ngmtcwattg cgcgccgcaw ncttgtmnas     60
agaatctcnn aaytcggcac anatgtcttt tstmtaktgt ggcggggngc cacgccktat    120
gtgygcctgg gytracccaa ccccgcggcs cgggccracc aggcggggra tscaggccgc    180
ggcggccgcg gcggytatat raagcgccgy ttttktrata acggtsccgc cgccgggtra    240
ttacgggcaa aaycggkktt ttgggtrtat aacgctaatt gcaaccawtt tttycgggtc    300
aaaaacycgg cgwgcanatc ncgggycnct raggcgcatt ymcgccaaaa wtntgggcgc    360
aaaaccccckt tsytattttn tgggctatsc ggytgcttcg gcaaacgcty cccgggttaa    420
tcccktccgc ggcgccgccn aaaaaccacc aatyccgytg ggggtgkycc cmcaggcsgt    480
tgctycgngy cacctggcca aayycccawt akattgggtg scycktscgg ttsytgggcy    540
caattacccc cncgggnaaa grraaaanaa atcntccntt tgctcggyca yctttmttgg    600
saaaaggggc atggcscggt tyytttacct caaycccna ncantwacct ytccscccgg    660
ggggncanaa cgsttngctc cgsggnakcc tkgtmcccgn atcnaaaggc cngaatttgg    720
tyysstycna attwtwkkky ccccwcnttg yaaaaakcca aaasakccck ycncammykt    780
nggggtyssg gccknycttk snmttaaacc cyccccaaaa yynsgggkkt tccgcynsat    840
kccaccncck gngggggna saaaaaaaay tttyccsaaa atcccaccyy tcyktkstry    900
```

amaccccctt tyymkkaytc ckyscnattc sgmttcwaaa tyccgyggct tnttccccck 960
csggngcccc aawtttgktt yncnanttyc cccnaamncm awtmggggks kccattctgg 1020
scytmaanta aaanaanggg nktttyycty manaaacacn gtgkcncncn cnaamaaasn 1080
akmaaakagn kkkmtknnsa aanccncccc ctstytnytt nktnmnckcc cyggkknkgm 1140
swswynttct ncccrccccc ynynktgana aammncyccs ggstmcrnan asnmntttck 1200
ststngmgcc kmbasnanan mcamwkwycc 1230

<210> SEQ ID NO 325
<211> LENGTH: 1022
<212> TYPE: DNA
<213> ORGANISM: Mycobacterium tuberculosis
<220> FEATURE:
<221> NAME/KEY: modified_base
<222> LOCATION: (1)..(1022)
<223> OTHER INFORMATION: n = g, a, c or t
<400> SEQUENCE: 325
ngngggknna tmaycwtctc acssggtcta tgcggcgcaw ctmgtmaasa gatctcnaay 60
tcggcamnan gcatmtcmmc catatataac cattgcgtcs gywtgcawct craawctgtc 120
cttcskgccg ttktacraag gtggmwtgyt cwtycctraa sccctcratc tcktktatyc 180
ctkgggctyc actttaacsg ratksctgcc ttktaycatt ratgcaawta wtggycrawt 240
kttgcaggcc racggcwyct tttyccgcra gracaatnga ttggawycgc tycgcraggc 300
ccggcaccar accgggcncc aaaggyccgc gcaawtscct ggktcaaaaa tggtgcaaac 360
aaamcnatcc ccggyttrac cgcagytamc acaakaaaat tcccwtggcc gcaccawnnt 420
ttycratcwy cwyccccacc ttraacttgk ytgcsgtatt gcctkcctgc ctcracagcm 480
ycncccktca aacctgcggt gactccaact ggtctggycg aasgggggyt camcggacaa 540
aaccccrann tcgccaaatt ttcnccccccc cycgggaaan gktgatmttc tcsnaaccsa 600
cmgggnnytw naaccctgaa csssgsnkga mynsccsgga antttttccct tyngggcgrn 660 aaanccttttt aaggtacccc kggnggggkg cccyyttggg aaaacaaccc ckattggktt 720
tggaaatntt tkcnccccca ttcnsggggg gggccccamc ccmmcttttn tcmscnmtyy 780
ycyygggaat tnytcgccsg gaayycggsm cckgycctaa nccccmnwgg gkystgsnar 840
ggratmawwt tystttyymc ccggcnnccc ccckakmcnt kgntgaacma aaakcsgggg 900
gscnmymwyy ycnnngnrtt tnrggssnmt tymaaamman ggggkywtyy ckccngscnn 960
gktysgggst tttccnttts gggssatykg macccccktmt ayccgggggt ntktkycccc 1020 sc 1022

<210> SEQ ID NO 326
<211> LENGTH: 1083
<212> TYPE: DNA
<213> ORGANISM: Mycobacterium tuberculosis
<220> FEATURE:
<221> NAME/KEY: modified_base
<222> LOCATION: (1)..(1083)
<223> OTHER INFORMATION: n = g, a, c or t
<400> SEQUENCE: 326
nncgnnknta tamaycwyct ncaccsggga tcwattgcgg ccgcaatctt stmaasagat 60
ctckaaytcg gcamganccg cawctatttg kgtgrascgc accagcgrga cctcgcsgkt 120
ckttycttgc agrgaggcck tgggtggcrc cggtggcaat gccaaccgcc ccccaaaacn 180
ccgcaaatmy craaaaacaa cccsggggta gktccsggcc gccaaatmaa taaccgtktt 240

-continued

```
aackcaggcn acggccaacc ggycccgccc aaccaagcna cctccccscc nataggyccg    300

gtgggggctg cck tatykcc aastcgtcay ctcnacgggm cggyccmcwt tccgcctcat    360

ccgtctctcc ttmmattttc crtccacykg gcggggaacy tttttnycnc ccttgscman    420

caccnaaggy cnaaaattnc ccmtgcckyg snncaaaygr gattggggty cgkkttttnt    480

tcnmccmaac ccccntttna cgccccmatc ccytwatacc cccwwmcmns angkttgnsa    540

aaktnncccc aaatrccaaa mttcttcgcc ntttmtwmcy yyccttt ccc cmcccwnaaa    600

ggsccrccyy tcgggaanty tccccncaaa awtcamwccm tttcccncca agaawttcsg    660

sactcctttn ttcngggnam atanatyytt ycktngggsk ttccgmtcnc ammaatntcc    720

rgggkaamcc agkntnntcc yyyyccccaa nntyccykgg rmcynnyycy ttaaanrasr    780

saacccksgg gkcyncncss tarcccccam kaaaatttcc cccsskt ttc tyynnkkmrw    840

gcccccsaam actmtwaytt tccckcgnnn tttsycckcs kcamwmwmtg kkncttttt t    900

ycscmatama cttnggkcct ntcnygsgcg cmaaanaagg cgcgsttctn ttcwmamaca    960

yntsgnmmma saakakwata awnntrkkyk tknnccencc ckckcttsnn tnkccmcsks   1020

gggknwnkkr gwctccwcnc ckcccncknk cckwatmccc ccccskccgm ncmmnttt kt   1080

ccc                                                                 1083
```

<210> SEQ ID NO 327
<211> LENGTH: 1069
<212> TYPE: DNA
<213> ORGANISM: Mycobacterium tuberculosis
<220> FEATURE:
<221> NAME/KEY: modified_base
<222> LOCATION: (1)..(1069)
<223> OTHER INFORMATION: n = g, a, c or t

<400> SEQUENCE: 327

```
ggggnnkyat mcaycwtcts yacsgggmnc tattgcggcc gcawytngtm gasagatctc     60

gaaytcggca mgaaaaaagw gatgtgctgg accttmccgc gcgggacgcr accracaaag    120

raascgcgcc anaatattgg ccacakttgg tcacatattt acccaattmt aycagggayt    180

mccattcckg ggaccraccg cacaatcccr atsktggttt gcraaccctr accgtcccca    240

mytycgccra sttgaaccag ggcraaaaaa cggccraawy ctcgccctga ntcccgctcs    300

gcgcnaataa ctaggcccat tkaacggaac cggnggccsc nanttggcca acaggtcctr    360

acaaaggggc cccasyycgg ccggwtcccw ttycacnccc tnktctcktg ccgaatycgg    420

wtccratnyc ccwtgggcct tktckyckyc kycggtncca awtctnggta tnctatrgkg    480

tcccctaaat scanatctgg gckyccattt nctggsnttc natttamman srrcggttct    540

ttcwttccra aaccgsntgg gcccnnmcca aaaaatgatn ataataatgk ygsctttcaa    600

accccgcccc cccattcrwt csgttccanc ccccngnggt taagktggga atttytnamc    660

ycnargccct natttsggna aaaaccycyc gggyctcaaa cmnytttttt gskssntcgg    720

gctcrttcsc caaaacccaa attntynygg ggyccktnaa acmcggycrc rccggaaatt    780

tttytggttc aaccccaacc ttttcaascc nttttytyyt trccsscsmn tngssgggnt    840

kssccnttcy rarkkccnmn gggggwycyn ccccrmnttt cttttttttt ccgtnnmaam    900

ngkttcttca aasmcccccc scccccnsaa accccctnar gttttycmma aannwynngn    960

kncccccccc mmnaaaaaay ycscccgnrn acsmsnggga mcccccggsn nttrkttttt   1020

tncmsgyccc csrmasyytt tkamamanrr gamnsmttty tnnrgnwnk               1069
```

<210> SEQ ID NO 328
<211> LENGTH: 1210
<212> TYPE: DNA
<213> ORGANISM: Mycobacterium tuberculosis
<220> FEATURE:
<221> NAME/KEY: modified_base
<222> LOCATION: (1)..(1210)
<223> OTHER INFORMATION: n = g, a, c or t

<400> SEQUENCE: 328
ngnggggkwk matacatcwt tcttcacgsg ggatcwattg cgggccgcaw tctngtmcaa 60
sagatctcga tytcgggcam nacccaccwc tccraaaaaa acccraawct cgggskctyc 120
garaagtgtt gcccgckttr aatttaacaa attcagtgtc anagtgtcac ggckttacwt 180
ycccggcaaa ggggccacaa cctgcagrga scacycratg gktgytgkts cncgggcggg 240
ccggktnaag ggacctgcct gggtktgcsc tmcaaanatc wyccgcgggt ycgctggrat 300
mcncaggggt gtcaaaaaac cgcaaacagg cacsccancc ntttacgggs cttaaaanga 360
aaaagggctg atgcccccaa gggggcccgc ncccaacctt ccgttggtca acaacccggt 420
ctctcktgcc raatccgrwt ccratnycnc cwtggccttk tckyctycty cggtacccaa 480
atctgggtat cctatastgt cccctaawtt ccaaatctgg gctgtccatt tscttggcnt 540
tccaaattta ccancaacgg tttcttncat nccaaaaacc gntkggckcc nracccraaa 600
aaatgaataa taataanngg kcnnttycna accnccccc cccnattcca tysngttcca 660 nmnccccag nggktaggtk gggaaanyyc tcmaccyyca ancccctwars ttttngraat 720 kaaaccctyc ycngggtcww tymaaaaama nttatttggn ngntttcggg mwnckrknst 780
sccaaaatcc maaatanttt yytggtycna twaaaaamcg ygnccmnccc ggaaaawttt 840
ttntgkttsa accccaaaac yttttcmnaa ncsskttttty cyttcccccc amnwtgggys 900
gggnatkgyg scytntctta tktkytymtw cmggggggnn mkmtcmmccc ccmtttyycy 960
nywrtttttn kccccktnmr nnraannggn ytcsynanaa aagcnccccc scckncccna 1020
aaaawccccn nnnaraktnt ttmkannrmn sckcnkngky ycccccccwc ynmnnaaaaa 1080
aatmyccncc rasanmcasm nmggrgnrsc cccccccstt nnnntmttnt ttttttcsra 1140
gagckccscg mnnanmknck ctttttkcnc nngnngngnn ggngmnckcc ccnagaamwk 1200 ctkstcccks 1210

<210> SEQ ID NO 329
<211> LENGTH: 1105
<212> TYPE: DNA
<213> ORGANISM: Mycobacterium tuberculosis
<220> FEATURE:
<221> NAME/KEY: modified_base
<222> LOCATION: (1)..(1105)
<223> OTHER INFORMATION: n = g, a, c or t

<400> SEQUENCE: 329
ngsssngnna tmcatcwyct gyacsgggmt cwattgcggc cgcaactngt maasagatct 60
cgaaytcggc aakanacacc accgccgtgt mtatacaccg caaatgttct gtktgccaaa 120
accgagacgc gccggccgcg gggytccaac gckttacytr acccgccagy tcagtgttra 180
aaccggtgyt ragggccgca cccaacwtaa acgctttakc caagrawytg gktggcccgc 240
agccacctgy tgtggytgcc ctcwycggtg gtagcgccgg ttancgccgg ttgcgcgytc 300
amcascscgc cggtratccc akcnwtcccc cggccmracc caccgggcac tttgracggt 360
gccgccaatt caaayckyct grwtccttcm aaacaccacr aaggccaccm ccmscaccna 420
atmgggract ttaaggccca ggcaaaacct ntrakcncct cccgggcraa ggtccsgcaa 480

-continued

```
scratccmaa aaaakcknat ttcccccagc akcaacccaa mmcgstttgc tgcttccgga    540

ttcgaamcca attmcwggkt ncnwgggaaa aacascnncc nwtakccmgg cccmcgggca    600

atttcsgraa saacccctny cccgggtttt ycctgctcmg gcccaanacc cccgggaatc    660

aaaaasggtc ggncaaangg gcmaaacccs sacccmactt wttccrcttn ggggggscwn    720

ccknqtttaa awkscctcyy ctscccaaay tcggkcmaaa nngrkttggk ttnggcnacc    780

ntttccggkc ccgggkgkgk wgkyctmnma cstttntttt sccccykaaa nyscccccccc   840

cggsscccg cccgggggga nntttttama gkktycccct ccccamaaaa anaccccnyc    900

ccsggsccct ttkrwaaamn kctsccccng gnnggggkcm ggkttattmt nnnccscccc    960

tccgcgsaaa aaatakmttt sycccccncc ctccknckr gkamsmscgc tcccyctcnc   1020

gcnkntwaan arsncckknn ccncykccgs nsngkcnwcd nccstssnct nkgcnckncn   1080

kaaanaaync ngsmstssmn cnkcc                                         1105
```

<210> SEQ ID NO 330
<211> LENGTH: 936
<212> TYPE: DNA
<213> ORGANISM: Mycobacterium tuberculosis
<220> FEATURE:
<221> NAME/KEY: modified_base
<222> LOCATION: (1)..(936)
<223> OTHER INFORMATION: n = g, a, c or t

<400> SEQUENCE: 330

```
ngsnsnknnn tamaycwyyc tscacsngga acwantgcgg ccrmawctns tmkasagatc     60

tmgaaytcgg caagagcggc aagagtgtgt gcatctggtc anagtstmma crcggtgccg    120

csggtgkgtr gascacmcat ntgcgracac caaacccktc gcgggycacc ggcktcgcct    180

gcaaawycct ccaggccacc tcraacaayw yctyctgcaa cgcargccgt tycgcggccg    240

ratcctggkt casyycgcck tgcggtgccc aagktactgg cscaycaaaa ccgctccggg    300

raacraackt aawtytgccg aatttcnttc ccctgcgcct tgataaattt ntnaagccac    360

cgcaamccty cgggcktctc ctcktgccra atycgrwtcc rataycgcca tggcctnktc    420

kyctyckycs gtacccaaat cttgggtatc ctatantkyc ccwaaanrca awtctgggck    480

ktccatktsc tggsktccra atttammaca ncggtttctt tcwtaccaaa aaccsntggg    540

ccccraccra aaaakgataa taataakgtg cwwwcaaaac cccgcccccc rrttcaaycg    600

gtccarcacc ccangnggtn aggtnggaat tytmaacccc cagcccataa snttnsgnaa    660

aaaccccccn gggymycaaa ammctttttg gggmttcsgs ccatkgykcc aaaaccaaaa    720

tmtttcyggt crwaaaaacc ggcccncccg naaatttttt gkcaacccca aacctttmam    780

ccnnnttcyy ycccnsacaa tnggsggnkn ngsscnttyt twtttyynna ggggggrrwc    840

snccccnaan yyccnaankg nkcccgsnma aaagagantt ycmkaaaaac ccccncnccc    900

naaayacccc maaakwttcm aaasmscnng yccccc                             936
```

<210> SEQ ID NO 331
<211> LENGTH: 1042
<212> TYPE: DNA
<213> ORGANISM: Mycobacterium tuberculosis
<220> FEATURE:
<221> NAME/KEY: modified_base
<222> LOCATION: (1)..(1042)
<223> OTHER INFORMATION: n = g, a, c or t

<400> SEQUENCE: 331

```
nnngnknnny atmmaytcwy yctscaccsg ggnnwcwatt gcggccrmaw kcttgtmaas     60
```

agatctmnaa ytcggcacag asssgcacag ascegcggcg ctatycmycc gytgctcatg 120
ctcaacacgc tcktcggcgw gratatggc ncgccgccgg cgccaacacg ytcaaytgct 180
tcgccaacgc catatntcaa caaggtrata aaascaaaac cgcscgccgy gcccttgggc 240
scggraascg gtgccaaccc raaacnckt gggcacycgg ktsracttta aasggtaatc 300
tcktcctcct gggctatggt gcgccacaaa cctsytggcg wgggtctggc cctgggycac 360
cgycrcnttt tatntntcck yctacacnct tkggtycaac caacccactt cacmaaattg 420
ttttgggktg gggssgccgg ytgtnnccgk taataatcsg ntgktcsgcc mycaccggwa 480 ccatanccctg gccggcsctg gcaaatttcc saaatcatyt ccttctgrac ccccacamrc 540
ctnsaaatcc gratcaatnc cccnkggctt ntcyctctcn gtrcccaaty tggtttctat 600
rktncccyaa tscaattggs ttyccrttsc ygsttccaan ttnacaamas ggtttytcmt 660
accaaaaccc ntggsccnna cmnaaaakna raaaanakgg kctttyaaac cccccccctat 720 tcawycggtn cmrnwccccg ngkaaggkgn gaaaytthra cccaancccmt arsttsgnak 780 aaacccyycg gggtsmcaaa mkntwttssc cttcggmctt yccaaatmsa aaatyytckk 840
krmnaaaamc ygnccccsaa anatttttgt naamccckma yytrttwmcc wttttccycc 900
ccmcnnsnsg gntnccccty tyatttcymm mcrnnsgacn ccccmntytt twttckcwcn 960
mmargsnnyt rgrmmnmncc ccnccccnak mtccncaaak ntttnaacnn nnkyckcccc 1020
cccmwmnknc ccccmncmtt tm 1042

<210> SEQ ID NO 332
<211> LENGTH: 1073
<212> TYPE: DNA
<213> ORGANISM: Mycobacterium tuberculosis
<220> FEATURE:
<221> NAME/KEY: modified_base
<222> LOCATION: (1)..(1073)
<223> OTHER INFORMATION: n = g, a, c or t

<400> SEQUENCE: 332
nnsgsgmkkk atamatcwct ctsyaccsng gmtcwattgc ggccgmawtc tngtmaasag 60
atctcgaayt cggcaaanak acgcmaygtc aagtgtrayy cggtcacata tcmtcgcgng 120
tcaacmccaa agccgngtca ccgyctccct ggggcgccac ccccatcggt ratgcaacyt 180
cgcgcgccac cgycaaaagg ktcwttragg cgctaaaggt camcaattcc traggtymcn 240
caccgttntt tggcccgccc rawtyctrac ccgcaatwtc ggtaatcggr aatttgggcw 300
ycggcttggg caataagktn ttgggcaacg gcggrwtcyc nctggccgra attcccncat 360
tcckttaacg gktgraccgt ttycccggyt gccgtaaytg ytycntgggc gccytcggcc 420
crnagcasyy crctaacggy cmccaggcaa tacckttggc tttraaccac cggratnaay 480
tgktacccac ytcaassgts ctgranttrk tntcntgraa aanmccaccn aacccggntt 540
ratctgcttc mtcancwttt sccgggttct gccgttttgr aaycttnatc cmtycaaaag 600
gtttamtttc ccaanraatt cggyttgcca ccttggccgs ggctggtttm cgmwccttrr 660
amatccnccs gcgggsaaan amttsggntt sgsccggtcc cccgnaatat ycntggncct 720
gnaaattgss gggatccccn gsgnayccgg ccwtkggggk tncccagttg gwacaattyc 780
wkccgttcca aacccgggnc cggggggtgg gscccntttt cctmynnaaa aagkgtttgn 840
nyyttttccg cnraanttca ccskcnktnt ggnccnaacy yyycaanttc canaccttta 900
aasaaancyk ygktyycccc ttttmccsgs sancccccccm nmssknc ggg aaaaaaagnk 960 tyngccttan cnsnktkttt tnktyccccc nmwnnsnmcy ncbkkcnkry ngnsnmncct 1020
mkyskcnnnn snnnnnkcgn gsncsgmkym cmnncngmyk ngnksnnccc msc 1073

<210> SEQ ID NO 333
<211> LENGTH: 1061
<212> TYPE: DNA
<213> ORGANISM: Mycobacterium tuberculosis
<220> FEATURE:
<221> NAME/KEY: modified_base
<222> LOCATION: (1)..(1061)
<223> OTHER INFORMATION: n = g, a, c or t
<400> SEQUENCE: 333
gnsngnkntn tmcaycwyct scacsgggtc tattgcggcc gcaatytngt ckasagatct 60
cgatytcggc amnanaartg tcgtcgtcaa tttcagkktg gtcktcaaay gggccaggcc 120
gngaccraca ccctgngtca cccaaaanac caacagcwtc aaatwtcaag gccraggcsc 180
trtcaatycc crascaktta accgtktccw tcraaggtgc craaccaggc acccagytca 240
ccgccsggca awtcgcgctg ccggccggtn tcagcctgat tyctgaccct rwtctgtsgg 300
tggycamcnt ggtgaaggcc cwwccgccna agaactggag ggcraattcc cagganccna 360
graacccnag gaacccgcgg takaanccgg craaaccrag gccgytggcn attccnatta 420
namsggtttg cracntggcc raaccgttty cttggtcggc ctcggcaacc ctggaccant 480
taccccktnc ccggnmcmac cycgggtnct tgkycccaat ntgcycccgc gnrantnggc 540
cnaattccag ggcnccanct ttccggcccn aattcccytg gttaatcacc gggcncncct 600
ggttttgggc aaccccncys cttmtttaaa cattccgscc caaatgggnc sttggsaaat 660
tctntycggt ggggcsggcr anmyttctct ycccnaasan cttamyccan ttcgssntcc 720
cggkcaaaws ngggggggna aagggccccc cggntsckcc ggggkkgccc cyggkttcaa 780
aantttcsgg gktstmscgg nvtcsccccc csgccaagra ccgnggtttt tttttgaacc 840
kcmantcssa amccgccssc cccmaaaggs gcctnaawgr rayttnkscc cnnaaacsgg 900
cccccakyty sggkttcnnc cnccsgkkgt ccmtstttmm mrccctttgn gnktttttan 960
mgsccttnnc cacccccyck gggkcsmnna gaaktmywkc cnggggnnan rscccccnn 1020 gsgkggggkg mgagyscckt ctkgcgncnn ykntttcccc c 1061

<210> SEQ ID NO 334
<211> LENGTH: 986
<212> TYPE: DNA
<213> ORGANISM: Mycobacterium tuberculosis
<220> FEATURE:
<221> NAME/KEY: modified_base
<222> LOCATION: (1)..(986)
<223> OTHER INFORMATION: n = g, a, c or t
<400> SEQUENCE: 334
gnngnnnkwn atmcaycwyy ctscaccsgg gmtcwattgc ggccgcawky tngtmaasag 60
atctmgaayt cggcacanag cggcacagag tgtgtgcatc tgtgtcanag ctgtcaacgc 120
ggtgccgcsg gtggtrasca cmcattgcgr aacaccaaac ccgtccgcgg gycaccggck 180
tcgcctgcaa aaycctccag gccaccycra aacaaywyct cctgcaacsc arsccgttyc 240
gcggccgrat cctggkycas ytcgccktgc ggtgcgccaa ggtactggcs cwycranacc 300
gctycgggra accnaacgta aatcttgccn aatttgcntt ccccctsccc ttratnaatt 360
tgttaaacca cgcaaaccty cgggcktctc ctcktgccra wtccgrwtcc ratnycgcca 420
tggcctnktc kyctyckycs gtmcccaaat cttggtatcc tatattgtcc ctaaatgcaa 480
atctkggctg tccatntgct ggcgttcaaa ttwamancag nggtttctty cttccnaaac 540
ccsttggccc caaaccnaaa aatgatnata ataatggtgc tntcaaaccc cgcncccaty 600
cnatcsgkcc ammccccrgn ggktankkgg gnaattctmm aaccccaagc cataasnttg 660
sganaaaccy ncncmggyca ccaaaacany nttnttggny ssnttcggmn ycatggctnn 720
cmaaaaccca aatactnyyg ggyccaataa aammmsggyc samccggaaa wttttyttgn 780
kynaaaccna aakccttttt cnaacccdan wntycctncc rcrcmantgg cnsggartkt 840
ssscttncca atgkyccmaa agngggrana ccarccccaa ttcctnnntn knkncccnst 900
trnaaaaggg gkntyncmaa aascnccncc ncnctcccaa aakamccccn aaagakntcn 960
naanaskysn nnnscccccc ccmmmn 986

<210> SEQ ID NO 335
<211> LENGTH: 1074
<212> TYPE: DNA
<213> ORGANISM: Mycobacterium tuberculosis
<220> FEATURE:
<221> NAME/KEY: modified_base
<222> LOCATION: (1)..(1074)
<223> OTHER INFORMATION: n = g, a, c or t

<400> SEQUENCE: 335
ngngggnkrn atmmaycwct satyyaccsn ggmnmwattg cggccrmawt ctngtmkasa 60
gatctmgaaa ytcggcaaag agyatkctcg ggggccagat ttntggcccg caaccgccgc 120
actttgcayw tcaacaktcc sggtgcccca aaaaawtcwt acccccatmc tycktgcasm 180
asytgcgccc rattraacac ccggccggcw tgctgcgcca ggtattycas cagytcaaay 240
yctttktagk taaaatccag csggcggcca cncagccggg cggtktaggt gcctycrtca 300
atmaccagcy cgcccagggy caccttgccc aaaayctcct gggtcagcca aattyccgcs 360
ccggccaacm accanccgca tyctggcntc aatcycaccg ggcccggtgy taaammanma 420
gratctcktc manccccccan tcagcsytna cngcmacagc ccgccttctt camaccgcca 480
rtaccgggwt caaccggccs gtcaaactca acaggcggnc aggcctcccc cggansaaag 540
gtcttacscc nnyaanaaaa maagntctgt tttccccctc casaasnaaa aanccccsgc 600
cgggccttcn nmmgggtttg gggmananaa aarcnccggn ggaacgnatc cgaaamctcc 660
caagtcncmt twawaacycn nnaacccccc antttttggga aaggntcccc nttmyccccc 720
ttttasgkts gggmmyycty taaaaaaatt ccccaaaaag ccccgggaag ggtcmamctg 780
ggnaaatttc caamccnwgk ttnttynggt tmcgggggra aattycnctc ccyynnnggg 840
cssgsnnnat tayggmsnmt tttnnaawtm nsgkktsamm ynnkccmnnn snnmsmannk 900
tnamckcccn cctcngngky cscynccccsg gnagnggras mkccnanmaa ayasgnttnk 960
cggaammcnn aatkgnnnsc ccggasmcmn nnnmaaatmt cncnkcnsnn aanrgmracn 1020
cccnsnsgmn rrgaarmtny ycccccgskm gkgnkaaaaw gkyccccccm aaag 1074

<210> SEQ ID NO 336
<211> LENGTH: 1195
<212> TYPE: DNA
<213> ORGANISM: Mycobacterium tuberculosis
<220> FEATURE:
<221> NAME/KEY: modified_base
<222> LOCATION: (1)..(1195)
<223> OTHER INFORMATION: n = g, a, c or t

<400> SEQUENCE: 336
ngngncnknt mtacatcwtt ctgcaccsgg gntcwantgc ggccgcawky ttgtcgasag 60
atctcgaayt cggcamgagg acwctcgcra cgcccccaca nactctggcg tgtgtacccc 120

```
attgngcgck tcacgcgccc aytganccak tncactgggg tgccgtycgc cktgcgcggc    180
ggcctcacgg ckctscwtct raaggcwtgg cgcaccgcat tcggttttct raacgctggg    240
aaawtggcca gccgtctggc tcatgggntc tacgcaacgc cngcccccaa crctttctta    300
aatccggycc ntcctgancs ctttgaaycc cggggsaaga actggttgcs cncgayctgc    360
tcgaacttrk tcnaaatccc gcanaktgtt tcntamgycc cnccggaagg ngaacctact    420
ttcnggwang tcggcnkccg gcgcttatca stcctgatca acggggaact ggyknnsttg    480
kgggaaaaag rrcctcaatg mtyggtcckc gctgcgkanc cgcscccctgk gycgcnaatg    540
gaaggcsmag ggttaangcc mttycnyccr rsccgtstga sgkwttycgg mgganknamnn   600
nnkmamwttk tcrgnggccw atstsccggg cksttakaga anactycckw wccgtntysc    660
saaagntkcs gcgmgtttts scckmgangn yctgatttsa gggggkykcc cccggggtyc    720
cgaawkwrky ccyagggggm gnycsagcsc cgmnnatnag agnaaggktt rygstskncc    780
tytnkggacc wscnncwsak anaacnnkkt tgcsccntms agnktnkgrt yccnktsttc    840
taagaggagc tatkmkcgcc cktggangmm gagwgmgcgc kycccsnkrt tcntngwaaa    900
tatksagmgg tkccgmagmk ccscgtttkt tktganaamn msmrknkktg cgmgytctsc    960
gggntttgta gagtaktcgs cscssmwgac wcsgmcmgng agknktnnts yantgarcgy   1020
mnnsktmkmt mscscgcgna ggagngcccc csangmstgy nkggnmssng arakgatggs   1080
ggccncgmnn mgmgganmga sanngmggmr gggggktgkc tckcsccgns csangragaa   1140
gktcngscgc cgmggkygkt ktktknktgg ystcmssmmm nagaaaagag agggc        1195
```

<210> SEQ ID NO 337
<211> LENGTH: 3572
<212> TYPE: DNA
<213> ORGANISM: Mycobacterium tuberculosis

<400> SEQUENCE: 337

```
ccatctgatc gttggcaacc agcatcgcag tgggaacgat gccctcattc agcatttgca     60
tggtttgttg aaaaccggac atggcactcc agtcgccttc ccgttccgct atcggctgaa    120
tttgattgcg agtgagatat ttatgccagc cagccagacg cagacgcgcc gagacagaac    180
ttaatgggcc cgctaacagc gcgatttgct ggtgacccaa tgcgaccaga tgctccacgc    240
ccagtcgcgt accgtcttca tgggagaaaa taatactgtt gatgggtgtc tggtcagaga    300
catcaagaaa taacgccgga acattagtgc aggcagcttc cacagcaatg gcatcctggt    360
catccagcgg atagttaatg atcagcccac tgacgcgttg cgcgagaaga ttgtgcaccg    420
ccgctttaca ggcttcgacg ccgcttcgtt ctaccatcga caccaccacg ctggcaccca    480
gttgatcggc gcgagattta atcgccgcga caatttgcga cggcgcgtgc agggccagac    540
tggaggtggc aacgccaatc agcaacgact gtttgcccgc cagttgttgt gccacgcggt    600
tgggaatgta attcagctcc gccatcgccg cttccacttt ttcccgcgtt ttcgcagaaa    660
cgtggctggc ctggttcacc acgcgggaaa cggtctgata agagacaccg gcatactctg    720
cgacatcgta taacgttact ggtttcacat tcaccaccct gaattgactc tcttccgggc    780
gctatcatgc catacgcga aaggttttgc gccattcgat ggtgtccggg atctcgacgc     840
tctcccttat gcgactcctg cattaggaag cagcccagta gtaggttgag gccgttgagc    900
accgccgccg caaggaatgg tgcatgcaag gagatggcgc ccaacagtcc cccggccacg    960
gggcctgcca ccatacccac gccgaaacaa gcgctcatga gcccgaagtg gcgagcccga   1020
tcttccccat cggtgatgtc ggcgatatag gcgccagcaa ccgcacctgt ggcgccggtg   1080
```

-continued

```
atgccggcca cgatgcgtcc ggcgtagagg atcgagatct cgatcccgcg aaattaatac   1140
gactcactat aggggaattg tgagcggata acaattcccc tctagaaata attttgttta   1200
actttaagaa ggagatatac atatgggcca tcatcatcat catcacgtga tcgacatcat   1260
cgggaccagc cccacatcct gggaacaggc ggcggcggag gcggtccagc gggcgcggga   1320
tagcgtcgat gacatccgcg tcgctcgggt cattgagcag gacatggccg tggacagcgc   1380
cggcaagatc acctaccgca tcaagctcga agtgtcgttc aagatgaggc cggcgcaacc   1440
gaggggctcg aaaccaccga gcggttcgcc tgaaacgggc gccggcgccg gtactgtcgc   1500
gactaccccc gcgtcgtcgc cggtgacgtt ggcggagacc ggtagcacgc tgctctaccc   1560
gctgttcaac ctgtggggtc cggcctttca cgagaggtat ccgaacgtca cgatcaccgc   1620
tcagggcacc ggttctggtg ccgggatcgc gcaggccgcc gccgggacgg tcaacattgg   1680
ggcctccgac gcctatctgt cggaaggtga tatggccgcg cacaaggggc tgatgaacat   1740
cgcgctagcc atctccgctc agcaggtcaa ctacaacctg cccggagtga gcgagcacct   1800
caagctgaac ggaaaagtcc tggcggccat gtaccagggc accatcaaaa cctgggacga   1860
cccgcagatc gctgcgctca accccggcgt gaacctgccc ggcaccgcgg tagttccgct   1920
gcaccgctcc gacgggtccg gtgacacctt cttgttcacc cagtacctgt ccaagcaaga   1980
tcccgagggc tggggcaagt cgcccggctt cggcaccacc gtcgacttcc cggcggtgcc   2040
gggtgcgctg ggtgagaacg gcaacggcgg catggtgacc ggttgcgccg agacaccggg   2100
ctgcgtggcc tatatcggca tcagcttcct cgaccaggcc agtcaacggg gactcggcga   2160
ggcccaacta ggcaatagct ctggcaattt cttgttgccc gacgcgcaaa gcattcaggc   2220
cgcggcggct ggcttcgcat cgaaaacccc ggcgaaccag gcgatttcga tgatcgacgg   2280
gcccgccccg gacggctacc cgatcatcaa ctacgagtac gccatcgtca acaaccggca   2340
aaaggacgcc gccaccgcgc agaccttgca ggcatttctg cactgggcga tcaccgacgg   2400
caacaaggcc tcgttcctcg accaggttca tttccagccg ctgccgcccg cggtggtgaa   2460
gttgtctgac gcgttgatcg cgacgatttc cagcgctgag atgaagaccg atgccgctac   2520
cctcgcgcag gaggcaggta atttcgagcg gatctccggc gacctgaaaa cccagatcga   2580
ccaggtggag tcgacggcag gttcgttgca gggccagtgg cgcggcgcgg cggggacggc   2640
cgcccaggcc gcggtggtgc gcttccaaga agcagccaat aagcagaagc aggaactcga   2700
cgagatctcg acgaatattc gtcaggccgg cgtccaatac tcgagggccg acgaggagca   2760
gcagcaggcg ctgtcctcgc aaatgggctt tggattcagc ttcgcgctgc ctgctggctg   2820
ggtggagtct gacgccgccc acttcgacta cggttcagca ctcctcagca aaaccaccgg   2880
ggacccgcca tttcccggac agccgccgcc ggtggccaat gacacccgta tcgtgctcgg   2940
ccggctagac caaaagcttt acgccagcgc cgaagccacc gactccaagg ccgcggcccg   3000
gttgggctcg gacatgggtg agttctatat gccctacccg ggcacccgga tcaaccagga   3060
aaccgtctcg ctygacgcca acggggtgtc tggaagcgcg tcgtattacg aagtcaagtt   3120
cagcgatccg agtaagccga acggccagat ctggacgggc gtaatcggct cgcccgcggc   3180
gaacgcaccg gacgccgggc cccctcagcg ctggtttgtg gtatggctcg ggaccgccaa   3240
caacccggtg gacaagggcg cggccaaggc gctggccgaa tcgatccggc ctttggtcgc   3300
cccgccgccg gcgccggccg gggaagtcgc tcctaccccg acgacaccga caccgcagcg   3360
gaccttaccg gcctgagaat tctgcagata tccatcacac tggcggccgc tcgagcacca   3420
ccaccaccac cactgagatc cggctgctaa caaagcccga aaggaagctg agttggctgc   3480
```

```
tgccaccgct gagcaataac tagcataacc ccttggggcc tctaaacggg tcttgagggg   3540

ttttttgctg aaaggaggaa ctatatccgg at                                 3572


<210> SEQ ID NO 338
<211> LENGTH: 20
<212> TYPE: PRT
<213> ORGANISM: Mycobacterium tuberculosis
<220> FEATURE:
<221> NAME/KEY: MOD_RES
<222> LOCATION: (1)..(20)
<223> OTHER INFORMATION: Xaa = any amino acid

<400> SEQUENCE: 338

Val Gln Phe Gln Ser Gly Gly Asp Asn Ser Pro Ala Val Tyr Xaa Xaa
  1               5                  10                  15

Asp Gly Xaa Arg
             20


<210> SEQ ID NO 339
<211> LENGTH: 10
<212> TYPE: PRT
<213> ORGANISM: Mycobacterium tuberculosis
<220> FEATURE:
<221> NAME/KEY: MOD_RES
<222> LOCATION: (5)
<223> OTHER INFORMATION: Xaa = any amino acid

<400> SEQUENCE: 339

Thr Thr Val Pro Xaa Val Thr Glu Ala Arg
  1               5                  10


<210> SEQ ID NO 340
<211> LENGTH: 10
<212> TYPE: PRT
<213> ORGANISM: Mycobacterium tuberculosis
<220> FEATURE:
<221> NAME/KEY: MOD_RES
<222> LOCATION: (5)
<223> OTHER INFORMATION: Xaa = any amino acid

<400> SEQUENCE: 340

Thr Thr Pro Ser Xaa Val Ala Phe Ala Arg
  1               5                  10


<210> SEQ ID NO 341
<211> LENGTH: 12
<212> TYPE: PRT
<213> ORGANISM: Mycobacterium tuberculosis
<220> FEATURE:
<221> NAME/KEY: MOD_RES
<222> LOCATION: (1)..(12)
<223> OTHER INFORMATION: Xaa = any amino acid

<400> SEQUENCE: 341

Asp Ala Gly Lys Xaa Ala Gly Xaa Asp Val Xaa Arg
  1               5                  10


<210> SEQ ID NO 342
<211> LENGTH: 18
<212> TYPE: PRT
<213> ORGANISM: Mycobacterium tuberculosis
<220> FEATURE:
<221> NAME/KEY: MOD_RES
<222> LOCATION: (1)..(18)
<223> OTHER INFORMATION: Xaa = any amino acid

<400> SEQUENCE: 342
```

```
Thr Xaa Glu Glu Xaa Gln Glu Ser Phe Asn Ser Ala Ala Pro Gly Asn
  1               5                  10                  15

Xaa Lys
```

```
<210> SEQ ID NO 343
<211> LENGTH: 27
<212> TYPE: DNA
<213> ORGANISM: Artificial Sequence
<220> FEATURE:
<223> OTHER INFORMATION: Description of Artificial Sequence:PCR primer
      PDM-157

<400> SEQUENCE: 343

ctagttagta ctcagtcgca gaccgtg                                          27


<210> SEQ ID NO 344
<211> LENGTH: 25
<212> TYPE: DNA
<213> ORGANISM: Artificial Sequence
<220> FEATURE:
<223> OTHER INFORMATION: Description of Artificial Sequence:PCR primer
      PDM-160

<400> SEQUENCE: 344

gcagtgacga attcacttcg actcc                                            25


<210> SEQ ID NO 345
<211> LENGTH: 2412
<212> TYPE: DNA
<213> ORGANISM: Artificial Sequence
<220> FEATURE:
<223> OTHER INFORMATION: Description of Artificial Sequence:DNA sequence
      of fusion protein TbF-6

<400> SEQUENCE: 345

catatgggcc atcatcatca tcatcacgtg atcgacatca tcgggaccag ccccacatcc      60

tgggaacagg cggcggcgga ggcggtccag cgggcgcggg atagcgtcga tgacatccgc     120

gtcgctcggg tcattgagca ggacatggcc gtggacagcg ccggcaagat cacctaccgc     180

atcaagctcg aagtgtcgtt caagatgagg ccggcgcaac cgaggggctc gaaaccaccg     240

agcggttcgc ctgaaacggg cgccggcgcc ggtactgtcg cgactacccc cgcgtcgtcg     300

ccggtgacgt tggcggagac cggtagcacg ctgctctacc cgctgttcaa cctgtggggt     360

ccggcctttc acgagaggta tccgaacgtc acgatcaccg ctcagggcac cggttctggt     420

gccgggatcg cgcaggccgc cgccgggacg gtcaacattg ggcctccga cgcctatctg     480

tcggaaggtg atatggccgc gcacaagggg ctgatgaaca tcgcgctagc catctccgct     540

cagcaggtca actacaacct gcccggagtg agcgagcacc tcaagctgaa cggaaaagtc     600

ctggcggcca tgtaccaggg caccatcaaa acctgggacg acccgcagat cgctgcgctc     660

aaccccggcg tgaacctgcc cggcaccgcg gtagttccgc tgcaccgctc cgacgggtcc     720

ggtgacacct tcttgttcac ccagtacctg tccaagcaag atcccgaggg ctggggcaag     780

tcgcccggct tcggcaccac cgtcgacttc ccggcggtgc cgggtgcgct gggtgagaac     840

ggcaacggcg gcatggtgac cggttgcgcc gagacaccgg gctgcgtggc ctatatcggc     900

atcagcttcc tcgaccaggc cagtcaacgg ggactcggcg aggcccaact aggcaatagc     960

tctggcaatt tcttgttgcc cgacgcgcaa agcattcagg ccgcggcggc tggcttcgca    1020

tcgaaaaccc cggcgaacca ggcgatttcg atgatcgacg ggcccgcccc ggacggctac    1080

ccgatcatca actacgagta cgccatcgtc aacaaccggc aaaaggacgc cgccaccgcg    1140
```

```
cagaccttgc aggcatttct gcactgggcg atcaccgacg gcaacaaggc ctcgttcctc   1200

gaccaggttc atttccagcc gctgccgccc gcggtggtga agttgtctga cgcgttgatc   1260

gcgacgattt ccagcgctga gatgaagacc gatgccgcta ccctcgcgca ggaggcaggt   1320

aatttcgagc ggatctccgg cgacctgaaa acccagatcg accaggtgga gtcgacggca   1380

ggttcgttgc agggccagtg gcgcggcgcg gcggggacgg ccgcccaggc cgcggtggtg   1440

cgcttccaag aagcagccaa taagcagaag caggaactcg acgagatctc gacgaatatt   1500

cgtcaggccg gcgtccaata ctcgagggcc gacgaggagc agcagcaggc gctgtcctcg   1560

caaatgggct ttgtgcccac aacggccgcc tcgccgccgt cgaccgctgc agcgccaccc   1620

gcaccggcga cacctgttgc ccccccacca ccggccgccg ccaacacgcc gaatgcccag   1680

ccgggcgatc ccaacgcagc acctccgccg gccgacccga acgcaccgcc gccacctgtc   1740

attgccccaa acgcacccca acctgtccgg atcgacaacc cggttggagg attcagcttc   1800

gcgctgcctg ctggctgggt ggagtctgac gccgcccact tcgactacgg ttcagcactc   1860

ctcagcaaaa ccaccgggga cccgccattt cccggacagc cgccgccggt ggccaatgac   1920

acccgtatcg tgctcggccg gctagaccaa aagctttacg ccagcgccga agccaccgac   1980

tccaaggccg cggcccggtt gggctcggac atgggtgagt tctatatgcc ctacccgggc   2040

acccggatca accaggaaac cgtctcgctc gacgccaacg gggtgtctgg aagcgcgtcg   2100

tattacgaag tcaagttcag cgatccgagt aagccgaacg gccagatctg gacgggcgta   2160

atcggctcgc ccgcggcgaa cgcaccggac gccgggcccc ctcagcgctg gtttgtggta   2220

tggctcggga ccgccaacaa cccggtggac aagggcgcgg ccaaggcgct ggccgaatcg   2280

atccggcctt tggtcgcccc gccgccggcg ccggcaccgg ctcctgcaga gcccgctccg   2340

gcgccggcgc cggccgggga agtcgctcct accccgacga caccgacacc gcagcggacc   2400

ttaccggcct ga                                                       2412
```

<210> SEQ ID NO 346
<211> LENGTH: 802
<212> TYPE: PRT
<213> ORGANISM: Artificial Sequence
<220> FEATURE:
<223> OTHER INFORMATION: Description of Artificial Sequence:amino acid sequence of fusion protein TbF-6

<400> SEQUENCE: 346

```
Met Gly His His His His His His Val Ile Asp Ile Ile Gly Thr Ser
  1               5                  10                  15

Pro Thr Ser Trp Glu Gln Ala Ala Ala Glu Ala Val Gln Arg Ala Arg
             20                  25                  30

Asp Ser Val Asp Asp Ile Arg Val Ala Arg Val Ile Glu Gln Asp Met
         35                  40                  45

Ala Val Asp Ser Ala Gly Lys Ile Thr Tyr Arg Ile Lys Leu Glu Val
     50                  55                  60

Ser Phe Lys Met Arg Pro Ala Gln Pro Arg Gly Ser Lys Pro Pro Ser
 65                  70                  75                  80

Gly Ser Pro Glu Thr Gly Ala Gly Ala Gly Thr Val Ala Thr Thr Pro
                 85                  90                  95

Ala Ser Ser Pro Val Thr Leu Ala Glu Thr Gly Ser Thr Leu Leu Tyr
            100                 105                 110

Pro Leu Phe Asn Leu Trp Gly Pro Ala Phe His Glu Arg Tyr Pro Asn
        115                 120                 125

Val Thr Ile Thr Ala Gln Gly Thr Gly Ser Gly Ala Gly Ile Ala Gln
```

```
    130                 135                 140

Ala Ala Ala Gly Thr Val Asn Ile Gly Ala Ser Asp Ala Tyr Leu Ser
145                 150                 155                 160

Glu Gly Asp Met Ala Ala His Lys Gly Leu Met Asn Ile Ala Leu Ala
                165                 170                 175

Ile Ser Ala Gln Gln Val Asn Tyr Asn Leu Pro Gly Val Ser Glu His
            180                 185                 190

Leu Lys Leu Asn Gly Lys Val Leu Ala Ala Met Tyr Gln Gly Thr Ile
        195                 200                 205

Lys Thr Trp Asp Asp Pro Gln Ile Ala Ala Leu Asn Pro Gly Val Asn
    210                 215                 220

Leu Pro Gly Thr Ala Val Val Pro Leu His Arg Ser Asp Gly Ser Gly
225                 230                 235                 240

Asp Thr Phe Leu Phe Thr Gln Tyr Leu Ser Lys Gln Asp Pro Glu Gly
                245                 250                 255

Trp Gly Lys Ser Pro Gly Phe Gly Thr Thr Val Asp Phe Pro Ala Val
            260                 265                 270

Pro Gly Ala Leu Gly Glu Asn Gly Asn Gly Gly Met Val Thr Gly Cys
        275                 280                 285

Ala Glu Thr Pro Gly Cys Val Ala Tyr Ile Gly Ile Ser Phe Leu Asp
    290                 295                 300

Gln Ala Ser Gln Arg Gly Leu Gly Glu Ala Gln Leu Gly Asn Ser Ser
305                 310                 315                 320

Gly Asn Phe Leu Leu Pro Asp Ala Gln Ser Ile Gln Ala Ala Ala Ala
                325                 330                 335

Gly Phe Ala Ser Lys Thr Pro Ala Asn Gln Ala Ile Ser Met Ile Asp
            340                 345                 350

Gly Pro Ala Pro Asp Gly Tyr Pro Ile Ile Asn Tyr Glu Tyr Ala Ile
        355                 360                 365

Val Asn Asn Arg Gln Lys Asp Ala Ala Thr Ala Gln Thr Leu Gln Ala
    370                 375                 380

Phe Leu His Trp Ala Ile Thr Asp Gly Asn Lys Ala Ser Phe Leu Asp
385                 390                 395                 400

Gln Val His Phe Gln Pro Leu Pro Pro Ala Val Val Lys Leu Ser Asp
                405                 410                 415

Ala Leu Ile Ala Thr Ile Ser Ser Ala Glu Met Lys Thr Asp Ala Ala
            420                 425                 430

Thr Leu Ala Gln Glu Ala Gly Asn Phe Glu Arg Ile Ser Gly Asp Leu
        435                 440                 445

Lys Thr Gln Ile Asp Gln Val Glu Ser Thr Ala Gly Ser Leu Gln Gly
    450                 455                 460

Gln Trp Arg Gly Ala Ala Gly Thr Ala Ala Gln Ala Ala Val Val Arg
465                 470                 475                 480

Phe Gln Glu Ala Ala Asn Lys Gln Lys Gln Glu Leu Asp Glu Ile Ser
                485                 490                 495

Thr Asn Ile Arg Gln Ala Gly Val Gln Tyr Ser Arg Ala Asp Glu Glu
            500                 505                 510

Gln Gln Gln Ala Leu Ser Ser Gln Met Gly Phe Val Pro Thr Thr Ala
        515                 520                 525

Ala Ser Pro Pro Ser Thr Ala Ala Ala Pro Pro Ala Pro Ala Thr Pro
    530                 535                 540

Val Ala Pro Pro Pro Pro Ala Ala Ala Asn Thr Pro Asn Ala Gln Pro
545                 550                 555                 560
```

-continued

```
Gly Asp Pro Asn Ala Ala Pro Pro Pro Ala Asp Pro Asn Ala Pro Pro
                565                 570                 575

Pro Pro Val Ile Ala Pro Asn Ala Pro Gln Pro Val Arg Ile Asp Asn
            580                 585                 590

Pro Val Gly Gly Phe Ser Phe Ala Leu Pro Ala Gly Trp Val Glu Ser
        595                 600                 605

Asp Ala Ala His Phe Asp Tyr Gly Ser Ala Leu Leu Ser Lys Thr Thr
    610                 615                 620

Gly Asp Pro Pro Phe Pro Gly Gln Pro Pro Pro Val Ala Asn Asp Thr
625                 630                 635                 640

Arg Ile Val Leu Gly Arg Leu Asp Gln Lys Leu Tyr Ala Ser Ala Glu
                645                 650                 655

Ala Thr Asp Ser Lys Ala Ala Ala Arg Leu Gly Ser Asp Met Gly Glu
            660                 665                 670

Phe Tyr Met Pro Tyr Pro Gly Thr Arg Ile Asn Gln Glu Thr Val Ser
        675                 680                 685

Leu Asp Ala Asn Gly Val Ser Gly Ser Ala Ser Tyr Tyr Glu Val Lys
    690                 695                 700

Phe Ser Asp Pro Ser Lys Pro Asn Gly Gln Ile Trp Thr Gly Val Ile
705                 710                 715                 720

Gly Ser Pro Ala Ala Asn Ala Pro Asp Ala Gly Pro Pro Gln Arg Trp
                725                 730                 735

Phe Val Val Trp Leu Gly Thr Ala Asn Asn Pro Val Asp Lys Gly Ala
            740                 745                 750

Ala Lys Ala Leu Ala Glu Ser Ile Arg Pro Leu Val Ala Pro Pro Pro
        755                 760                 765

Ala Pro Ala Pro Ala Pro Ala Glu Pro Ala Pro Ala Pro Ala Pro Ala
    770                 775                 780

Gly Glu Val Ala Pro Thr Pro Thr Thr Pro Thr Pro Gln Arg Thr Leu
785                 790                 795                 800

Pro Ala
```

```
<210> SEQ ID NO 347
<211> LENGTH: 34
<212> TYPE: DNA
<213> ORGANISM: Artificial Sequence
<220> FEATURE:
<223> OTHER INFORMATION: Description of Artificial Sequence:PCR primer
      PDM-176

<400> SEQUENCE: 347

ggatccaaac caccgagcgg ttcgcctgaa acgg                                34


<210> SEQ ID NO 348
<211> LENGTH: 37
<212> TYPE: DNA
<213> ORGANISM: Artificial Sequence
<220> FEATURE:
<223> OTHER INFORMATION: Description of Artificial Sequence:PCR primer
      PDM-175

<400> SEQUENCE: 348

cgctgcgaat tcacctccgg aggaaatcgt cgcgatc                             37


<210> SEQ ID NO 349
<211> LENGTH: 1962
<212> TYPE: DNA
<213> ORGANISM: Artificial Sequence
<220> FEATURE:
<223> OTHER INFORMATION: Description of Artificial Sequence:DNA sequence
```

of fusion protein TbF-8

<400> SEQUENCE: 349

```
catatgggcc atcatcatca tcatcacgga tccaaaccac cgagcggttc gcctgaaacg     60
ggcgccggcg ccggtactgt cgcgactacc cccgcgtcgt cgccggtgac gttggcggag    120
accggtagca cgctgctcta cccgctgttc aacctgtggg gtccggcctt tcacgagagg    180
tatccgaacg tcacgatcac cgctcagggc accggttctg gtgccgggat cgcgcaggcc    240
gccgccggga cggtcaacat tggggcctcc gacgcctatc tgtcggaagg tgatatggcc    300
gcgcacaagg ggctgatgaa catcgcgcta gccatctccg ctcagcaggt caactacaac    360
ctgcccggag tgagcgagca cctcaagctg aacggaaaag tcctggcggc catgtaccag    420
ggcaccatca aaacctggga cgacccgcag atcgctgcgc tcaaccccgg cgtgaacctg    480
cccggcaccg cggtagttcc gctgcaccgc tccgacgggt ccggtgacac cttcttgttc    540
acccagtacc tgtccaagca agatcccgag ggctggggca agtcgcccgg cttcggcacc    600
accgtcgact tcccggcggt gccgggtgcg ctgggtgaga acggcaacgg cggcatggtg    660
accggttgcg ccgagacacc gggctgcgtg gcctatatcg gcatcagctt cctcgaccag    720
gccagtcaac ggggactcgg cgaggcccaa ctaggcaata gctctggcaa tttcttgttg    780
cccgacgcgc aaagcattca ggccgcggcg gctggcttcg catcgaaaac cccggcgaac    840
caggcgattt cgatgatcga cgggcccgcc ccggacggct acccgatcat caactacgag    900
tacgccatcg tcaacaaccg gcaaaaggac gccgccaccg cgcagacctt gcaggcattt    960
ctgcactggg cgatcaccga cggcaacaag gcctcgttcc tcgaccaggt tcatttccag   1020
ccgctgccgc ccgcggtggt gaagttgtct gacgcgttga tcgcgacgat ttcctccgga   1080
ggtggcagtg gggaggctc aggtggaggt tctggcggga gcgtgcccac aacggccgcc   1140
tcgccgccgt cgaccgctgc agcgccaccc gcaccggcga cacctgttgc ccccccacca   1200
ccggccgccg ccaacacgcc gaatgcccag ccgggcgatc ccaacgcagc acctccgccg   1260
gccgacccga acgcaccgcc gccacctgtc attgccccaa acgcacccca acctgtccgg   1320
atcgacaacc cggttggagg attcagcttc gcgctgcctg ctggctgggt ggagtctgac   1380
gccgcccact tcgactacgg ttcagcactc ctcagcaaaa ccaccgggga cccgccattt   1440
cccggacagc cgccgccggt ggccaatgac acccgtatcg tgctcggccg gctagaccaa   1500
aagctttacg ccagcgccga agccaccgac tccaaggccg cggcccggtt gggctcggac   1560
atgggtgagt tctatatgcc ctacccgggc acccggatca accaggaaac cgtctcgctc   1620
gacgccaacg gggtgtctgg aagcgcgtcg tattacgaag tcaagttcag cgatccgagt   1680
aagccgaacg gccagatctg gacgggcgta atcggctcgc ccgcggcgaa cgcaccggac   1740
gccgggcccc ctcagcgctg gtttgtggta tggctcggga ccgccaacaa cccggtggac   1800
aagggcgcgg ccaaggcgct ggccgaatcg atccggcctt tggtcgcccc gccgccggcg   1860
ccggcaccgg ctcctgcaga gcccgctccg gcgccggcgc cggccgggga agtcgctcct   1920
accccgacga caccgacacc gcagcggacc ttaccggcct ga                       1962
```

<210> SEQ ID NO 350
<211> LENGTH: 652
<212> TYPE: PRT
<213> ORGANISM: Artificial Sequence
<220> FEATURE:
<223> OTHER INFORMATION: Description of Artificial Sequence:amino acid
sequence of fusion protein TbF-8

<400> SEQUENCE: 350

```
Met Gly His His His His His His Gly Ser Lys Pro Pro Ser Gly Ser
  1               5                  10                  15

Pro Glu Thr Gly Ala Gly Ala Gly Thr Val Ala Thr Thr Pro Ala Ser
             20                  25                  30

Ser Pro Val Thr Leu Ala Glu Thr Gly Ser Thr Leu Leu Tyr Pro Leu
         35                  40                  45

Phe Asn Leu Trp Gly Pro Ala Phe His Glu Arg Tyr Pro Asn Val Thr
     50                  55                  60

Ile Thr Ala Gln Gly Thr Gly Ser Gly Ala Gly Ile Ala Gln Ala Ala
 65                  70                  75                  80

Ala Gly Thr Val Asn Ile Gly Ala Ser Asp Ala Tyr Leu Ser Glu Gly
                 85                  90                  95

Asp Met Ala Ala His Lys Gly Leu Met Asn Ile Ala Leu Ala Ile Ser
            100                 105                 110

Ala Gln Gln Val Asn Tyr Asn Leu Pro Gly Val Ser Glu His Leu Lys
        115                 120                 125

Leu Asn Gly Lys Val Leu Ala Ala Met Tyr Gln Gly Thr Ile Lys Thr
    130                 135                 140

Trp Asp Asp Pro Gln Ile Ala Ala Leu Asn Pro Gly Val Asn Leu Pro
145                 150                 155                 160

Gly Thr Ala Val Val Pro Leu His Arg Ser Asp Gly Ser Gly Asp Thr
                165                 170                 175

Phe Leu Phe Thr Gln Tyr Leu Ser Lys Gln Asp Pro Glu Gly Trp Gly
            180                 185                 190

Lys Ser Pro Gly Phe Gly Thr Thr Val Asp Phe Pro Ala Val Pro Gly
        195                 200                 205

Ala Leu Gly Glu Asn Gly Asn Gly Gly Met Val Thr Gly Cys Ala Glu
    210                 215                 220

Thr Pro Gly Cys Val Ala Tyr Ile Gly Ile Ser Phe Leu Asp Gln Ala
225                 230                 235                 240

Ser Gln Arg Gly Leu Gly Glu Ala Gln Leu Gly Asn Ser Ser Gly Asn
                245                 250                 255

Phe Leu Leu Pro Asp Ala Gln Ser Ile Gln Ala Ala Ala Ala Gly Phe
            260                 265                 270

Ala Ser Lys Thr Pro Ala Asn Gln Ala Ile Ser Met Ile Asp Gly Pro
        275                 280                 285

Ala Pro Asp Gly Tyr Pro Ile Ile Asn Tyr Glu Tyr Ala Ile Val Asn
    290                 295                 300

Asn Arg Gln Lys Asp Ala Ala Thr Ala Gln Thr Leu Gln Ala Phe Leu
305                 310                 315                 320

His Trp Ala Ile Thr Asp Gly Asn Lys Ala Ser Phe Leu Asp Gln Val
                325                 330                 335

His Phe Gln Pro Leu Pro Pro Ala Val Val Lys Leu Ser Asp Ala Leu
            340                 345                 350

Ile Ala Thr Ile Ser Ser Gly Gly Gly Ser Gly Gly Gly Ser Gly Gly
        355                 360                 365

Gly Ser Gly Gly Ser Val Pro Thr Thr Ala Ala Ser Pro Pro Ser Thr
    370                 375                 380

Ala Ala Ala Pro Pro Ala Pro Ala Thr Pro Val Ala Pro Pro Pro Pro
385                 390                 395                 400

Ala Ala Ala Asn Thr Pro Asn Ala Gln Pro Gly Asp Pro Asn Ala Ala
                405                 410                 415

Pro Pro Pro Ala Asp Pro Asn Ala Pro Pro Pro Pro Val Ile Ala Pro
```

-continued

```
            420                 425                 430

Asn Ala Pro Gln Pro Val Arg Ile Asp Asn Pro Val Gly Gly Phe Ser
        435                 440                 445

Phe Ala Leu Pro Ala Gly Trp Val Glu Ser Asp Ala Ala His Phe Asp
    450                 455                 460

Tyr Gly Ser Ala Leu Leu Ser Lys Thr Thr Gly Asp Pro Pro Phe Pro
465                 470                 475                 480

Gly Gln Pro Pro Pro Val Ala Asn Asp Thr Arg Ile Val Leu Gly Arg
                485                 490                 495

Leu Asp Gln Lys Leu Tyr Ala Ser Ala Glu Ala Thr Asp Ser Lys Ala
            500                 505                 510

Ala Ala Arg Leu Gly Ser Asp Met Gly Glu Phe Tyr Met Pro Tyr Pro
        515                 520                 525

Gly Thr Arg Ile Asn Gln Glu Thr Val Ser Leu Asp Ala Asn Gly Val
    530                 535                 540

Ser Gly Ser Ala Ser Tyr Tyr Glu Val Lys Phe Ser Asp Pro Ser Lys
545                 550                 555                 560

Pro Asn Gly Gln Ile Trp Thr Gly Val Ile Gly Ser Pro Ala Ala Asn
                565                 570                 575

Ala Pro Asp Ala Gly Pro Pro Gln Arg Trp Phe Val Val Trp Leu Gly
            580                 585                 590

Thr Ala Asn Asn Pro Val Asp Lys Gly Ala Ala Lys Ala Leu Ala Glu
        595                 600                 605

Ser Ile Arg Pro Leu Val Ala Pro Pro Pro Ala Pro Ala Pro Ala Pro
    610                 615                 620

Ala Glu Pro Ala Pro Ala Pro Ala Pro Ala Gly Glu Val Ala Pro Thr
625                 630                 635                 640

Pro Thr Thr Pro Thr Pro Gln Arg Thr Leu Pro Ala
                645                 650


<210> SEQ ID NO 351
<211> LENGTH: 8
<212> TYPE: PRT
<213> ORGANISM: Artificial Sequence
<220> FEATURE:
<223> OTHER INFORMATION: Description of Artificial Sequence:linker in
      TbF-8

<400> SEQUENCE: 351

Met Gly His His His His His His
  1               5
```

COMPOUND AND METHODS FOR DIAGNOSIS OF TUBERCULOSIS

CROSS-REFERENCE TO RELATED APPLICATIONS

This application is a continuation of U.S. application Ser. No. 11/082,005, filed Mar. 15, 2005, now U.S. Pat. No. 7,122,196, which is a division of U.S. application Ser. No. 10/193,002, filed Jul. 10, 2002, now U.S. Pat. No. 6,949,246, which is a continuation of U.S. application Ser. No. 09/072,596, filed May 5, 1998, now U.S. Pat. No. 6,458,366, which is a continuation-in-part of U.S. application Ser. No. 09/024,753, filed Feb. 18, 1998, now abandoned; which is a continuation-in-part of U.S. application Ser. No. 08/942,341, filed Oct. 1, 1997, now abandoned; which is a continuation-in-part of U.S. application Ser. No. 08/818,111, filed Mar. 13, 1997, now U.S. Pat. No. 6,338,852, which is a continuation-in-part of U.S. application Ser. No. 08/729,622 filed Oct. 11, 1996, now abandoned; which claims priority from PCT Application No. PCT/US96/14675, filed Aug. 30, 1996; and is a continuation-in-part of U.S. application Ser. No. 08/680,574, filed Jul. 12, 1996, now abandoned; which is a continuation-in-part of U.S. application Ser. No. 08/658,800 filed Jun. 5, 1996, now abandoned; which is a continuation-in-part of U.S. application Ser. No. 08/620,280, filed Mar. 22, 1996, now abandoned; which is a continuation-in-part of U.S. application Ser. No. 08/532,136, filed Sep. 22, 1995, now abandoned; which is a continuation of U.S. application Ser. No. 08/523,435, filed Sep. 1, 1995, now abandoned.

TECHNICAL FIELD

The present invention relates generally to the detection of *Mycobacterium tuberculosis* infection. The invention is more particularly related to polypeptides comprising a *Mycobacterium tuberculosis* antigen, or a portion or other variant thereof, and the use of such polypeptides for the serodiagnosis of *Mycobacterium tuberculosis* infection.

BACKGROUND OF THE INVENTION

Tuberculosis is a chronic, infectious disease, that is generally caused by infection with *Mycobacterium tuberculosis*. It is a major disease in developing countries, as well as an increasing problem in developed areas of the world, with about 8 million new cases and 3 million deaths each year. Although the infection may be asymptomatic for a considerable period of time, the disease is most commonly manifested as an acute inflammation of the lungs, resulting in fever and a nonproductive cough. If left untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance.

Inhibiting the spread of tuberculosis will require effective vaccination and accurate, early diagnosis of the disease. Currently, vaccination with live bacteria is the most efficient method for inducing protective immunity. The most common *Mycobacterium* for this purpose is *Bacillus* Calmette-Guerin (BCG), an avirulent strain of *Mycobacterium bovis*. However, the safety and efficacy of BCG is a source of controversy and some countries, such as the United States, do not vaccinate the general public. Diagnosis is commonly achieved using a skin test, which involves intradermal exposure to tuberculin PPD (protein-purified derivative). Antigen-specific T cell responses result in measurable incubation at the injection site by 48-77 hours after injection, which indicates exposure to Mycobacterial antigens. Sensitivity and specificity have, however, been a problem with this test, and individuals vaccinated with BCG cannot be distinguished from infected individuals.

While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in AIDS patients, due to the depletion of CD4 T cells associated with human immunodeficiency virus (HIV) infection. *Mycobacterium*-reactive CD4 T cells have been shown to be potent producers of gamma-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25-dihydroxy-vitamin D3. Similarly, IL-12 has been shown to play a role in stimulating resistance to *M. tuberculosis* infection. For a review of the immunology of *M. tuberculosis* infection see Chan and Kaufmann, in *Tuberculosis: Pathogenesis, Protection and Control*, Bloom (ed.), ASM Press, Washington, D.C., 1994.

Accordingly, there is a need in the art for improved diagnostic methods for detecting tuberculosis. The present invention fulfills this need and further provides other related advantages.

SUMMARY OF THE INVENTION

Briefly stated, the present invention provides compositions and methods for diagnosing tuberculosis. In one aspect, polypeptides are provided comprising an antigenic portion of a soluble *M. tuberculosis* antigen, or a variant of such an antigen that differs only in conservative substitutions and/or modifications. In one embodiment of this aspect, the soluble antigen has one of the following N-terminal sequences:

```
(a) Asp-Pro-Val-Asp-Ala-Val-Ile-      (SEQ ID NO: 115)
    Asn-Thr-Thr-Cys-Asn-Tyr-Gly-
    Gln-Val-Val-Ala-Ala-Leu;

(b) Ala-Val-Glu-Ser-Gly-Met-Leu-      (SEQ ID NO: 116)
    Ala-Leu-Gly-Thr-Pro-Ala-Pro-
    Ser;

(c) Ala-Ala-Met-Lys-Pro-Arg-Thr-      (SEQ ID NO: 117)
    Gly-Asp-Gly-Pro-Leu-Glu-Ala-
    Ala-Lys-Glu-Gly-Arg;

(d) Tyr-Tyr-Trp-Cys-Pro-Gly-Gln-      (SEQ ID NO: 118)
    Pro-Phe-Asp-Pro-Ala-Trp-Gly-
    Pro;

(e) Asp-Ile-Gly-Ser-Glu-Ser-Thr-      (SEQ ID NO: 119)
    Glu-Asp-Gln-Gln-Xaa-Ala-Val;

(f) Ala-Glu-Glu-Ser-Ile-Ser-Thr-      (SEQ ID NO: 120)
    Xaa-Glu-Xaa-Ile-Val-Pro;
```

-continued

```
(g) Asp-Pro-Glu-Pro-Ala-Pro-Pro-    (SEQ ID NO: 121)
    Val-Pro-Thr-Thr-Ala-Ala-Ser-
    Pro-Pro-Ser;

(h) Ala-Pro-Lys-Thr-Tyr-Xaa-Glu-    (SEQ ID NO: 122)
    Glu-Leu-Lys-Gly-Thr-Asp-Thr-
    Gly;

(i) Asp-Pro-Ala-Ser-Ala-Pro-Asp-    (SEQ ID NO: 123)
    Val-Pro-Thr-Ala-Ala-Gln-Leu-
    Thr-Ser-Leu-Leu-Asn-Ser-Leu-
    Ala-Asp-Pro-Asn-Val-Ser-Phe-
    Ala-Asn;

(j) Xaa-Asp-Ser-Glu-Lys-Ser-Ala-    (SEQ ID NO: 129)
    Thr-Ile-Lys-Val-Thr-Asp-Ala-
    Ser;

(k) Ala-Gly-Asp-Thr-Xaa-Ile-Tyr-    (SEQ ID NO: 130)
    Ile-Val-Gly-Asn-Leu-Thr-Ala-
    Asp;
or

(l) Ala-Pro-Glu-Ser-Gly-Ala-Gly-    (SEQ ID NO: 131)
    Leu-Gly-Gly-Thr-Val-Gln-Ala-
    Gly;
```

wherein Xaa may be any amino acid.

In a related aspect, polypeptides are provided comprising an immunogenic portion of an *M. tuberculosis* antigen, or a variant of such an antigen that differs only in conservative substitutions and/or modifications, the antigen having one of the following N-terminal sequences:

```
(m) Xaa-Tyr-Ile-Ala-Tyr-Xaa-Thr-    (SEQ ID NO: 132)
    Thr-Ala-Gly-Ile-Val-Pro-Gly-
    Lys-Ile-Asn-Val-His-Leu-Val;
or

(n) Asp-Pro-Pro-Asp-Pro-His-Gln-    (SEQ ID NO: 124)
    Xaa-Asp-Met-Thr-Lys-Gly-Tyr-
    Tyr-Pro-Gly-Gly-Arg-Arg-Xaa-
    Phe;
```

wherein Xaa may be any amino acid.

In another embodiment, the soluble *M. tuberculosis* antigen comprises an amino acid sequence encoded by a DNA sequence selected from the group consisting of the sequences recited in SEQ ID NOS: 1, 2, 4-10, 13-25, 52, 94 and 96, the complements of said sequences, and DNA sequences that hybridize to a sequence recited in SEQ ID NOS: 1, 2, 4-10, 13-25, 52, 94 and 96 or a complement thereof under moderately stringent conditions.

In a related aspect, the polypeptides comprise an antigenic portion of a *M. tuberculosis* antigen, or a variant of such an antigen that differs only in conservative substitutions and/or modifications, wherein the antigen comprises an amino acid sequence encoded by a DNA sequence selected from the group consisting of the sequences recited in SEQ ID NOS: 26-51, 133, 134, 158-178, 184-188, 194-196, 198, 210-220, 232, 234, 235, 237-242, 248-251, 256-271, 287, 288, 290-293 and 298-337, the complements of said sequences, and DNA sequences that hybridize to a sequence recited in SEQ ID NOS: 26-51, 133, 134, 158-178, 184-188, 194-196, 198, 210-220, 232, 234, 235, 237-242, 248-251, 256-271, 287, 288, 290-293 and 298-337, or a complement thereof under moderately stringent conditions.

In related aspects, DNA sequences encoding the above polypeptides, recombinant expression vectors comprising these DNA sequences and host cells transformed or transfected with such expression vectors are also provided.

In another aspect, the present invention provides fusion proteins comprising a first and a second inventive polypeptide or, alternatively, an inventive polypeptide and a known *M. tuberculosis* antigen.

In further aspects of the subject invention, methods and diagnostic kits are provided for detecting tuberculosis in a patient. The methods comprise: (a) contacting a biological sample with at least one of the above polypeptides; and (b) detecting in the sample the presence of antibodies that bind to the polypeptide or polypeptides, thereby detecting *M. tuberculosis* infection in the biological sample. Suitable biological samples include whole blood, sputum, serum, plasma, saliva, cerebrospinal fluid and urine. The diagnostic kits comprise one or more of the above polypeptides in combination with a detection reagent.

The present invention also provides methods for detecting *M. tuberculosis* infection comprising: (a) obtaining a biological sample from a patient; (b) contacting the sample with at least one oligonucleotide primer in a polymerase chain reaction, the oligonucleotide primer being specific for a DNA sequence encoding the above polypeptides; and (c) detecting in the sample a DNA sequence that amplifies in the presence of the first and second oligonucleotide primers. In one embodiment, the oligonucleotide primer comprises at least about 10 contiguous nucleotides of such a DNA sequence.

In a further aspect, the present invention provides a method for detecting *M. tuberculosis* infection in a patient comprising: (a) obtaining a biological sample from the patient; (b) contacting the sample with an oligonucleotide probe specific for a DNA sequence encoding the above polypeptides; and (c) detecting in the sample a DNA sequence that hybridizes to the oligonucleotide probe. In one embodiment, the oligonucleotide probe comprises at least about 15 contiguous nucleotides of such a DNA sequence.

In yet another aspect, the present invention provides antibodies, both polyclonal and monoclonal, that bind to the polypeptides described above, as well as methods for their use in the detection of *M. tuberculosis* infection.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS AND SEQUENCE IDENTIFIERS

FIGS. 1A, 1B, 1C, and 1D illustrate the stimulation of proliferation and interferon-γ production in T cells derived from a first and a second *M. tuberculosis*-immune donor, respectively, by the 14 Kd, 20 Kd and 26 Kd antigens described in Example 1.

FIGS. 2A-D illustrate the reactivity of antisera raised against secretory *M. tuberculosis* proteins, the known *M. tuberculosis* antigen 85b and the inventive antigens Tb38-1 and TbH-9, respectively, with *M. tuberculosis* lysate (lane 2), *M. tuberculosis* secretory proteins (lane 3), recombinant Tb38-1 (lane 4), recombinant TbH-9 (lane 5) and recombinant 85b (lane 5).

Figure 10:
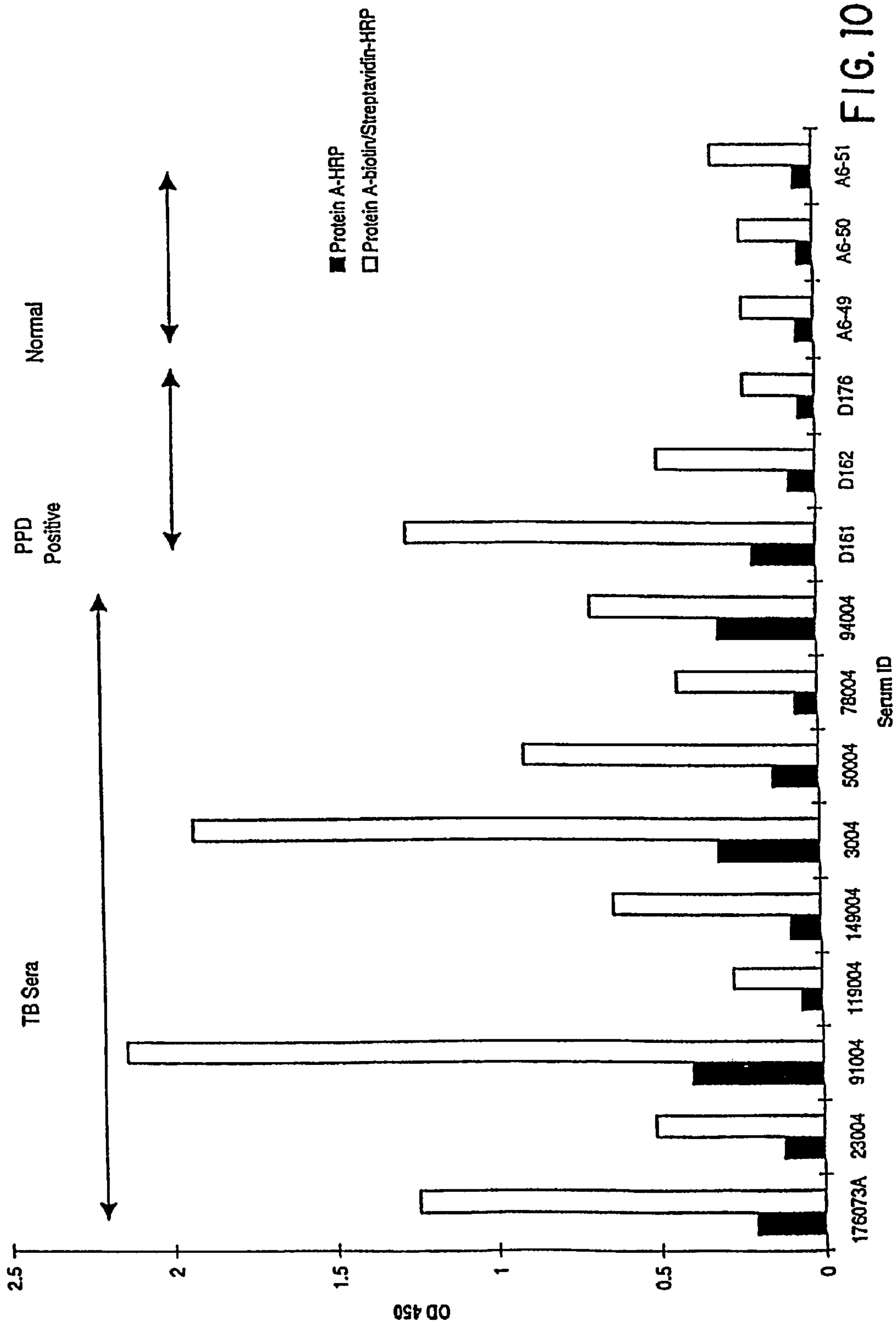
Figure 11:
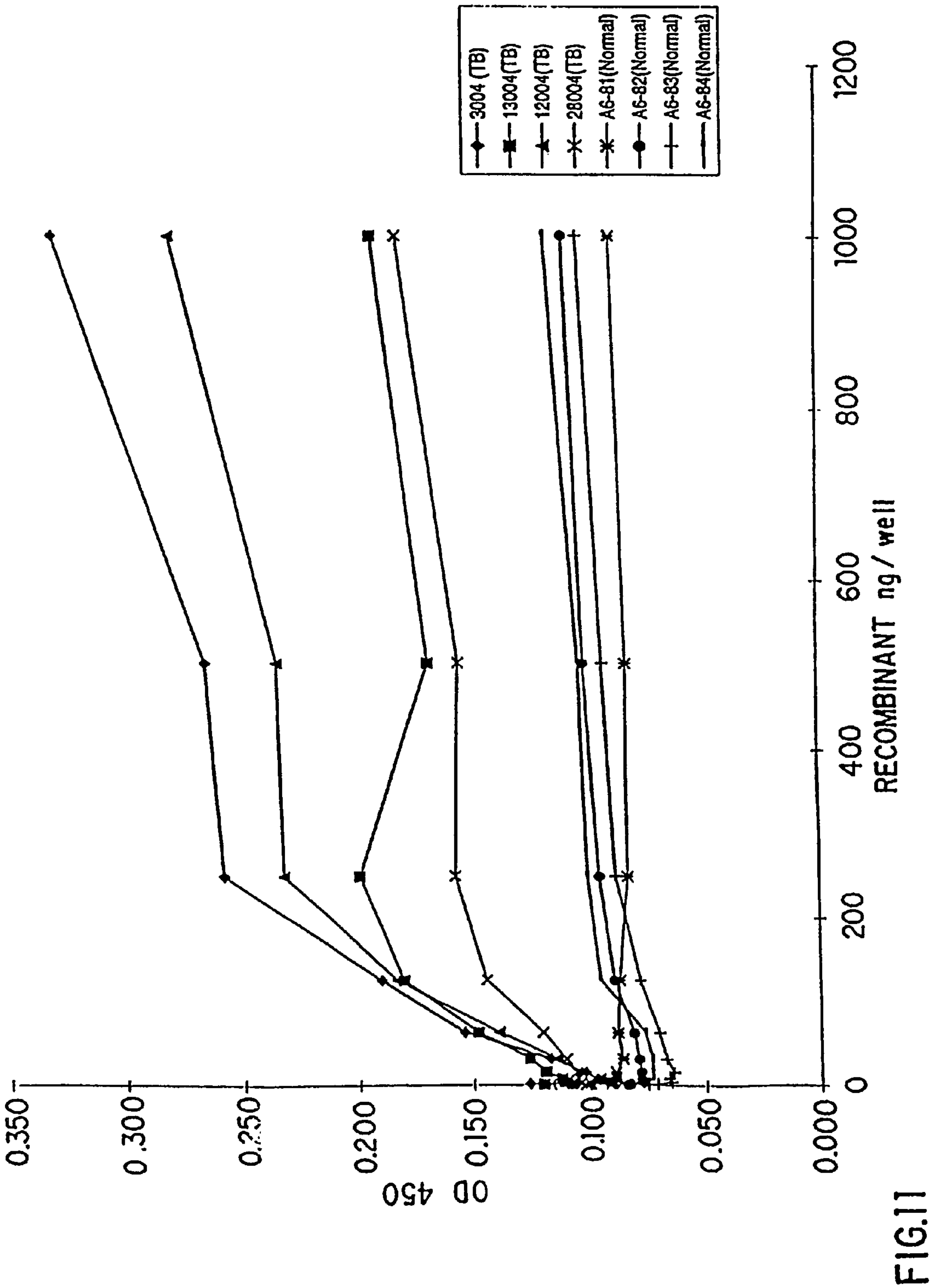
Figure 12A:
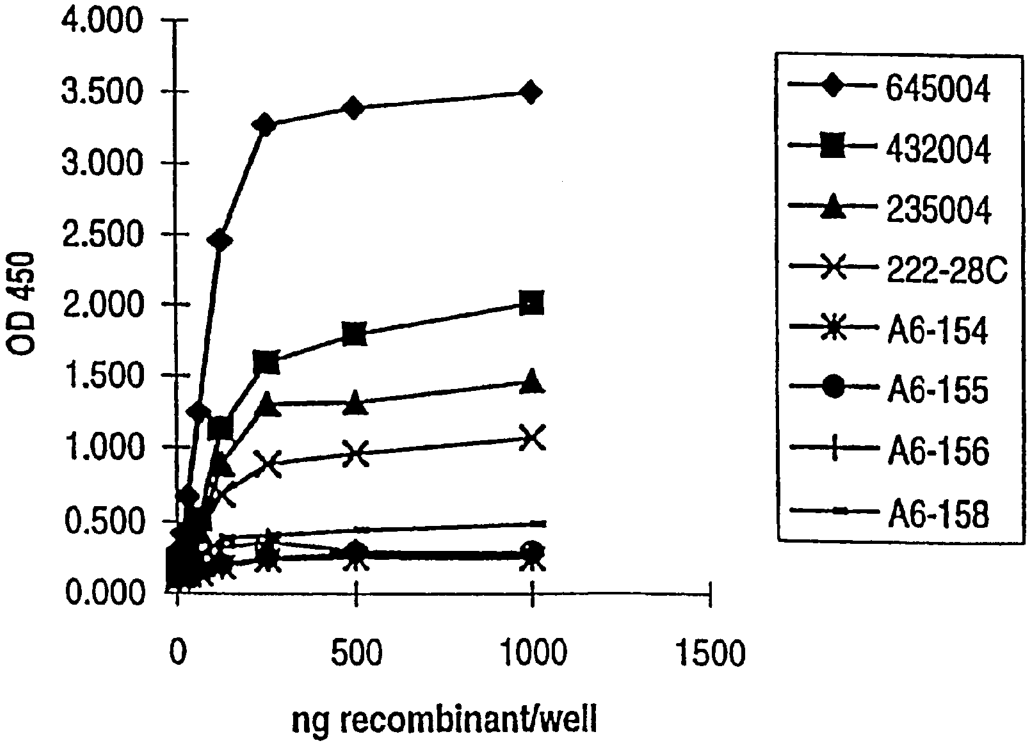
Figure 12B:
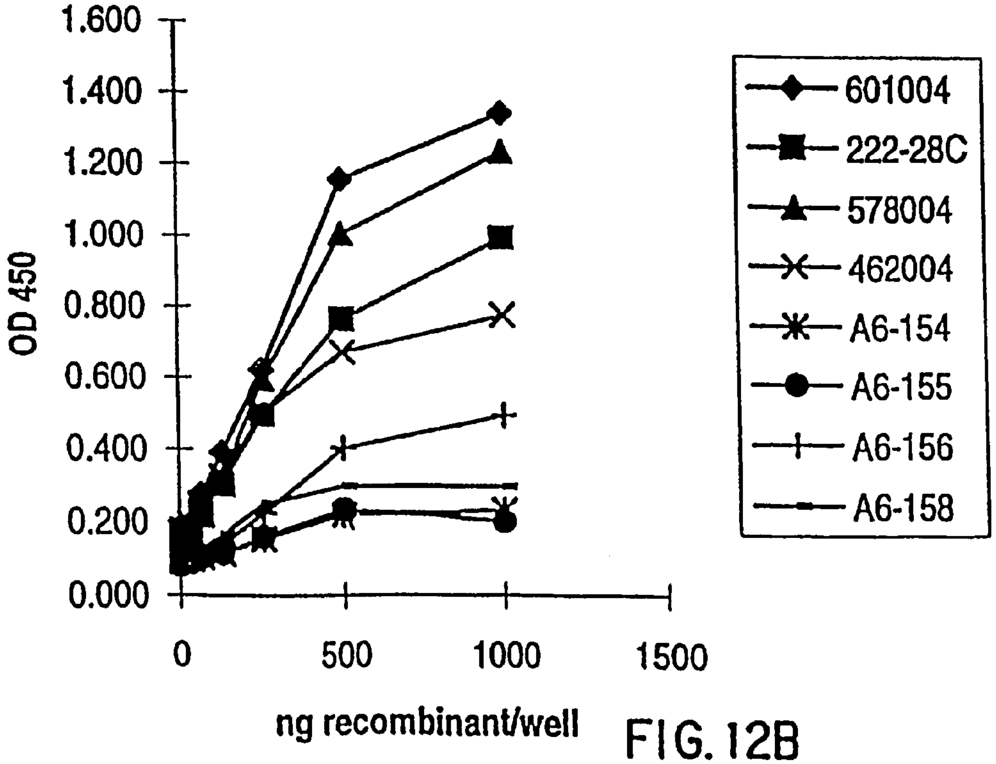
Figure 12C:
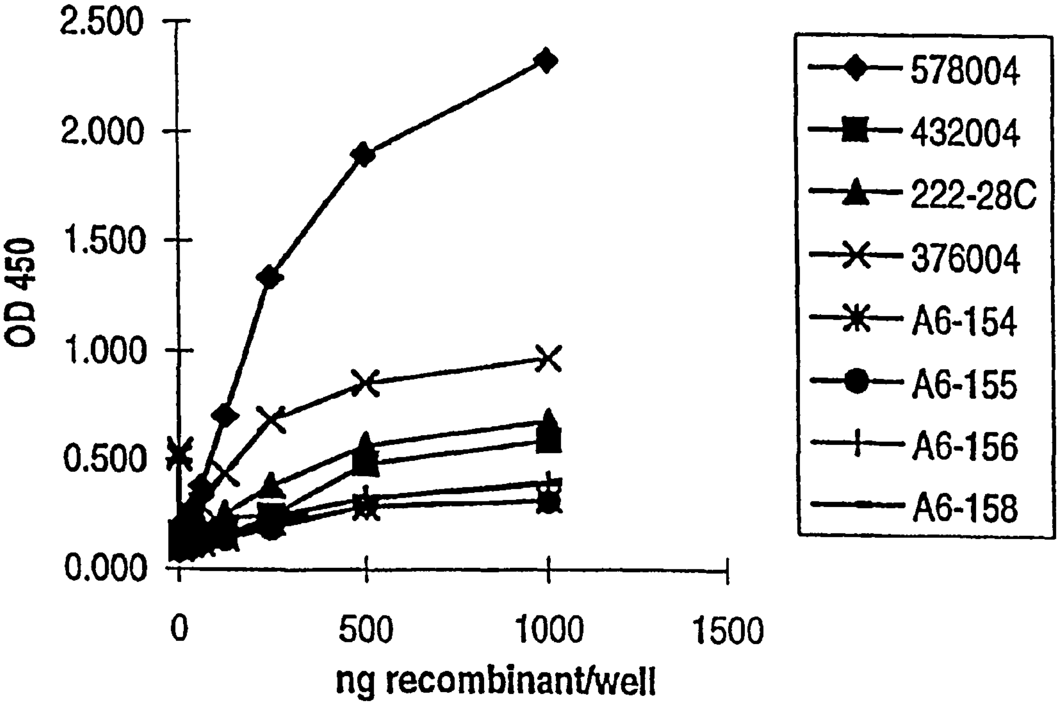
Figure 12D:
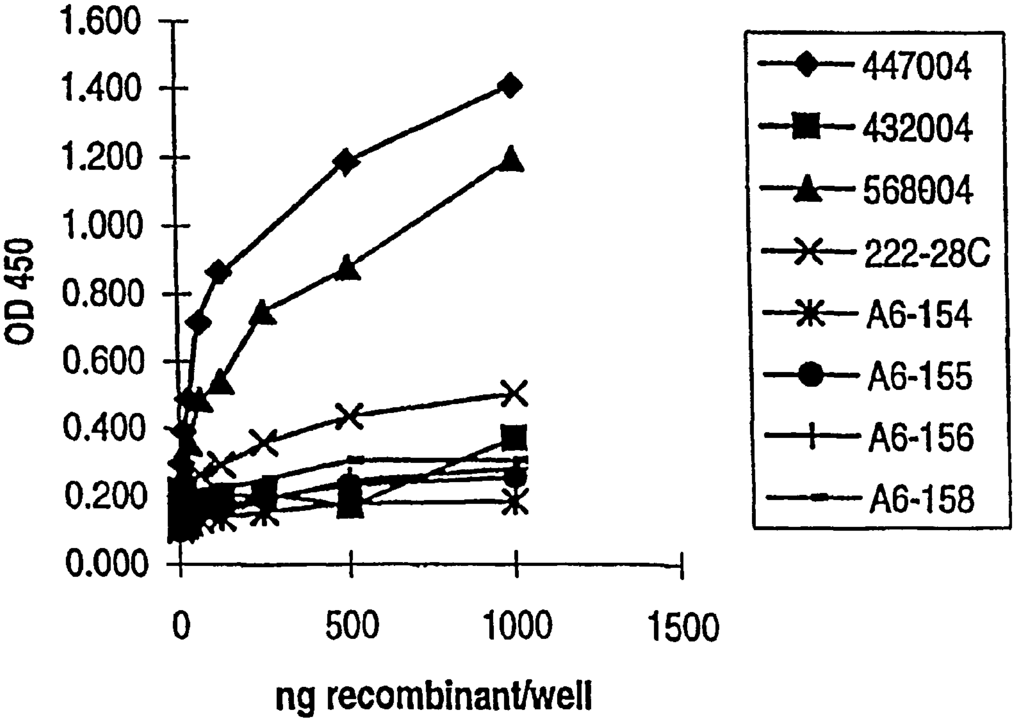
Figure 12E:
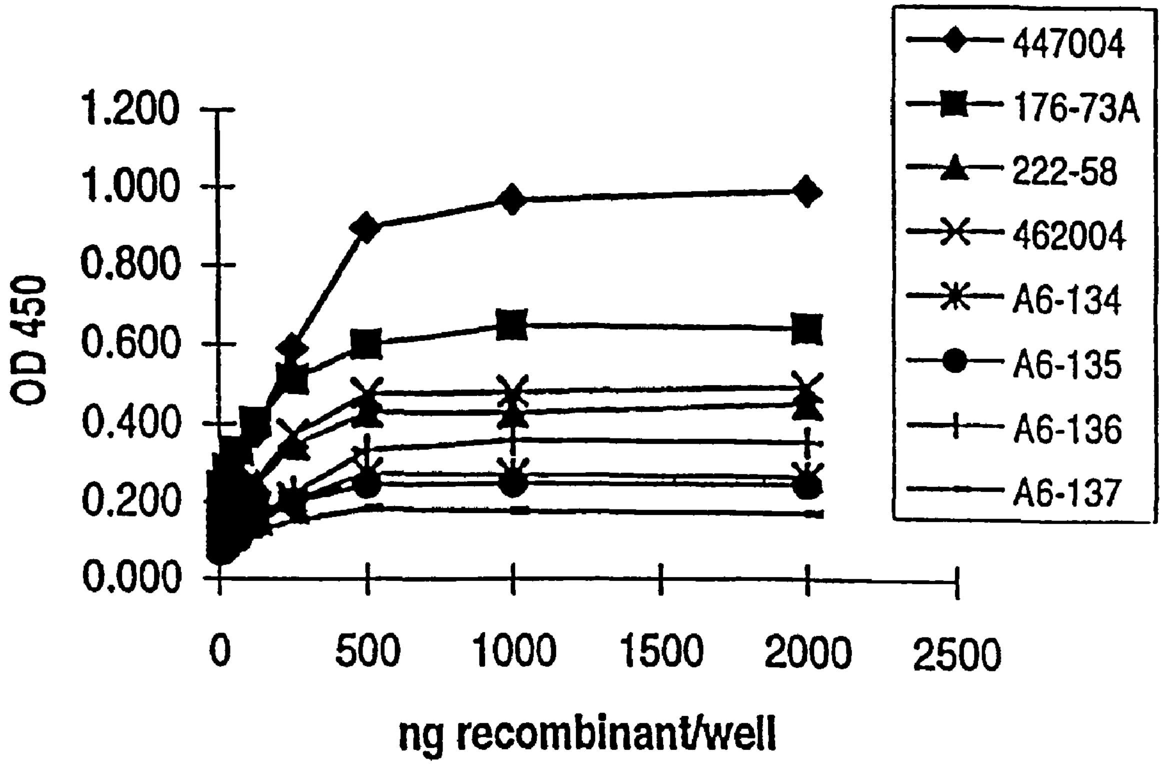

FIG. 10 illustrates the reactivity of the recombinant antigen TbH-33 (SEQ ID NO: 140) with sera from *M. tuberculosis* patients and from normal donors, and with a pool of sera from *M. tuberculosis* patients, as determined both by direct and indirect ELISA FIG. 11 illustrates the reactivity of increasing concentrations of the recombinant antigen TbH-33 (SEQ ID NO: 140) with sera from *M. tuberculosis* patients and from normal donors as determined by ELISA.

FIGS. 12A-E illustrate the reactivity of the recombinant antigens MO-1, MO-2, MO-4, MO-28 and MO-29, respectively, with sera from *M. tuberculosis* patients and from normal donors as determined by ELISA.

SEQ. ID NO. 1 is the DNA sequence of TbRa1.

SEQ. ID NO. 2 is the DNA sequence of TbRa10.

SEQ. ID NO. 3 is the DNA sequence of TbRa11.

SEQ. ID NO. 4 is the DNA sequence of TbRa12.

SEQ. ID NO. 5 is the DNA sequence of TbRa13.

SEQ. ID NO. 6 is the DNA sequence of TbRa16.

SEQ. ID NO. 7 is the DNA sequence of TbRa17.

SEQ. ID NO. 8 is the DNA sequence of TbRa18.

SEQ. ID NO. 9 is the DNA sequence of TbRa19.

SEQ. ID NO. 10 is the DNA sequence of TbRa24.

SEQ. ID NO. 11 is the DNA sequence of TbRa26.

SEQ. ID NO. 12 is the DNA sequence of TbRa28.

SEQ. ID NO. 13 is the DNA sequence of TbRa29.

SEQ. ID NO. 14 is the DNA sequence of TbRa2A.

SEQ. ID NO. 15 is the DNA sequence of TbRa3.

SEQ. ID NO. 16 is the DNA sequence of TbRa32.

SEQ. ID NO. 17 is the DNA sequence of TbRa35.

SEQ. ID NO. 18 is the DNA sequence of TbRa36.

SEQ. ID NO. 19 is the DNA sequence of TbRa4.

SEQ. ID NO. 20 is the DNA sequence of TbRa9.

SEQ. ID NO. 21 is the DNA sequence of TbRaB.

SEQ. ID NO. 22 is the DNA sequence of TbRaC.

SEQ. ID NO. 23 is the DNA sequence of TRaD.

SEQ. ID NO. 24 is the DNA sequence of YYWCPG.

SEQ. ID NO. 25 is the DNA sequence of AAMK.

SEQ. ID NO. 26 is the DNA sequence of TbL-23.

SEQ. ID NO. 27 is the DNA sequence of TbL-24.

SEQ. ID NO. 28 is the DNA sequence of TbL-25.

SEQ. ID NO. 29 is the DNA sequence of TbL-28.

SEQ. ID NO. 30 is the DNA sequence of TbL-29.

SEQ. ID NO. 31 is the DNA sequence of TbH-5.

SEQ. ID NO. 32 is the DNA sequence of TbH-8.

SEQ. ID NO. 33 is the DNA sequence of TbH-9.

SEQ. ID NO. 34 is the DNA sequence of TbM-1.

SEQ. ID NO. 35 is the DNA sequence of TbM-3.

SEQ. ID NO. 36 is the DNA sequence of TbM-6.

SEQ. ID NO. 37 is the DNA sequence of TbM-7.

SEQ. ID NO. 38 is the DNA sequence of TbM-9.

SEQ. ID NO. 39 is the DNA sequence of TbM-12.

SEQ. ID NO. 40 is the DNA sequence of TbM-13.

SEQ. ID NO. 41 is the DNA sequence of TbM-14.

SEQ. ID NO. 42 is the DNA sequence of TbM-15.

SEQ. ID NO. 43 is the DNA sequence of TbH-4.

SEQ. ID NO. 44 is the DNA sequence of TbH-4-FWD.

SEQ. ID NO. 45 is the DNA sequence of TbH-12.

SEQ. ID NO. 46 is the DNA sequence of Tb38-1.

SEQ. ID NO. 47 is the DNA sequence of Tb38-4.

SEQ. ID NO. 48 is the DNA sequence of TbL-17.

SEQ. ID NO. 49 is the DNA sequence of TbL-20.

SEQ. ID NO. 50 is the DNA sequence of TbL-21.

SEQ. ID NO. 51 is the DNA sequence of TbH-16.

SEQ. ID NO. 52 is the DNA sequence of DPEP.

SEQ. ID NO. 53 is the deduced amino acid sequence of DPEP.

SEQ. ID NO. 54 is the protein sequence of DPV N-terminal Antigen.

SEQ. ID NO. 55 is the protein sequence of AVGS N-terminal Antigen.

SEQ. ID NO. 56 is the protein sequence of AAMK N-terminal Antigen.

SEQ. ID NO. 57 is the protein sequence of YYWC N-terminal Antigen.

SEQ. ID NO. 58 is the protein sequence of DIGS N-terminal Antigen.

SEQ. ID NO. 59 is the protein sequence of AEES N-terminal Antigen.

SEQ. ID NO. 60 is the protein sequence of DPEP N-terminal Antigen.

SEQ. ID NO. 61 is the protein sequence of APKT N-terminal Antigen.

SEQ. ID NO. 62 is the protein sequence of DPAS N-terminal Antigen.

SEQ. ID NO. 63 is the deduced amino acid sequence of TbM-1 Peptide.

SEQ. ID NO. 64 is the deduced amino acid sequence of TbRa1.

SEQ. ID NO. 65 is the deduced amino acid sequence of TbRa1.

SEQ. ID NO. 66 is the deduced amino acid sequence of TbRa11.

SEQ. ID NO. 67 is the deduced amino acid sequence of TbRa12.

SEQ. ID NO. 68 is the deduced amino acid sequence of TbRa13.

SEQ. ID NO. 69 is the deduced amino acid sequence of TbRa16.

SEQ. ID NO. 70 is the deduced amino acid sequence of TbRa17.

SEQ. ID NO. 71 is the deduced amino acid sequence of TbRa18.

SEQ. ID NO. 72 is the deduced amino acid sequence of TbRa19.

SEQ. ID NO. 73 is the deduced amino acid sequence of TbRa24.

SEQ. ID NO. 74 is the deduced amino acid sequence of TbRa26.

SEQ. ID NO. 75 is the deduced amino acid sequence of TbRa28.

SEQ. ID NO. 76 is the deduced amino acid sequence of TbRa29.

SEQ. ID NO. 77 is the deduced amino acid sequence of TbRa2A.

SEQ. ID NO. 78 is the deduced amino acid sequence of TbRa3.

SEQ. ID NO. 79 is the deduced amino acid sequence of TbRa32.

SEQ. ID NO. 80 is the deduced amino acid sequence of TbRa35.

SEQ. ID NO. 81 is the deduced amino acid sequence of TbRa36.

SEQ. ID NO. 82 is the deduced amino acid sequence of TbRa4.

SEQ. ID NO. 83 is the deduced amino acid sequence of TbRa9.

SEQ. ID NO. 84 is the deduced amino acid sequence of TbRaB.

SEQ. ID NO. 85 is the deduced amino acid sequence of TbRaC.

SEQ. ID NO. 86 is the deduced amino acid sequence of TbRaD.

SEQ. ID NO. 87 is the deduced amino acid sequence of YYWCPG.

SEQ. ID NO. 88 is the deduced amino acid sequence of TbAAMK.

SEQ. ID NO. 89 is the deduced amino acid sequence of Tb38-1.

SEQ. ID NO. 90 is the deduced amino acid sequence of TbH-4.

SEQ. ID NO. 91 is the deduced amino acid sequence of TbH-8.

SEQ. ID NO. 92 is the deduced amino acid sequence of TbH-9.

SEQ. ID NO. 93 is the deduced amino acid sequence of TbH-12.

SEQ. ID NO. 94 is the DNA sequence of DPAS.

SEQ. ID NO. 95 is the deduced amino acid sequence of DPAS.

SEQ. ID NO. 96 is the DNA sequence of DPV.

SEQ. ID NO. 97 is the deduced amino acid sequence of DPV.

SEQ. ID NO. 98 is the DNA sequence of ESAT-6.

SEQ. ID NO. 99 is the deduced amino acid sequence of ESAT-6.

SEQ. ID NO. 100 is the DNA sequence of TbH-8-2.

SEQ. ID NO. 101 is the DNA sequence of TbH-9FL.

SEQ. ID NO. 102 is the deduced amino acid sequence of TbH-9FL.

SEQ. ID NO. 103 is the DNA sequence of TbH-9-1.

SEQ. ID NO. 104 is the deduced amino acid sequence of TbH-9-1.

SEQ. ID NO. 105 is the DNA sequence of TbH-9-4.

SEQ. ID NO. 106 is the deduced amino acid sequence of TbH-9-4.

SEQ. ID NO. 107 is the DNA sequence of Tb38-1F2 IN.

SEQ. ID NO. 108 is the DNA sequence of Tb38-1F2 RP.

SEQ. ID NO. 109 is the deduced amino acid sequence of Tb37-FL.

SEQ. ID NO. 110 is the deduced amino acid sequence of Tb38-IN.

SEQ. ID NO. 111 is the DNA sequence of Tb38-1F3.

SEQ. ID NO. 112 is the deduced amino acid sequence of Tb38-1F3.

SEQ. ID NO. 113 is the DNA sequence of Tb38-1F5.

SEQ. ID NO. 114 is the DNA sequence of Tb38-1F6.

SEQ. ID NO. 115 is the deduced N-terminal amino acid sequence of DPV.

SEQ. ID NO. 116 is the deduced N-terminal amino acid sequence of AVGS.

SEQ. ID NO. 117 is the deduced N-terminal amino acid sequence of AAMK.

SEQ. ID NO. 118 is the deduced N-terminal amino acid sequence of YYWC.

SEQ. ID NO. 119 is the deduced N-terminal amino acid sequence of DIGS.

SEQ. ID NO. 120 is the deduced N-terminal amino acid sequence of AAES.

SEQ. DD NO. 121 is the deduced N-terminal amino acid sequence of DPEP.

SEQ. ID NO. 122 is the deduced N-terminal amino acid sequence of APKT.

SEQ. ID NO. 123 is the deduced N-terminal amino acid sequence of DPAS.

SEQ. ID NO. 124 is the protein sequence of DPPD N-terminal Antigen.

SEQ ID NO. 125-128 are the protein sequences of four DPPD cyanogen bromide fragments.

SEQ ID NO. 129 is the N-terminal protein sequence of XDS antigen.

SEQ ID NO. 130 is the N-terminal protein sequence of AGD antigen.

SEQ ID NO. 131 is the N-terminal protein sequence of APE antigen.

SEQ ID NO. 132 is the N-terminal protein sequence of XYI antigen.

SEQ ID NO. 133 is the DNA sequence of TbH-29.

SEQ ID NO. 134 is the DNA sequence of TbH-30.

SEQ ID NO. 135 is the DNA sequence of TbH-32.

SEQ ID NO. 136 is the DNA sequence of TbH-33.

SEQ ID NO. 137 is the predicted amino acid sequence of TbH-29.

SEQ ID NO. 138 is the predicted amino acid sequence of TbH-30.

SEQ ID NO. 139 is the predicted amino acid sequence of TbH-32.

SEQ ID NO. 140 is the predicted amino acid sequence of TbH-33.

SEQ ID NO: 141-146 are PCR primers used in the preparation of a fusion protein containing TbRa3, 38 kD and Tb38-1.

SEQ ID NO: 147 is the DNA sequence of the fusion protein containing TbRa3, 38 kD and Tb38-1.

SEQ ID NO: 148 is the amino acid sequence of the fusion protein containing TbRa3, 38 kD and Tb38-1.

SEQ ID NO: 149 is the DNA sequence of the *M. tuberculosis* antigen 38 kD.

SEQ ID NO: 150 is the amino acid sequence of the *M. tuberculosis* antigen 38 kD.

SEQ ID NO: 151 is the DNA sequence of XP14.

SEQ ID NO: 152 is the DNA sequence of XP14.

SEQ ID NO: 153 is the DNA sequence of XP31.

SEQ ID NO: 154 is the 5' DNA sequence of XP32.

SEQ ID NO: 155 is the 3' DNA sequence of XP32.

SEQ ID NO: 156 is the predicted amino acid sequence of XP 14.

SEQ ID NO: 157 is the predicted amino acid sequence encoded by the reverse complement of XP14.

SEQ ID NO: 158 is the DNA sequence of XP27.

SEQ ID NO: 159 is the DNA sequence of XP36.

SEQ ID NO: 160 is the 5' DNA sequence of XP4.

SEQ ID NO: 161 is the 5' DNA sequence of XP5.

SEQ ID NO: 162 is the 5' DNA sequence of XP17.

SEQ ID NO: 163 is the 5' DNA sequence of XP30.

SEQ ID NO: 164 is the 5' DNA sequence of XP2.

SEQ ID NO: 165 is the 3' DNA sequence of XP2.

SEQ ID NO: 166 is the 5' DNA sequence of XP3.

SEQ ID NO: 167 is the 3' DNA sequence of XP3.
SEQ ID NO: 168 is the 5' DNA sequence of XP6.
SEQ ID NO: 169 is the 3' DNA sequence of XP6.
SEQ ID NO: 170 is the 5' DNA sequence of XP18.
SEQ ID NO: 171 is the 3' DNA sequence of XP18.
SEQ ID NO: 172 is the 5' DNA sequence of XP19.
SEQ ID NO: 173 is the 3' DNA sequence of XP19.
SEQ ID NO: 174 is the 5' DNA sequence of XP22.
SEQ ID NO: 175 is the 3' DNA sequence of XP22.
SEQ ID NO: 176 is the 5' DNA sequence of XP25.
SEQ ID NO: 177 is the 3' DNA sequence of XP25.
SEQ ID NO: 178 is the full-length DNA sequence of TbH4-XP1.
SEQ ID NO: 179 is the predicted amino acid sequence of TbH4-XP1.
SEQ ID NO: 180 is the predicted amino acid sequence encoded by the reverse complement of TbH4-XP1.
SEQ ID NO: 181 is a first predicted amino acid sequence encoded by XP36.
SEQ ID NO: 182 is a second predicted amino acid sequence encoded by XP36.
SEQ ID NO: 183 is the predicted amino acid sequence encoded by the reverse complement of XP36.
SEQ ID NO: 184 is the DNA sequence of RDIF2.
SEQ ID NO: 185 is the DNA sequence of RDIF5.
SEQ ID NO: 186 is the DNA sequence of RDIF8.
SEQ ID NO: 187 is the DNA sequence of RDIF10.
SEQ ID NO: 188 is the DNA sequence of RDIF11.
SEQ ID NO: 189 is the predicted amino acid sequence of RDIF2.
SEQ ID NO: 190 is the predicted amino acid sequence of RDIF5.
SEQ ID NO: 191 is the predicted amino acid sequence of RDIF8.
SEQ ID NO: 192 is the predicted amino acid sequence of RDIF10.
SEQ ID NO: 193 is the predicted amino acid sequence of RDIF11.
SEQ ID NO: 194 is the 5' DNA sequence of RDIF12.
SEQ ID NO: 195 is the 3' DNA sequence of RDIF12.
SEQ ID NO: 196 is the DNA sequence of RDIF7.
SEQ ID NO: 197 is the predicted amino acid sequence of RDIF7.
SEQ ID NO: 198 is the DNA sequence of DIF2-1.
SEQ ID NO: 199 is the predicted amino acid sequence of DIF2-1.
SEQ ID NO: 200-207 are PCR primers used in the preparation of a fusion protein containing TbRa3, 38 kD, Tb38-1 and DPEP (hereinafter referred to as TbF-2).
SEQ ID NO: 208 is the DNA sequence of the fusion protein TbF-2.
SEQ ID NO: 209 is the amino acid sequence of the fusion protein TbF-2.
SEQ ID NO: 210 is the 5' DNA sequence of MO-1.
SEQ ID NO: 211 is the 5' DNA sequence for MO-2
SEQ ID NO: 212 is the 5' DNA sequence for MO-4.
SEQ ID NO: 213 is the 5' DNA sequence for MO-8.
SEQ ID NO: 214 is the 5' DNA sequence for MO-9.
SEQ ID NO: 215 is the 5' DNA sequence for MO-26.
SEQ ID NO: 216 is the 5' DNA sequence for MO-28.
SEQ ID NO: 217 is the 5' DNA sequence for MO-29.
SEQ ID NO: 218 is the 5' DNA sequence for MO-30.
SEQ ID NO: 219 is the 5' DNA sequence for MO-34.
SEQ ID NO: 220 is the 5' DNA sequence for MO-35.
SEQ ID NO: 221 is the predicted amino acid sequence for MO-1.
SEQ ID NO: 222 is the predicted amino acid sequence for MO-2.
SEQ ID NO: 223 is the predicted amino acid sequence for MO-4.
SEQ ID NO: 224 is the predicted amino acid sequence for MO-8.
SEQ ID NO: 225 is the predicted amino acid sequence for MO-9.
SEQ ID NO: 226 is the predicted amino acid sequence for MO-26.
SEQ ID NO: 227 is the predicted amino acid sequence for MO-28.
SEQ ID NO: 228 is the predicted amino acid sequence for MO-29.
SEQ ID NO: 229 is the predicted amino acid sequence for MO-30.
SEQ ID NO: 230 is the predicted amino acid sequence for MO-34.
SEQ ID NO: 231 is the predicted amino acid sequence for MO-35.
SEQ ID NO: 232 is the determined DNA sequence for MO-10.
SEQ ID NO: 233 is the predicted amino acid sequence for MO-10.
SEQ ID NO: 234 is the 3' DNA sequence for MO-27.
SEQ ID NO: 235 is the full-length DNA sequence for DPPD.
SEQ ID NO: 236 is the predicted full-length amino acid sequence for DPPD
SEQ ID NO: 237 is the determined 5' cDNA sequence for LSER-10
SEQ ID NO: 238 is the determined 5' cDNA sequence for LSER-11
SEQ ID NO: 239 is the determined 5' cDNA sequence for LSER-12
SEQ ID NO: 240 is the determined 5' cDNA sequence for LSER-13
SEQ ID NO: 241 is the determined 5' cDNA sequence for LSER-16
SEQ ID NO: 242 is the determined 5' cDNA sequence for LSER-25.
SEQ ID NO: 243 is the predicted amino acid sequence for LSER-10
SEQ ID NO: 244 is the predicted amino acid sequence for LSER-12
SEQ ID NO: 245 is the predicted amino acid sequence for LSER-13
SEQ ID NO: 246 is the predicted amino acid sequence for LSER-16
SEQ ID NO: 247 is the predicted amino acid sequence for LSER-25
SEQ ID NO: 248 is the determined cDNA sequence for LSER-18
SEQ ID NO: 249 is the determined cDNA sequence for LSER-23
SEQ ID NO: 250 is the determined cDNA sequence for LSER-24
SEQ ID NO: 251 is the determined cDNA sequence for LSER-27
SEQ ID NO: 252 is the predicted amino acid sequence for LSER-18
SEQ ID NO: 253 is the predicted amino acid sequence for LSER-23
SEQ ID NO: 254 is the predicted amino acid sequence for LSER-24
SEQ ID NO: 255 is the predicted amino acid sequence for LSER-27

SEQ ID NO: 256 is the determined 5' cDNA sequence for LSER-1
SEQ ID NO: 257 is the determined 5' cDNA sequence for LSER-3
SEQ ID NO: 258 is the determined 5' cDNA sequence for LSER-4
SEQ ID NO: 259 is the determined 5' cDNA sequence for LSER-5
SEQ ID NO: 260 is the determined 5' cDNA sequence for LSER-6
SEQ ID NO: 261 is the determined 5' cDNA sequence for LSER-8
SEQ ID NO: 262 is the determined 5' cDNA sequence for LSER-14
SEQ ID NO: 263 is the determined 5' cDNA sequence for LSER-15
SEQ ID NO: 264 is the determined 5' cDNA sequence for LSER-17
SEQ ID NO: 265 is the determined 5' cDNA sequence for LSER-19
SEQ ID NO: 266 is the determined 5' cDNA sequence for LSER-20
SEQ ID NO: 267 is the determined 5' cDNA sequence for LSER-22
SEQ ID NO: 268 is the determined 5 cDNA sequence for LSER-26
SEQ ID NO: 269 is the determined 5' cDNA sequence for LSER-28
SEQ ID NO: 270 is the determined 5' cDNA sequence for LSER-29
SEQ ID NO: 271 is the determined 5' cDNA sequence for LSER-30
SEQ ID NO: 272 is the predicted amino acid sequence for LSER-1
SEQ ID NO: 273 is the predicted amino acid sequence for LSER-3
SEQ ID NO: 274 is the predicted amino acid sequence for LSER-5
SEQ ID NO: 275 is the predicted amino acid sequence for LSER-6
SEQ ID NO: 276 is the predicted amino acid sequence for LSER-8
SEQ ID NO: 277 is the predicted amino acid sequence for LSER-14
SEQ ID NO: 278 is the predicted amino acid sequence for LSER-15
SEQ ID NO: 279 is the predicted amino acid sequence for LSER-17
SEQ ID NO: 280 is the predicted amino acid sequence for LSER-19
SEQ ID NO: 281 is the predicted amino acid sequence for LSER-20
SEQ ID NO: 282 is the predicted amino acid sequence for LSER-22
SEQ ID NO: 283 is the predicted amino acid sequence for LSER-26
SEQ ID NO: 284 is the predicted amino acid sequence for LSER-28
SEQ ID NO: 285 is the predicted amino acid sequence for LSER-29
SEQ ID NO: 286 is the predicted amino acid sequence for LSER-30
SEQ ID NO: 287 is the determined cDNA sequence for LSER-9
SEQ ID NO: 288 is the determined cDNA sequence for the reverse complement of LSER-6
SEQ ID NO: 289 is the predicted amino acid sequence for the reverse complement of LSER-6
SEQ ID NO: 290 is the determined 5' cDNA sequence for MO-12
SEQ ID NO: 291 is the determined 5' cDNA sequence for MO-13
SEQ ID NO: 292 is the determined 5' cDNA sequence for MO-19
SEQ ID NO: 293 is the determined 5' cDNA sequence for MO-39
SEQ ID NO: 294 is the predicted amino acid sequence for MO-12
SEQ ID NO: 295 is the predicted amino acid sequence for MO-13
SEQ ID NO: 296 is the predicted amino acid sequence for MO-19
SEQ ID NO: 297 is the predicted amino acid sequence for MO-39
SEQ ID NO: 298 is the determined 5' cDNA sequence for Erdsn-1
SEQ ID NO: 299 is the determined 5' cDNA sequence for Erdsn-2
SEQ ID NO: 300 is the determined 5' cDNA sequence for Erdsn-4
SEQ ID NO: 301 is the determined 5' cDNA sequence for Erdsn-5
SEQ ID NO: 302 is the determined 5' cDNA sequence for Erdsn-6
SEQ ID NO: 303 is the determined 5' cDNA sequence for Erdsn-7
SEQ ID NO: 304 is the determined 5' cDNA sequence for Erdsn-8
SEQ ID NO: 305 is the determined 5' cDNA sequence for Erdsn-9
SEQ ID NO: 306 is the determined 5' cDNA sequence for Erdsn-10
SEQ ID NO: 307 is the determined 5' cDNA sequence for Erdsn-12
SEQ ID NO: 308 is the determined 5' cDNA sequence for Erdsn-13
SEQ ID NO: 309 is the determined 5' cDNA sequence for Erdsn-14
SEQ ID NO: 310 is the determined 5' cDNA sequence for Erdsn-15
SEQ ID NO: 311 is the determined 5' cDNA sequence for Erdsn-16
SEQ ID NO: 312 is the determined 5' cDNA sequence for Erdsn-17
SEQ ID NO: 313 is the determined 5' cDNA sequence for Erdsn-18
SEQ ID NO: 314 is the determined 5' cDNA sequence for Erdsn-21
SEQ ID NO: 315 is the determined 5' cDNA sequence for Erdsn-22
SEQ ID NO: 316 is the determined 5' cDNA sequence for Erdsn-23
SEQ ID NO: 317 is the determined 5' cDNA sequence for Erdsn-25
SEQ ID NO: 318 is the determined 3' cDNA sequence for Erdsn-1
SEQ ID NO: 319 is the determined 3' cDNA sequence for Erdsn-2
SEQ ID NO: 320 is the determined 3' cDNA sequence for Erdsn-4
SEQ ID NO: 321 is the determined 3' cDNA sequence for Erdsn-5

SEQ ID NO: 322 is the determined 3' cDNA sequence for Erdsn-7

SEQ ID NO: 323 is the determined 3' cDNA sequence for Erdsn-8

SEQ ID NO: 324 is the determined 3' cDNA sequence for Erdsn-9

SEQ ID NO: 325 is the determined 3' cDNA sequence for Erdsn-10

SEQ ID NO: 326 is the determined 3' cDNA sequence for Erdsn-12

SEQ ID NO: 327 is the determined 3' cDNA sequence for Erdsn-13

SEQ ID NO: 328 is the determined 3' cDNA sequence for Erdsn-14

SEQ ID NO: 329 is the determined 3' cDNA sequence for Erdsn-15

SEQ ID NO: 330 is the determined 3' cDNA sequence for Erdsn-16

SEQ ID NO: 331 is the determined 3' cDNA sequence for Erdsn-17

SEQ ID NO: 332 is the determined 3' cDNA sequence for Erdsn-18

SEQ ID NO: 333 is the determined 3' cDNA sequence for Erdsn-21

SEQ ID NO: 334 is the determined 3' cDNA sequence for Erdsn-22

SEQ ID NO: 335 is the determined 3' cDNA sequence for Erdsn-23

SEQ ID NO: 336 is the determined 3' cDNA sequence for Erdsn-25

SEQ ID NO: 337 is the determined cDNA sequence for Erdsn-24

SEQ ID NO: 338 is the determined amino acid sequence for a *M. tuberculosis* 85b precursor homolog SEQ ID NO: 339 is the determined amino acid sequence for spot 1

SEQ ID NO: 340 is a determined amino acid sequence for spot 2

SEQ ID NO: 341 is a determined amino acid sequence for spot 2

SEQ ID NO: 342 is the determined amino acid seq for spot 4

SEQ ID NO: 343 is the sequence of primer PDM-157

SEQ ID NO: 344 is the sequence of primer PDM-160

SEQ ID NO: 345 is the DNA sequence of the fusion protein TbF-6

SEQ ID NO: 346 is the amino acid sequence of fusion protein TbF-6

SEQ ID NO: 347 is the sequence of primer PDM-176

SEQ ID NO: 348 is the sequence of primer PDM-175

SEQ ID NO: 349 is the DNA sequence of the fusion protein TbF-8

SEQ ID NO: 350 is the amino acid sequence of the fusion protein TbF-8

DETAILED DESCRIPTION OF THE INVENTION

As noted above, the present invention is generally directed to compositions and methods for diagnosing tuberculosis. The compositions of the subject invention include polypeptides that comprise at least one antigenic portion of a *M. tuberculosis* antigen, or a variant of such an antigen that differs only in conservative substitutions and/or modifications. Polypeptides within the scope of the present invention include, but are not limited to, soluble *M. tuberculosis* antigens. A "soluble *M. tuberculosis* antigen" is a protein of *M. tuberculosis* origin that is present in *M. tuberculosis* culture filtrate. As used herein, the term "polypeptide" encompasses amino acid chains of any length, including full length proteins (i.e., antigens), wherein the amino acid residues are linked by covalent peptide bonds. Thus, a polypeptide comprising an antigenic portion of one of the above antigens may consist entirely of the antigenic portion, or may contain additional sequences. The additional sequences may be derived from the native *M. tuberculosis* antigen or may be heterologous, and such sequences may (but need not) be antigenic.

An "antigenic portion" of an antigen (which may or may not be soluble) is a portion that is capable of reacting with sera obtained from an *M. tuberculosis*-infected individual (i.e., generates an absorbance reading with sera from infected individuals that is at least three standard deviations above the absorbance obtained with sera from uninfected individuals, in a representative ELISA assay described herein). An "*M. tuberculosis*-infected individual" is a human who has been infected with *M. tuberculosis* (e.g., has an intradermal skin test response to PPD that is at least 0.5 cm in diameter). Infected individuals may display symptoms of tuberculosis or may be free of disease symptoms. Polypeptides comprising at least an antigenic portion of one or more *M. tuberculosis* antigens as described herein may generally be used, alone or in combination, to detect tuberculosis in a patient.

The compositions and methods of the present invention also encompass variants of the above polypeptides and DNA molecules. A polypeptide "variant," as used herein, is a polypeptide that differs from the recited polypeptide only in conservative substitutions and/or modifications, such that the therapeutic, antigenic and/or immunogenic properties of the polypeptide are retained. Polypeptide variants preferably exhibit at least about 70%, more preferably at least about 90% and most preferably at least about 95% identity to the identified polypeptides. For polypeptides with immunoreactive properties, variants may, alternatively, be identified by modifying the amino acid sequence of one of the above polypeptides, and evaluating the immunoreactive of the modified polypeptide. For polypeptides useful for the generation of diagnostic binding agents, a variant may be identified by evaluating a modified polypeptide for the ability to generate antibodies that detect the presence or absence of tuberculosis. Such modified sequences may be prepared and tested using, for example, the representative procedures described herein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gan, asn, ser, thr, (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA,* 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity to the recited sequence. Such variant nucleotide sequences will generally hybridize to the recite nucleotide sequence under stringent conditions. As used herein, "stringent conditions" refers to prewashing in a solution of 6×SSC, 0.2% SDS; hybridizing at 65° C., 6×SSC, 0.2%, SDS overnight; followed by two washes of 30 minutes each in 1×SSC, 0.1% SDS at 65° C. and two washes of 30 minutes each in 0.2×SSC, 0.1% SDS at 65° C.

In a related aspect, combination, or fusion, polypeptides are disclosed. A "fusion polypeptide" is a polypeptide comprising at least one of the above antigenic portions and one or more additional antigenic *M. tuberculosis* sequences, which are joined via a peptide linkage into a single amino acid chain. The sequences may be joined directly (i.e., with no intervening amino acids) or may be joined by way of a linker sequence (e.g., Gly-Cys-Gly) that does not significantly diminish the antigenic properties of the component polypeptides.

In general, *M. tuberculosis* antigens, and DNA sequences encoding such antigens, may be prepared using any of a variety of procedures. For example, soluble antigens may be isolated from *M. tuberculosis* culture filtrate by procedures known to those of ordinary skill in the art, including anion-exchange and reverse phase chromatography. Purified antigens may then be evaluated for a desired property, such as the ability to react with sera obtained from an *M. tuberculosis*-infected individual. Such screens may be performed using the representative methods described herein. Antigens may then be partially sequenced using, for example, traditional Edman chemistry. See Edman and Berg, *Eur. J. Biochem.* 80:116-132, 1967.

Antigens may also be produced recombinantly using a DNA sequence that encodes the antigen, which has been inserted into an expression vector and expressed in an appropriate host. DNA molecules encoding soluble antigens may be isolated by screening an appropriate *M. tuberculosis* expression library with anti-sera (e.g., rabbit) raised specifically against soluble *M. tuberculosis* antigens. DNA sequences encoding antigens that may or may not be soluble may be identified by screening an appropriate *M. tuberculosis* genomic or cDNA expression library with sera obtained from patients infected with if tuberculosis. Such screens may generally be performed using techniques well known in the art, such as those described in Sambrook et al., *Molecular Cloning: A Laboratory Manual*, Cold Spring Harbor Laboratories, Cold Spring Harbor. NY, 1989.

DNA sequences encoding soluble antigens may also be obtained by screening an appropriate *M. tuberculosis* cDNA or genomic DNA library for DNA sequences that hybridize to degenerate oligonucleotides derived from partial amino acid sequences of isolated soluble antigens. Degenerate oligonucleotide sequences for use in such a screen may be designed and synthesized, and the screen may be performed, as described (for example) in Sambrook et al., *Molecular Cloning: A Laboratory Manual*, Cold Spring Harbor Laboratories, Cold Spring Harbor, N.Y. (and references cited therein). Polymerase chain reaction (PCR) may also be employed, using the above oligonucleotides in methods well known in the art, to isolate a nucleic acid probe from a cDNA or genomic library. The library screen may then be performed using the isolated probe.

Regardless of the method of preparation, the antigens described herein are "antigenic." More specifically, the antigens have the ability to react with sera obtained from an *M. tuberculosis-infected* individual. Reactivity may be evaluated using, for example, the representative ELISA assays described herein, where an absorbance reading with sera from infected individuals that is at least three standard deviations above the absorbance obtained with sera from uninfected individuals is considered positive.

Antigenic portions of *M. tuberculosis* antigens may be prepared and identified using well known techniques, such as those summarized in Paul, *Fundamental Immunology,* 3d ed., Raven Press, 1993, pp. 243-247 and references cited therein. Such techniques include screening polypeptide portions of the native antigen for antigenic properties. The representative ELISAs described herein may generally be employed in these screens. An antigenic portion of a polypeptide is a portion that, within such representative assays, generates a signal in such assays that is substantially similar to that generated by the full length antigen. In other words, an antigenic portion of a *M. tuberculosis* antigen generates at least about 20%, and preferably about 100%, of the signal induced by the full length antigen in a model ELISA as described herein.

Portions and other variants of *M. tuberculosis* antigens may be generated by synthetic or recombinant means. Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146, 1963. Equipment for automated synthesis of polypeptides is commercially available from suppliers such as Applied BioSystems, Inc., Foster City, Calif., and may be operated according to the manufacturer's instructions. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

Recombinant polypeptides containing portions and/or variants of a native antigen may be readily prepared from a DNA sequence encoding the polypeptide using a variety of techniques well known to those of ordinary skill in the art. For example, supernatants from suitable host/vector systems which secrete recombinant protein into culture media may be first concentrated using a commercially available to filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides as described herein. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line, such as COS or CHO. The DNA sequences expressed in this manner may encode naturally occurring antigens, portions of naturally occurring antigens, or other variants thereof.

In general, regardless of the method of preparation, the polypeptides disclosed herein are prepared in substantially pure form. Preferably, the polypeptides are at least about 80% pure, more preferably at least about 90% pure and most preferably at least about 99% pure. For use in the methods described herein, however, such substantially pure polypeptides may be combined.

In certain specific embodiments, the subject invention discloses polypeptides comprising at least an antigenic portion of a soluble *M. tuberculosis* antigen (or a variant of such an antigen), where the antigen has one of the following N-terminal sequences:

```
(a) Asp-Pro-Val-Asp-Ala-Val-Ile-     (SEQ ID NO: 115)
    Asn-Thr-Thr-Cys-Asn-Tyr-Gly-
    Gln-Val-Val-Ala-Ala-Leu;

(b) Ala-Val-Glu-Ser-Gly-Met-Leu-     (SEQ ID NO: 116)
    Ala-Leu-Gly-Thr-Pro-Ala-Pro-
    Ser;

(c) Ala-Ala-Met-Lys-Pro-Arg-Thr-     (SEQ ID NO: 117)
    Gly-Asp-Gly-Pro-Leu-Glu-Ala-
    Ala-Lys-Glu-Gly-Arg;

(d) Tyr-Tyr-Trp-Cys-Pro-Gly-Gln-     (SEQ ID NO: 118)
    Pro-Phe-Asp-Pro-Ala-Trp-Gly-
    Pro;

(e) Asp-Ile-Gly-Ser-Glu-Ser-Thr-     (SEQ ID NO: 119)
    Glu-Asp-Gln-Gln-Xaa-Ala-Val;

(f) Ala-Glu-Glu-Ser-Ile-Ser-Thr-     (SEQ ID NO: 120)
    Xaa-Glu-Xaa-Ile-Val-Pro;

(g) Asp-Pro-Glu-Pro-Ala-Pro-Pro-     (SEQ ID NO: 121)
    Val-Pro-Thr-Thr-Ala-Ala-Ser-
    Pro-Pro-Ser;

(h) Ala-Pro-Lys-Thr-Tyr-Xaa-Glu-     (SEQ ID NO: 122)
    Glu-Leu-Lys-Gly-Thr-Asp-Thr-
    Gly;

(i) Asp-Pro-Ala-Ser-Ala-Pro-Asp-     (SEQ ID NO: 123)
    Val-Pro-Thr-Ala-Ala-Gln-Gln-
    Thr-Ser-Leu-Leu-Asn-Ser-Leu-
    Ala-Asp-Pro-Asn-Val-Ser-Phe-
    Ala-Asn;

(j) Xaa-Asp-Ser-Glu-Lys-Ser-Ala-     (SEQ ID NO: 129)
    Thr-Ile-Lys-Val-Thr-Asp-Ala-
    Ser;

(k) Ala-Gly-Asp-Thr-Xaa-Ile-Tyr-     (SEQ ID NO: 130)
    Ile-Val-Gly-Asn-Leu-Thr-Ala-
    Asp;
or

(l) Ala-Pro-Glu-Ser-Gly-Ala-Gly-     (SEQ ID NO: 131)
    Leu-Gly-Gly-Thr-Val-Gln-Ala-
    Gly;
```

wherein Xaa may be any amino acid, preferably a cysteine residue. A DNA sequence encoding the antigen identified as (g) above is provided in SEQ ID NO: 52, the deduced amino acid sequence of which is provided in SEQ ID NO: 53. A DNA sequence encoding the antigen identified as (a) above is provided in SEQ ID NO: 96; its deduced amino acid sequence is provided in SEQ ID NO: 97. A DNA sequence corresponding to antigen (d) above is provided in SEQ ID NO: 24, a DNA sequence corresponding to antigen (c) is provided in SEQ ID NO: 25 and a DNA sequence corresponding to antigen (I) is disclosed in SEQ ID NO: 94 and its deduced amino acid sequence is provided in SEQ ID NO: 95.

In a further specific embodiment, the subject invention discloses polypeptides comprising at least an immunogenic portion of an *M. tuberculosis* antigen having one of the following N-terminal sequences, or a variant thereof that differs only in conservative substitutions and/or modifications:

```
(m) Xaa-Tyr-Ile-Ala-Tyr-Xaa-Thr-     (SEQ ID NO: 132)
    Thr-Ala-Gly-Ile-Val-Pro-Gly-
    Lys-Ile-Asn-Val-His-Leu-Val;
or

(n) Asp-Pro-Pro-Asp-Pro-His-Gln-     (SEQ ID NO: 124)
    Xaa-Asp-Met-Thr-Lys-Gly-Tyr-
    Tyr-Pro-Gly-Gly-Arg-Arg-Xaa-
    Phe;
```

wherein Xaa may be any amino acid, preferably a cysteine residue. A DNA sequence encoding the antigen of (n) above is provided in SEQ ID NO: 235, with the corresponding predicted fall-length amino acid sequence being provided in SEQ ID NO: 236.

In other specific embodiments, the subject invention discloses polypeptides comprising at least an antigenic portion of a soluble *M. tuberculosis* antigen (or a variant of such an antigen) that comprises one or more of the amino acid sequences encoded by (a) the DNA sequences of SEQ ID NOS: 1, 2, 4-10, 13-25, 52, 94 and 96, (b) the complements of such DNA sequences, or (c) DNA sequences substantially homologous to a sequence in (a) or (b).

In further specific embodiments, the subject invention discloses polypeptides comprising at least an antigenic portion of a *M. tuberculosis* antigen (or a variant of such an antigen), which may or may not be soluble, that comprises one or more of the amino acid sequences encoded by (a) the DNA sequences of SEQ ID NOS: 26-51, 133, 134, 158-178, 184-188, 194-196, 198, 210-220, 232, 234, 235, 237-242, 248-251, 256-271, 287, 288, 290-293 and 298-337, (b) the complements of such DNA sequences or (c) DNA sequences substantially homologous to a sequence in (a) or (b).

In a related aspect, the present invention provides fusion proteins comprising a first and a second inventive polypeptide or, alternatively, a polypeptide of the present invention and a known *M. tuberculosis* antigen, such as the 38 kD antigen described in Andersen and Hansen, *Infect. Immun.* 57:2481-2488, 1989, (Genbank Accession No. M30046) or ESAT-6 (SEQ ID) NOS: 98 and 99), together with variants of such fusion proteins. The fusion proteins of the present invention may also include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8562, 1986; U.S. Pat. No. 4,935,233 and U.S. Pat. No. 4,751,180. The linker sequence may be from 1 to about 50 amino acids in length. Peptide linker sequences are not required when the first and second polypeptides have non-essential N-terminal amino acid regions that can be used to separate the functional domains and prevent steric hindrance.

In another aspect, the present invention provides methods for using the polypeptides described above to diagnose tuberculosis. In this aspect, methods are provided for detecting *M. tuberculosis* infection in a biological sample, using one or more of the above polypeptides, alone or in combination. In embodiments in which multiple polypeptides are employed, polypeptides other than those specifically described herein, such as the 38 kD antigen described in Andersen and Hansen, *Infect. Immun.* 57:2481-2488, 1989, may be included. As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient or a blood supply. The polypeptide(s) are used in an assay, as described below, to determine the presence or absence of antibodies to the polypeptide(s) in the sample, relative to a predetermined cut-off value. The presence of such antibodies indicates previous sensitization to mycobacterial antigens which may be indicative of tuberculosis.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with *M. tuberculosis*. After determining which samples test positive (as described below) with each polypeptide, combinations of two or more polypeptides may be formulated that are capable of detecting infection in most, or all, of the samples tested. Such polypeptides are complementary. For example, approximately 25-30% of sera from tuberculosis-infected individuals are negative for antibodies to any single protein, such as the 38 kD antigen mentioned above. Complementary polypeptides may, therefore, be used in combination with the 38 kD antigen to improve sensitivity of a diagnostic test.

There are a variety of assay formats known to those of ordinary skill in the art for using one or more polypeptides to detect antibodies in a sample. See, e.g., Harlow and Lane, *Antibodies: A Laboratory Manual*, Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art, which are amply described in the patent and scientific literature. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 μg, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12-A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time (i.e., incubation time) is that period of time that is sufficient to detect the presence of antibody within a *M. tuberculosis*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups, biotin and colliodal particles, such as colloidal gold and selenium. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-*M. tuberculosis* antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for tuberculosis. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, pp. 106-107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for tuberculosis.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-*M. tuberculosis* antibodies in the sample. Typically, the concentration of detection reagent at that site generates a pattern, such as a line, that can be read visually. The absence of such a pattern indicates a negative result. In general the amount of polypeptide immobilized on the membrane is selected to generate a visually discernible pattern when the biological sample contains a level of antibodies that would be sufficient to generate a positive signal in an ELISA as discussed above. Preferably, the amount of polypeptide immobilized on the membrane ranges from about 25 ng to about 1 μg, and more preferably from about 50 ng to about 500 ng. Such tests can typically be performed with a very small amount (e.g., one drop) of patient serum or blood.

Of course, numerous other assay protocols exist that are suitable for use with the polypeptides of the present invention. The above descriptions are intended to be exemplary only.

In yet another aspect, the present invention provides antibodies to the inventive polypeptides. Antibodies may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Antibodies may be used in diagnostic tests to detect the presence of *M. tuberculosis* antigens using assays similar to those detailed above and other techniques well known to those of skill in the art, thereby providing a method for detecting *M. tuberculosis* infection in a patient.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify *M. tuberculosis*-specific cDNA derived from a biological sample, wherein at least one of the oligonucleotide primers is specific for a DNA molecule encoding a polypeptide of the present invention. The presence of the amplified cDNA is then detected using techniques well known in the art, such as gel electrophoresis. Similarly, oligonucleotide probes specific for a DNA molecule encoding a polypeptide of the present invention may be used in a hybridization assay to detect the presence of an inventive polypeptide in a biological sample.

As used herein, the term "oligonucleotide primer/probe specific for a DNA molecule" means an oligonucleotide sequence that has at least about 80%, preferably at least about 90% and more preferably at least about 95%, identity to the DNA molecule in question. Oligonucleotide primers and/or probes which may be usefully employed in the inventive diagnostic methods preferably have at least about 10-40 nucleotides. In a preferred embodiment, the oligonucleotide primers comprise at least about 10 contiguous nucleotides of a DNA molecule encoding one of the polypeptides disclosed herein. Preferably, oligonucleotide probes for use in the inventive diagnostic methods comprise at least about 15 contiguous oligonucleotides of a DNA molecule encoding one of the polypeptides disclosed herein. Techniques for both PCR based assays and hybridization assays are well known in the art (see, for example, Mullis et al. *Ibid*; Ehrlich, Ibid). Primers or probes may thus be used to detect *M. tuberculosis*-specific sequences in biological samples. DNA probes or primers comprising oligonucleotide sequences described above may be used alone, in combination with each other, or with previously identified sequences, such as the 38 kD antigen discussed above.

The following Examples are offered by way of illustration and not by way of limitation.

EXAMPLES

Example 1

Purification and Characterization of Polypeptides from *M. tuberculosis* Culture Filtrate This example illustrates the preparation of *M. tuberculosis* soluble polypeptides from culture filtrate. Unless otherwise noted, all percentages in the following example are weight per volume.

*M. tuberculosis* (either H37Ra, ATCC No. 25177, or H37Rv, ATCC No. 25618) was cultured in sterile GAS media at 37° C. for fourteen days. The media was then vacuum filtered (leaving the bulk of the cells) through a 0.45μ filter into a sterile 2.5 L bottle. The media was then filtered through a 0.2μ filter into a sterile 4 L bottle. $NaN_3$ was then added to the culture filtrate to a concentration of 0.04%. The bottles were then placed in a 4° C. cold room.

The culture filtrate was concentrated by placing the filtrate in a 12 L reservoir that had been autoclaved and feeding the filtrate into a 400 ml Amicon stir cell which had been rinsed with ethanol and contained a 10,000 kDa MWCO membrane. The pressure was maintained at 60 psi using nitrogen gas. This procedure reduced the 12 L volume to approximately 50 ml.

The culture filtrate was then dialyzed into 0.1% ammonium bicarbonate using a 8.000 kDa MWCO cellulose ester membrane with two changes of ammonium bicarbonate solution. Protein concentration was then determined by a commercially available BCA assay (Pierce, Rockford, Ill.).

The dialyzed culture filtrate was then lyophilized, and the polypeptides resuspended in distilled water. The polypeptides were then dialyzed against 0.01 mM 1,3bis[tris(hydroxymethyl)-methylamino]propane, pH 7.5 (Bis-Tris propane buffer), the initial conditions for anion exchange chromatography. Fractionation was performed using gel profusion chromatography on a POROS 146 II Q/M anion exchange column 4.6 mm×100 mm (Perseptive BioSystems, Framingham. MA) equilibrated in 0.01 mM Bis-Tris propane buffer pH 7.5. Polypeptides were eluted with a linear 0-0.5 M NaCl gradient in the above buffer system. The column eluent was monitored at a wavelength of 220 nm.

The pools of polypeptides eluting from the ion exchange column were dialyzed against distilled water and lyophilized. The resulting material was dissolved in 0.1% trifluoroacetic acid (TFA) pH 1.9 in water, and the polypeptides were purified on a Delta-Pak C18 column (Waters, Milford, Mass.) 300 Angstrom pore size, 5 micron particle size (3.9×150 mm). The polypeptides were eluted from the column with a linear gradient from 0-60% dilution buffer (0.1% TFA in acetonitrile). The flow rate was 0.75 ml/minute and the HPLC eluent was monitored at 214 nm. Fractions containing the eluted polypeptides were collected to maximize the purity of the individual samples. Approximately 200 purified polypeptides were obtained.

The purified polypeptides were then screened for the ability to induce T-cell proliferation in PBMC preparations. The PBMCs from donors known to be PPD skin test positive and whose T cells were shown to proliferate in response to PPD and crude soluble proteins from MTB were cultured in medium comprising RPMI 1640 supplemented with 10% pooled human serum and 50 μg/ml gentamicin. Purified polypeptides were added in duplicate at concentrations of 0.5 to 10 μg/mL. After six days of culture in 96-well round-bottom plates in a volume of 200 μl, 50 μl of medium was removed from each well for determination of IFN-γ levels, as described below. The plates were then pulsed with 1 μCi/well of tritiated thymidine for a further 18 hours, harvested and tritium uptake determined using a gas scintillation counter. Fractions that resulted in proliferation in both replicates three fold greater than the proliferation observed in cells cultured in medium alone were considered positive.

IFN-γ was measured using an enzyme-linked immunosorbent assay (ELISA). ELISA plates were coated with a mouse monoclonal antibody directed to human IFN-γ (Chemicon) in PBS for four hours at room temperature. Wells were then blocked with PBS containing 5% (W/V) non-fat dried milk for 1 hour at room temperature. The plates were then washed six times in PBS/0.2% TWEEN-20 and samples diluted 1:2 in culture medium in the ELISA plates were incubated overnight at room temperature. The plates were again washed and a polyclonal rabbit anti-human IFN-γ serum diluted 1:3000 in PBS/10% normal goat serum was added to each well. The plates were then incubated for two hours at room temperature, washed and horseradish peroxidase-coupled anti-rabbit IgG (Jackson Labs.) was added at a 1:2000 dilution in PBS/5% non-fat dried milk. After a further two hour incubation at room temperature, the plates were washed and TMB substrate added. The reaction was stopped after 20 min with 1 N sulfuric acid. Optical density was determined at 450 nm using 570 nm as a reference wavelength. Fractions that resulted in both replicates giving an OD two fold greater than the mean OD from cells cultured in medium alone, plus 3 standard deviations, were considered positive.

For sequencing, the polypeptides were individually dried onto Biobrene™ (Perkin Elmer/Applied BioSystems Division, Foster City, Calif.) treated glass fiber filters. The filters with polypeptide were loaded onto a Perkin Elmer/Applied BioSystems Division Procise 492 protein sequencer. The polypeptides were sequenced from the amino terminal and using traditional Edman chemistry. The amino acid sequence was determined for each polypeptide by comparing the retention time of the PTH amino acid derivative to the appropriate PTH derivative standards.

Using the procedure described above, antigens having the following N-terminal sequences were isolated:

```
(a) Asp-Pro-Val-Asp-Ala-Val-Ile-    (SEQ ID NO: 54)
    Asn-Thr-Thr-Xaa-Asn-Tyr-Gly-
    Gln-Val-Val-Ala-Ala-Leu;

(b) Ala-Val-Glu-Ser-Gly-Met-Leu-    (SEQ ID NO: 55)
    Ala-Leu-Gly-Thr-Pro-Ala-Pro-
    Ser;

(c) Ala-Ala-Met-Lys-Pro-Arg-Thr-    (SEQ ID NO: 56)
    Gly-Asp-Gly-Pro-Leu-Glu-Ala-
    Ala-Lys-Glu-Gly-Arg;

(d) Tyr-Tyr-Trp-Cys-Pro-Gly-Gln-    (SEQ ID NO: 57)
    Pro-Phe-Asp-Pro-Ala-Trp-Gly-
    Pro;

(e) Asp-Ile-Gly-Ser-Glu-Ser-Thr-    (SEQ ID NO: 58)
    Glu-Asp-Gln-Gln-Xaa-Ala-Val;

(f) Ala-Glu-Glu-Ser-Ile-Ser-Thr-    (SEQ ID NO: 59)
    Xaa-Glu-Xaa-Ile-Val-Pro;
```

-continued

```
(g) Asp-Pro-Glu-Pro-Ala-Pro-Pro-    (SEQ ID NO: 60)
    Val-Pro-Thr-Ala-Ala-Ala-Ala-
    Pro-Pro-Ala;
and

(h) Ala-Pro-Lys-Thr-Tyr-Xaa-Glu-    (SEQ ID NO: 61)
    Glu-Leu-Lys-Gly-Thr-Asp-Thr-
    Gly;
```

wherein Xaa may be any amino acid.

An additional antigen was isolated employing a microbore HPLC purification step in addition to the procedure described above. Specifically, 20 μl of a fraction comprising a mixture of antigens from the chromatographic purification step previously described, was purified on an Aquapore C18 column (Perkin Elmer/Applied Biosystems Division, Foster City, Calif.) with a 7 micron pore size, column size 1 mm×100 mm, in a Perkin Elmer/Applied Biosystems Division Model 172 HPLC. Fractions were eluted from the column with a linear gradient of 1%/minute of acetonitrile (containing 0.05% TFA) in water (0.05% TFA) at a flow rate of 80 μl/minute. The eluent was monitored at 250 nm. The original fraction was separated into 4 major peaks plus other smaller components and a polypeptide was obtained which was shown to have a molecular weight of 12.054 Kd (by mass spectrometry) and the following N-terminal sequence:

```
(i) Asp-Pro-Ala-Ser-Ala-Pro-Asp-    (SEQ ID NO: 62)
    Val-Pro-Thr-Ala-Ala-Gln-Gln-
    Thr-Ser-Leu-Leu-Asn-Asn-Leu-
    Ala-Asp-Pro-Asp-Val-Ser-Phe-
    Ala-Asp.
```

This polypeptide was shown to induce proliferation and IFN-γ production in PBMC preparations using the assays described above.

Additional soluble antigens were isolated from *M. tuberculosis* culture filtrate as follows. *M. tuberculosis* culture filtrate was prepared as described above. Following dialysis against Bis-Tris propane buffer, at pH 5.5, fractionation was performed using anion exchange chromatography on a Poros QE column 4.6×100 mm (Perseptive Biosystems) equilibrated in Bis-Tris propane buffer pH 5.5. Polypeptides were eluted with a linear 0-1.5 M NaCl gradient in the above buffer system at a flow rate of 10 ml/min. The column eluent was monitored at a wavelength of 214 nm.

The fractions eluting from the ion exchange column were pooled and subjected to reverse phase chromatography using a Poros R2 column 4.6×100 mm (Perseptive Biosystems). Polypeptides were eluted from the column with a linear gradient from 0-100% acetonitrile (0.1% TFA) at a flow rate of 5 ml/min. The eluent was monitored at 214 nm.

Fractions containing the eluted polypeptides were lyophilized and resuspended in 80 μl of aqueous 0.1% TFA and further subjected to reverse phase chromatography on a Vydac C4 column 4.6×150 mm (Western Analytical, Temecula, Calif.) with a linear gradient of 0-100% acetonitrile (0.1% TFA) at a flow rate of 2 ml/min. Eluent was monitored at 214 nm.

The fraction with biological activity was separated into one major peak plus other smaller components. Western blot of this peak onto PVDF membrane revealed three major bands of molecular weights 14 Kd, 20 Kd and 26 Kd. These polypeptides were determined to have the following N-terminal sequences, respectively:

```
(j) Xaa-Asp-Ser-Glu-Lys-Ser-Ala-    (SEQ ID NO: 129)
    Thr-Ile-Lys-Val-Thr-Asp-Ala-
    Ser;

(k) Ala-Gly-Asp-Thr-Xaa-Ile-Tyr-    (SEQ ID NO: 130)
    Ile-Val-Gly-Asn-Leu-Thr-Ala-
    Asp;
and

(l) Ala-Pro-Glu-Ser-Gly-Ala-Gly-    (SEQ ID NO: 131)
    Leu-Gly-Gly-Thr-Val-Gln-Ala-
    Gly;,
wherein Xaa may be any amino acid.
```

Figure 1A:
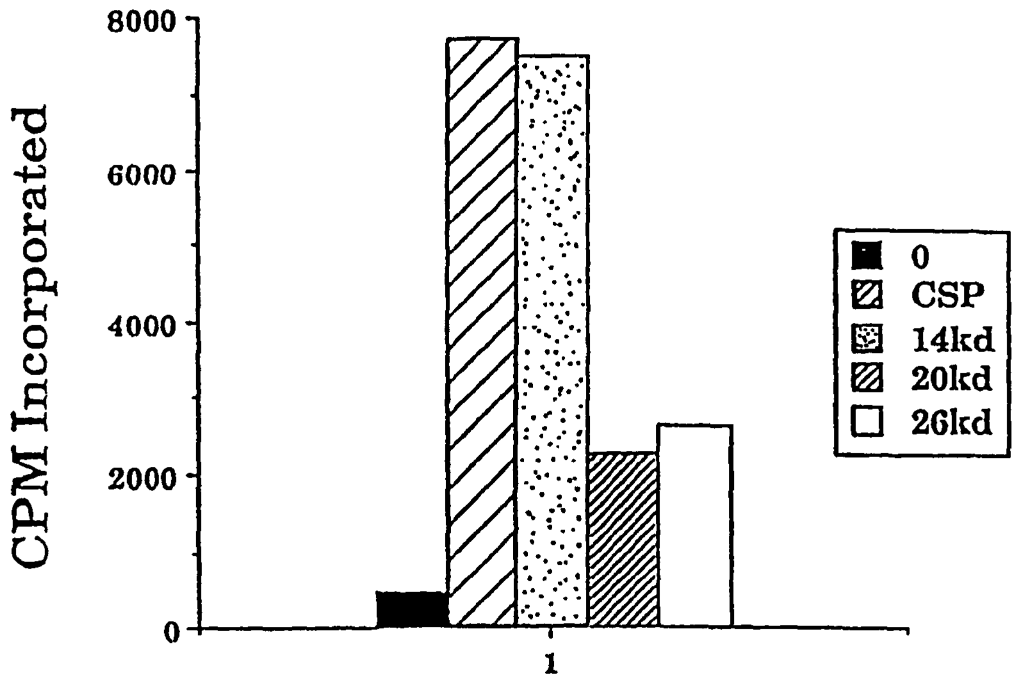
Figure 1B:
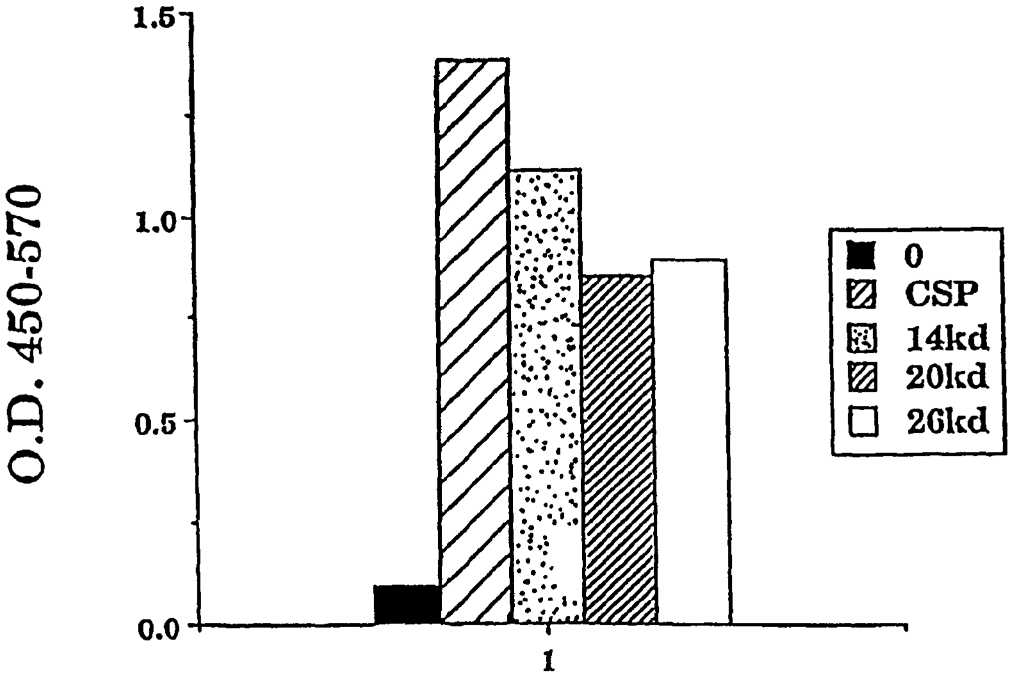
Figure 1C:
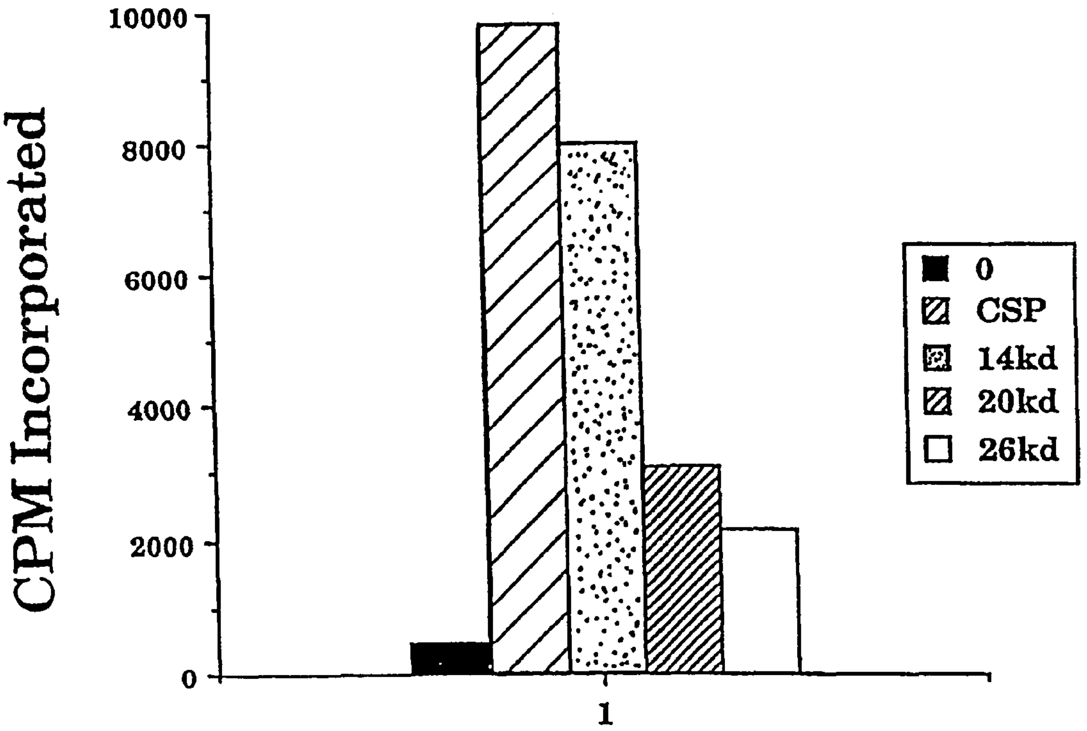
Figure 1D:
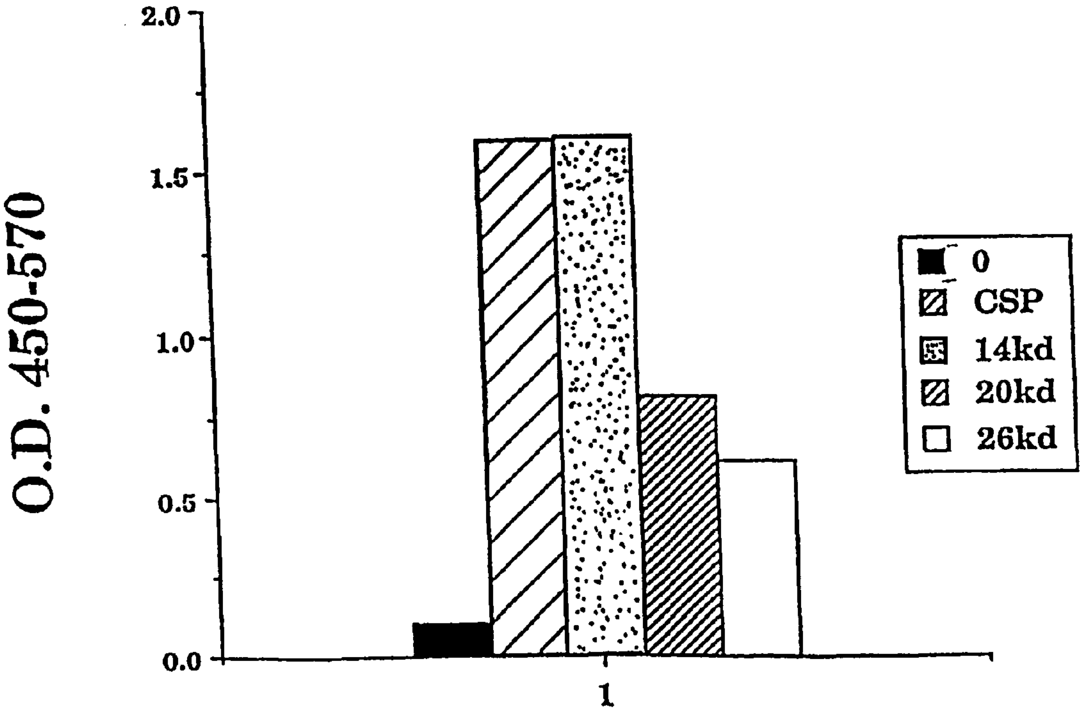

Using the assays described above, these polypeptides were shown to induce proliferation and IFN-γ production in PBMC preparations. FIGS. 1A and B show the results of such assays using PBMC preparations from a first and a second donor, respectively.

DNA sequences that encode the antigens designated as (a), (c), (d) and (g) above were obtained by screening a *M. tuberculosis* genomic library using $^{32}P$ end labeled degenerate oligonucleotides corresponding to the N-terminal sequence and containing *M. tuberculosis* codon bias. The screen performed using a probe corresponding to antigen (a) above identified a clone having the sequence provided in SEQ ID NO: 96. The polypeptide encoded by SEQ ID NO: 96 is provided in SEQ ID NO: 97. The screen performed using a probe corresponding to antigen (g) above identified a clone having the sequence provided in SEQ ID NO: 52. The polypeptide encoded by SEQ ID NO: 52 is provided in SEQ ID NO: 53. The screen performed using a probe corresponding to antigen (d) above identified a clone having the sequence provided in SEQ ID NO: 24, and the screen performed with a probe corresponding to antigen (c) identified a clone having the sequence provided in SEQ ID NO: 25.

The above amino acid sequences were compared to known amino acid sequences in the gene bank using the DNA STAR system. The database searched contains some 173,000 proteins and is a combination of the Swiss, PIR databases along with translated protein sequences (Version 87). No significant homologies to the amino acid sequences for antigens (a)-(h) and (I) were detected.

The amino acid sequence for antigen (i) was found to be homologous to a sequence from *M. leprae*. The full length *M. leprae* sequence was amplified from genomic DNA using the sequence obtained from GENBANK. This sequence was then used to screen an *M. tuberculosis* library and a full length copy of the *M. tuberculosis* homologue was obtained (SEQ ID NO: 94).

The amino acid sequence for antigen (O) was found to be homologous to a known *M. tuberculosis* protein translated from a DNA sequence. To the best of the inventors' knowledge, this protein has not been previously shown to possess T-cell stimulatory activity. The amino acid sequence for antigen (k) was found to be related to a sequence from *M. leprae*.

In the proliferation and IFN-γ assays described above, using three PPD positive donors, the results for representative antigens provided above are presented in Table 1:

TABLE 1

RESULTS OF PBMC PROLIFERATION AND IFN-γ ASSAYS

| Sequence | Proliferation | IFN-γ |
|---|---|---|
| (a) | + | − |
| (c) | +++ | +++ |
| (d) | ++ | ++ |

TABLE 1-continued

RESULTS OF PBMC PROLIFERATION AND IFN-γ ASSAYS

| Sequence | Proliferation | IFN-γ |
|---|---|---|
| (g) | +++ | +++ |
| (h) | +++ | +++ |

In Table 1, responses that gave a stimulation index (SI) of between 2 and 4 (compared to cells cultured in medium alone) were scored as +, as SI of 48 or 2-4 at a concentration of 1 μg or less was scored as ++ and an SI of greater than 8 was scored as +++. The antigen of sequence (i) was found to have a high SI (+++) for one donor and lower SI (++ and +) for the two other donors in both proliferation and IFN-γ assays. These results indicate that these antigens are capable of inducing proliferation and/or interferon-γ production.

Example 2

Use of Patent Sera to Isolate *M. tuberculosis* Antigens

This example illustrates the isolation of antigens from *M. tuberculosis* lysate by screening with serum from *M. tuberculosis*-infected individuals.

Dessicated *M. tuberculosis* H37Ra (Difco Laboratories) was added to, a 2% NP40 solution, and alternately homogenized and sonicated three times. The resulting suspension was centrifuged at 13,000 rpm in microfuge tubes and the supernatant put through a 0.2 micron syringe filter. The filtrate was bound to Macro Prep DEAE beads (BioRad, Hercules, Calif.). The beads were extensively washed with 20 mM Tris pH 7.5 and bound proteins eluted with 1M NaCl. The NaCl elute was dialyzed overnight against 10 mM Tris, pH 7.5. Dialyzed solution was treated with DNase and RNase at 0.05 mg/ml for 30 min. at room temperature and then with α-D-mannosidase, 0.5 U/mg at pH 4.5 for 3-4 hours at room temperature. After returning to pH 7.5, the material was fractionated via FPLC over a Bio Scale-Q-20 column (BioRad). Fractions were combined into nine pools, concentrated in a Centriprep 10 (Amicon, Beverley, Mass.) and screened by Western blot for serological activity using a serum pool from *M. tuberculosis*-infected patients which was not immunoreactive with other antigens of the present invention.

The most reactive fraction was run in SDS-PAGE and transferred to PVDF. A band at approximately 85 Kd was cut out yielding the sequence:

```
(m) Xaa-Tyr-Ile-Ala-Tyr-Xaa-Thr-    (SEQ ID NO: 132)
    Thr-Ala-Gly-Ile-Val-Pro-Gly-
    Lys-Ile-Asn-Val-His-Leu-
    Val;,
wherein Xaa may be any amino acid.
```

Comparison of this sequence with those in the gene bank as described above, revealed no significant homologies to known sequences.

A DNA sequence that encodes the antigen designated as (m) above was obtained by screening a genomic *M. tuberculosis* Erdman strain library using labeled degenerate oligonucleotides corresponding to the N-terminal sequence of SEQ ID NO: 137. A clone was identified having the DNA sequence provided in SEQ ID NO: 198. This sequence was found to encode the amino acid sequence provided in SEQ ID NO: 199. Comparison of these sequences with those in the genebank revealed some similarity to sequences previously identified in *M. tuberculosis* and *M. bovis.*

Example 3

Preparation of DNA Sequences Encoding *M. tuberculosis* Antigens

This example illustrates the preparation of DNA sequences encoding *M. tuberculosis* antigens by screening a *M. tuberculosis* expression library with sera obtained from patients infected with *M. tuberculosis*, or with anti-sera raised against *M. tuberculosis* antigens.

A. Preparation of *M. tuberculosis* Soluble Antigens Using Rabbit Anti-Sera Raised Against *M. tuberculosis* Supernatant Genomic DNA was isolated from the *M. tuberculosis* strain H37Ra. The DNA was randomly sheared and used to construct an expression library using the Lambda ZAP expression system (Stratagene, La Jolla, Calif.). Rabbit anti-sera was generated against secretory proteins of the *M. tuberculosis* strains H37Ra, H37Rv and Erdman by immunizing a rabbit with concentrated supernatant of the *M. tuberculosis* cultures. Specifically, the rabbit was first immunized subcutaneously with 200 μg of protein antigen in a total volume of 2 ml containing 100 μg muramyl dipeptide (Calbiochem, La Jolla, Calif.) and 1 ml of incomplete Freund's adjuvant. Four weeks later the rabbit was boosted subcutaneously with 100 μg antigen in incomplete Freund's adjuvant. Finally, the rabbit was immunized intravenously four weeks later with 50 μg protein antigen. The anti-sera were used to screen the expression library as described in Sambrook et al., *Molecular Cloning: A Laboratory Manual*, Cold Spring Harbor Laboratories, Cold Spring Harbor, N.Y., 1989. Bacteriophage plaques expressing immunoreactive antigens were purified. Phagemid from the plaques was rescued and the nucleotide sequences of the *M. tuberculosis* clones deduced.

Thirty two clones were purified. Of these, 25 represent sequences that have not been previously identified in *M. tuberculosis*. Proteins were induced by IPTG and purified by gel elution, as described in Skeiky et al., *J. Exp. Med.* 181: 1527-1537, 1995. Representative partial sequences of DNA molecules identified in this screen are provided in SEQ ID NOS: 1-25. The corresponding predicted amino acid sequences are shown in SEQ ID NOS: 64-88.

On comparison of these sequences with known sequences in the gene bank using the databases described above, it was found that the clones referred to hereinafter as TbRA2A, TbRA16, TbRA18, and TbRA29 (SEQ ID NOS: 77, 69, 71, 76) show some homology to sequences previously identified in *Mycobacterium leprae* but not in *M. tuberculosis*. TbRA2A was found to be a lipoprotein, with a six residue lipidation sequence being located adjacent to a hydrophobic secretory sequence. TbRA11, TbRA26, TbRA28 and TbDPEP (SEQ ID NOS: 66, 74, 75, 53) have been previously identified in *M. tuberculosis*. No significant homologies were found to TbRA1, TbRA3, TbRA4, TbRA9, TbRA10, TbRA13, TbRA17, TbRA19, TbRA29, TbRA32, TbRA36 and the overlapping clones TbRA35 and TbRA12 (SEQ ID NOS: 64, 78, 82, 83, 65, 68, 76, 72, 76, 79, 81, 80, 67, respectively). The clone TbRa24 is overlapping with clone TbRa29.

B. Use of Sera from Patients Having Pulmonary or Pleural Tuberculosis to Identify DNA Sequences Encoding *M. tuberculosis* Antigens The genomic DNA library described above, and an additional H37Rv library, were screened using pools of sera obtained from patients with active tuberculosis. To prepare the H37Rv library, *M. tuberculosis* strain H37Rv genomic DNA was isolated, subjected to partial Sau3A digestion and used to construct an expression library using the Lambda Zap expression system (Stratagene, La Jolla, Calif.). Three different pools of sera, each containing sera obtained from three individuals with active pulmonary or pleural disease, were used in the expression screening. The pools were designated TbL, TbM and TbH, referring to relative reactivity with H37Ra lysate (i.e., TbL=low reactivity, TbM=medium reactivity and TbH=high reactivity) in both ELISA and immunoblot format. A fourth pool of sera from seven patients with active pulmonary tuberculosis was also employed. All of the sera lacked increased reactivity with the recombinant 38 kD *M. tuberculosis* H37Ra phosphate-binding protein.

All pools were pre-adsorbed with *E. coli* lysate and used to screen the H37Ra and H37Rv expression libraries, as described in Sambrook et al., *Molecular Cloning: A Laboratory Manual*, Cold Spring Harbor Laboratories. Cold Spring Harbor. NY, 1989. Bacteriophage plaques expressing immunoreactive antigens were purified. Phagemid from the plaques was rescued and the nucleotide sequences of the *M. tuberculosis* clones deduced.

Thirty two clones were purified. Of these, 31 represented sequences that had not been previously identified in human *M. tuberculosis*. Representative sequences of the DNA molecules identified are provided in SEQ ID NOS: 26-51 and 100. Of these. TbH-8-2 (SEQ. ID NO. 100) is a partial clone of TbH-8, and TbH-4 (SEQ. ID NO. 43) and TbH-4-FWD (SEQ. ID NO. 44) are non-contiguous sequences from the same clone. Amino acid sequences for the antigens hereinafter identified as Tb38-1, TbH-4, TbH-8, TbH-9, and TbH-12 are shown in SEQ ID NOS.: 89-93. Comparison of these sequences with known sequences in the gene bank using the databases identified above revealed no significant homologies to TbH-4, TbH-8, TbH-9 and TbM-3, although weak homologies were found to TbH-9. TbH-12 was found to be homologous to a 34 kD antigenic protein previously identified in *M. paratuberculosis* (Acc. No. S28515). Tb38-1 was found to be located 34 base pairs upstream of the open reading frame for the antigen ESAT-6 previously identified in *M. bovis* (Acc. No. U34848) and in *M. tuberculosis* (Sorensen et al., *Infec. Immun.* 63:1710-1717, 1995).

Probes derived from Tb38-1 and TbH-9, both isolated from an H37Ra library, were used to identify clones in an H37Rv library. Tb38-1 hybridized to Tb38-1F2, Tb38-1F3, Tb38-1F5 and Tb38-1F6 (SEQ. ID NOS: 107, 108, 111, 113, and 114). (SEQ ID NOS: 107 and 108 are non-contiguous sequences from clone Tb38-1F2.) Two open reading frames were deduced in Tb38-1F2; one corresponds to Tb37FL (SEQ. ID. NO. 109), the second, a partial sequence, may be the homologue of Tb38-1 and is called Tb38-IN (SEQ. ID NO. 110). The deduced amino acid sequence of Tb38-1F3 is presented in SEQ. ID. NO. 112. A TbH-9 probe identified three clones in the H37Rv library: TbH-9-FL (SEQ. ID NO. 101), which may be the homologue of TbH-9 (R37Ra), TbH-9-1 (SEQ. ID NO. 103), and TbH-8-2 (SEQ. ID NO. 105) is a partial clone of TbH-8. The deduced amino acid sequences for these three clones are presented in SEQ ID NOS: 102, 104 and 106.

Further screening of the *M. tuberculosis* genomic DNA library, as described above, resulted in the recovery of ten additional reactive clones, representing seven different genes. One of these genes was identified as the 38 Kd antigen discussed above, one was determined to be identical to the 14 Kd alpha crystallin heat shock protein previously shown to be present in *M. tuberculosis*, and a third was determined to be identical to the antigen TbH-8 described above. The determined DNA sequences for the remaining five clones (hereinafter referred to as TbH-29, TbH-30, TbH-32 and TbH-33) are provided in SEQ ID NO: 133-136, respectively, with the corresponding predicted amino acid sequences being provided in SEQ ID NO: 137-140, respectively. The DNA and amino acid sequences for these antigens were compared with those in the gene bank as described above. No homologies were found to the 5' end of TbH-29 (which contains the reactive open reading frame), although the 3' end of TbH-29 was found to be identical to the *M. tuberculosis* cosmid Y227. TbH-32 and TbH-33 were found to be identical to the previously identified *M. tuberculosis* insertion element IS6110 and to the *M. tuberculosis* cosmid Y50, respectively. No significant homologies to TbH-30 were found.

Positive phagemid from this additional screening were used to infect *E. coli* XL-1 Blue MRF', as described in Sambrook et al., supra. Induction of recombinant protein was accomplished by the addition of IPTG. Induced and uninduced lysates were run in duplicate on SDS-PAGE and transferred to nitrocellulose filters. Filters were reacted with human *M. tuberculosis* sera (1:200 dilution) reactive with TbH and a rabbit sera (1:200 or 1:250 dilution) reactive with the N-terminal 4 Kd portion of lacZ. Sera incubations were performed for 2 hours at room temperature. Bound antibody was detected by addition of $^{125}$I-labeled Protein A and subsequent exposure to film for variable times ranging from 16 hours to 11 days. The results of the immunoblots are summarized in Table 2.

TABLE 2

| Antigen | Human M. tb Sera | Anti-lacZ Sera |
|---|---|---|
| TbH-29 | 45 Kd | 45 Kd |
| TbH-30 | No reactivity | 29 Kd |
| TbH-32 | 12 Kd | 12 Kd |
| TbH-33 | 16 Kd | 16 Kd |

Positive reaction of the recombinant human *M. tuberculosis* antigens with both the human *M. tuberculosis* sera and anti-lacZ sera indicate that reactivity of the human *M. tuberculosis* sera is directed towards the fusion protein. Antigens reactive with the anti-lacZ sera but not with the human *M. tuberculosis* sera may be the result of the human *M. tuberculosis* sera recognizing conformational epitopes, or the antigen-antibody binding kinetics may be such that the 2 hour sera exposure in the immunoblot is not sufficient.

Studies were undertaken to determine whether the antigens TbH-9 and Tb38-1 represent cellular proteins or are secreted into *M. tuberculosis* culture media. In the first study, rabbit sera were raised against A) secretory proteins of *M. tuberculosis*, B) the known secretory recombinant *M. tuberculosis* antigen 85b, C) recombinant Tb38-1 and D) recombinant TbH-9, using protocols substantially as described in Example 3A. Total *M. tuberculosis* lysate, concentrated supernatant of *M. tuberculosis* cultures and the recombinant antigens 85b, TbH-9 and Tb38-1 were resolved on denaturing gels, immobilized on nitrocellulose membranes and duplicate blots were probed using the rabbit sera described above.

Figure 2A:
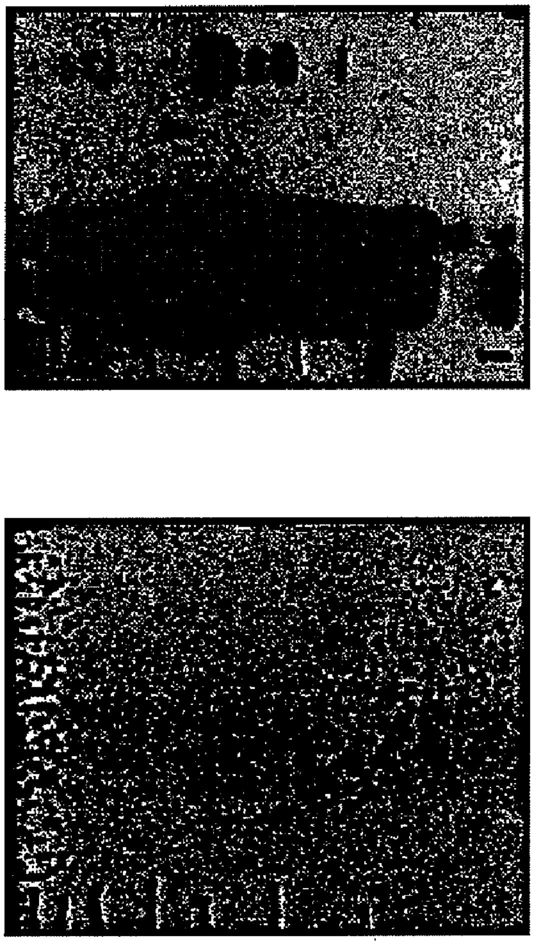
Figure 2B:
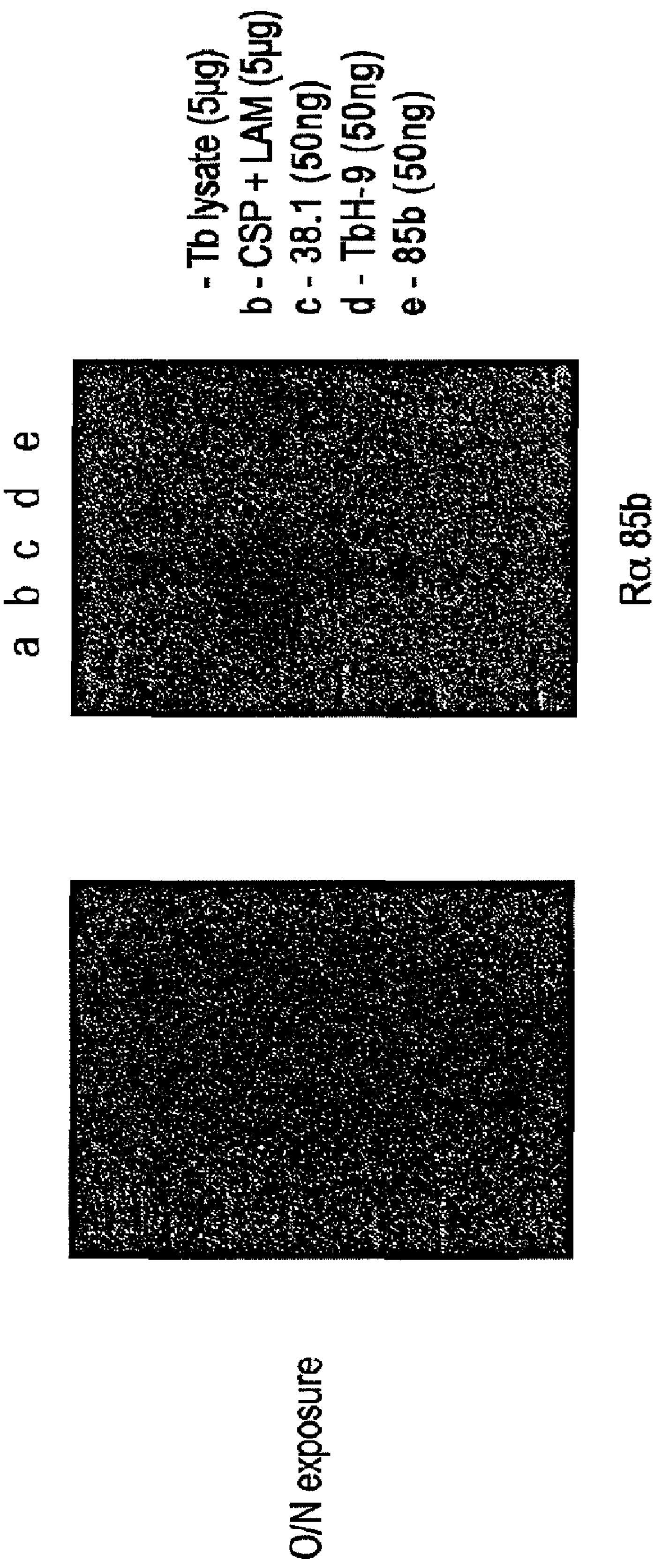
Figure 2C:
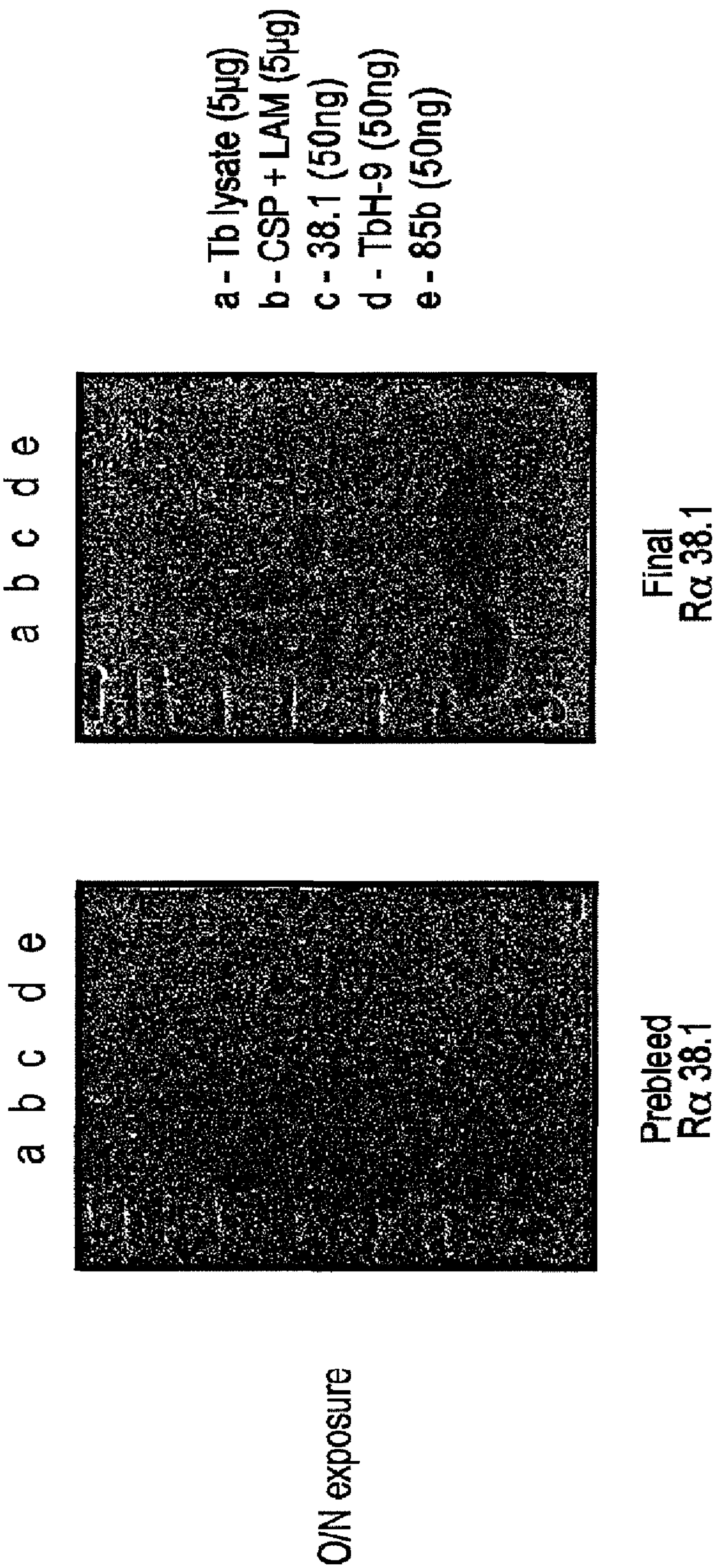
Figure 2D:
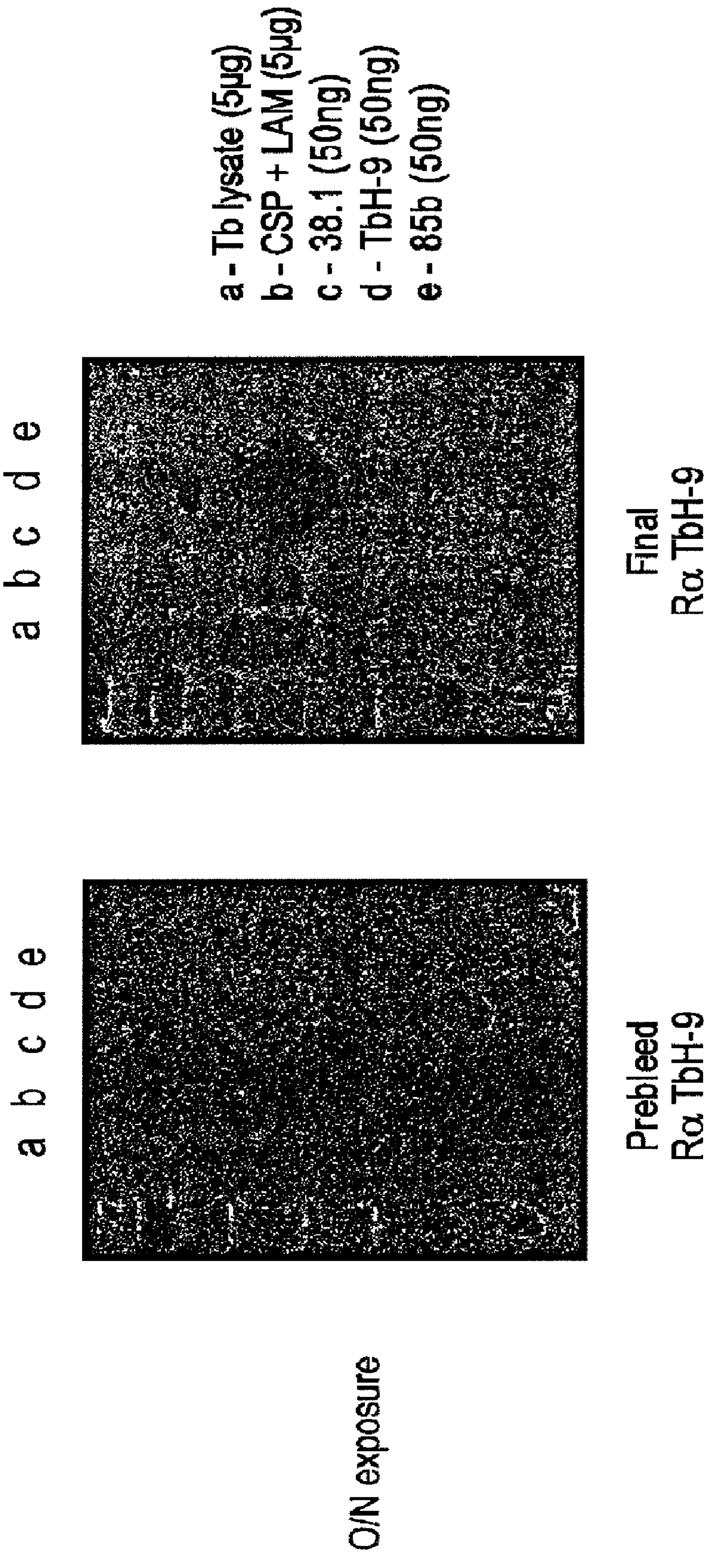

The results of this analysis using control sera (panel I) and antisera (panel II) against secretory proteins, recombinant 85b, recombinant Tb38-1 and recombinant TbH-9 are shown in FIGS. 2A-D, respectively, wherein the lane designations are as follows: 1) molecular weight protein standards; 2) 5 μg of *M. tuberculosis* lysate; 3) 5 μg secretory proteins; 4) 50 ng recombinant Tb38-1; 5) 50 ng recombinant TbH-9; and 6) 50 ng recombinant 85b. The recombinant antigens were engineered with six terminal histidine residues and would therefore be expected to migrate with a mobility approximately 1 kD larger that the native protein. In FIG. 2D, recombinant TbH-9 is lacking approximately 10 kD of the full-length 42 kD antigen, hence the significant difference in the size of the immunoreactive native TbH-9 antigen in the lysate lane (indicated by an arrow). These results demonstrate that Tb38-1 and TbH-9 are intracellular antigens and are not actively secreted by *M. tuberculosis.*

Figure 3A:
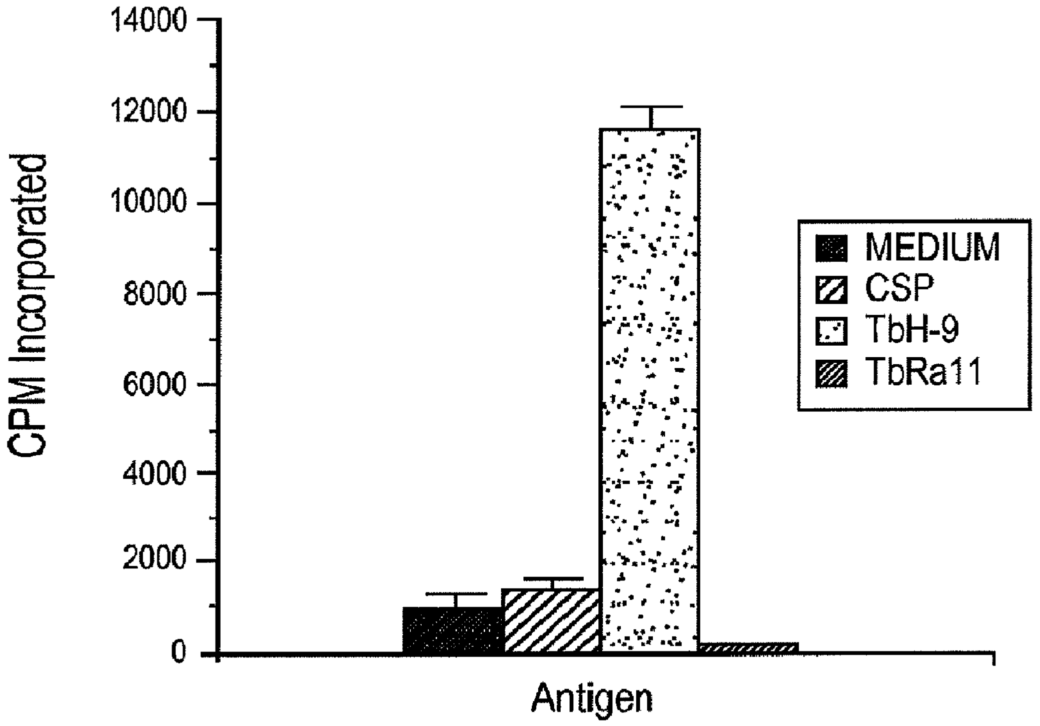
FIG. 3A illustrates the stimulation of proliferation in a TbH-9-specific T cell clone by secretory *M. tuberculosis* proteins, recombinant TbH-9 and a control antigen, TbRa11.
Figure 3B:
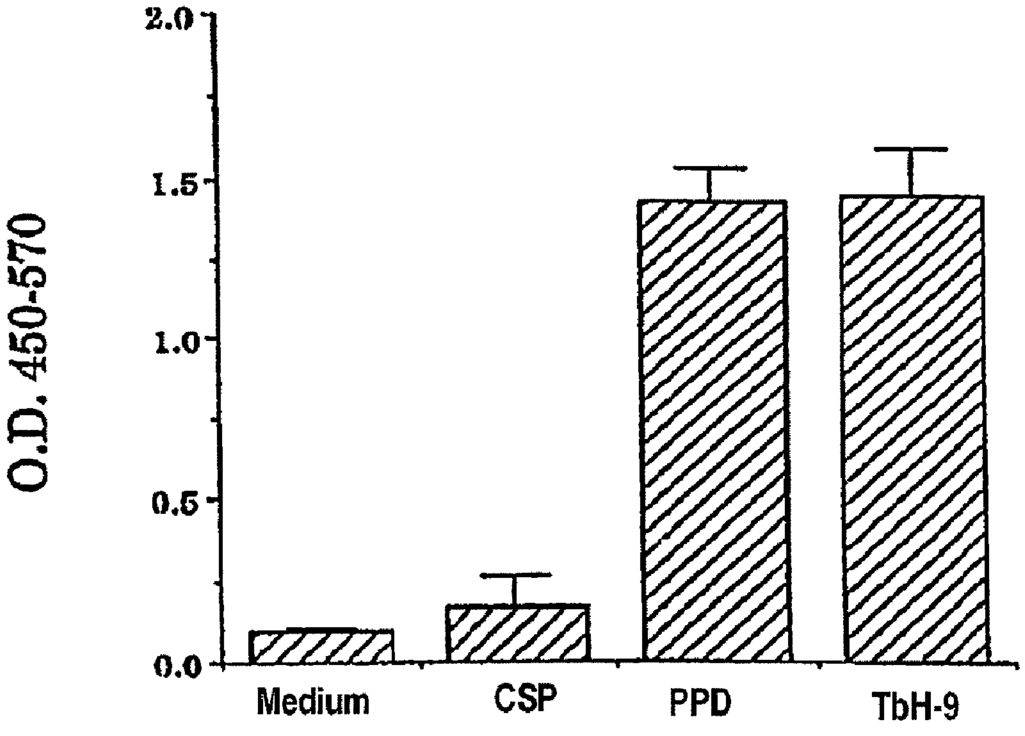
FIG. 3B illustrates the stimulation of interferon-γ production in a TbH-9-specific T cell clone by secretory *M. tuberculosis* proteins, PPD and recombinant TbH-9.

The finding that TbH-9 is an intracellular antigen was confirmed by determining the reactivity of TbH-9-specific human T cell clones to recombinant TbH-9, secretory *M. tuberculosis* proteins and PPD. A TbH-9-specific T cell clone (designated 131TbH-9) was generated from PBMC of a healthy PPD-positive donor. The proliferative response of 131TbH-9 to secretory proteins, recombinant TbH-9 and a control *M. tuberculosis* antigen, TbRa11, was determined by measuring uptake of tritiated thymidine, as described in Example 1. As shown in FIG. 3A, the clone 131TbH-9 responds specifically to TbH-9, showing that TbH-9 is not a significant component of *M. tuberculosis* secretory proteins. FIG. 3B shows the production of IFN-γ by a second TbH-9-specific T cell clone (designated PPD 800-10) prepared from PBMC from a healthy PPD-positive donor, following stimulation of the T cell clone with secretory proteins, PPD or recombinant TbH-9. These results further confirm that TbH-9 is not secreted by *M. tuberculosis.*

C. Use of Sera from Patients Having Extra Pulmonary Tuberculosis to Identify DNA Sequences Encoding *M. tuberculosis* Antigens Genomic DNA was isolated from *M. tuberculosis* Erdman strain, randomly sheared and used to construct an expression library employing the Lambda ZAP expression system (Stratagene, La Jolla, Calif.). The resulting library was screened using pools of sera obtained from individuals with extrapulmonary tuberculosis, as described above in Example 3B, with the secondary antibody being goat anti-human IgG+A+M (H+L) conjugated with alkaline phosphatase.

Eighteen clones were purified. Of these, 4 clones (hereinafter referred to as XP14, XP24, XP31 and XP32) were found to bear some similarity to known sequences. The determined DNA sequences for XP14, XP24 and XP31 are provided in SEQ ID NOS: 151-153, respectively, with the 5' and 3' DNA sequences for XP32 being provided in SEQ ID NOS: 154 and 155, respectively. The predicted amino acid sequence for XP14 is provided in SEQ ID NO: 156. The reverse complement of XP14 was found to encode the amino acid sequence provided in SEQ ID NO: 157.

Comparison of the sequences for the remaining 14 clones (hereinafter referred to as XP1-XP6, XP17-XP19, XP22, XP25, XP27, XP30 and XP36) with those in the genebank as described above, revealed no homologies with the exception of the 3' ends of XP2 and XP6 which were found to bear some homology to known *M. tuberculosis* cosmids. The DNA sequences for XP27 and XP36 are shown in SEQ ID NOS: 158 and 159, respectively, with the 5' sequences for XP4, XP5, XP17 and XP30 being shown in SEQ ID NOS: 160-163, respectively, and the 5' and 3' sequences for XP2, XP3, XP6, XP18, XP19, XP22 and XP25 being shown in SEQ E) NOS: 164 and 165; 166 and 167; 168 and 169; 170 and 171; 172 and 173; 174 and 175; and 176 and 171, respectively. XP1 was found to overlap with the DNA sequences for TbH4, disclosed above. The full-length DNA sequence for TbH4-XP1 is provided in SEQ ID NO: 178. This DNA sequence was found to contain an open reading frame encoding the amino acid sequence shown in SEQ ID NO: 179. The reverse complement of TbH4-XP1 was found to contain an open reading frame encoding the amino acid sequence shown in SEQ ID NO: 180. The DNA sequence for XP36 was found to contain two open reading frames encoding the amino acid sequence shown in SEQ ID NOS: 181 and 182, with the reverse complement containing an open reading frame encoding the amino acid sequence shown in SEQ ID NO: 183.

Recombinant XP1 protein was prepared as described above in Example 3B, with a metal ion affinity chromatography column being employed for purification. Recombinant XP1 was found to stimulate cell proliferation and IFN-γ production in T cells isolated from an *M. tuberculosis*-immune donors.

D. Use of a Lysate Positive Serum Pool from Patients Having Tuberculosis to Identify DNA Sequences Encoding *M. tuberculosis* Antigens Genomic DNA was isolated from *M. tuberculosis* Erdman strain randomly sheared and used to construct an expression library employing the Lambda Screen expression system (Novagen, Madison, Wis.), as described below in Example 6. Pooled serum obtained from *M. tuberculosis*-infected patients and that was shown to react with *M. tuberculosis* lysate but not with the previously expressed proteins 38 kD, Tb38-1, TbRa3. TbH4, DPEP and TbRa11, was used to screen the expression library as described above in Example 3B, with the secondary antibody being goat anti-human IgG+A+M(H+L) conjugated with alkaline phosphatase.

Twenty-seven clones were purified. Comparison of the determined cDNA sequences for these clones revealed no significant homologies to 10 of the clones (hereinafter referred to as LSER-10, LSER-11, LSER-12, LSER-13, LSER-16, LSER-18, LSER-23, LSER-24, LSER-25 and LSER-27). The determined 5' cDNA sequences for LSER-10, LSER-11, LSER-12, LSER-13, LSER-16 and LSER-25 are provided in SEQ ID NO: 237-242, respectively, with the corresponding predicted amino acid sequences for LSER-10, LSER-12, LSER-13, LSER-16 and LSER-25 being provided in SEQ ID NO: 243-247, respectively. The determined full-length cDNA sequences for LSER-18, LSER-23, LSER-24 and LSER-27 are shown in SEQ ID NO: 248-251, respectively, with the corresponding predicted amino acid sequences being provided in SEQ ID NO: 252-255. The remaining seventeen clones were found to show similarities to unknown sequences previously identified in *M. tuberculosis*. The determined 5' cDNA sequences for sixteen of these clones (hereinafter referred to as LSER-1, LSER-3, LSER-4, LSER-5, LSER-6, LSER-8, LSER-14, LSER-15, LSER-17, LSER-19, LSER-20, LSER-22, LSER-26, LSER-28, LSER-29 and LSER-30) are provided in SEQ ID NO: 256-271, respectively, with the corresponding predicted amino acid sequences for LSER-1, LSER-3, LSER-5, LSER-6, LSER-8, LSER-14, LSER-15, LSER-17, LSER-19, LSER-20, LSER-22, LSER-26, LSER-28, LSER-29 and LSER-30 being provided in SEQ ID NO: 272-286, respectively. The determined full-length cDNA sequence for the clone LSER-9 is provided in SEQ ID NO: 287. The reverse complement of LSER-6 (SEQ ID NO: 288) was found to encode the predicted amino acid sequence of SEQ ID NO: 289.

E. Preparation of *M. tuberculosis* Soluble Antigens Using Rabbit Anti-Sera Raised Against *M. tuberculosis* Fractionated Proteins

*M. tuberculosis* lysate was prepared as described above in Example 2. The resulting material was fractionated by HPLC and the fractions screened by Western blot for serological activity with a serum pool from *M. tuberculosis*-infected patients which showed little or no immunoreactivity with other antigens of the present invention. Rabbit anti-sera was generated against the most reactive fraction using the method described in Example 3A. The anti-sera was used to screen an *M. tuberculosis* Erdman strain genomic DNA expression library prepared as described above. Bacteriophage plaques expressing immunoreactive antigens were purified. Phagemid from the plaques was rescued and the nucleotide sequences of the *M. tuberculosis* clones determined.

Ten different clones were purified. Of these, one was found to be TbRa35, described above, and one was found to be the previously identified *M. tuberculosis* antigen, HSP60. Of the remaining eight clones, six (hereinafter referred to as RDIF2, RDIF5, RDIF8, RDIF10, RDIF11 and RDIF12) were found to bear some similarity to previously identified *M. tuberculosis* sequences. The determined DNA sequences for RDIF2, RDIF5, RDIF8, RDIF10 and RDIF11 are provided in SEQ ID NOS: 184188, respectively, with the corresponding predicted amino acid sequences being provided in SEQ ID NOS: 189-193, respectively. The 5' and 3' DNA sequences for RDIF12 are provided in SEQ ID NOS: 194 and 195, respectively. No significant homologies were found to the antigen RDIF-7. The determined DNA and predicted amino acid sequences for RDIF7 are provided in SEQ ID NOS: 196 and 197, respectively. One additional clone, referred to as RDIF6 was isolated, however, this was found to be identical to RDIF5.

Recombinant RDIF6, RDIF8, RDIF10 and RDIF11 were prepared as described above. These antigens were found to stimulate cell proliferation and IFN-γ production in T cells isolated from *M. tuberculosis*-immune donors.

Example 4

Purification and Characterization of a Polypeptide from Tuberculin Purified Protein Derivative An *M. tuberculosis* polypeptide was isolated from tuberculin purified protein derivative (PPD) as follows.

PPD was prepared as published with some modification (Seibert, F. et al., Tuberculin purified protein derivative. Preparation and analyses of a large quantity for standard. *The American Review of Tuberculosis* 44:9-25, 1941). *M. tuberculosis* Rv strain was grown for 6 weeks in synthetic medium in roller bottles at 37° C. Bottles containing the bacterial growth were then heated to 100° C. in water vapor for 3 hours. Cultures were sterile filtered using a 0.22μ filter and the liquid phase was concentrated 20 times using a 3 kD cut-off membrane. Proteins were precipitated once with 50% ammonium sulfate solution and eight times with 25% ammonium sulfate solution. The resulting proteins (PPD) were fractionated by reverse phase liquid chromatography (RP-HPLC) using a C18 column (7.8×300 mM; Waters, Milford, Mass.) in a Biocad HPLC system (Perseptive Biosystems, Framingham, Mass.). Fractions were eluted from the column with a linear gradient from 0-100% buffer (0.1% TFA in acetonitrile). The flow rate was 10 ml/minute and eluent was monitored at 214 nm and 280 nm.

Six fractions were collected, dried, suspended in PBS and tested individually in *M. tuberculosis*-infected guinea pigs for induction of delayed type hypersensitivity (DTH) reaction. One fraction was found to induce a strong DTH reaction and was subsequently fractionated further by RP-HPLC on a microbore Vydac C18 column (Cat. No. 218TP5115) in a Perkin Elmer/Applied Biosystems Division Model 172 HPLC. Fractions were eluted with a linear gradient from 5-100% buffer (0.05% TFA in acetonitrile) with a flow rate of 80 μl/minute. Eluent was monitored at 215 nm. Eight fractions were collected and tested for induction of DTH in *M. tuberculosis*-infected guinea pigs. One fraction was found to induce strong DTH of about 16 mm induration. The other fractions did not induce detectable DTH. The positive fraction was submitted to SDS-PAGE gel electrophoresis and found to contain a single protein band of approximately 12 kD molecular weight.

This polypeptide, herein after referred to as DPPD, was sequenced from the amino terminal using a Perkin Elmer/Applied Biosystems Division Procise 492 protein sequencer as described above and found to have the N-terminal sequence shown in SEQ ID NO: 124. Comparison of this sequence with known sequences in the gene bank as described above revealed no known homologies. Four cyanogen bromide fragments of DPPD were isolated and found to have the sequences shown in SEQ ID NOS: 125-128. A subsequent search of the *M. tuberculosis* genome database released by the Institute for Genomic Research revealed a match of the DPPD partial amino acid sequence with a sequence present within the *M. tuberculosis* cosmid MTY21C12. An open reading frame of 336 bp was identified. The full-length DNA sequence for DPPD is provided in SEQ ID NO: 235, with the corresponding full-length amino acid sequence being provided in SEQ ID NO: 236.

Example 5

Use of Sera from Tuberculosis-Infected Monkeys to Identify DNA Sequences Encoding *M. tuberculosis* Antigens Genomic DNA was isolated from *M. tuberculosis* Erdman strain, randomly sheared and used to construct an expression library employing the Lambda ZAP expression system (Stratagene, La Jolla, Calif.). Serum samples were obtained from a cynomolgous monkey 18, 33, 51 and 56 days following infection with *M. tuberculosis* Erdman strain. These samples were pooled and used to screen the *M. tuberculosis* genomic DNA expression library using the procedure described above in Example 3C.

Twenty clones were purified. The determined 5' DNA sequences for the clones referred to as MO-1, MO-2, MO-4, MO-8, MO-9, MO-26, MO-28, MO-29, MO-30. MO-34 and MO-35 are provided in SEQ ID NO: 210-220, respectively, with the corresponding predicted amino acid sequences being provided in SEQ ID NO: 221-231. The full-length DNA sequence of the clone MO-10 is provided in SEQ ID NO: 232, with the corresponding predicted amino acid sequence being provided in SEQ ID NO: 233. The 3' DNA sequence for the clone MO-27 is provided in SEQ ID NO: 234.

Clones MO-1, MO-30 and MO-35 were found to show a high degree of relatedness and showed some homology to a previously identified unknown *M. tuberculosis* sequence and to cosmid MTC1237. MO-2 was found to show some homology to aspartokinase from *M. tuberculosis*. Clones MO-3, MO-7 and MO-27 were found to be identical and to show a high degree of relatedness to MO-5. All four of these clones showed some homology to *M. tuberculosis* heat shock protein 70. MO-27 was found to show some homology to *M. tuberculosis* cosmid MTCY339. MO-4 and MO-34 were found to show some homology to cosmid SCY21B4 and *M. smegmatis* integration host factor, and were both found to show some homology to a previously identified, unknown *M. tuberculosis* sequence. MO-6 was found to show some homology to *M. tuberculosis* heat shock protein 65. MO-8, MO-9, MO-10, MO-26 and MO-29 were found to be highly related to each other and to show some homology to *M. tuberculosis* dihydrolipamide succinyltransferase. MO-28, MO-31 and MO-32 were found to be identical and to show some homology to a previously identified *M. tuberculosis* protein. MO-33 was found to show some homology to a previously identified 14 kDa *M tuberculosis* heat shock protein.

Further studies using the above protocol resulted in the isolation of an additional four clones, hereinafter referred to as MO-12, MO-13, MO-19 and MO-39. The determined 5' cDNA sequences for these clones are provided in SEQ ID NO: 290-293, respectively, with the corresponding predicted protein sequences being provided in SEQ ID NO: 294-297, respectively. Comparison of these sequences with those in the gene bank as described above revealed no significant homologies to MO-39. MO-12, MO-13 and MO-19 were found to show some homologies to unknown sequences previously isolated from *M. tuberculosis.*

Example 6

Isolation of DNA Sequences Encoding *M. tuberculosis* Antigens by Screening of a Novel Expression Library This example illustrates isolation of DNA sequences encoding *M. tuberculosis* antigens by screening of a novel expression library with sera from *M. tuberculosis*-infected patients that were shown to be unreactive with a panel of the recombinant *M. tuberculosis* antigens TbRa11, TbRa3, Tb38-1, TbH4, TbF and 38 kD.

Genomic DNA from *M. tuberculosis* Erdman strain was randomly sheared to an average size of 2 kb, and blunt ended with Klenow polymerase, followed by the addition of EcoRI adaptors. The insert was subsequently ligated into the Screen phage vector (Novagen, Madison, Wis.) and packaged in vitro using the PhageMaker extract (Novagen). The resulting library was screened with sera from several *M. tuberculosis* donors that had been shown to be negative on a panel of previously identified *M. tuberculosis* antigens as described above in Example 3B.

A total of 22 different clones were isolated. By comparison, screening of the λZap library described above using the same sera did not result in any positive hits. One of the clones was found to represent TbRa11, described above. The determined 5' cDNA sequences for 19 of the remaining 21 clones (hereinafter referred to as Erdsn1, Erdsn2, Erdsn4Erdsn10, Erdsn12-18, Erdsn21-Erdsn23 and Erdsn25) are provided in SEQ ID NO: 298-317, respectively, with the determined 3' cDNA sequences for Erdsn1, Erdsn2, Erdsn4, Erdsn5, Erdsn7-Erdsn10, Erdsn12-Erdsn18, Erdsn21-Erdsn23 and Erdsn25 being provided in SEQ ID NO: 318-336, respectively. The complete cDNA insert sequence for the clone Erdsn24 is provided in SEQ ID NO: 337. Comparison of the determined cDNA sequences with those in the gene bank revealed no significant homologies to the sequences provided in SEQ ID NO: 304, 311, 313-315, 317, 319, 324, 326, 329, 331, 333, 335 and 337. The sequences of SEQ ID NO: 298-303, 305-310, 312, 316, 318, 320-321, 324-326, 328, 330, 332, 334 and 336 were found to show some homology to unknown sequences previously identified in *M. tuberculosis.*

Example 7

Isolation of Soluble *M. tuberculosis* Antigens Using Mass Spectrometry

This example illustrates the use of mass spectrometry to identify soluble *M. tuberculosis* antigens.

In a first approach, *M. tuberculosis* culture filtrate was screened by Western analysis using serum from a tuberculosis-infected individual. The reactive bands were excised from a silver stained gel and the amino acid sequences determined by mass spectrometry. The determined amino acid sequence for one of the isolated antigens is provided in SEQ ID NO: 338. Comparison of this sequence with those in the gene bank revealed homology to the 85b precursor antigen previously identified in *M. tuberculosis.*

In a second approach, the high molecular weight region of *M. tuberculosis* culture supernatant was studied. This area may contain immunodominant antigens which may be useful in the diagnosis of *M. tuberculosis* infection. Two known monoclonal antibodies, IT42 and IT57 (available from the Center for Disease Control, Atlanta, Ga.), show reactivity by Western analysis to antigens in this vicinity, although the identity of the antigens remains unknown. In addition, unknown high-molecular weight proteins have been described as containing a surrogate marker for *M. tuberculosis* infection in HIV-positive individuals (*Jnl. Infect. Dis.,* 76:133-143, 1997). To determine the identity of these antigens, two-dimensional gel electrophoresis and two-dimensional Western analysis were performed using the antibodies IT57 and IT42. Five protein spots in the high molecular weight region were identified, individually excised, enzymatically digested and subjected to mass spectrometric analysis.

The determined amino acid sequences for three of these spots (referred to as spots 1, 2 and 4) are provided in SEQ ID NO: 339, 340-341 and 342, respectively. Comparison of these sequences with those in the gene bank revealed that spot 1 is the previously identified PcK-1, a phosphoenolpyruvate kinase. The two sequences isolated from spot 2 were determined to be from two DNAks, previously identified in *M. tuberculosis* as heat shock proteins. Spot 4 was determined to be the previously identified *M. tuberculosis* protein Kat G. To the best of the inventors' knowledge, neither PcK-1 nor the two DNAks have previously been shown to have utility in the diagnosis of *M. tuberculosis* infection.

Example 8

Synthesis of Synthetic Polypeptides

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation or labeling of the peptide. Cleavage of the peptides from the solid support may be carried out using the following cleavage mixture: trifluoroacetic acid: ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0-60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

This procedure was used to synthesize a TbM-1 peptide that contains one and a half repeats of a TbM-1 sequence. The TbM-1 peptide has the sequence GCGDRSGGNLDQIRLRRDRSGGNL (SEQ ID NO: 63).

Example 9

Use of Representative Antigens for Serodiagnosis of Tuberculosis

This Example illustrates the diagnostic properties of several representative antigens.

Assays were performed in 96-well plates were coated with 200 ng antigen diluted to 50 μL in carbonate coating buffer, pH 9.6. The wells were coated overnight at 4° C. (or 2 hours at 37° C.). The plate contents were then removed and the wells were blocked for 2 hours with 200 μL of PBS/1% BSA. After the blocking step, the wells were washed five times with PBS/0.1% Tween 20™. 50 μL sera, diluted 1:100 in PBS/0.1% Tween 20™/0.1% BSA, was then added to each well and incubated for 30 minutes at room temperature. The plates were then washed again five times with PBS/0.1% Tween 20™.

The enzyme conjugate (horseradish peroxidase—Protein A, Zymed, San Francisco, Calif.) was then diluted 1:10,000 in PBS/0.1% Tween 20™/0.1% BSA, and 50 μL of the diluted conjugate was added to each well and incubated for 30 minutes at room temperature. Following incubation, the wells were washed five times with PBS/0.1% Tween 20™. 100 μL of tetramethylbenzidine peroxidase (TMB) substrate (Kirkegaard and Perry Laboratories, Gaithersburg, Md.) was added, undiluted, and incubated for about 15 minutes. The reaction was stopped with the addition of 100 μL of 1 N $H_2SO_4$ to each well, and the plates were read at 450 nm.

Figure 4:
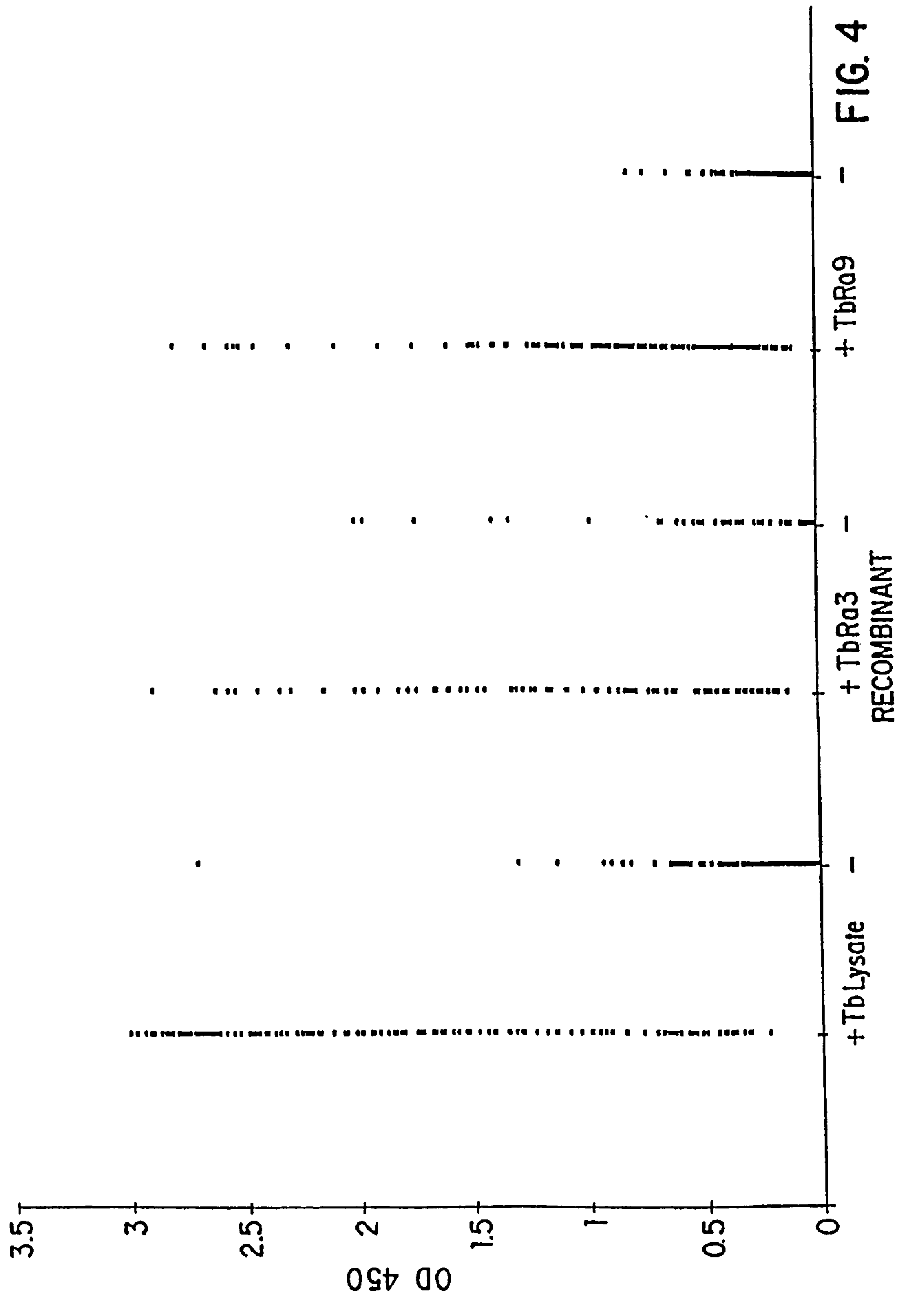
FIG. 4 illustrates the reactivity of two representative polypeptides with sera from *M. tuberculosis*-infected and uninfected individuals, as compared to the reactivity of bacterial lysate.

FIG. 4 shows the ELISA reactivity of two recombinant antigens isolated using method A in Example 3 (TbRa3 and TbRa9) with sera from *M. tuberculosis* positive and negative patients. The reactivity of these antigens is compared to that of bacterial lysate isolated from *M. tuberculosis* strain H37Ra (Difco, Detroit, Mich.). In both cases, the recombinant antigens differentiated positive from negative sera. Based on cut-off values obtained from receiver-operator curves, TbRa3 detected 56 out of 87 positive sera, and TbRa9 detected 111 out of 165 positive sera.

Figure 5:
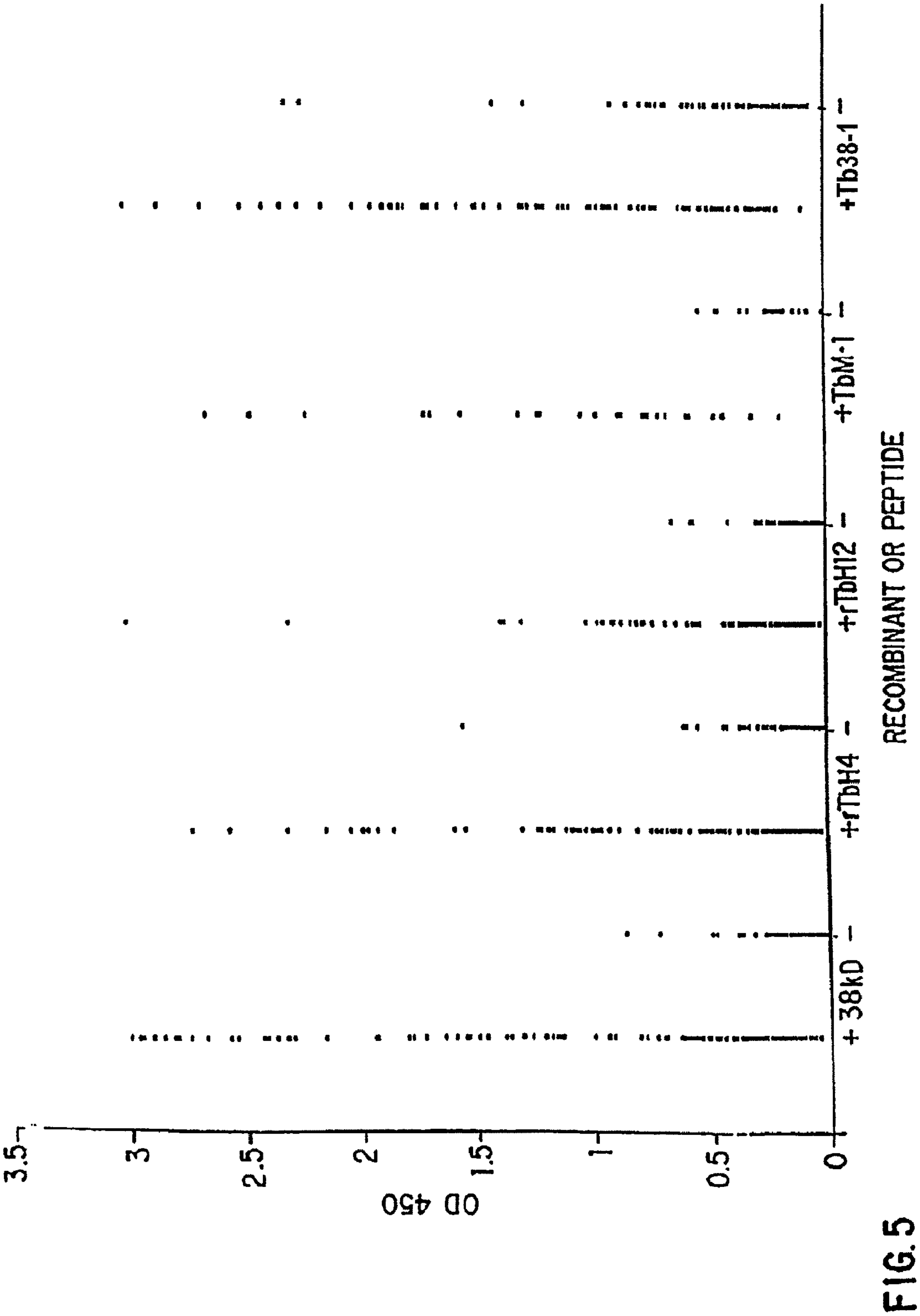
FIG. 5 shows the reactivity of four representative polypeptides with sera from *M. tuberculosis*-infected and uninfected individuals, as compared to the reactivity of the 38 kD antigen.

FIG. 5 illustrates the ELISA reactivity of representative antigens isolated using method B of Example 3. The reactivity of the recombinant antigens TbH4, TbH12, Tb38-1 and the peptide TbM-1 (as described in Example 4) is compared to that of the 38 kD antigen described by Andersen and Hansen, *Infect. Immun.* 57:2481-2488, 1989. Again, all of the polypeptides tested differentiated positive from negative sera. Based on cut-off values obtained from receiver-operator curves, TbH4 detected 67 out of 126 positive sera, TbH12 detected 50 out of 125 positive sera, 38-1 detected 61 out of 101 positive sera and the TbM-1 peptide detected 25 out of 30 positive sera.

The reactivity of four antigens (TbRa3, TbRa9, TbH4 and TbH12) with sera from a group of *M. tuberculosis* infected patients with differing reactivity in the acid fast stain of sputum (Smithwick and David, *Tubercle* 52:226, 1971) was also examined, and compared to the reactivity of *M. tuberculosis* lysate and the 38 kD antigen. The results are presented in Table 3, below:

TABLE 3

REACTIVITY OF ANTIGENS WITH SERA FROM *M. TUBERCULOSIS* PATIENTS

| Patient | Acid Fast Sputum | ELISA Values | | | | | |
|---|---|---|---|---|---|---|---|
| | | Lysate | 38 kD | TbRa9 | TbH12 | TbH4 | TbRa3 |
| Tb01B93I-2 | ++++ | 1.853 | 0.634 | 0.998 | 1.022 | 1.030 | 1.314 |
| Tb01B93I-19 | ++++ | 2.657 | 2.322 | 0.608 | 0.837 | 1.857 | 2.335 |
| Tb01B93I-8 | +++ | 2.703 | 0.527 | 0.492 | 0.281 | 0.501 | 2.002 |
| Tb01B93I-10 | +++ | 1.665 | 1.301 | 0.685 | 0.216 | 0.448 | 0.458 |
| Tb01B93I-11 | +++ | 2.817 | 0.697 | 0.509 | 0.301 | 0.173 | 2.608 |
| Tb01B93I-15 | +++ | 1.28 | 0.283 | 0.808 | 0.218 | 1.537 | 0.811 |
| Tb01B93I-16 | +++ | 2.908 | >3 | 0.899 | 0.441 | 0.593 | 1.080 |
| Tb01B93I-25 | +++ | 0.395 | 0.131 | 0.335 | 0.211 | 0.107 | 0.948 |
| Tb01B93I-87 | +++ | 2.653 | 2.432 | 2.282 | 0.977 | 1.221 | 0.857 |
| Tb01B93I-89 | +++ | 1.912 | 2.370 | 2.436 | 0.876 | 0.520 | 0.952 |
| Tb01B94I-108 | +++ | 1.639 | 0.341 | 0.797 | 0.368 | 0.654 | 0.798 |
| Tb01B94I-201 | +++ | 1.721 | 0.419 | 0.661 | 0.137 | 0.064 | 0.692 |
| Tb01B93I-88 | ++ | 1.939 | 1.269 | 2.519 | 1.381 | 0.214 | 0.530 |
| Tb01B93I-92 | ++ | 2.355 | 2.329 | 2.78 | 0.685 | 0.997 | 2.527 |
| Tb01B94I-109 | ++ | 0.993 | 0.620 | 0.574 | 0.441 | 0.5 | 2.558 |
| Tb01B94I-210 | ++ | 2.777 | >3 | 0.393 | 0.367 | 1.004 | 1.315 |
| Tb01B94I-224 | ++ | 2.913 | 0.476 | 0.251 | 1.297 | 1.990 | 0.256 |
| Tb01B93I-9 | + | 2.649 | 0.278 | 0.210 | 0.140 | 0.181 | 1.586 |
| Tb01B93I-14 | + | >3 | 1.538 | 0.282 | 0.291 | 0.549 | 2.880 |
| Tb01B93I-21 | + | 2.645 | 0.739 | 2.499 | 0.783 | 0.536 | 1.770 |
| Tb01B93I-22 | + | 0.714 | 0.451 | 2.082 | 0.285 | 0.269 | 1.159 |
| Tb01B93I-31 | + | 0.956 | 0.490 | 1.019 | 0.812 | 0.176 | 1.293 |
| Tb01B93I-32 | – | 2.261 | 0.786 | 0.668 | 0.273 | 0.535 | 0.405 |
| Tb01B93I-52 | – | 0.658 | 0.114 | 0.434 | 0.330 | 0.273 | 1.140 |
| Tb01B93I-99 | – | 2.118 | 0.584 | 1.62 | 0.119 | 0.977 | 0.729 |
| Tb01B94I-130 | – | 1.349 | 0.224 | 0.86 | 0.282 | 0.383 | 2.146 |
| Tb01B94I-131 | – | 0.685 | 0.324 | 1.173 | 0.059 | 0.118 | 1.431 |
| AT4-0070 | Normal | 0.072 | 0.043 | 0.092 | 0.071 | 0.040 | 0.039 |
| AT4-0105 | Normal | 0.397 | 0.121 | 0.118 | 0.103 | 0.078 | 0.390 |
| 3/15/94-1 | Normal | 0.227 | 0.064 | 0.098 | 0.026 | 0.001 | 0.228 |
| 4/15/93-2 | Normal | 0.114 | 0.240 | 0.071 | 0.034 | 0.041 | 0.264 |
| 5/26/94-4 | Normal | 0.089 | 0.259 | 0.096 | 0.046 | 0.008 | 0.053 |
| 5/26/94-3 | Normal | 0.139 | 0.093 | 0.085 | 0.019 | 0.067 | 0.01 |

Based on cut-off values obtained from receiver-operator curves, TbRa3 detected 23 out of 27 positive sera, TbRa9 detected 22 out of 27, TbH4 detected 18 out of 27 and TbH12 detected 15 out of 27. If used in combination, these four antigens would have a theoretical sensitivity of 27 out of 27, indicating that these antigens should complement each other in the serological detection of *M. tuberculosis* infection. In addition, several of the recombinant antigens detected positive sera that were not detected using the 38 kD antigen, indicating that these antigens may be complementary to the 38 kD antigen.

Figure 6:
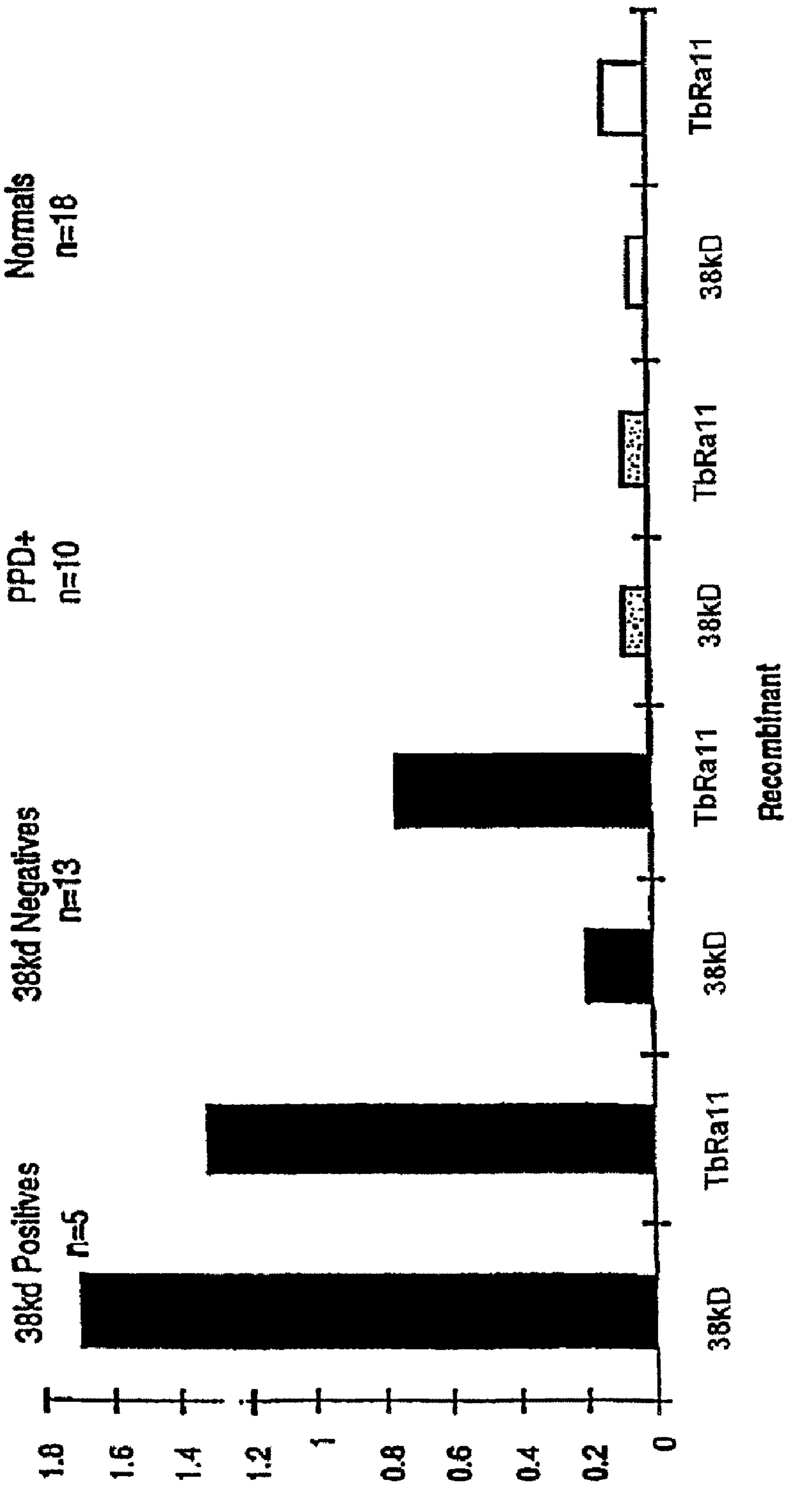
FIG. 6 shows the reactivity of recombinant 38 kD and TbRa11 antigens with sera from *M. tuberculosis* patients, PPD positive donors and normal donors.

The reactivity of the recombinant antigen TbRa11 with sera from *M. tuberculosis* patients shown to be negative for the 38 kD antigen, as well as with sera from PPD positive and normal donors, was determined by ELISA as described above. The results are shown in FIG. 6 which indicates that TbRa11, while being negative with sera from PPD positive and normal donors, detected sera that were negative with the 38 kD antigen. Of the thirteen 38 kD negative sera tested, nine were positive with TbRa11, indicating that this antigen may be reacting with a sub-group of 38 kD antigen negative sera. In contrast, in a group of 38 kD positive sera where TbRa11 was reactive, the mean OD 450 for TbRa11 was lower than that for the 38 kD antigen. The data indicate an inverse relationship between the presence of TbRa11 activity and 38 kD positivity.

Figure 7:
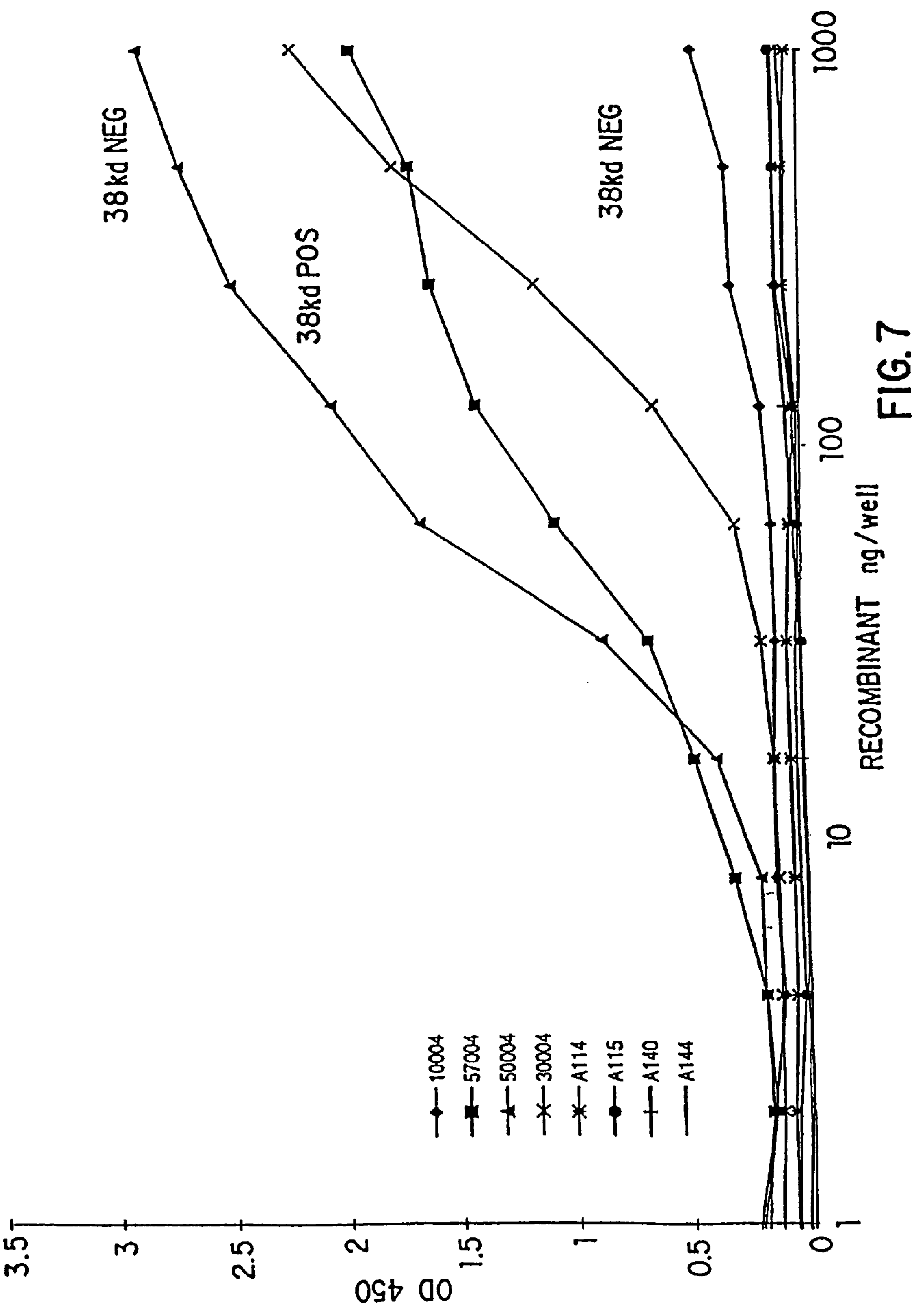
FIG. 7 shows the reactivity of the antigen TbRa2a with 38 kD negative and positive sera.

The antigen TbRa2A was tested in an indirect ELISA using initially 50 μl of serum at 1:100 dilution for 30 minutes at room temperature followed by washing in PBS Tween and incubating for 30 minutes with biotinylated Protein A (Zymed, San Francisco, Calif.) at a 1:10,000 dilution. Following washing, 50 μl of streptavidin-horseradish peroxidase (Zymed) at 1:10,000 dilution was added and the mixture incubated for 30 minutes. After washing, the assay was developed with TMB substrate as described above. The reactivity of TbRa2A with sera from *M. tuberculosis* patients and normal donors in shown in Table 4. The mean value for reactivity of TbRa2A with sera from *M. tuberculosis* patients was 0.444 with a standard deviation of 0.309. The mean for reactivity with sera from normal donors was 0.109 with a standard deviation of 0.029. Testing of 38 kD negative sera (FIG. 7) also indicated that the TbRa2A antigen was capable of detecting sera in this category.

TABLE 4

REACTIVITY OF TBRA2A WITH SERA FROM *M. TUBERCULOSIS* PATIENTS AND FROM NORMAL DONORS

| Serum ID | Status | OD 450 |
|---|---|---|
| Tb85 | TB | 0.680 |
| Tb86 | TB | 0.450 |
| Tb87 | TB | 0.263 |
| Tb88 | TB | 0.275 |
| Tb89 | TB | 0.403 |
| Tb91 | TB | 0.393 |
| Tb92 | TB | 0.401 |
| Tb93 | TB | 0.232 |
| Tb94 | TB | 0.333 |
| Tb95 | TB | 0.435 |
| Tb96 | TB | 0.284 |

TABLE 4-continued

REACTIVITY OF TBRA2A WITH SERA FROM *M. TUBERCULOSIS* PATIENTS AND FROM NORMAL DONORS

| Serum ID | Status | OD 450 |
|---|---|---|
| Tb97 | TB | 0.320 |
| Tb99 | TB | 0.328 |
| Tb100 | TB | 0.817 |
| Tb101 | TB | 0.607 |
| Tb102 | TB | 0.191 |
| Tb103 | TB | 0.228 |
| Tb107 | TB | 0.324 |
| Tb109 | TB | 1.572 |
| Tb112 | TB | 0.338 |
| DL4-0176 | Normal | 0.036 |
| AT4-0043 | Normal | 0.126 |
| AT4-0044 | Normal | 0.130 |
| AT4-0052 | Normal | 0.135 |
| AT4-0053 | Normal | 0.133 |
| AT4-0062 | Normal | 0.128 |
| AT4-0070 | Normal | 0.088 |
| AT4-0091 | Normal | 0.108 |
| AT4-0100 | Normal | 0.106 |
| AT4-0105 | Normal | 0.108 |
| AT4-0109 | Normal | 0.105 |

Figure 8:
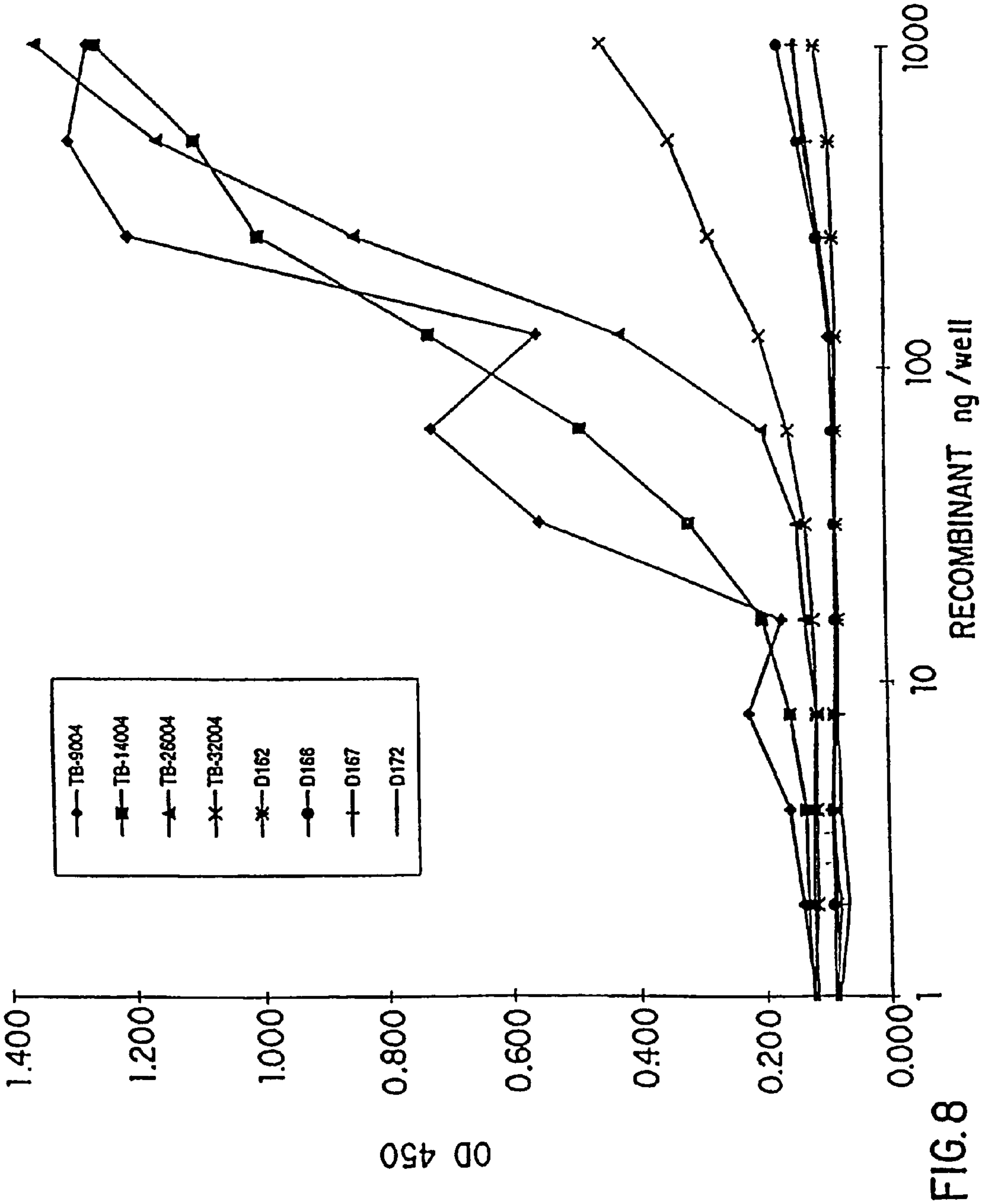
FIG. 8 shows the reactivity of the antigen of SEQ ID NO: 60 with sera from *M. tuberculosis* patients and normal donors.

The reactivity of the recombinant antigen (g) (SEQ ID NO: 60) with sera from *M. tuberculosis* patients and normal donors was determined by ELISA as described above. FIG. 8 shows the results of the titration of antigen (g) with four *M. tuberculosis* positive sera that were all reactive with the 38 kD antigen and with four donor sera. All four positive sera were reactive with antigen (g).

Figure 9:
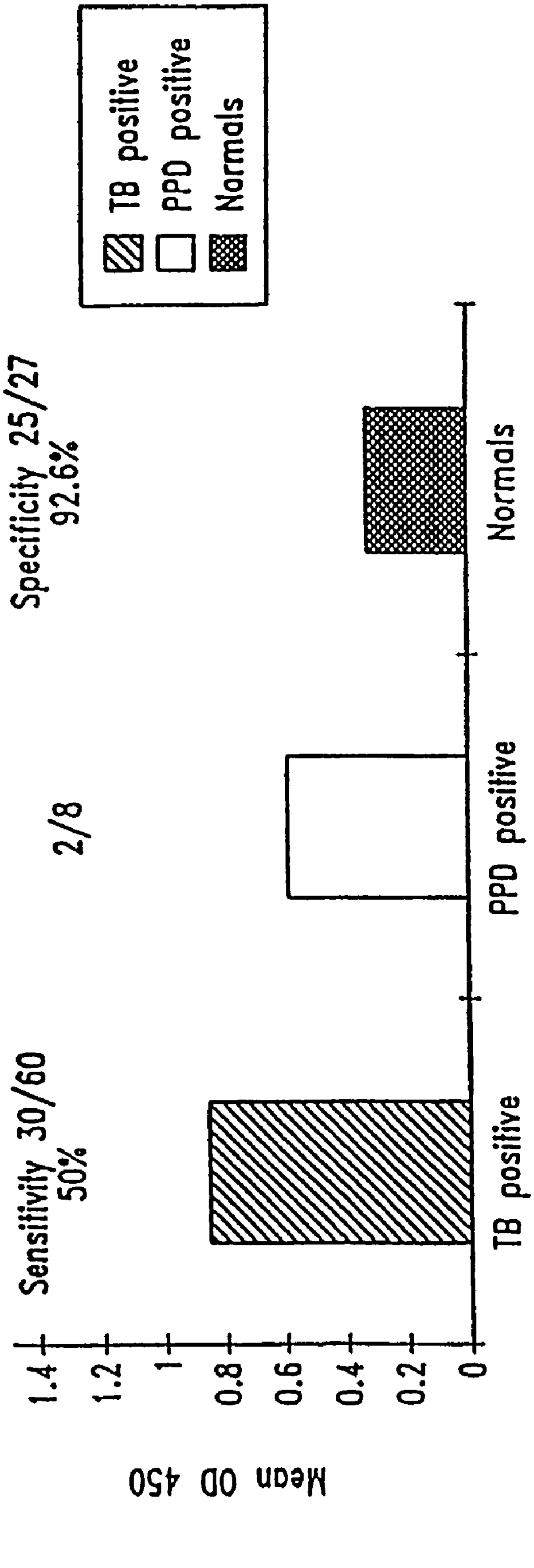
FIG. 9 illustrates the reactivity of the recombinant antigen TbH-29 (SEQ ID NO: 137) with sera from *M. tuberculosis* patients, PPD positive donors and normal donors as determined by indirect ELISA.

The reactivity of the recombinant antigen TbH-29 (SEQ ID NO: 137) with sera from *M. tuberculosis* patients, PPD positive donors and normal donors was determined by indirect ELISA as described above. The results are shown in FIG. 9. TbH-29 detected 30 out of 60 *M. tuberculosis* sera, 2 out of 8 PPD positive sera and 2 out of 27 normal sera.

FIG. 10 shows the results of ELISA tests (both direct and indirect) of the antigen TbH-33 (SEQ ID NO: 140) with sera from *M. tuberculosis* patients and from normal donors and with a pool of sera from *M. tuberculosis* patients. The mean OD 450 was demonstrated to be higher with sera from *M. tuberculosis* patients than from normal donors, with the mean OD 450 being significantly higher in the indirect ELISA than in the direct ELISA. FIG. 11 is a titration curve for the reactivity of recombinant TbH-33 with sera from *M. tuberculosis* patients and from normal donors showing an increase in OD 450 with increasing concentration of antigen.

The reactivity of the recombinant antigens RDIF6, RDIF8 and RDIF10 (SEQ ID NOS: 184-187, respectively) with sera from *M. tuberculosis* patients and normal donors was determined by ELISA as described above. RDIF6 detected 6 out of 32 *M. tuberculosis* sera and 0 out of 15 normal sera; RDEF8 detected 14 out of 32 *M. tuberculosis* sera and 0 out of 15 normal sera; and RDIF10 detected 4 out of 27 *M. tuberculosis* sera and 1 out of 15 normal sera. In addition, RDIF10 was found to detect 0 out of 5 sera from PPD-positive donors.

The antigens MO-1, MO-2, MO-4, MO-28 and MO-29 described above in Example 5, were expressed in *E. coli* and purified using a hexahistidine tag. The reactivity of these antigens with both *M. tuberculosis* positive and negative sera was examined by ELISA as described above. Titration curves showing the reactivity of MO-1, MO-2, MO-4, MO-28 and MO-29 at different solid phase coat levels when tested against four *M. tuberculosis* positive sera and four *M. tuberculosis* negative sera are shown in FIGS. 12A-E, respectively. Three of the clones, MO-1, MO-2 and MO-29 were further tested on panels of HIV positive/tuberculosis (HIV/TB) positive and extrapulmonary sera MO-1 detected 3/20 extrapulmonary and 2/38 HIV/TB sera. On the same sera groups, MO-2 detected 2/20 and 10/38, and MO-29 detected 2/20 and 8/38 sera. In combination these three clones would have detected 4/20 extrapulmonary sera and 16/38 HIV/TB sera. In addition, MO-1 detected 6/17 sera that had previously been shown only to react with *M. tuberculosis* lysate and not with either 38 kD or with other antigens of the subject invention.

Example 10

Preparation and Characterization of *M. tuberculosis* Fusion Proteins

A fusion protein containing TbRa3, the 38 kD antigen and Tb38-1 was prepared as follows.

Each of the DNA constructs TbRa3, 38 kD and Tb38-1 were modified by PCR in order to facilitate their fusion and the subsequent expression of the fusion protein TbRa3-38 kD-Tb38-1. TbRa3, 38 kD and Tb38-1 DNA was used to perform PCR using the primers PDM-64 and PDM-65 (SEQ ID NO: 141 and 142), PDM-57 and PDM-58 (SEQ ID NO: 143 and 144), and PDM-69 and PDM-60 (SEQ ID NO: 145-146), respectively. In each case, the DNA amplification was performed using 10 μl 10×Pfu buffer, 2 μl 10 mM dNTPs, 2 μl each of the PCR primers at 10 μM concentration, 81.5 μl water, 1.5 μl Pfu DNA polymerase (Stratagene, La Jolla, Calif.) and 1 μl DNA at either 70 ng/μl (for TbRa3) or 50 ng/μl (for 38 kD and Tb38-1). For TbRa3, denaturation at 94° C. was performed for 2 min, followed by 40 cycles of 96° C. for 15 sec and 72° C. for 1 min, and lastly by 72° C. for 4 min. For 38 kD, denaturation at 96° C. was performed for 2 min, followed by 40 cycles of 96° C. for 30 sec, 68° C. for 15 sec and 72° C. for 3 min, and finally by 72° C. for 4 min. For Tb38-1 denaturation at 94° C. for 2 min was followed by 10 cycles of 96° C. for 15 sec, 68° C. for 15 sec and 72° C. for 1.5 min, 30 cycles of 96° C. for 15 sec, 64° C. for 15 sec and 72° C. for 1.5, and finally by 72° C. for 4 min.

The TbRa3 PCR fragment was digested with NdeI and EcoRI and cloned directly into pT7^L2 IL 1 vector using NdeI and EcoRI sites. The 38 kD PCR fragment was digested with Sse83871, treated with T4 DNA polymerase to make blunt ends and then digested with EcoRI for direct cloning into the pT7^L2Ra3-1 vector which was digested with StuI and EcoRI. The 38-1 PCR fragment was digested with Eco47III and EcoRI and directly subcloned into pT7^Ra3/38 kD-17 digested with the same enzymes. The whole fusion was then transferred to pET28b using NdeI and EcoRI sites. The fusion construct was confirmed by DNA sequencing.

The expression construct was transformed to BLR pLys S *E. coli* (Novagen, Madison, Wis.) and grown overnight in LB broth with kanamycin (30 μg/ml) and chloramphenicol (34 μg/ml). This culture (12 ml) was used to inoculate 500 ml 2XYT with the same antibiotics and the culture was induced with IPTG at an OD560 of 0.44 to a final concentration of 1.2 mM. Four hours post-induction, the bacteria were harvested and sonicated in 20 mM Tris (8.0), 100 mM NaCl, 0.1% DOC, 20 μg/ml Leupeptin, 20 mM PMSF followed by centrifugation at 26,000×g. The resulting pellet was resuspended in 82 M urea, 20 mM Tris (8.0), 100 mM NaCl and bound to Pro-bond nickel resin (Invitrogen, Carlsbad, Calif.). The column was washed several times with the above buffer then eluted with an imidazole gradient (50 mM, 100 mM, 500 mM imidazole was added to 8 M urea, 20 mM Tris (8.0), 100 mM NaCl). The eluates containing the protein of interest were then dialzyed against 10 mM Tris (8.0).

The DNA and amino acid sequences for the resulting fusion protein (hereinafter referred to as TbRa3-38 kD-Tb38-1) are provided in SEQ ID NO: 147 and 148, respectively.

A fusion protein containing the two antigens TbH-9 and Tb38-1 (hereinafter referred to as TbH9-Tb38-1) without a hinge sequence, was prepared using a similar procedure to that described above.

A fusion protein containing TbRa3, the antigen 38 kD, Tb38-1 and DPEP was prepared as follows.

Each of the DNA constructs TbRa3, 38 kD and Tb38-1 were modified by PCR and cloned into vectors essentially as described above, with the primers PDM-69 (SEQ ID NO:145 and PDM-83 (SEQ ID NO: 200) being used for amplification of the Tb38-1A fragment. Tb38-1A differs from Tb38-1 by a DraI site at the 3' end of the coding region that keeps the final amino acid intact while creating a blunt restriction site that is in frame. The TbRa3/38 kD/Tb38-1A fusion was then transferred to pET28b using NdeI and EcoRI sites.

DPEP DNA was used to perform PCR using the primers PDM-84 and PDM-85 (SEQ ID NO: 201 and 202, respectively) and 1 μl DNA at 50 ng/μl. Denaturation at 94° C. was performed for 2 min, followed by 10 cycles of 96° C. for 15 sec, 68° C. for 15 sec and 72° C. for 1.5 min; 30 cycles of 96° C. for 15 sec, 64° C. for 15 sec and 72° C. for 1.5 min; and finally by 72° C. for 4 min. The DPEP PCR fragment was digested with EcoRI and Eco72I and cloned directly into the pET28Ra3/38 kD/38-1A construct which was digested with DraI and EcoRI. The fusion construct was confirmed to be correct by DNA sequencing. Recombinant protein was prepared as described above. The DNA and amino acis sequences for the resulting fusion protein (hereinafter referred to as TbF-2) are provided in SEQ ID NO: 208 and 209, respectively.

A fusion protein containing TbRa3, the antigen 38 kD, Tb38-1 and TbH4 was prepared as follows.

Genomic *M. tuberculosis* DNA was used to PCR full-length TbH4 (FL TbH4) with the primers PDM-157 and PDM-160 (SEQ ID NO: 343 and 344, respectively) and 2 μl DNA at 100 ng/μl. Denaturation at 96° C. was performed for 2 min, followed by 40 cycles of 96° C. for 30 sec, 61° C. for 20 sec and 72° C. for 5 min; and finally by annealing at 72° C. for 10 min. The FL TbH4 PCR fragment was digested with EcoRI and Sca I (New England Biolabs.) and cloned directly into the pET28Ra3/38 kD/38-1A construct described above which was digested with DraI and EcoRI. The fusion construct was confirmed to be correct by DNA sequencing. Recombinant protein was prepared as described above. The DNA and amino acid sequences for the resulting fusion protein (hereinafter referred to as TbF-6) are provided in SEQ ID NO: 345 and 346, respectively.

A fusion protein containing the antigen 38 kD and DPEP separated by a linker was prepared as follows.

38 kD DNA was used to perform PCR using the primers PDM-176 and PDM-175 (SEQ ID NO: 347 and 348, respectively), and 1 μl PET28Ra3/38 kD/38-1/Ra2A-12 DNA at 110 ng/μl. Denaturation at 96° C. was performed for 2 min, followed by 40 cycles of 96° C. for 30 sec, 71° C. for 15 sec and 72° C. for 5 min and 40 sec; and finally by annealing at 72° C. for 4 min. The two sets of primers PDM-171, PDM-172, and PDM-173, PDM-174 were annealed by heating to 95° C. for 2 min and then ramping down to 25° C. slowly at 0.1° C./sec. DPEP DNA was used to perform PCR as described above. The 38 kD fragment was digested with Eco RI (New England Biolabs) and cloned into a modified pT7ΔL2 vector which was cut with Eco 72 I (Promega) and Eco RI. The modified pT7ΔL2 construct was designed to have a MGHHHHHH (SEQ ID NO:351) amino acid coding region in frame just 5' of the Eco 72 I site. The construct was digested with Kpn 2I(Gibco, BRL) and Pst I (New England Biolabs) and the annealed sets of phosphorylated primers (PDM-171, PDM-172 and PDM-173, PDM-174) were cloned in. The DPEP PCR fragment was digested with Eco RI and Eco 72 I and cloned into this second construct which was digested with Eco 47 III (New England Biolabs) and Eco RI. Ligations were done with a ligation kit from Panvera (Madison, Wis.). The resulting construct was digested with NdeI (New England Biolabs) and Eco RI, and transferred to a modified pET28 vector. The fusion construct was confirmed to be correct by DNA sequencing.

Recombinant protein was prepared essentially as described above. The DNA and amino acid sequences for the resulting fusion protein (hereinafter referred to as TbF-8) are provided in SEQ ID NO: 349 and 350, respectively.

Example 11

Use of *M. tuberculosis* Fusion Proteins for Serodiagnosis of Tuberculosis

The effectiveness of the fusion protein TbRa3-38 kD-Tb38-1, prepared as described above, in the serodiagnosis of tuberculosis infection was examined by ELISA.

The ELISA protocol was as described above in Example 6, with the fusion protein being coated at 200 ng/well. A panel of sera was chosen from a group of tuberculosis patients previously shown, either by ELISA or by western blot analysis, to react with each of the three antigens individually or in combination. Such a panel enabled the dissection of the serological reactivity of the fusion protein to determine if all three epitopes functioned with the fusion protein. As shown in Table 5, all four sera that reacted with TbRa3 only were detectable with the fusion protein. Three sera that reacted only with Tb38-1 were also detectable, as were two sear that reacted with 38 kD alone. The remaining 15 sera were all positive with the fusion protein based on a cut-off in the assay of mean negatives +3 standard deviations. This data demonstrates the functional activity of all three epitopes in the fusion protein.

TABLE 5

REACTIVITY OF TRI-PEPTIDE FUSION PROTEIN WITH SERA FROM *M. TUBERCULOSIS* PATIENTS

| | | ELISA and/or Western Blot Reactivity with Individual proteins | | | Fusion Recom-binant | Fusion Recom-binant |
|---|---|---|---|---|---|---|
| Serum ID | Status | 38 kd | Tb38-1 | TbRa3 | OD 450 | Status |
| 01B93I-40 | TB | − | − | + | 0.413 | + |
| 01B93I-41 | TB | − | + | + | 0.392 | + |
| 01B93I-29 | TB | + | − | + | 2.217 | + |
| 01B93I-109 | TB | + | ± | + | 0.522 | + |
| 01B93I-132 | TB | + | + | + | 0.937 | + |
| 5004 | TB | ± | + | ± | 1.098 | + |
| 15004 | TB | + | + | + | 2.077 | + |
| 39004 | TB | + | + | + | 1.675 | + |
| 68004 | TB | + | + | + | 2.388 | + |
| 99004 | TB | − | + | ± | 0.607 | + |
| 107004 | TB | − | + | ± | 0.667 | + |
| 92004 | TB | + | ± | ± | 1.070 | + |
| 97004 | TB | + | − | ± | 1.152 | + |
| 118004 | TB | + | − | ± | 2.694 | + |
| 173004 | TB | + | + | + | 3.258 | + |
| 175004 | TB | + | − | + | 2.514 | + |
| 274004 | TB | − | − | + | 3.220 | + |
| 276004 | TB | − | + | − | 2.991 | + |

TABLE 5-continued

REACTIVITY OF TRI-PEPTIDE FUSION PROTEIN WITH SERA FROM *M. TUBERCULOSIS* PATIENTS

| | | ELISA and/or Western Blot Reactivity with Individual proteins | | | Fusion Recombinant | Fusion Recombinant |
|---|---|---|---|---|---|---|
| Serum ID | Status | 38 kd | Tb38-1 | TbRa3 | OD 450 | Status |
| 282004 | TB | + | − | − | 0.824 | + |
| 289004 | TB | − | − | + | 0.848 | + |
| 308004 | TB | − | + | − | 3.338 | + |
| 314004 | TB | − | + | − | 1.362 | + |
| 317004 | TB | + | − | − | 0.763 | + |
| 312004 | TB | − | − | + | 1.079 | + |
| D176 | PPD | − | − | − | 0.145 | − |
| D162 | PPD | − | − | − | 0.073 | − |
| D161 | PPD | − | − | − | 0.097 | − |
| D27 | PPD | − | − | − | 0.082 | − |
| A6-124 | NORMAL | − | − | − | 0.053 | − |
| A6-125 | NORMAL | − | − | − | 0.087 | − |
| A6-126 | NORMAL | − | − | − | 0.346 | ± |
| A6-127 | NORMAL | − | − | − | 0.064 | − |
| A6-128 | NORMAL | − | − | − | 0.034 | − |
| A6-129 | NORMAL | − | − | − | 0.037 | − |
| A6-130 | NORMAL | − | − | − | 0.057 | − |
| A6-131 | NORMAL | − | − | − | 0.054 | − |
| A6-132 | NORMAL | − | − | | 0.022 | − |
| A6-133 | NORMAL | − | − | | 0.147 | − |
| A6-134 | NORMAL | − | − | − | 0.101 | − |
| A6-135 | NORMAL | − | − | | 0.066 | − |
| A6-136 | NORMAL | − | − | | 0.054 | − |
| A6-137 | NORMAL | − | − | − | 0.065 | − |
| A6-138 | NORMAL | − | − | − | 0.041 | − |
| A6-139 | NORMAL | − | − | − | 0.103 | − |
| A6-140 | NORMAL | − | − | − | 0.212 | − |
| A6-141 | NORMAL | − | − | − | 0.056 | − |
| A6-142 | NORMAL | − | − | − | 0.051 | − |

The reactivity of the fusion protein TbF-2 with sera from *M. tuberculosis*-infected patients was examined by ELISA using the protocol described above. The results of these studies (Table 6) demonstrate that all four antigens function independently in the fusion protein.

TABLE 6

REACTIVITY OF TBF-2 FUSION PROTEIN WITH TB AND NORMAL SERA

| | | TbF | | TbF-2 | | ELISA Reactivity | | | |
|---|---|---|---|---|---|---|---|---|---|
| Serum ID | Status | OD450 | Status | OD450 | Status | 38 kD | TbRa3 | Tb38-1 | DPEP |
| B931-40 | TB | 0.57 | + | 0.321 | + | − | + | − | + |
| B931-41 | TB | 0.601 | + | 0.396 | + | + | + | + | − |
| B931-109 | TB | 0.494 | + | 0.404 | + | + | + | ± | − |
| B931-132 | TB | 1.502 | + | 1.292 | + | + | + | + | ± |
| 5004 | TB | 1.806 | + | 1.666 | + | ± | ± | + | − |
| 15004 | TB | 2.862 | + | 2.468 | + | + | + | + | − |
| 39004 | TB | 2.443 | + | 1.722 | + | + | + | + | − |
| 68004 | TB | 2.871 | + | 2.575 | + | + | − | + | − |
| 99004 | TB | 0.691 | + | 0.971 | + | − | ± | − | − |
| 107004 | TB | 0.875 | + | 0.732 | + | − | ± | − | − |
| 92004 | TB | 1.632 | + | 1.394 | + | + | ± | ± | − |
| 97004 | TB | 1.491 | + | 1.979 | + | + | ± | − | + |
| 118004 | TB | 3.182 | + | 3.045 | + | + | ± | − | − |
| 173004 | TB | 3.644 | + | 3.578 | + | + | + | + | − |
| 175004 | TB | 3.332 | + | 2.916 | + | + | + | − | − |
| 274004 | TB | 3.696 | + | 3.716 | + | − | + | − | + |
| 276004 | TB | 3.243 | + | 2.56 | + | − | − | + | − |
| 282004 | TB | 1.249 | + | 1.234 | + | + | − | − | − |
| 289004 | TB | 1.373 | + | 1.17 | + | − | + | − | − |
| 308004 | TB | 3.708 | + | 3.355 | + | − | − | + | − |
| 314004 | TB | 1.663 | + | 1.399 | + | − | − | + | − |
| 317004 | TB | 1.163 | + | 0.92 | + | + | − | − | − |
| 312004 | TB | 1.709 | + | 1.453 | + | − | + | − | − |
| 380004 | TB | 0.238 | − | 0.461 | + | − | ± | − | + |
| 451004 | TB | 0.18 | − | 0.2 | − | − | − | − | ± |
| 478004 | TB | 0.188 | − | 0.469 | + | − | − | − | ± |
| 410004 | TB | 0.384 | + | 2.392 | + | ± | − | − | + |
| 411004 | TB | 0.306 | + | 0.874 | + | − | + | − | + |
| 421004 | TB | 0.357 | + | 1.456 | + | − | + | − | + |
| 528004 | TB | 0.047 | − | 0.196 | − | − | − | − | + |
| A6-87 | Normal | 0.094 | − | 0.063 | − | − | − | − | − |
| A6-88 | Normal | 0.214 | − | 0.19 | − | − | − | − | − |
| A6-89 | Normal | 0.248 | − | 0.125 | − | − | − | − | − |
| A6-90 | Normal | 0.179 | − | 0.206 | − | − | − | − | − |
| A6-91 | Normal | 0.135 | − | 0.151 | − | − | − | − | − |
| A6-92 | Normal | 0.064 | − | 0.097 | − | − | − | − | − |
| A6-93 | Normal | 0.072 | − | 0.098 | − | − | − | − | − |
| A6-94 | Normal | 0.072 | − | 0.064 | − | − | − | − | − |
| A6-95 | Normal | 0.125 | − | 0.159 | − | − | − | − | − |
| A6-96 | Normal | 0.121 | − | 0.12 | − | − | − | − | − |
| Cut-off | | 0.284 | | 0.266 | | | | | |

One of skill in the art will appreciate that the order of the individual antigens within the fusion protein may be changed and that comparable activity would be expected provided each of the epitopes is still functionally available. In addition, truncated forms of the proteins containing active epitopes may be used in the construction of fusion proteins.

From the foregoing, it will be appreciated that, although specific embodiments of the invention have been described herein for the purpose of illustration, various modifications may be made without deviating from the spirit and scope of the invention.

We claim:

1. A method for detecting *M. tuberculosis* infection in a patient, the method comprising:

(a) contacting a biological sample from said patient with an isolated polypeptide comprising an *M. tuberculosis* antigen encoded by the polynucleotide consisting of SEQ ID NO:46, (b) detecting in the sample antibodies that specifically bind the *M. tuberculosis* antigen, wherein the presence of such antibodies indicates *M. tuberculosis* infection in the patient.

2. The method according to claim 1, wherein the polypeptide is bound to a solid support.

3. The method according to claim 2, wherein the solid support comprises nitrocellulose, latex or a plastic material.

4. The method according to claim 1, wherein the biological sample is selected from the group consisting of whole blood, sputum, serum, plasma, saliva, cerebrospinal fluid, and urine.

5. The method according to claim 4, wherein the biological sample is whole blood, serum, or plasma.

6. A method for detecting *M. tuberculosis* infection in a patient, the method comprising:

(a) contacting a biological sample from said patient with an isolated polypeptide comprising an antigenic portion of the *M. tuberculosis* antigen encoded by the polynucleotide consisting of SEQ ID NO:46; and detecting in the sample antibodies that specifically bind said antigenic portion of the *M. tuberculosis* antigen;

wherein the presence of such antibodies indicates *M. tuberculosis* infection in the patient.

7. The method according to claim 6, wherein the polypeptide is bound to a solid support.

8. The method according to claim 7, wherein the solid support comprises nitrocellulose, latex or a plastic material.

9. The method according to claim 6, wherein the biological sample is selected from the group consisting of whole blood, sputum, serum, plasma, saliva, cerebrospinal fluid, and urine.

10. The method according to claim 9, wherein the biological sample is whole blood, serum, or plasma.

11. A method for detecting *M. tuberculosis* infection in a patient, the method comprising:

(a) contacting a biological sample from said patient with an isolated polypeptide comprising a variant of the *M. tuberculosis* antigen encoded by the polynucleotide consisting of SEQ ID NO:46, said variant having at least about 95% identity to said *M. tuberculosis* antigen; and detecting in the sample antibodies that specifically bind said variant of the M tuberculosis antigen;

wherein the presence of such antibodies indicates *M. tuberculosis* infection in the patient.

12. The method according to claim 11, wherein the polypeptide is bound to a solid support.

13. The method according to claim 12, wherein the solid support comprises nitrocellulose, latex or a plastic material.

14. The method according to claim 11, wherein the biological sample is selected from the group consisting of whole blood, sputum, serum, plasma, saliva, cerebrospinal fluid, and urine.

15. The method according to claim 14, wherein the biological sample is whole blood, serum, or plasma.

* * * * *